United States Patent
Zhang et al.

(10) Patent No.: US 11,639,388 B2
(45) Date of Patent: May 2, 2023

(54) CD3 ANTIGEN BINDING FRAGMENT AND APPLICATION THEREOF

(71) Applicant: Wuhan YZY Biopharma Co., Ltd., Wuhan (CN)

(72) Inventors: Jing Zhang, Wuhan (CN); Lijuan Fang, Wuhan (CN); Yongxiang Yan, Wuhan (CN); Liang Zeng, Wuhan (CN); Pengfei Zhou, Wuhan (CN)

(73) Assignee: Wuhan YZY Biopharma Co., Ltd., Wuhan (CN)

( * ) Notice: Subject to any disclaimer, the term of this patent is extended or adjusted under 35 U.S.C. 154(b) by 0 days.

(21) Appl. No.: 17/432,892

(22) PCT Filed: Feb. 22, 2019

(86) PCT No.: PCT/CN2019/075901
§ 371 (c)(1),
(2) Date: Aug. 20, 2021

(87) PCT Pub. No.: WO2020/168555
PCT Pub. Date: Aug. 27, 2020

(65) Prior Publication Data
US 2022/0041721 A1 Feb. 10, 2022

(51) Int. Cl.
*C07K 16/28* (2006.01)

(52) U.S. Cl.
CPC ...... *C07K 16/2809* (2013.01); *C07K 2317/31* (2013.01); *C07K 2317/524* (2013.01); *C07K 2317/526* (2013.01); *C07K 2317/53* (2013.01)

(58) Field of Classification Search
CPC ............ C07K 16/2809; C07K 2317/31; C07K 2317/524; C07K 2317/526; C07K 2317/53; C07K 16/2851; C07K 16/2896; C07K 2317/24; C07K 2317/33; C07K 2317/567; C07K 2317/73; C07K 2317/92; C07K 2317/94; C07K 16/468; A61P 35/00; A61K 2039/505
See application file for complete search history.

(56) References Cited

U.S. PATENT DOCUMENTS 8,216,805 B2 * 7/2012 Carter .................. C07K 16/46
435/71.1
8,846,042 B2 * 9/2014 Zhou .................... C07K 14/705
530/387.3
9,822,186 B2 * 11/2017 Bernett ............... C07K 16/2809
2014/0243505 A1 * 8/2014 Zhou .................. C07K 16/2809
530/387.3
2014/0377270 A1 * 12/2014 Moore ............... C07K 16/2803
435/69.6
2016/0058857 A1 * 3/2016 Spencer ......... A61K 39/001171
435/325

FOREIGN PATENT DOCUMENTS

| WO | WO2007019620 A1 | 2/2007 | |
| WO | WO2013158856 A2 | 10/2013 | |
| WO | WO2017023761 A1 | 2/2017 | |
| WO | WO-2017157305 A1 * | 9/2017 | ......... A61K 31/573 |

OTHER PUBLICATIONS

Piche-Nicholas et al., MABS 10(1): 81-94 (Year: 2018).*
Rudikoff et al., Proc Natl Acad Sci USA 79: 1979-1983 (Year: 1982).*
Wu et al., J. Mol. Biol. 294: 151-162 (Year: 1999).*
Lloyd et al., Protein Engineering, Design & Selection 22:159-168 (Year: 2009).*
Edwards et al., J Mol Biol. 334(1): 103-118 (Year: 2003).*
International Search Report and Written Opinion for PCT/CN2019/075901, dated Nov. 28, 2019 (8 pages).

* cited by examiner

*Primary Examiner* — Phuong Huynh
(74) *Attorney, Agent, or Firm* — Sheppard Mullin Richter & Hampton LLP

(57) ABSTRACT

Provided in the present application is a humanized and multifunctional CD3 antibody; a heavy chain variable region of the CD3 antibody comprised herein contains the amino acid sequence of any one of SEQ ID NOs: 1-3 or a variant sequence thereof; and a light chain variable region thereof contains the amino acid sequence of any one of SEQ ID NOs: 26-28 or a variant sequence thereof. Further provided in the present application is a multifunctional antibody comprising (a) a light chain-heavy chain pair that has specificity for tumor cells or microorganisms; and (b) a fusion peptide that comprises a single-chain variable fragment and an Fc fragment having a CH2 domain and/or a CH3 domain, the fusion peptide having specificity for immune cells. The antibodies provided in the present application have improved biological activity, thermal stability and/or acid resistance.

5 Claims, 12 Drawing Sheets
Specification includes a Sequence Listing.

US 11,639,388 B2

CD3 ANTIGEN BINDING FRAGMENT AND APPLICATION THEREOF

CROSS REFERENCE TO RELATED APPLICATIONS

This application is a U.S. National Stage Application under 35 U.S.C. 371 of International Application No. PCT/CN2019/075901, filed Feb. 22, 2019, the content of which is incorporated by reference in its entirety into the present disclosure.

SEQUENCE LISTING

The instant application contains a Sequence Listing which has been submitted electronically in ASCII format and is hereby incorporated by reference in its entirety. Said ASCII copy, created on Aug. 20, 2021, is named YZY022_SEQLT.txt and is 188 kb size.

FIELD OF THE INVENTION

The present invention relates to the field of genetic engineering, and in particular to the field of antibody engineering. Specifically, the present application relates to antibodies, such as multi-functional antibodies, such as antibodies against CD3, in particular humanized antibodies, antigen-binding fragments of the antibodies, and related uses.

BACKGROUND ART

CD3 is a T cell surface molecule that can bind to T cell receptors on the surface of T cells to form a TCR-CD3 complex to activate T cells, and play an important role in antigen recognition and immune signal transduction. Anti-CD3 antibodies are widely used in the treatment of transplant rejection and autoimmune diseases. It is known that murine anti-CD3 antibodies, such as OKT3, may cause a significant human anti-mouse antibody (HAMA) response, which is not conducive to use in humans. Therefore, it is necessary to subject these mouse antibodies to humanization or other treatments to reduce adverse reactions. At present, the main way to avoid or reduce the HAMA response is to humanize murine monoclonal antibodies or develop fully humanized antibodies. For example, the HAMA response can be reduced by introducing sequence fragments identical to the human antibody protein into the murine antibody. However, there may not be structurally similar proteins in humans, and such treatment may not be possible. Moreover, bottlenecks such as decreased antibody affinity, low activity, poor stability or low yield of humanized antibodies often occur and active therapeutic proteins cannot be obtained.

SUMMARY OF THE INVENTION

The present invention provides an antibody, such as a multi-functional antibody, such as an antibody for CD3, in particular a humanized antibody, an antigen-binding fragment of the antibody, and a related use.

In some embodiments, the invention provides an antibody or an antigen binding fragment thereof, in particular a humanized antibody or an antigen binding fragment thereof, the antibody specifically binding to CD3 of primates, e.g., humans and/or monkeys, the antibody comprising framework regions, which are FR-H1, FR-H2, FR-H3, FR-H4, FR-L1, FR-L2, FR-L3 and FR-L4, respectively, and complementarity-determining regions (CDRs), wherein CDR-H1, CDR-H2 and CDR-H3 amino acid sequences of heavy chain variable regions are amino acid sequences shown in SEQ ID NOs:1, 2 and 3, respectively, or variant sequences thereof, such as any one of sequences shown in the CDR3 variant sequences SEQ ID Nos: 4-14 and 190-191; CDR-H1, CDR-H2 and CDR-H3 amino acid sequences of light chain variable regions are amino acid sequences shown in SEQ ID NOs:26, 27 and 28, respectively, or variant sequences thereof, wherein the framework regions of the humanized antibody comprise one or more of the following sequences:
  a) FR-H1 of SEQ ID No: 15 or 16;
  b) FR-H2 of SEQ ID No: 17;
  c) FR-H3 of any one of SEQ ID Nos: 18-24;
  d) FR-H4 of SEQ ID No: 25;
  e) FR-L1 of any one of SEQ ID Nos: 29-31;
  f) FR-L2 of any one of SEQ ID Nos: 32-38;
  g) FR-L3 of any one of SEQ ID Nos: 39-42; and/or
  h) FR-L4 of any one of SEQ ID Nos: 43-44.

In some embodiments, the invention provides an antibody or an antigen binding fragment thereof, in particular a humanized antibody or an antigen binding fragment thereof, the antibody specifically binding to CD3 of primates, e.g., humans and/or monkeys, wherein the antibody comprises a heavy chain variable region and a light chain variable region, and the heavy chain variable region comprises any one of the following sequences:
  a) amino acid sequences of SEQ ID NOs: 45-62;
  b) amino acid sequences having 80%, 85%, 90%, 91%, 92%, 93%, 94%, 95%, 96%, 97%, 98%, 99% or higher amino acid identity with at least one amino acid sequence of SEQ ID NOs: 45-62;
  c) amino acid sequences having one or more (preferably one or several, and more preferably 1, 2, or 3) different amino acids with at least one amino acid sequence of SEQ ID NOs: 45-62; and the light chain variable region comprises any one of the following sequences:
  d) amino acid sequences of SEQ ID NOs: 63-73;
  e) amino acid sequences having 80%, 85%, 90%, 91%, 92%, 93%, 94%, 95%, 96%, 97%, 98%, 99% or higher amino acid identity with at least one amino acid sequence of SEQ ID NOs: 63-73;
  f) amino acid sequences having one or more (preferably one or several, and more preferably 1, 2, or 3) different amino acids with at least one amino acid sequence of SEQ ID NOs: 63-73.

In some embodiments, the invention provides an antibody or an antigen binding fragment thereof, in particular a humanized antibody or an antigen binding fragment thereof, the antibody specifically binding to CD3 of primates, e.g., humans and/or monkeys, wherein the antibody comprises a heavy chain variable region and a light chain variable region, and the heavy chain variable region and the light chain variable region respectively comprise amino acid sequences selected from the group consisting of:
  a) SEQ ID Nos: 46, 63; SEQ ID Nos: 47, 63; SEQ ID Nos: 49, 63; SEQ ID Nos: 50, 63; SEQ ID Nos: 51, 63; SEQ ID Nos: 46, 71; SEQ ID Nos: 47, 71; SEQ ID Nos: 49, 71; SEQ ID Nos: 51, 71; SEQ ID Nos: 52, 72; SEQ ID Nos: 53, 72; SEQ ID Nos: 54, 72; SEQ ID Nos: 55, 72; SEQ ID Nos: 56, 72; SEQ ID Nos: 57, 72; SEQ ID Nos: 58, 72; SEQ ID Nos: 62, 72; SEQ ID Nos: 52, 73; SEQ ID Nos: 53, 73; SEQ ID Nos: 54, 73; SEQ ID Nos: 55, 73; SEQ ID Nos: 56, 73; SEQ ID Nos: 57, 73; SEQ ID Nos: 58, 73; SEQ ID Nos: 61, 73; SEQ ID Nos: 62, 73; SEQ ID Nos: 45, 63; SEQ ID Nos: 48, 63; SEQ ID Nos: 45, 64; SEQ ID Nos: 45, 67; SEQ ID Nos: 48, 64; SEQ ID Nos: 48, 67; SEQ ID Nos: 45, 71; SEQ ID Nos: 48, 71; SEQ ID Nos: 50, 71; SEQ ID Nos: 61, 72; SEQ ID Nos: 60, 73; SEQ ID Nos: 60, 72; SEQ ID Nos: 59, 72;
b) amino acid sequences having 80%, 85%, 90%, 91%, 92%, 93%, 94%, 95%, 96%, 97%, 98%, 99% or higher amino acid identity with at least one amino acid sequence in a);
c) amino acid sequences having one or more (preferably one or several, and more preferably 1, 2, or 3) different amino acids with at least one amino acid sequence in a).

In some embodiments, the invention provides a polyspecific antibody, preferably bispecific antibody, comprising the antibody or an antigen binding fragment thereof according to any one of claims 1-3, and an antibody against another antigen and/or antigenic epitope, or an antigen binding fragment thereof, for example, a protein over-expressed in tumor cells compared to corresponding non-tumor cells; tumor antigen, such as CD38, BCMA, PD-L1, SLAMF7, Claudin18.2 or CEA; viruses; bacteria; and/or endotoxins.

In some embodiments, the invention provides a polypeptide, comprising an amino acid sequence selected from SEQ ID NOs: 45-62, or an amino acid sequence having 80%, 85%, 90%, 91%, 92%, 93%, 94%, 95%, 96%, 97%, 98%, 99% or higher amino acid identity with at least one amino acid sequence of SEQ ID NOs: 45-62, or an amino acid sequence having one or more (preferably one or several, and more preferably 1, 2, or 3) different amino acids with at least one amino acid sequence of SEQ ID NOs: 45-62.

In some embodiments, the invention provides a polypeptide, comprising an amino acid sequence selected from SEQ ID NOs: 63-73, or an amino acid sequence having 80%, 85%, 90%, 91%, 92%, 93%, 94%, 95%, 96%, 97%, 98%, 99% or higher amino acid identity with at least one amino acid sequence of SEQ ID NOs: 63-73, or an amino acid sequence having one or more (preferably one or several, and more preferably 1, 2, or 3) different amino acids with at least one amino acid sequence of SEQ ID NOs: 63-73.

In some embodiments, the humanized antibody has comparable affinity and improved biological activity, thermal stability, and/or acid resistance compared to a control antibody.

In some embodiments, the invention provides a polynucleotide, which codes the polypeptide of the invention.

In some embodiments, the invention provides an antibody, comprising (a) a light chain-heavy chain pair that is specific for tumor cells or microorganisms; and (b) fusion peptide, comprising a single-chain variable fragment and a single-chain Fc fragment, and the fusion peptide is specific for immune cells. In some embodiments, the single-chain Fc fragment comprises the CH2 and/or CH3 sequence described herein, for example, CH2 having a sequence selected from any one of SEQ ID Nos: 155-161 and 192 and/or CH3 having a sequence selected from any one of SEQ ID Nos:162-183. In some embodiments, the fusion peptide comprises the corresponding sequence or a partial sequence thereof of the antibody described herein, for example, the fusion peptide comprises the light chain and/or heavy chain variable region and/or framework region sequences of the humanized antibody described herein. In some embodiments, the single-chain variable fragment (scFv) of the fusion peptide comprises the scFV of the humanized antibody described herein.

In some embodiments, the fusion peptide in the antibody of the present invention comprises VHs-linker1-VLs-hinge 1-CH2-CH3-b, the heavy chain comprises VHm-CH1-hinge 2-CH2-CH3-a, and the light chain comprises VLm-CL.

In some embodiments, the light chain-heavy chain pair in the antibody of the present invention specifically binds to
a) a protein over-expressed in tumor cells compared to corresponding non-tumor cells;
b) tumor antigen, such as CD38, BCMA, PD-L1, SLAMF7, Claudin18.2 or CEA;
c) viruses;
d) bacteria; and/or
e) endotoxins.

In some embodiments, the fusion peptide in the antibody of the present invention specifically binds to immune cell antigens, for example, the fusion peptide comprises an antigen binding site that specifically binds to CD3 of primates, e.g., humans and/or monkeys, such as the fusion peptide comprises the variable regions of the light and heavy chains of the antibodies described herein.

In some embodiments, the VH of the fusion peptide of the antibody of the present invention comprises a sequence selected from any one of SEQ ID Nos: 45-62, 74, 76, 78, 80, 82, 84, 86, and 88; VL of the fusion peptide comprises a sequence selected from any one of SEQ ID Nos: 63-73, 75, 77, 79, 81, 83, 85, 87, and 89; linker1 of the fusion peptide comprises a sequence selected from any one of SEQ ID Nos: 120-138; hinge 1 of the fusion peptide and hinge 2 of the heavy chain comprise a sequence selected from any one of SEQ ID Nos: 139-147; CH2 of the fusion peptide and CH2 of the heavy chain comprise a sequence selected from any one of SEQ ID Nos: 155-161 and 192; CH3-b of the fusion peptide comprises a sequence selected from any one of SEQ ID Nos: 163, 165, 167, 169, 171, 173, 175, 177, 179, 181, and 183; CH3-a of the heavy chain comprises a sequence selected from any one of SEQ ID Nos: 162, 164, 166, 168, 170, 172, 174, 176, 178, 180, and 182; VHm of the heavy chain comprises a sequence selected from any one of SEQ ID Nos: 90, 92, 94, 96, 98, 100, 102, 104, 106, 108, 110, 112, 114, 116, 118, and 193; CH1 of the heavy chain comprises the sequence of SEQ ID Nos: 154; VLm of the light chain comprises a sequence selected from any one of SEQ ID Nos: 91, 93, 95, 97, 99, 101, 103, 105, 107, 109, 111, 113, 115, 117, 119, and 194; and/or CL of the light chain comprises a sequence selected from any one of SEQ ID Nos: 148-153.

In some embodiments, the VH of the fusion peptide and VL of the fusion peptide of the antibody of the present invention respectively comprise amino acid sequences selected from the group consisting of: a) SEQ ID Nos: 45, 63; SEQ ID Nos: 48, 63; SEQ ID Nos: 48, 71; SEQ ID Nos: 49, 63; SEQ ID Nos: 49, 71; SEQ ID Nos: 51, 71; SEQ ID Nos: 58, 72; SEQ ID Nos: 60, 72; SEQ ID Nos: 60, 73; SEQ ID Nos: 59, 72; SEQ ID Nos: 61, 73; SEQ ID Nos: 62, 73; SEQ ID Nos: 58, 72; SEQ ID Nos: 74, 75; SEQ ID Nos: 76, 77; SEQ ID Nos: 78, 79; SEQ ID Nos: 80, 81; SEQ ID Nos: 82, 83; SEQ ID Nos: 84, 85; SEQ ID Nos: 86, 87; SEQ ID Nos: 88, 89;
b) amino acid sequences having 80%, 85%, 90%, 91%, 92%, 93%, 94%, 95%, 96%, 97%, 98%, 99% or higher amino acid identity with at least one amino acid sequence in a);
c) amino acid sequences having one or more (preferably one or several, and more preferably 1, 2, or 3) different amino acids with at least one amino acid sequence in a); and/or VHm of the heavy chain and VLm of the light chain respectively comprise amino acid sequences selected from the group consisting of: d) SEQ ID Nos: 90, 91; SEQ ID Nos: 92, 93; SEQ ID Nos: 94, 95; SEQ ID Nos: 96, 97; SEQ ID Nos: 98, 99; SEQ ID Nos: 100, 101; SEQ ID Nos: 102, 103; SEQ ID Nos: 104, 105; SEQ ID Nos: 106, 107; SEQ ID Nos: 108, 109; SEQ ID Nos: 110, 111; SEQ ID Nos: 112, 113; SEQ ID Nos: 114, 115; SEQ ID Nos: 116, 117; SEQ ID Nos: 118, 119; SEQ ID Nos: 193, 194;
- e) amino acid sequences having 80%, 85%, 90%, 91%, 92%, 93%, 94%, 95%, 96%, 97%, 98%, 99% or higher amino acid identity with at least one amino acid sequence in d);
- f) amino acid sequences having one or more (preferably one or several, and more preferably 1, 2, or 3) different amino acids with at least one amino acid sequence in d).

In some embodiments, in the antibody of the present invention:
- a) CH3-b of the fusion peptide and CH3-a of the heavy chain have substitution pairs forming knob-into-hole structures, for example, T366 in one CH3 domain is substituted by a larger amino acid residue, such as Tyrosine (Y) or Tryptophan (W), and Y407 in the other CH3 domain is substituted by a smaller amino acid residue, such as Threonine (T), Alanine (A), or Valine (V), and for example, comprises one or more substitutions in Table 15;
- b) CH3-b of the fusion peptide and CH3-a of the heavy chain have substitution pairs forming ionic bonds, for example, one of the CH3 domains comprises one or more substitutions by amino acid residues having a positive charge under physiological conditions, while the other CH3 domain comprises one or more substitutions by one or more amino acid residues having a negative charge under physiological conditions; for example, the amino acid residue having a positive charge is Arginine (R), Histidine (H) or Lysine (K); for example, the amino acid residue having a negative charge may be Aspartic acid (D) or Glutamic acid (E); for example, the substituted amino acid residues include one or more of D356, L368, K392, D399 and K409, such as one or more substitutions in Table 16;
- c) CH3-b of the fusion peptide and CH3-a of the heavy chain have substitution pairs forming disulfide bonds, for example, the substitutions in Table 17; and/or
- d) CH3-b of the fusion peptide and CH3-a of the heavy chain have substitutions leading to weakened binding capability with protein A, for example, H435 and Y436 in one of the CH3 domains are substituted by Arginine and Phenylalanine, respectively, as shown in Table 18.

In some embodiments, the Fc fragment in the antibody of the present invention comprises CH2 having a sequence selected from any one of SEQ ID Nos: 155-161 and 192 and/or CH3 having a sequence selected from any one of SEQ ID Nos:162-183.

In some embodiments, the heavy chain or the heavy chain of the fusion peptide of the antibody of the present invention comprises a human or humanized Fc fragment, such as a human IgG Fc fragment, for example, IgG1, IgG2, IgG3, IgG4, and IgG5 Fc fragments.

In some embodiments, compared with wild-type antibodies, the Fc fragment of the heavy chain of the antibody, the heavy chain of the fusion peptide, and/or the fusion peptide of the present invention comprises one or more substitutions that form knob-into-hole structural pairs between the heavy chain and the fusion peptide.

In some embodiments, the Fc fragment of the heavy chain and/or the fusion peptide of the antibody of the present invention comprises one or more substitutions that form salt bridge pairs between the heavy chain and the fusion peptide.

In some embodiments, the antibody of the present invention comprises Y101, Y102, Y103, Y104, Y105, Y150-8-3, Y150-F8-4, Y150-F8-5, Y150-F8-6, Y150-F8-7, Y150-F8-8, Y150-F8-9, Y150-F8-10, Y150-F8-11, Y150-F8-12, Y150-F8-13, Y150-F8-14, Y150-F8-15, Y150-F9-7, Y150-F9-11, Y150-F9-12, MS-hCD3-IC15, MS-hCD3-IC16, MS-hCD3-IC17 and MS-hCD3-IC18, and wherein according to the order of components in the fusion peptide VHs-linker1-VLs-hinge 1-CH2-CH3-b, the heavy chain VHm-CH1-hinge 2-CH2-CH3-a, and the light chain VLm-CL, Y101 respectively comprises SEQ ID Nos: 45, 129, 63, 142, 159, 167, 106, 154, 139, 159, 166, 107, 148; or amino acid sequences having 80%, 85%, 90%, 91%, 92%, 93%, 94%, 95%, 96%, 97%, 98%, 99% or higher amino acid identity with at least one of the above amino acid sequences; or amino acid sequences having one or more (preferably one or several, and more preferably 1, 2, or 3) different amino acids with at least one of the above amino acid sequences;

Y102 respectively comprises SEQ ID Nos: 48, 129, 63, 142, 159, 167, 106, 154, 139, 159, 166, 107, 148; or amino acid sequences having 80%, 85%, 90%, 91%, 92%, 93%, 94%, 95%, 96%, 97%, 98%, 99% or higher amino acid identity with at least one of the above amino acid sequences; or amino acid sequences having one or more (preferably one or several, and more preferably 1, 2, or 3) different amino acids with at least one of the above amino acid sequences;

Y103 respectively comprises SEQ ID Nos: 48, 129, 71, 142, 159, 167, 106, 154, 139, 159, 166, 107, 148; or amino acid sequences having 80%, 85%, 90%, 91%, 92%, 93%, 94%, 95%, 96%, 97%, 98%, 99% or higher amino acid identity with at least one of the above amino acid sequences; or amino acid sequences having one or more (preferably one or several, and more preferably 1, 2, or 3) different amino acids with at least one of the above amino acid sequences;

Y104 respectively comprises SEQ ID Nos: 49, 129, 63, 142, 139, 167, 106, 154, 139, 159, 166, 107, 148; or amino acid sequences having 80%, 85%, 90%, 91%, 92%, 93%, 94%, 95%, 96%, 97%, 98%, 99% or higher amino acid identity with at least one of the above amino acid sequences; or amino acid sequences having one or more (preferably one or several, and more preferably 1, 2, or 3) different amino acids with at least one of the above amino acid sequences;

Y105 respectively comprises SEQ ID Nos: 49, 129, 71, 142, 139, 167, 106, 154, 139, 159, 166, 107, 148; or amino acid sequences having 80%, 85%, 90%, 91%, 92%, 93%, 94%, 95%, 96%, 97%, 98%, 99% or higher amino acid identity with at least one of the above amino acid sequences; or amino acid sequences having one or more (preferably one or several, and more preferably 1, 2, or 3) different amino acids with at least one of the above amino acid sequences;

Y150-8-3 respectively comprises SEQ ID Nos: 45, 129, 63, 141, 157, 167, 90, 154, 139, 157, 166, 91, 148; or amino acid sequences having 80%, 85%, 90%, 91%, 92%, 93%, 94%, 95%, 96%, 97%, 98%, 99% or higher amino acid identity with at least one of the above amino acid sequences; or amino acid sequences having one or more (preferably one or several, and more preferably 1, 2, or 3) different amino acids with at least one of the above amino acid sequences;

Y150-F8-4 respectively comprises SEQ ID Nos: 48, 129, 63, 141, 157, 167, 90, 154, 139, 157, 166, 91, 148; or amino acid sequences having 80%, 85%, 90%, 91%, 92%, 93%, 94%, 95%, 96%, 97%, 98%, 99% or higher amino acid identity with at least one of the above amino acid sequences; or amino acid sequences having one or more (preferably one or several, and more preferably 1, 2, or 3) different amino acids with at least one of the above amino acid sequences;

Y150-F8-5 respectively comprises SEQ ID Nos: 49, 129, 71, 141, 139, 167, 90, 154, 139, 157, 166, 91, 148; or amino acid sequences having 80%, 85%, 90%, 91%, 92%, 93%, 94%, 95%, 96%, 97%, 98%, 99% or higher amino acid identity with at least one of the above amino acid sequences; or amino acid sequences having one or more (preferably one or several, and more preferably 1, 2, or 3) different amino acids with at least one of the above amino acid sequences;

Y150-F8-6 respectively comprises SEQ ID Nos: 51, 129, 71, 141, 139, 167, 90, 154, 139, 157, 166, 91, 148; or amino acid sequences having 80%, 85%, 90%, 91%, 92%, 93%, 94%, 95%, 96%, 97%, 98%, 99% or higher amino acid identity with at least one of the above amino acid sequences; or amino acid sequences having one or more (preferably one or several, and more preferably 1, 2, or 3) different amino acids with at least one of the above amino acid sequences;

Y150-F8-7 respectively comprises SEQ ID Nos: 49, 129, 71, 144, 158, 167, 90, 154, 139, 158, 166, 91, 148; or amino acid sequences having 80%, 85%, 90%, 91%, 92%, 93%, 94%, 95%, 96%, 97%, 98%, 99% or higher amino acid identity with at least one of the above amino acid sequences; or amino acid sequences having one or more (preferably one or several, and more preferably 1, 2, or 3) different amino acids with at least one of the above amino acid sequences;

Y150-F8-8 respectively comprises SEQ ID Nos: 49, 129, 71, 144, 161, 167, 90, 154, 139, 161, 166, 91, 148; or amino acid sequences having 80%, 85%, 90%, 91%, 92%, 93%, 94%, 95%, 96%, 97%, 98%, 99% or higher amino acid identity with at least one of the above amino acid sequences; or amino acid sequences having one or more (preferably one or several, and more preferably 1, 2, or 3) different amino acids with at least one of the above amino acid sequences;

Y150-F8-9 respectively comprises SEQ ID Nos: 49, 129, 71, 144, 161, 167, 96, 154, 139, 161, 166, 97, 148; or amino acid sequences having 80%, 85%, 90%, 91%, 92%, 93%, 94%, 95%, 96%, 97%, 98%, 99% or higher amino acid identity with at least one of the above amino acid sequences; or amino acid sequences having one or more (preferably one or several, and more preferably 1, 2, or 3) different amino acids with at least one of the above amino acid sequences;

Y150-F8-10 respectively comprises SEQ ID Nos: 58, 129, 72, 144, 161, 167, 96, 154, 139, 161, 166, 97, 148; or amino acid sequences having 80%, 85%, 90%, 91%, 92%, 93%, 94%, 95%, 96%, 97%, 98%, 99% or higher amino acid identity with at least one of the above amino acid sequences; or amino acid sequences having one or more (preferably one or several, and more preferably 1, 2, or 3) different amino acids with at least one of the above amino acid sequences;

Y150-F8-11 respectively comprises SEQ ID Nos: 60, 129, 72, 144, 161, 167, 96, 154, 139, 161, 166, 97, 148; or amino acid sequences having 80%, 85%, 90%, 91%, 92%, 93%, 94%, 95%, 96%, 97%, 98%, 99% or higher amino acid identity with at least one of the above amino acid sequences; or amino acid sequences having one or more (preferably one or several, and more preferably 1, 2, or 3) different amino acids with at least one of the above amino acid sequences;

Y150-F8-12 respectively comprises SEQ ID Nos: 60, 129, 73, 144, 161, 167, 96, 154, 139, 161, 166, 97, 148; or amino acid sequences having 80%, 85%, 90%, 91%, 92%, 93%, 94%, 95%, 96%, 97%, 98%, 99% or higher amino acid identity with at least one of the above amino acid sequences; or amino acid sequences having one or more (preferably one or several, and more preferably 1, 2, or 3) different amino acids with at least one of the above amino acid sequences;

Y150-F8-13 respectively comprises SEQ ID Nos: 59, 129, 72, 144, 161, 167, 96, 154, 139, 161, 166, 97, 148; or amino acid sequences having 80%, 85%, 90%, 91%, 92%, 93%, 94%, 95%, 96%, 97%, 98%, 99% or higher amino acid identity with at least one of the above amino acid sequences; or amino acid sequences having one or more (preferably one or several, and more preferably 1, 2, or 3) different amino acids with at least one of the above amino acid sequences;

Y150-F8-14 respectively comprises SEQ ID Nos: 61, 129, 73, 144, 161, 167, 96, 154, 139, 161, 166, 97, 148; or amino acid sequences having 80%, 85%, 90%, 91%, 92%, 93%, 94%, 95%, 96%, 97%, 98%, 99% or higher amino acid identity with at least one of the above amino acid sequences; or amino acid sequences having one or more (preferably one or several, and more preferably 1, 2, or 3) different amino acids with at least one of the above amino acid sequences;

Y150-F8-15 respectively comprises 62, 129, 73, 144, 161, 167, 96, 154, 139, 161, 166, 97, 148; or amino acid sequences having 80%, 85%, 90%, 91%, 92%, 93%, 94%, 95%, 96%, 97%, 98%, 99% or higher amino acid identity with at least one of the above amino acid sequences; or amino acid sequences having one or more (preferably one or several, and more preferably 1, 2, or 3) different amino acids with at least one of the above amino acid sequences;

Y150-F9-7 respectively comprises 49, 129, 71, 141, 139, 167, 92, 154, 139, 157, 166, 93, 150; or amino acid sequences having 80%, 85%, 90%, 91%, 92%, 93%, 94%, 95%, 96%, 97%, 98%, 99% or higher amino acid identity with at least one of the above amino acid sequences; or amino acid sequences having one or more (preferably one or several, and more preferably 1, 2, or 3) different amino acids with at least one of the above amino acid sequences;

Y150-F9-11 respectively comprises 49, 129, 71, 144, 161, 167, 92, 154, 139, 161, 166, 93, 148; or amino acid sequences having 80%, 85%, 90%, 91%, 92%, 93%, 94%, 95%, 96%, 97%, 98%, 99% or higher amino acid identity with at least one of the above amino acid sequences; or amino acid sequences having one or more (preferably one or several, and more preferably 1, 2, or 3) different amino acids with at least one of the above amino acid sequences;

Y150-F9-12 respectively comprises 49, 129, 71, 144, 192, 167, 92, 154, 139, 192, 166, 93, 148; or amino acid sequences having 80%, 85%, 90%, 91%, 92%, 93%, 94%, 95%, 96%, 97%, 98%, 99% or higher amino acid identity with at least one of the above amino acid sequences; or amino acid sequences having one or more (preferably one or several, and more preferably 1, 2, or 3) different amino acids with at least one of the above amino acid sequences;

MS-hCD3-IC15 respectively comprises 49, 129, 71, 141, 159, 167, 118, 154, 139, 159, 166, 119, 148; or amino acid sequences having 80%, 85%, 90%, 91%, 92%, 93%, 94%, 95%, 96%, 97%, 98%, 99% or higher amino acid identity with at least one of the above amino acid sequences; or amino acid sequences having one or more (preferably one or several, and more preferably 1, 2, or 3) different amino acids with at least one of the above amino acid sequences;

MS-hCD3-IC16 respectively comprises 49, 129, 71, 141, 157, 167, 118, 154, 139, 157, 166, 119, 148; or amino acid sequences having 80%, 85%, 90%, 91%, 92%, 93%, 94%, 95%, 96%, 97%, 98%, 99% or higher amino acid identity with at least one of the above amino acid sequences; or amino acid sequences having one or more (preferably one or several, and more preferably 1, 2, or 3) different amino acids with at least one of the above amino acid sequences;

MS-hCD3-IC17 respectively comprises 49, 129, 71, 141, 161, 167, 118, 154, 139, 161, 166, 119, 148; or amino acid sequences having 80%, 85%, 90%, 91%, 92%, 93%, 94%, 95%, 96%, 97%, 98%, 99% or higher amino acid identity with at least one of the above amino acid sequences; or amino acid sequences having one or more (preferably one or several, and more preferably 1, 2, or 3) different amino acids with at least one of the above amino acid sequences;

MS-hCD3-IC18 respectively comprises 58, 129, 72, 141, 161, 167, 118, 154, 139, 161, 166, 119, 148; or amino acid sequences having 80%, 85%, 90%, 91%, 92%, 93%, 94%, 95%, 96%, 97%, 98%, 99% or higher amino acid identity with at least one of the above amino acid sequences; or amino acid sequences having one or more (preferably one or several, and more preferably 1, 2, or 3) different amino acids with at least one of the above amino acid sequences.

In some embodiments, the antibody or an antigen binding fragment thereof of the present invention can bind to a target with KD less than about $10^{-8}$ M, for example, less than about $10^{-8}$ M, $10^{-9}$ M, $10^{-10}$ M, or less, or binds to a target with EC50 less than about 100 nM, for example, less than about 10 nM, 1 nM, 0.9 nM, 0.8 nM, 0.7 nM, 0.6 nM, 0.5 nM, 0.4 nM, 0.3 nM, 0.2 nM, 0.1 nM or smaller, and preferably, the antigen binding fragment is selected from F(ab')$_2$, F(ab)$_2$, Fab', Fab, Fv, Fd, and scFv.

In some embodiments, the invention provides a polynucleotide, which codes the antibody or an antigen binding fragment thereof described herein.

In some embodiments, the invention provides an expression vector, comprising the polynucleotide described herein.

In some embodiments, the invention provides a host cell, comprising the polynucleotide or the expression vector described herein.

In some embodiments, the invention provides a method for preparing the antibody of the present invention, comprising introducing the polynucleotide or the expression vector described herein into a host cell, so as to prepare the antibody.

In some embodiments, the invention provides an antibody conjugate, comprising the antibody or an antigen binding fragment thereof described herein and a conjugating moiety conjugated thereto, preferably, the conjugating moiety is selected from purification tags (e.g., a His tag), cytotoxic agents, detectable marks, radioactive isotopes, luminescent substances, colored substances, enzymes, or polyethylene glycol.

In some embodiments, the invention provides an antibody conjugate, wherein the antibody may be conjugated to therapeutic agents, prodrugs, peptides, proteins, enzymes, viruses, lipids, biological response modifiers, pharmaceutical agents, or PEG.

In some embodiments, the antibodies may be conjugated or fused to a therapeutic agent, which may include detectable labels such as radioactive labels, an immunomodulator, a hormone, an enzyme, an oligonucleotide, a photoactive therapeutic or diagnostic agent, a cytotoxic agent, which may be a drug or a toxin, an ultrasound enhancing agent, a non-radioactive label, a combination thereof and other such agents known in the art.

In some embodiments, the antibodies can be detectably labeled by coupling it to a chemiluminescent compound. The presence of the chemiluminescent-tagged antigen-binding polypeptide is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

In some embodiments, the antibodies can also be detectably labeled using fluorescence emitting metals such as 152Eu, or other labels of the lanthanide series. These metals can be attached to the antibody using such metal chelating groups as diethylenetriaminepentacetic acid (DTPA) or ethylenediaminetetraacetic acid (EDTA). Techniques for conjugating various groups to an antibody are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. (1985); Hellstrom et al., "Antibodies For Drug Delivery", in Controlled Drug Delivery (2nd Ed.), Robinson et al., (eds.), Marcel Dekker, Inc., pp. 623-53 (1987); Thorpe, "Antibody Carriers Of Cytotoxic Agents In Cancer Therapy: A Review", in Monoclonal Antibodies "84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), Academic Press pp. 303-16 (1985), and Thorpe et al., "The Preparation And Cytotoxic Properties Of Antibody-Toxin Conjugates", Immunol. Rev. (52:119-58 (1982)).

In some embodiments, the invention provides a fusion protein, comprising the antibody or an antigen binding fragment thereof described herein.

In some embodiments, the invention provides a pharmaceutical composition, comprising the antibody or an antigen binding fragment thereof, the antibody conjugate, or the fusion protein described herein, and optionally, further comprising a pharmaceutically acceptable carrier and/or excipient.

In some embodiments, the pharmaceutical composition described herein is a formulation suitable for oral administration to gastrointestinal (GI) tract, preferably, the formulation is selected from tablet, capsule, pill, powder, granule, emulsion, micro-emulsion, solution, suspension, syrup, and elixir; or the drug is a formulation suitable for subcutaneous injection, intradermal injection, intravenous injection, intramuscular injection, and intralesional injection.

In some embodiments, the invention provides a kit, comprising the antibody or an antigen binding fragment thereof, the antibody conjugate, or the fusion protein described herein, and preferably, further comprising a secondary antibody that specifically recognizes the antibody or an antigen binding fragment thereof, the antibody conjugate, or the fusion protein described herein; wherein, optionally, the secondary antibody further comprises a detectable label, such as a radioactive isotope, a luminescent substance, a colored substance, or an enzyme.

In some embodiments, the invention provides the antibody or an antigen binding fragment thereof described herein used for treating a disease, or a use of the antibody or an antigen binding fragment thereof described herein in treating a disease, or a use of the antibody or an antigen binding fragment thereof described herein in preparing a medicament for treating a disease.

In some embodiments, the antibodies provided herein can be used in combination with another therapeutic agent (e.g., a therapeutic agent used to treat tumors or cancer).

In some embodiments, the invention provides a kit that includes the antibody or antigen-binding fragment thereof provided herein and a pharmaceutical acceptable carrier, instructions for use, and optional another therapeutic agent (e.g., a therapeutic agent used to treat tumors or cancer).

In some embodiments, in the compositions and/or kits provided herein, the antibody or antigen-binding fragment thereof is conjugated to a cytotoxic moiety, an enzyme, a radioactive compound, a cytokine, an interferon, a target, or a reporter moiety.

In some embodiments, the antibodies or antigen-binding fragments thereof provided herein can be used to treat a disease such as cancer or tumors.

In some embodiments, the invention provides the use of the antibody or antigen-binding fragment thereof for the treatment of a disease such as cancer or tumors.

In some embodiments, the antibodies or antigen-binding fragments thereof provided herein are used in the preparation of drugs for the treatment of a disease such as cancer or tumors.

In some embodiments, the antibodies or antigen-binding fragments provided herein can be used to treat a disease such as cancer or tumors, including but not limited to multiple myeloma, lung cancer (e.g., small cell lung cancer, non-small cell lung cancer, lung adenocarcinoma, and lung squamous cell cancer), etc.

In some embodiments, the invention provides a method of humanizing CD3 antibodies and the obtained humanized sequences. Monoclonal antibodies and multifunctional antibodies prepared based on the humanized antibody sequence have suitable affinity, high stability and good cell killing ability.

In some embodiments, compared with control antibodies such as the original antibody SP34 and CD3 antibodies with high homology provided in other documents, the humanized CD3 antibody provided herein shows better biological activity and/or stability than other CD3 antibodies in terms of the biological activity and stability of the multifunctional antibody.

In some embodiments, the invention provides a multifunctional antibody and a preparation method, the antibody comprising: (a) a light chain-heavy chain pair having specificity to tumor cells or microorganisms; and (b) a fusion peptide comprising a single chain variable fragment (scFv) and an Fc fragment comprising a CH2 domain and/or a CH3 domain, wherein the fusion peptide has specificity to immune cells.

In some embodiments, the light chain-heavy chain pair or VLm-VHm pair of the antibody of the invention has specificity to a tumor antigen. In some embodiments, the tumor antigen is selected from: PD-L1, SLAMF7, CD38, BCMA and the like. In some embodiments, the light chain-heavy chain pair or VLm-VHm pair has specificity to a protein that is overexpressed on a tumor cell compared to a corresponding non-tumor cell.

In some aspects, the light chain-heavy chain pair or VLm-VHm pair has specificity to a virus or bacterium. In one aspect, the light chain-heavy chain pair or VLm-VHm pair has specificity to an endotoxin.

In some embodiments, the immune cell is selected from the group consisting of T cells, CIK cells, NKT cells, B cells, monocytes, macrophages, neutrophils, dendritic cells, macrophages, natural killer cells, eosinocytes, basophils and mast cells.

In some embodiments, the ScFv or VLs-VHs pair has specificity to the antigens including, for example, CD3, CD4, CD8, CD40L, CD152, CD16, CD56, CD94, CD158, CD161, CD19, CD20, CD21, CD40. In some embodiments, the antigen is CD3.

In some embodiments, the light chain is bound to the heavy chain or fusion heavy chain through a disulfide bond. In some embodiments, the heavy chain is bound to the fusion peptide through one or more disulfide bonds. In some embodiments, the fusion heavy chain 1 is bound to the fusion heavy chain 2 through one or more disulfide bonds. In some embodiments, the heavy chain or fusion heavy chain comprises a human or humanized Fc fragment. In some embodiments, the Fc fragment of the heavy chain or fusion heavy chain comprises a human IgG Fc fragment. In some embodiments, the Fc fragment of the fusion peptide comprises a human or a humanized Fc fragment. In some embodiments, the Fc fragment of the fusion peptide comprises a human IgG Fc fragment.

In some aspects, the Fc fragment of the heavy chain, the fusion heavy chain and/or the fusion peptide comprises one or more substitutions that form knobs-into-holes structure pairing between the heavy chain and the fusion peptide, as compared to a wild-type antibody fragment. The pairing can significantly improve the heterodimer pairing efficiency of the heavy chain and the fusion peptide.

In some aspects, the Fc fragment of the heavy chain and/or the fusion peptide comprise one or more substitutions that form a salt-bridge pairing between the heavy chain and the fusion peptide. The pairing can significantly improve the heterodimer pairing efficiency of the heavy chain and the fusion peptide.

In some aspects, the CH2 domain of the fusion peptide is located between the scFv fragment and the CH3 domain. In one aspect, the fusion peptide does not contain a CH1 domain.

In one embodiment, the application also provides a composition comprising the antibody in any of the above embodiments. In one aspect, the carrier is a drug carrier.

Another embodiment provides a complex comprising the antibody of any of the above embodiments that binds to one or more antigens.

DESCRIPTION OF THE SPECIFIC EMBODIMENTS

Definitions

Figure 1A:
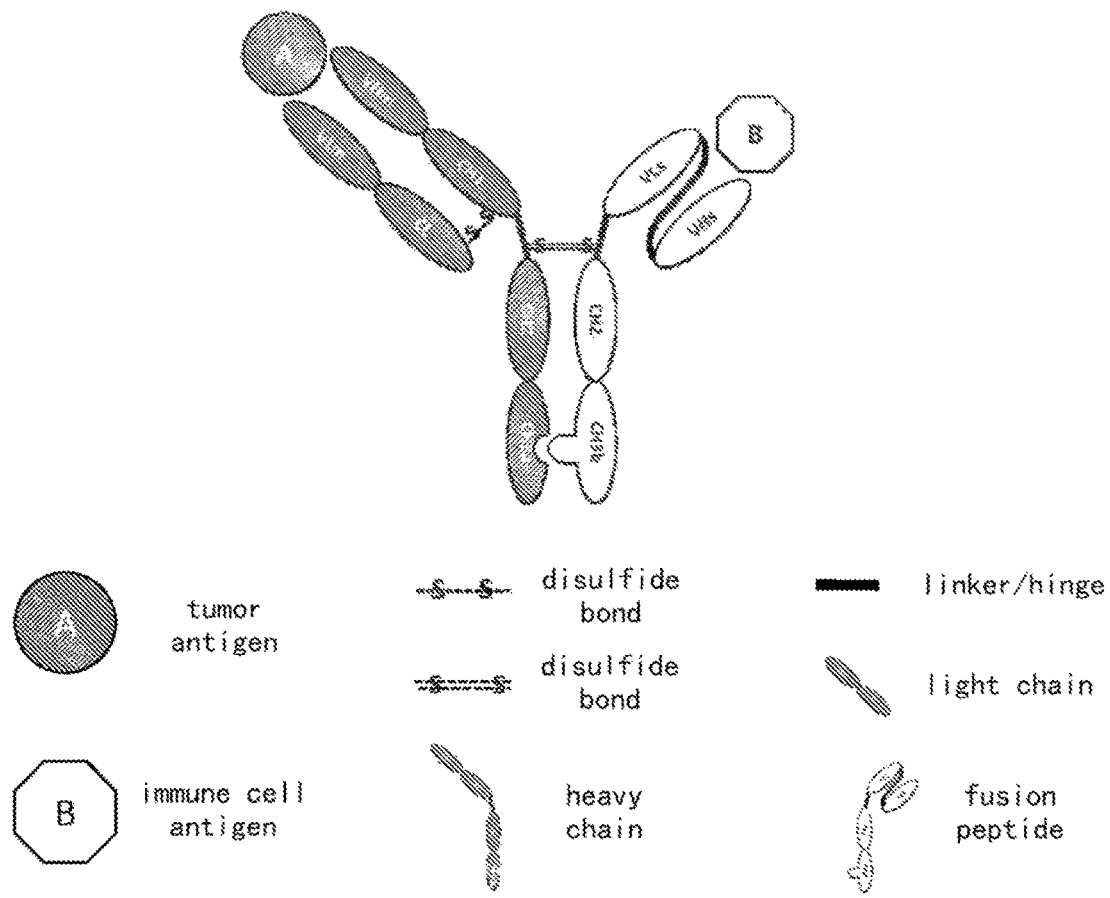
FIG. 1A is a schematic structural diagram of an antibody.

There are six "complementarily determining regions" or "CDRs" in naturally occurring antibodies which are specifically positioned to form the antigen-binding domain. The remainder of the amino acids in the antigen-binding domains, referred to as "framework" regions, show less inter-molecular variability. The framework regions largely adopt a β-sheet configuration and the CDRs form loops which connect, and in some cases form part of, the β-sheet structure. Thus, framework regions act to form a scaffold that provides for positioning the CDRs in correct orientation by inter-chain, non-covalent interactions. The antigen-binding domain formed by the positioned CDRs defines a surface complementary to the epitope on the immunoreactive antigen. This complementary surface promotes the non-covalent binding of the antibody to its cognate epitope. The amino acids of the CDRs and the framework regions, respectively, can be readily identified for any given heavy or light chain variable region by one of ordinary skill in the art (see "Sequences of Proteins of Immunological Interest," Kabat, E., et al., U.S. Department of Health and Human Services, (1983); and Chothia and Lesk, J. Mol. Biol., 196:901-917 (1987)).

The term "complementarity determining region" ("CDR") is used herein to describe the noncontinous antigen binding sites within the variable regions of both heavy and light chain polypeptides. This particular region has been described by Kabat et al., U.S. Dept. of Health and Human Services, "Sequences of Proteins of Immunological Interest" (1983) and by Chothia et al., J. Mol. Biol. 196:901-917 (1987). The CDRs include overlapping amino acid residues or amino acid substructure when compared against each other according to Kabat and Chothia's definitions. Nevertheless, use of definition of CDRs of an antibody or variants thereof is intended to be within the scope of the term as defined and used herein. Those skilled in the art can routinely determine which residues comprise a particular CDR given the variable region amino acid sequence of the antibody.

Kabat et al. also defined a numbering system for variable domain sequences that is applicable to any antibody. One of ordinary skill in the art can unambiguously assign this system of "Kabat numbering" to any variable domain sequence, independent of any experimental data beyond the sequence itself. As used herein, "Kabat numbering" refers to the numbering system described by Kabat et al., also in U.S. Dept. of Health and Human Services, "Sequence of Proteins of Immunological Interest" (1983).

The Kabat number system describes the CDR regions as follows: CDR-H1 begins at approximately amino acid 31 (i.e., approximately 9 residues behind the first cysteine residue), includes approximately 5-7 amino acids, and ends at the next tryptophan residue. CDR-H2 begins at the fifteenth residue behind the end of CDR-H1, includes approximately 16-19 amino acids, and ends at the next arginine or lysine residue. CDR-H3 begins at approximately the thirty third amino acid residue behind the end of CDR-H2; includes 3-25 amino acids; and ends at the sequence W-G-X-G, where X is any amino acid. CDR-L1 begins at approximately residue 24 (i.e., behind a cysteine residue); includes approximately 10-17 residues; and ends at the next tryptophan residue. CDR-L2 begins at approximately the sixteenth residue behind the end of CDR-L1 and includes approximately 7 residues. CDR-L3 begins at approximately the thirty third residue behind the end of CDR-L2 (i.e., behind a cysteine residue); includes approximately 7-11 residues and ends at the sequence F or W-G-X-G, where X is any amino acid.

Antibodies described herein may be from any animal source including birds and mammals, including primates. Preferably, the antibody is a human, baboon, rhesus monkey, cynomolgus monkey, mouse, donkey, rabbit, goat, guinea pig, camel, llama, horse or chicken antibody.

The humanized antibodies described herein are capable of specifically binding to CD3, such as primate CD3, including, for example, human and/or monkey CD3.

As used herein, the term "heavy chain constant region" includes amino acid sequences derived from an immunoglobulin heavy chain. A polypeptide comprising a heavy chain constant region comprises at least one of: a CH1 domain, a hinge (e.g., upper, middle, and/or lower hinge region) domain, a CH2 domain, a CH3 domain, or a variant or fragment thereof. For example, an antigen-binding polypeptide for use in the present application may comprise a polypeptide chain comprising a CH1 domain; a polypeptide chain comprising a CH1 domain, at least a portion of a hinge domain, and a CH2 domain; a polypeptide chain comprising a CH1 domain and a CH3 domain; a polypeptide chain comprising a CH1 domain, at least a portion of a hinge domain, and a CH3 domain, or a polypeptide chain comprising a CH1 domain, at least a portion of a hinge domain, a CH2 domain, and a CH3 domain. In another embodiment, a polypeptide of the disclosure comprises a polypeptide chain comprising a CH3 domain. Further, an antibody for use in the disclosure may lack at least a portion of a CH2 domain (e.g., all or part of a CH2 domain). It will be understood by one of ordinary skill in the art that the heavy chain constant region may be modified such that they vary in amino acid sequence from the naturally occurring immunoglobulin molecule.

The heavy chain constant region of an antibody disclosed herein may be derived from different immunoglobulin molecules. For example, a heavy chain constant region of a polypeptide may comprise a CH1 domain derived from an IgG1 molecule and a hinge region derived from an IgG3 molecule. In another example, a heavy chain constant region can comprise a hinge region derived, in part, from an IgG1 molecule and, in part, from an IgG3 molecule. In another example, a heavy chain portion can comprise a chimeric hinge derived, in part, from an IgG1 molecule and, in part, from an IgG4 molecule.

As used herein, the term "light chain constant region" includes amino acid sequences derived from antibody light chain. Preferably, the light chain constant region comprises at least one of a constant kappa domain or constant lambda domain.

A "light chain-heavy chain pair" refers to the collection of a light chain and heavy chain that can form a dimer through a disulfide bond between the CL domain of the light chain and the CH1 domain of the heavy chain.

The subunit structures and three dimensional configuration of the constant regions of the various immunoglobulin classes are well known. The term "VH domain" includes the amino terminal variable domain of an immunoglobulin heavy chain and the term "CH1 domain" includes the first (most amino terminal) constant region domain of an immunoglobulin heavy chain. The CH1 domain is adjacent to the VH domain and is amino terminal to the hinge region of an immunoglobulin heavy chain molecule.

As used herein the term "CH2 domain" includes the portion of a heavy chain molecule that extends, e.g., from about residue 244 to residue 360 of an antibody using conventional numbering schemes (residues 244 to 360, Kabat numbering system; and residues 231-340, EU numbering system; see Kabat et al., U.S. Dept. of Health and Human Services, "Sequences of Proteins of Immunological Interest" (1983). The CH2 domain is unique in that it is not closely paired with another domain. Rather, two N-linked branched carbohydrate chains are interposed between the two CH2 domains of an intact native IgG molecule. It is also well documented that the CH3 domain extends from the CH2 domain to the C-terminal of the IgG molecule and comprises approximately 108 residues.

As used herein, the term "hinge region" includes the portion of a heavy chain molecule that joins the CH1 domain to the CH2 domain This hinge region comprises approximately 25 residues and is flexible, thus allowing the two N-terminal antigen binding regions to move independently. Hinge regions can be subdivided into three distinct domains: upper, middle, and lower hinge domains (Roux et al., J. Immunol 161:4083 (1998)).

As used herein the term "disulfide bond" includes the covalent bond formed between two sulfur atoms. The amino acid cysteine comprises a thiol group that can form a disulfide bond or bridge with a second thiol group. In most naturally occurring IgG molecules, the CH1 and CK regions are linked by a disulfide bond and the two heavy chains are linked by two disulfide bonds at positions corresponding to position 239 and 242 using the Kabat numbering system (position 226 or 229, EU numbering system).

As used herein, the term "chimeric antibody" will be held to mean any antibody wherein the immunoreactive region or site is obtained or derived from a first species and the constant region (which may be intact, partial or modified in accordance with the instant disclosure) is obtained from a second species. In certain embodiments the target binding region or site will be from a non-human source (e.g. mouse or primate) and the constant region is from huma.

As used herein, "percent humanization" is calculated by determining the number of framework amino acid differences (i.e., non-CDR difference) between the humanized domain and the germline domain, subtracting that number from the total number of amino acids, and then dividing that by the total number of amino acids and multiplying by 100.

By "specifically binds" or "has specificity to," it is generally meant that an antibody binds to an epitope via its antigen-binding domain, and that the binding entails some complementarity between the antigen-binding domain and the epitope. According to this definition, an antibody is said to "specifically bind" to an epitope when it binds to that epitope, via its antigen-binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D." In some embodiments, the antibody of the present invention bind to the target with an KD of less than about $10^{-8}$M, $10^{-9}$M, $10^{-19}$M or less. In some embodiments, the antibody of the present invention bind to the target with an EC50 of less than about 100 nM, such as less than about 10 nM, 1 nM, 0.9 nM, 0.8 nM, 0.7 nM, 0.6 nM, 0.5 nM, 0.4 nM, 0.3 nM, 0.2 nM, 0.1 nM or less.

It is to be noted that the term "a" or "an" entity refers to one or more of that entity; for example, "a multifunctional antibody," is understood to represent one or more multifunctional antibodies. As such, the terms "a" (or "an"), "one or more," and "at least one" can be used interchangeably herein.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" may be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by nonnaturally occurring amino acids. A polypeptide may be derived from a natural biological source or produced by recombinant technology, but is not necessarily translated from a designated nucleic acid sequence. It may be generated in any manner, including by chemical synthesis.

The term "isolated" as used herein with respect to cells, nucleic acids, such as DNA or RNA, refers to molecules separated from other DNAs or RNAs, respectively, that are present in the natural source of the macromolecule. The term "isolated" as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to cells or polypeptides which are isolated from other cellular proteins or tissues. Isolated polypeptides is meant to encompass both purified and recombinant polypeptides.

As used herein, the term "recombinant" as it pertains to polypeptides or polynucleotides intends a form of the polypeptide or polynucleotide that does not exist naturally, a non-limiting example of which can be created by combining polynucleotides or polypeptides that would not normally occur together.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, though preferably less than 25% identity, with one of the sequences of the present disclosure.

A polynucleotide or polynucleotide region (or a polypeptide or polypeptide region) has a certain percentage (for example, 60%, 65%, 70%, 75%, 80%, 85%, 90%, 95%, 98% or 99%) of "sequence identity" to another sequence means that, when aligned, that percentage of bases (or amino acids) are the same in comparing the two sequences. This alignment and the percent homology or sequence identity can be determined using software programs known in the art, for example those described in Ausubel et al. eds. (2007) Current Protocols in Molecular Biology. Preferably, default parameters are used for alignment. Biologically equivalent polynucleotides are those having the above-noted specified percent homology and encoding a polypeptide having the same or similar biological activity.

The term "an equivalent nucleic acid or polynucleotide" refers to a nucleic acid having a nucleotide sequence having a certain degree of homology, or sequence identity, with the nucleotide sequence of the nucleic acid or complement thereof. A homolog of a double stranded nucleic acid is intended to include nucleic acids having a nucleotide sequence which has a certain degree of homology with another nucleic acid or with the complement thereof. In one aspect, homologs of a nucleic acid are capable of hybridizing to the nucleic acid or complement thereof. Likewise, "an equivalent polypeptide" refers to a polypeptide having a certain degree of homology, or sequence identity, with the amino acid sequence of a reference polypeptide. In some aspects, the sequence identity is at least about 70%, 75%, 80%, 85%, 90%, 95%, 98%, or 99%. In some aspects, the equivalent sequence retains the activity (e.g., epitope-binding) or structure (e.g., salt-bridge) of the reference sequence.

Hybridization reactions can be performed under conditions of different "stringency". In general, a low stringency hybridization reaction is carried out at about 40° C. in about 10×SSC or a solution of equivalent ionic strength/temperature. A moderate stringency hybridization is typically performed at about 50° C. in about 6×SSC, and a high stringency hybridization reaction is generally performed at about 60° C. in about 1×SSC. Hybridization reactions can also be performed under "physiological conditions" which is well known to one of skill in the art. A non-limiting example of a physiological condition is the temperature, ionic strength, pH and concentration of Mg2+ normally found in a cell.

A polynucleotide is composed of a specific sequence of four nucleotide bases: adenine (A); cytosine (C); guanine (G); thymine (T); and uracil (U) for thymine when the polynucleotide is RNA. Thus, the term "polynucleotide sequence" is the alphabetical representation of a polynucleotide molecule. This alphabetical representation can be input into databases in a computer having a central processing unit and used for bioinformatics applications such as functional genomics and homology searching. The term "polymorphism" refers to the coexistence of more than one form of a gene or portion thereof. A portion of a gene of which there are at least two different forms, i.e., two different nucleotide sequences, is referred to as a "polymorphic region of a gene". A polymorphic region can be a single nucleotide, the identity of which differs in different alleles.

The terms "polynucleotide" and "oligonucleotide" are used interchangeably and refer to a polymeric form of nucleotides of any length, either deoxyribonucleotides or ribonucleotides or analogs thereof. Polynucleotides can have any three-dimensional structure and may perform any function, known or unknown. The following are nonlimiting examples of polynucleotides: a gene or gene fragment (for example, a probe, primer, EST or SAGE tag), exons, introns, messenger RNA (mRNA), transfer RNA, ribosomal RNA, ribozymes, cDNA, dsRNA, siRNA, miRNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of this disclosure that is a polynucleotide encompasses both the double-stranded form and each of two complementary single-stranded forms known or predicted to make up the double-stranded form.

The term "encode" as it is applied to polynucleotides refers to a polynucleotide which is said to "encode" a polypeptide if, in its native state or when manipulated by methods well known to those skilled in the art, it can be transcribed and/or translated to produce the mRNA for the polypeptide and/or a fragment thereof. The antisense strand is the complement of such a nucleic acid, and the encoding sequence can be deduced therefrom.

As used herein, the term "detectable label" intends a directly or indirectly detectable compound or composition that is conjugated directly or indirectly to the composition to be detected, e.g., polynucleotide or protein such as an antibody so as to generate a "labeled" composition. The term also includes sequences conjugated to the polynucleotide that will provide a signal upon expression of the inserted sequences, such as green fluorescent protein (GFP) and the like. The label may be detectable by itself (e.g. radioisotope labels or fluorescent labels) or, in the case of an enzymatic label, may catalyze chemical alteration of a substrate compound or composition which is detectable. The labels can be suitable for small scale detection or more suitable for high throughput screening. As such, suitable labels include, but are not limited to radioisotopes, fluorochromes, chemiluminescent compounds, dyes, and proteins, including enzymes. The label may be simply detected or it may be quantified. A reaction that is simply detected generally comprises a reaction whose existence merely is confirmed, whereas a reaction that is quantified generally comprises a reaction having a quantifiable (e.g., numerically reportable) value such as an intensity, polarization, and/or other property. In luminescence or fluorescence assays, the detectable reaction may be generated directly using a luminophore or fluorophore associated with an assay component actually involved in binding, or indirectly using a luminophore or fluorophore associated with another (e.g., reporter or indicator) component.

As used herein, an "antibody" or "antigen-binding polypeptide" refers to a polypeptide or a polypeptide complex that specifically recognizes and binds to an antigen. An antibody can be a whole antibody and any antigen binding fragment or a single chain thereof. Thus the term "antibody" includes any protein or peptide containing molecule that comprises at least a portion of an immunoglobulin molecule having biological activity of binding to the antigen. Examples of such include, but are not limited to a complementarity determining region (CDR) of a heavy or light chain or a ligand binding portion thereof, a heavy chain or light chain variable region, a heavy chain or light chain constant region, a framework (FR) region, or any portion thereof, or at least one portion of a binding protein.

The terms "antibody fragment" or "antigen-binding fragment", as used herein, is a portion of an antibody such as F(ab')2, F(ab)2, Fab', Fab, Fv, scFv and the like. Regardless of structure, an antibody fragment binds with the same antigen is recognized as an intact antibody. The term "antibody fragment" includes aptamers, spiegelmers, and diabodies. The term "antibody fragment" also includes any synthetic or genetically engineered protein that acts like an antibody by binding to a specific antigen to form a complex.

A "single-chain variable fragment" or "scFv" refers to a fusion protein of the variable regions of the heavy (VH) and light chains (VL) of an immunoglobulin. In some aspects, the regions are connected with a short linker peptide of 10 to about 25 amino acids. The linker can be rich in glycine for flexibility, as well as serine or threonine for solubility, and can either connect the N-terminus of the VH with the C-terminus of the VL, or vice versa. This protein retains the properties of the original immunoglobulin, despite removal of the constant regions and the introduction of the linker. ScFv molecules are known in the art, such as those described in U.S. Pat. No. 5,892,019.

Those skilled in the art will appreciate that heavy chains are classified as gamma, mu, alpha, delta, or epsilon ($\gamma, \mu, \alpha, \delta, \epsilon$) with some subclasses among them (e.g., $\gamma 1$-$\gamma 4$). It is the nature of this chain that determines the "class" of the antibody as IgG, IgM, IgA, IgG, or IgE, respectively. The immunoglobulin subclasses (isotypes) e.g., IgG1, IgG2, IgG3, IgG4, IgG5, etc. are well characterized and are known to confer functional specialization. Modified versions of each of these classes and isotypes are readily discernable to the skilled artisan in view of the instant disclosure and, accordingly, are within the scope of the instant disclosure. All immunoglobulin classes are clearly within the scope of the present disclosure, the following discussion will generally be directed to the IgG class of immunoglobulin molecules. With regard to IgG, a standard immunoglobulin molecule comprises two identical light chain polypeptides of molecular weight approximately 23,000 Daltons, and two identical heavy chain polypeptides of molecular weight 53,000-70,000. The four chains are typically joined by disulfide bonds in a "Y" configuration wherein the light chains bracket the heavy chains starting at the mouth of the "Y" and continuing through the variable region.

Antibodies, antigen-binding polypeptides, variants, or derivatives thereof of the disclosure include, but are not limited to, polyclonal, monoclonal, multispecific, human, humanized, primatized, or chimeric antibodies, single chain antibodies, epitope-binding fragments, e.g., Fab, Fab' and F(ab')2, Fd, Fvs, single-chain Fvs (scFv), single-chain antibodies, disulfide-linked Fvs (sdFv), fragments comprising either a VK or VH domain, fragments produced by a Fab expression library, and anti-idiotypic (anti-Id) antibodies (including, e.g., anti-Id antibodies to LIGHT antibodies disclosed herein) Immunoglobulin or antibody molecules of the disclosure can be of any type (e.g., IgG, IgE, IgM, IgD, IgA, and IgY), class (e.g., IgG1, IgG2, IgG3, IgG4, IgA1 and IgA2) or subclass of immunoglobulin molecule.

Light chains are classified as either kappa or lambda (K, 4 Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain.

Both the light and heavy chains are divided into regions of structural and functional homology. The terms "constant" and "variable" are used functionally. In this regard, it will be appreciated that the variable domains of both the light (VL) and heavy (VH) chain portions determine antigen recognition and specificity. Conversely, the constant domains of the light chain (CL) and the heavy chain (CH1, CH2 or CH3) confer important biological properties such as secretion, transplacental mobility, Fc receptor binding, complement binding, and the like. By convention the numbering of the constant region domains increases as they become more distal from the antigen binding site or amino-terminus of the antibody. The N-terminal portion is a variable region and at the C-terminal portion is a constant region; the CH3 and CL domains actually comprise the carboxy-terminus of the heavy and light chain, respectively.

As indicated above, the variable region allows the antibody to selectively recognize and specifically bind epitopes on antigens. That is, the VK domain and VH domain, or subset of the complementarity determining regions (CDRs), of an antibody combine to form the variable region that defines a three dimensional antigen-binding site. This quaternary antibody structure forms the antigen-binding site present at the end of each arm of the Y configuration. More specifically, the antigen-binding site is defined by three CDRs on each of the VH and VK chains (i.e. CDR-H1, CDR-H2, CDR-H3, CDR-L1, CDR-L2 and CDR-L3). In some instances, e.g., certain immunoglobulin molecules derived from camelid species or engineered based on camelid immunoglobulins, a complete immunoglobulin molecule may consist of heavy chains only, with no light chains. See, e.g., Hamers-Casterman et al., Nature 363:446-448 (1993).

As used herein, the terms "treat" or "treatment" refer to both therapeutic treatment and prophylactic or preventative measures, wherein the object is to prevent or slow down (lessen) an undesired physiological change or disorder, such as the progression of cancer. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Conditions in need of treatment include those already with the condition or disorder as well as those prone to have the condition or disorder or those in which the condition or disorder is to be prevented.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, and zoo, sport, or pet animals such as dogs, cats, guinea pigs, rabbits, rats, mice, horses, cattle, cows, primates (for example, humans, monkeys such as cynomolgus, macaques, baboons, and chimpanzees, etc.), and so on.

As used herein, phrases such as "a patient in need of treatment" or "a subject in need of treatment" includes mammalian subjects, such as a human that would benefit from administration of an antibody or composition used in the present application, e.g., for detection, for a diagnostic procedure and/or for treatment.

Multifunctional Antibody

One embodiment of the present disclosure provides a heterodimer antibody, which comprises two different antigen-binding polypeptide units. In some aspects, the heterodimer differs in size from its corresponding homodimer, and the size difference can be utilized to facilitate separation of hetero- and homo-dimers.

In some aspects, as shown in FIG. 1, one of the two antigen-binding polypeptide units comprises a light chain-heavy chain pair like a wild-type antibody. Throughout the disclosure, this unit is also referred to as a "monovalent unit."

In some aspects, as shown in FIG. 1, the other antigen-binding polypeptide unit, comprises a single chain variable fragment (scFv). Such a scFv can be fused to the N-terminus of the constant fragment (Fc) of an antibody, which is called a fusion peptide. Throughout the disclosure, this fusion peptide is also referred to as "single-chain unit".

The present application provides a multifunctional antibody and a preparation method, the antibody comprising: (a) a light chain-heavy chain pair having specificity to tumor cells; and (b) a fusion peptide comprising a single chain variable fragment (scFv) and an Fc fragment comprising a CH2 domain and/or a CH3 domain, wherein the fusion peptide has specificity to immune cells. This antibody is called a multifunctional antibody.

Any of the antibodies or polypeptides described above may further include additional polypeptides, e.g., a signal peptide to direct secretion of the encoded polypeptide, antibody constant regions as described herein, or other heterologous polypeptides as described herein.

It will also be understood by one of ordinary skill in the art that antibodies as disclosed herein may be modified such that they vary in amino acid sequence from the naturally occurring binding polypeptide from which they were derived. For example, a polypeptide or amino acid sequence derived from a designated protein may be similar, e.g., have a certain percent identity to the starting sequence, e.g., it may be 60%, 70%, 75%, 80%, 85%, 90%, 95%, 98%, or 99% identical to the starting sequence.

Furthermore, nucleotide or amino acid substitutions, deletions, or insertions leading to conservative substitutions or changes at "non-essential" amino acid regions may be made. For example, a polypeptide or amino acid sequence derived from a designated protein may be identical to the starting sequence except for one or more individual amino acid substitutions, insertions, or deletions, e.g., one, two, three, four, five, six, seven, eight, nine, ten, fifteen, twenty or more individual amino acid substitutions, insertions, or deletions. In certain embodiments, a polypeptide or amino acid sequence derived from a designated protein has one to five, one to ten, one to fifteen, or one to twenty individual amino acid substitutions, insertions, or deletions relative to the starting sequence.

In certain embodiments, an antigen-binding polypeptide comprises an amino acid sequence or one or more moieties not normally associated with an antibody. Exemplary modifications are described in more detail below. For example, a single chain Fv antibody fragment of the disclosure may comprise a flexible linker sequence, or may be modified to add a functional moiety (e.g., PEG, a drug, a toxin, or a label).

Antibodies, variants, or derivatives thereof of the disclosure include derivatives that are modified, i.e., by the covalent attachment of any type of molecule to the antibody such that covalent attachment does not prevent the antibody from binding to the epitope. For example, but not by way of limitation, the antibodies can be modified, e.g., by glycosylation, acetylation, pegylation, phosphorylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the antibodies may contain one or more non-classical amino acids.

In other embodiments, the antigen-binding polypeptides of the present disclosure may contain conservative amino acid substitutions.

A "conservative amino acid substitution" is one in which the amino acid residue is substituted with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in an immunoglobulin polypeptide is preferably substituted with another amino acid residue from the same side chain family In another embodiment, a string of amino acids can be substituted with a structurally similar string that differs in order and/or composition of side chain family members.

Methods of Making Antibodies

Methods of making antibodies are well known in the art and described herein. In certain embodiments, both the variable and constant regions of the antigen-binding polypeptides of the present disclosure are fully human Fully human antibodies can be made using techniques described in the art and as described herein. For example, fully human antibodies against a specific antigen can be prepared by administering the antigen to a transgenic animal which has been modified to produce such antibodies in response to antigenic challenge, but whose endogenous loci have been disabled. Exemplary techniques that can be used to make such antibodies are described in U.S. Pat. Nos. 6,150,584; 6,458,592; 6,420,140 which are incorporated by reference in their entireties.

In certain embodiments, the prepared antibodies will not elicit a deleterious immune response in the animal to be treated, e.g., in a human. In one embodiment, antigen binding polypeptides, variants, or derivatives thereof of the disclosure are modified to reduce their immunogenicity using art-recognized techniques. For example, antibodies can be humanized, primatized, deimmunized, or chimeric antibodies can be made. These types of antibodies are derived from a non-human antibody, typically a murine or primate antibody, that retains or substantially retains the antigen-binding properties of the parent antibody, but which is less immunogenic in humans. This may be achieved by various methods, including (a) grafting the entire non-human variable domains onto human constant regions to generate chimeric antibodies; (b) grafting at least a part of one or more of the non-human complementarity determining regions (CDRs) into a human framework and constant regions with or without retention of critical framework residues; or (c) transplanting the entire non-human variable domains, but "cloaking" them with a human-like section by substitution of surface residues.

De-immunization can also be used to decrease the immunogenicity of an antibody. As used herein, the term "de-immunization" includes alteration of an antibody to modify T-cell epitopes (see, e.g., International Application Publication Nos.: WO/9852976 A1 and WO/0034317 A2). For example, variable heavy chain and variable light chain sequences from the starting antibody are analyzed and a human T-cell epitope "map" from each V region showing the location of epitopes in relation to complementarity-determining regions (CDRs) and other key residues within the sequence is created. Individual T-cell epitopes from the T-cell epitope map are analyzed in order to identify alternative amino acid substitutions with a low risk of altering activity of the final antibody. A range of alternative variable heavy and variable light sequences are designed comprising combinations of amino acid substitutions and these sequences are subsequently incorporated into a range of binding polypeptides. Typically, between 12 and 24 variant antibodies are generated and tested for binding and/or function. Complete heavy and light chain genes comprising modified variable and human constant regions are then cloned into expression vectors and the subsequent plasmids introduced into cell lines for the production of whole antibody. The antibodies are then compared in appropriate biochemical and biological assays, and the optimal variant is identified.

The binding specificity of antigen-binding polypeptides of the present disclosure can be determined by in vitro assays such as immunoprecipitation, radioimmunoassay (RIA) or enzyme-linked immunoabsorbent assay (ELISA).

Techniques described for the production of single-chain units (U.S. Pat. No. 4,694,778; Bird, Science 242:423-442 (1988); Huston et al., Proc. Natl. Acad. Sci. USA 55:5879-5883 (1988); and Ward et al., Nature 334:544-554 (1989)) can be adapted to produce single-chain units of the present disclosure. Single-chain units are formed by linking the heavy and light chain fragments of the Fv region via an amino acid bridge, resulting in a single-chain fusion peptide. Techniques for the assembly of functional Fv fragments in E. coli may also be used (Skerra et al., Science 242: 1038-1041 (1988)).

Examples of techniques which can be used to produce single-chain Fvs (scFvs) and antibodies include those described in U.S. Pat. Nos. 4,946,778 and 5,258,498; Huston et al., Methods in Enzymology 203:46-88 (1991); Shu et al., Proc. Natl. Sci. USA 90:1995-1999 (1993); and Skerra et al., Science 240:1038-1040 (1988). For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See, e.g., Morrison, Science 229:1202 (1985); Oi et al., BioTechniques 4:214 (1986); Gillies et al., J. Immunol. Methods 125:191-202 (1989); U.S. Pat. Nos. 5,807,715; 4,816,567; and 4,816397, which are incorporated herein by reference in their entireties.

Humanized antibodies are antibody molecules derived from a non-human species antibody that bind the desired antigen having one or more complementarity determining regions (CDRs) from the non-human species and framework regions from a human immunoglobulin molecule. Often, framework residues in the human framework regions will be substituted with the corresponding residue from the CDR donor antibody to alter, preferably improve, antigen-binding. These framework substitutions are identified by methods well known in the art, e.g., by modeling of the interactions of the CDR and framework residues to identify framework residues important for antigen-binding and sequence comparison to identify unusual framework residues at particular positions. (See, e.g., Queen et al., U.S. Pat. No. 5,585,089; Riechmann et al., Nature 332:323 (1988), which are incorporated herein by reference in their entireties.) Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, Molecular Immunology 28(4/5):489-498 (1991); Studnicka et al., Protein Engineering 7(6):805-814 (1994); Roguska. et al., Proc. Natl. Sci. USA 91:969-973 (1994)), and chain shuffling (U.S. Pat. No. 5,565,332, which is incorporated by reference in its entirety).

Completely human antibodies are particularly desirable for therapeutic treatment of human patients. Human antibodies can be made by a variety of methods known in the art including phage display methods using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring that express human antibodies. The transgenic mice are immunized in the normal fashion with a selected antigen, e.g., all or a portion of a desired target polypeptide. Monoclonal antibodies directed against the antigen can be obtained from the immunized, transgenic mice using conventional hybridoma technology. The human immunoglobulin transgenes harbored by the transgenic mice rearrange during B-cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar Int. Rev. Immunol. 73:65-93 (1995). For a detailed discussion of this technology for producing human antibodies and human monoclonal antibodies and protocols for producing such antibodies, see, e.g., PCT publications WO 98/24893; WO 96/34096; WO 96/33735; U.S. Pat. Nos. 5,413,923; 5,625,126; 5,633,425; 5,569,825; 5,661,016; 5,545,806; 5,814,318; and 5,939,598, which are incorporated by reference herein in their entirety. In addition, companies such as Abgenix, Inc. (Freemont, Calif.) and GenPharm (San Jose, Calif.) can be engaged to provide human antibodies directed against a selected antigen using technology similar to that described above.

Completely human antibodies which recognize a selected epitope can also be generated using a technique referred to as "guided selection." In this approach a selected non-human monoclonal antibody, e.g., a mouse antibody, is used to guide the selection of a completely human antibody recognizing the same epitope. (Jespers et al., Bio/Technology 72:899-903 (1988). See also, U.S. Pat. No. 5,565,332, which is incorporated by reference in its entirety.)

In some embodiments, DNA encoding desired monoclonal antibodies may be readily isolated and sequenced using conventional procedures (e.g., by using oligonucleotide probes that are capable of binding specifically to genes encoding the heavy and light chains of murine antibodies). The isolated and subcloned hybridoma cells serve as a preferred source of such DNA. Once isolated, the DNA may be placed into expression vectors, which are then transfected into prokaryotic or eukaryotic host cells such as E. coli cells, simian COS cells, Chinese Hamster Ovary (CHO) cells, human embryonic kidney cell 293 or myeloma cells that do not otherwise produce immunoglobulins. More particularly, the isolated DNA (which may be synthetic as described herein) may be used to clone constant and variable region sequences for the manufacture of antibodies as described in Newman et al., U.S. Pat. No. 5,658,570, filed Jan. 25, 1995, which is incorporated by reference herein. Essentially, this entails extraction of RNA from the selected cells, conversion to cDNA, and amplification by PCR using Ig specific primers. Suitable primers for this purpose are also described in U.S. Pat. No. 5,658,570. As will be discussed in more detail below, transformed cells expressing the desired antibody may be grown up in relatively large quantities to provide clinical and commercial supplies of the immunoglobulin.

Additionally, using routine recombinant DNA techniques, one or more of the CDRs of the antigen-binding polypeptides of the present disclosure, may be inserted within framework regions, e.g., into human framework regions to humanize a non-human antibody. The framework regions may be naturally occurring or consensus framework regions, and preferably human framework regions (see, e.g., Chothia et al., J. Mol. Biol. 278:457-479 (1998) for a listing of human framework regions). Preferably, the polynucleotide generated by the combination of the framework regions and CDRs encodes a polypeptide that specifically binds to at least one epitope of a desired polypeptide, e.g., LIGHT. Preferably, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in formation of intra-chain disulfide bond to generate antibody molecules lacking one or more intrachain disulfide bonds. Other alterations to the polynucleotide are encompassed by the present disclosure and within the skill of the art.

In addition, techniques developed for the production of "chimeric antibodies" (Morrison et al., Proc. Natl. Acad. Sci. USA: 851-855 (1984); Neuberger et al., Nature 372:604-608 (1984); Takeda et al., Nature 314:452-454 (1985)) by splicing genes from a mouse antibody molecule, of appropriate antigen specificity, together with genes from a human antibody molecule of appropriate biological activity can be used. As used herein, a chimeric antibody is a molecule in which different portions are derived from different animal species, such as those having a variable region derived from a murine monoclonal antibody and a human immunoglobulin constant region.

Yet another highly efficient means for generating recombinant antibodies is disclosed by Newman, Biotechnology 10: 1455-1460 (1992). Specifically, this technique results in the generation of primatized antibodies that contain monkey variable domains and human constant sequences. This reference is incorporated by reference in its entirety herein. Moreover, this technique is also described in commonly assigned U.S. Pat. Nos. 5,658,570, 5,693,780 and 5,756,096 each of which is incorporated herein by reference.

In some embodiments, antibody-producing cell lines may be selected and cultured using techniques well known to the skilled artisan. Such techniques are described in a variety of laboratory manuals and primary publications. In this respect, techniques suitable for use in the disclosure as described below are described in Current Protocols in Immunology, Coligan et al., Eds., Green Publishing Associates and Wiley-Interscience, John Wiley and Sons, New York (1991) which is herein incorporated by reference in its entirety, including supplements.

In some embodiments, standard techniques known to those of skill in the art can be used to introduce mutations in the nucleotide sequence encoding an antibody of the present disclosure, including, but not limited to, site-directed mutagenesis and PCR-mediated mutagenesis which result in amino acid substitutions. Preferably, the variants (including derivatives) encode less than 50 amino acid substitutions, less than 40 amino acid subsitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the reference variable heavy chain region, CDRH1, CDR-H2, CDR-H3, variable light chain region, CDR-L1, CDR-L2, or CDR-L3. Alternatively, mutations can be introduced randomly along all or part of the coding sequence, such as by saturation mutagenesis, and the resultant mutants can be screened for biological activity to identify mutants that retain activity.

Treatment and Diagnostic Methods

As described herein, the antigen-binding polypeptides, variants or derivatives of the present disclosure may be used in certain treatments and diagnostic methods associated with cancer or an infectious disease.

The present disclosure is further directed to antibody-based therapies which involve administering the bispecific antibodies of the disclosure to a patient such as an animal, a mammal, and a human for treating one or more of the disorders or conditions described herein. Therapeutic compounds of the disclosure include, but are not limited to, antibodies of the disclosure (including variants and derivatives thereof as described herein) and nucleic acids or polynucleotides encoding antibodies of the disclosure (including variants and derivatives thereof as described herein).

The antibodies of the disclosure can also be used to treat, inhibit or prevent diseases, disorders or conditions including malignant diseases, disorders, or conditions associated with such diseases or disorders, such as diseases associated with immune response. In some embodiments, the antibodies of the invention can be used as immunosuppressive agents. In some embodiments, the antibodies of the invention can be used to treat autoimmune diseases. The antigen-binding polypeptides, variants or derivatives thereof of the disclosure are used to inhibit the growth, development and/or metastasis of cancer, especially those listed above or in the following paragraphs.

Additional diseases or conditions associated with increased cell survival, that may be treated, prevented, diagnosed and/or prognosed with the antibodies or variants, or derivatives thereof of the disclosure include, but are not limited to cancer or tumors, including the development and/or metastasis of malignant tumors, and related diseases, such as multiple myeloma, lung cancer (such as small cell lung cancer, non-small cell lung cancer, lung adenocarcinoma, lung squamous cell carcinoma), etc.

A specific dosage and treatment regimen for any particular patient will depend upon a variety of factors, including the particular antigen-binding polypeptide, variant or derivative thereof used, the patient's age, body weight, general health, sex, and diet, and the time of administration, rate of excretion, drug combination, and the severity of the particular disease being treated. Judgment of such factors by medical caregivers is within the ordinary skill in the art. The amount will also depend on the individual patient to be treated, the route of administration, the type of formulation, the characteristics of the compound used, the severity of the disease, and the desired effect. The amount used can be determined by pharmacological and pharmacokinetic principles well known in the art.

Methods of administration of the antigen-binding polypeptides, variants or derivatives thereof include but are not limited to intradermal, intramuscular, intraperitoneal, intravenous, subcutaneous, intranasal, epidural, and oral routes. The antigen-binding polypeptides or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Thus, pharmaceutical compositions containing the antigen-binding polypeptides of the disclosure may be administered orally, rectally, parenterally, intracisternally, intravaginally, intraperitoneally, topically (as by powders, ointments, drops or transdermal patch), bucally, or as an oral or nasal spray.

The term "parenteral" as used herein refers to modes of administration which include intravenous, intramuscular, intraperitoneal, intrasternal, subcutaneous and intraarticular injection and infusion.

Administration can be systemic or local. In addition, it may be desirable to introduce the antibodies of the disclosure into the central nervous system by any suitable route, including intraventricular and intrathecal injection; intraventricular injection may be facilitated by an intraventricular catheter, for example, attached to a reservoir. Pulmonary administration can also be employed, e.g., by use of an inhaler or nebulizer, and formulation with an aerosolizing agent.

It may be desirable to administer the antigen-binding polypeptides or compositions of the disclosure locally to the area in need of treatment; this may be achieved by, for example, and not by way of limitation, local infusion during surgery, topical application, e.g., in conjunction, with a wound dressing after surgery, by injection, by means of a catheter, by means of a suppository, or by means of an implant, said implant being of a porous, non-porous, or gelatinous material, including membranes, or fibers. Preferably, when administering a protein, including an antibody, of the disclosure, care must be taken to use materials to which the protein does not absorb.

The amount of the antibodies of the disclosure which will be effective in the treatment, inhibition and prevention of an inflammatory, immune or malignant disease, disorder or condition can be determined by standard clinical techniques. In addition, in vitro assays may optionally be employed to help identify optimal dosage ranges. The precise dose to be employed in the formulation will also depend on the route of administration, and the seriousness of the disease, disorder or condition, and should be decided according to the judgment of the practitioner and each patient's circumstances. Effective doses may be extrapolated from dose-response curves derived from in vitro or animal model test systems.

The methods for treating an infectious or malignant disease, condition or disorder comprising administration of an antibody, variant, or derivative thereof of the disclosure are typically tested in vitro, and then in vivo in an acceptable animal model, for the desired therapeutic or prophylactic activity, prior to use in humans. Suitable animal models, including transgenic animals, are well known to those of ordinary skill in the art. For example, in vitro assays to demonstrate the therapeutic utility of antigen-binding polypeptide described herein include the effect of an antigen-binding polypeptide on a cell line or a patient tissue sample. The effect of the antigen-binding polypeptide on the cell line and/or tissue sample can be determined utilizing techniques known to those of skill in the art, such as the assays disclosed elsewhere herein. In accordance with the disclosure, in vitro assays which can be used to determine whether administration of a specific antigen-binding polypeptide is indicated, include in vitro cell culture assays in which a patient tissue sample is grown in culture, and exposed to or otherwise administered a compound, and the effect of such compound upon the tissue sample is observed.

Antibody Structure Information

The structure of monoclonal antibody is: symmetrical monospecific antibody, including two identical light chains and two identical heavy chains, with light-heavy chain pairings and a heavy chain-heavy chain pairing; the light-heavy chain pairings target the same kind target.

The structure of the multifunctional antibody is: asymmetric bispecific antibody, including a light chain, a heavy chain and a fusion peptide, with a light-heavy chain pairing and a heavy chain-fusion peptide pairing; the light-heavy chain pairing targets tumor antigen, and the fusion peptide ScFv targets the immune cell antigen CD3.

In some aspects, the heavy chain is bound to the fusion peptide through one or more disulfide bonds, or one or more disulfide bonds are formed between two different fusion heavy chains. In one aspect, the one or more disulfide bonds are formed between the amino acid residues at the hinge region between the CH1 (or VLs) and the CH2 domains.

In some aspects, the CH2 domain of the fusion peptide is located between the scFv fragment and the CH3 domain. In other words, the scFv fragment is connected at the CH2 end of the Fc fragment. In some aspects, the single chain unit does not contain a CH1 domain.

In one aspect, either or both of the monovalent unit and the single-chain unit comprise human antibody sequences or humanized sequences. For instance, in one aspect, the heavy chain of the monovalent unit comprises a human or humanized Fc fragment. In a particular aspect, the Fc fragment of the heavy chain comprises a human IgG Fc fragment.

In one aspect, the Fc fragment of the fusion peptide comprises a human or humanized Fc fragment. In a particular aspect, the Fc fragment of the fusion peptide comprises a human IgG Fc fragment.

Figure 1B:
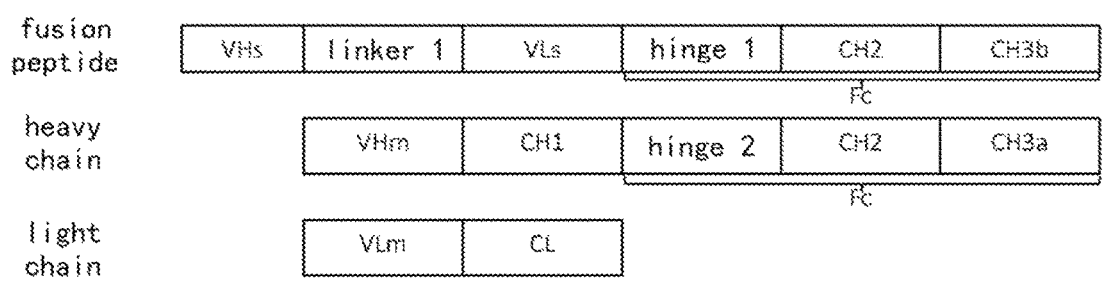
FIG. 1B is a schematic diagram of a primary structure of protein of each component of the antibody.

FIG. 1A is a schematic structural diagram of a multifunctional antibody 1. FIG. 1B is a schematic diagram of a primary structure of protein of each component of the antibody.

Humanized CD3 Antibody Engineered According to the Present Invention (1) CDR and FR Sequences of the Variable Region of the Humanized CD3 Antibody

TABLE 1

CDR and FR sequences of the variable regions of the humanized CD3 antibody

| Domain | Amino acid sequences (those in bold and underlined being replaceable amino acids | Sequence No. |
|---|---|---|
| CDR-H1 | TYAMN | 1 |
| CDR-H2 | RIRSKYNNYATYYADSVKD | 2 |
| CDR-H3 | HGNFGNSYVSWFAY | 3 |
| CDR-H3a | HGNFGNSYVTWFAY | 4 |
| CDR-H3b | HGNFGNSYVSYFAY | 5 |
| CDR-H3c | HGNFGNSYVSFFAY | 6 |
| CDR-H3d | HGNFGNSYVSWLAY | 7 |

TABLE 1-continued

CDR and FR sequences of the variable regions of the humanized CD3 antibody

| Domain | Amino acid sequences (those in bold and underlined being replaceable amino acids | Sequence No. |
|---|---|---|
| CDR-H3e | HGNFGNSYVSWVAY | 8 |
| CDR-H3f | HGNFGNSYVSWIAY | 9 |
| CDR-H3g | HGNFGNSYVSWAAY | 10 |
| CDR-H3h | HGNFGNSYVSWYAY | 11 |
| CDR-H3i | HGNFGNSYVSWFVY | 12 |
| CDR-H3j | HGNFGNSYVSWFLY | 13 |
| CDR-H3k | HGNFGNSYVSWFIY | 14 |
| CDR-H3l | HGNFGNSYVSWGAY | 190 |
| CDR-H3m | HGNFGNSYVSWFGY | 191 |
| FR-H1 | EVQLVESGGGLVQPGGSLRLSCAASGFTFS | 15 |
| FR-H1a | QVQLVESGGGVVQPGRSLRLSCAASGFTFS | 16 |
| FR-H2 | WVRQAPGKGLEWVA | 17 |
| FR-H3 | RFTISRDNAKNSLYLQMNSLRAEDTAVYYCAR | 18 |
| FR-H3a | RFTISRDDSKNSLYLQMNSLRAEDTAVYYCAR | 19 |
| FR-H3b | RFTISRDDSKNSLYLQMNSLRAEDTAVYYCVR | 20 |
| FR-H3c | RFTISRDNSKNTLYLQMNSLRAEDTAVYYCAR | 21 |
| FR-H3d | RFTISRDNSKNTLYLQMNSLRAEDTAVYYCVR | 22 |
| FR-H3e | RFTISRDDSKNTLYLQMNSLRAEDTAVYYCAR | 23 |
| FR-H3f | RFTISRDDSKNTLYLQMNSLRAEDTAVYYCVR | 24 |
| FR-H4 | WGQGTLVTVSS | 25 |
| CDR-L1 | RSSTGAVTTSNYAN | 26 |
| CDR-L2 | GTNKRAP | 27 |
| CDR-L3 | ALWYSNLWV | 28 |
| FR-L1 | EIVLTQSPATLSLSPGERATLSC | 29 |
| FR-L1a | EIVMTQSPATLSLSPGERATLSC | 30 |
| FR-L1b | QTVVTQEPSLTVSPGGTVTLTC | 31 |
| FR-L2 | WFQQKPGQAPRALIY | 32 |
| FR-L2a | WFQQKPGQAPRGLIG | 33 |
| FR-L2b | WVQQKPGQAPRALIG | 34 |
| FR-L2c | WYQQKPGQAPRALIY | 35 |
| FR-L2d | WVQQKPGQAPRGLIG | 36 |
| FR-L2e | WVQQKPGQAPKGLIG | 37 |
| FR-L2f | WVQQKPGKAPKLLIG | 38 |
| FR-L3 | GVPARFSGSLSGTDATLTISSLQPEDFAVYYC | 39 |

TABLE 1-continued

CDR and FR sequences of the variable regions of the humanized CD3 antibody

| Domain | Amino acid sequences (those in bold and underlined being replaceable amino acids | Sequence No. |
|---|---|---|
| FR-L3a | WTPARFSGSLLGGKAALTLSGVQPEDEAE**YYC | 40 |
| FR-L3b | GVPARFSGSLLGGKAALTLSGVQPEDEAE**YYC | 41 |
| FR-L3c | GTPARFSGSLLGGKAALTLSGVQPEDEAE**YYC | 42 |
| FR-L4 | FGGGTKVEIK | 43 |
| FR-L4a | FGGGTKLTVL | 44 |

(2) New Humanized CD3 Antibody Sequences (Some Examples)

TABLE 2

Sequences of the variable regions of the new humanized CD3 antibody

| Domian | Code | Amino acid sequences of the variable regions of the humanized CD3 antibody (those in bold and underlined being CDR regions) | Sequence No. |
|---|---|---|---|
| Heavy chain variable region (VHs) | VH1 | EVQLVESGGGLVQPGGSLRLSCAASGFTFSTYAMNWVRQAPGKGLEWVARIRSKYNNYATYYADSVKDRFTISRDNAKNSLYLQMNSLRAEDTAVYYCARHGNFGNSYVSWFAYWGQGTLVTVSS | 45 |
| | VH1a | EVQLVESGGGLVQPGGSLRLSCAASGFTFSTYAMNWVRQAPGKGLEWVARIRSKYNNYATYYADSVKDRFTISRDDSKNSLYLQMNSLRAEDTAVYYCARHGNFGNSYVSWFAYWGQGTLVTVSS | 46 |
| | VH1b | EVQLVESGGGLVQPGGSLRLSCAASGFTFSTYAMNWVRQAPGKGLEWVARIRSKYNNYATYYADSVKDRFTISRDDSKNSLYLQMNSLRAEDTAVYYCVRHGNFGNSYVSWFAYWGQGTLVTVSS | 47 |
| | VH2 | QVQLVESGGGVVQPGRSLRLSCAASGFTFSTYAMNWVRQAPGKGLEWVARIRSKYNNYATYYADSVKDRFTISRDNSKNTLYLQMNSLRAEDTAVYYCARHGNFGNSYVSWFAYWGQGTLVTVSS | 48 |
| | VH2a | QVQLVESGGGVVQPGRSLRLSCAASGFTFSTYAMNWVRQAPGKGLEWVARIRSKYNNYATYYADSVKDRFTISRDDSKNTLYLQMNSLRAEDTAVYYCARHGNFGNSYVSWFAYWGQGTLVTVSS | 49 |
| | VH2b | QVQLVESGGGVVQPGRSLRLSCAASGFTFSTYAMNWVRQAPGKGLEWVARIRSKYNNYATYYADSVKDRFTISRDNSKNTLYLQMNSLRAEDTAVYYCVRHGNFGNSYVSWFAYWGQGTLVTVSS | 50 |
| | VH2c | QVQLVESGGGVVQPGRSLRLSCAASGFTFSTYAMNWVRQAPGKGLEWVARIRSKYNNYATYYADSVKDRFTISRDDSKNTLYLQMNSLRAEDTAVYYCVRHGNFGNSYVSWFAYWGQGTLVTVSS | 51 |
| | VH2d | QVQLVESGGGVVQPGRSLRLSCAASGFTFSTYAMNWVRQAPGKGLEWVARIRSKYNNYATYYADSVKDRFTISRDDSKNTLYLQMNSLRAEDTAVYYCARHGNFGNSYVTWFAYWGQGTLVTVSS | 52 |
| | VH2e | QVQLVESGGGVVQPGRSLRLSCAASGFTFSTYAMNWVRQAPGKGLEWVARIRSKYNNYATYYADSVKDRFTISRDDSKNTLYLQMNSLRAEDTAVYYCARHGNFGNSYVSYFAYWGQGTLVTVSS | 53 |
| | VH2f | QVQLVESGGGVVQPGRSLRLSCAASGFTFSTYAMNWVRQAPGKGLEWVARIRSKYNNYATYYADSVKDRFTISRDDSKNTLYLQMNSLRAEDTAVYYCARHGNFGNSYVSFFAYWGQGTLVTVSS | 54 |
| | VH2g | QVQLVESGGGVVQPGRSLRLSCAASGFTFSTYAMNWVRQAPGKGLEWVARIRSKYNNYATYYADSVKDRFTISRDDSKNTLYLQMNSLRAEDTAVYYCARHGNFGNSYVSWLAYWGQGTLVTVSS | 55 |
| | VH2h | QVQLVESGGGVVQPGRSLRLSCAASGFTFSTYAMNWVRQAPGKGLEWVARIRSKYNNYATYYADSVKDRFTISRDDSKNTLYLQMNSLRAEDTAVYYCARHGNFGNSYVSWVAYWGQGTLVTVSS | 56 |
| | VH2i | QVQLVESGGGVVQPGRSLRLSCAASGFTFSTYAMNWVRQAPGKGLEWVARIRSKYNNYATYYADSVKDRFTISRDDSKNTLYLQMNSLRAEDTAVYYCARHGNFGNSYVSWIAYWGQGTLVTVSS | 57 |
| | VH2j | QVQLVESGGGVVQPGRSLRLSCAASGFTFSTYAMNWVRQAPGKGLEWVARIRSKYNNYATYYADSVKDRFTISRDDSKNTLYLQMNSLRAEDTAVYYCARHGNFGNSYVSWAAYWGQGTLVTVSS | 58 |
| | VH2k | QVQLVESGGGVVQPGRSLRLSCAASGFTFSTYAMNWVRQAPGKGLEWVARIRSKYNNYATYYADSVKDRFTISRDDSKNTLYLQMNSLRAEDTAVYYCARHGNFGNSYVSWYAYWGQGTLVTVSS | 59 |
| | VH2l | QVQLVESGGGVVQPGRSLRLSCAASGFTFSTYAMNWVRQAPGKGLEWVARIRSKYNNYATYYADSVKDRFTISRDDSKNTLYLQMNSLRAEDTAVYYCARHGNFGNSYVSWFVYWGQGTLVTVSS | 60 |
| | VH2m | QVQLVESGGGVVQPGRSLRLSCAASGFTFSTYAMNWVRQAPGKGLEWVARIRSKYNNYATYYADSVKDRFTISRDDSKNTLYLQMNSLRAEDTAVYYCARHGNFGNSYVSWFLYWGQGTLVTVSS | 61 |
| | VH2n | QVQLVESGGGVVQPGRSLRLSCAASGFTFSTYAMNWVRQAPGKGLEWVARIRSKYNNYATYYADSVKDRFTISRDDSKNTLYLQMNSLRAEDTAVYYCARHGNFGNSYVSWFIYWGQGTLVTVSS | 62 |
| Light chain variable region (VLs) | VL3 | EIVLTQSPATLSLSPGERATLSCRSSTGAVTTSNYANWVQQKPGQAPRGLIGGTNKRAPGVPARFSGSLSGTDATLTISSLQPEDFAVYYCALWYSNLWVFGGGTKVEIK | 63 |
| | VL3a | EIVLTQSPATLSLSPGERATLSCRSSTGAVTTSNYANWVQQKPGQAPKGLIGGTNKRAPGVPARFSGSLSGTDATLTISSLQPEDFAVYYCALWYSNLWVFGGGTKVEIK | 64 |
| | VL3b | EIVLTQSPATLSLSPGERATLSCRSSTGAVTTSNYANWVQQKPGKAPKLLIGGTNKRAPGVPARFSGSLSGTDATLTISSLQPEDFAVYYCALWYSNLWVFGGGTKVEIK | 65 |
| | VL3c | EIVLTQSPATLSLSPGERATLSCRSSTGAVTTSNYANWVQQKPGKAPKSLIGGTNKRAPGVPARFSGSLSGTDATLTISSLQPEDFAVYYCALWYSNLWVFGGGTKVEIK | 66 |
| | VL3d | EIVMTQSPATLSLSPGERATLSCRSSTGAVTTSNYANWVQQKPGQAPKGLIGGTNKRAPGVPARFSGSLSGTDATLTISSLQPEDFAVYYCALWYSNLWVFGGGTKVEIK | 67 |
| | VL3e | EIVMTQSPATLSLSPGERATLSCRSSTGAVTTSNYANWVQQKPGKAPKLLIGGTNKRAPGVPARFSGSLSGTDATLTISSLQPEDFAVYYCALWYSNLWVFGGGTKVEIK | 68 |
| | VL3f | EIVMTQSPATLSLSPGERATLSCRSSTGAVTTSNYANWVQQKPGKAPKSLIGGTNKRAPGVPARFSGSLSGTDATLTISSLQPEDFAVYYCALWYSNLWVFGGGTKVEIK | 69 |
| | VL4 | QAVVTQEPSLTVSPGGTVTLTCRSSTGAVTTSNYANWFQQKPGQAPRALIYGTNKRAPWTPARFSGSLLGGKAALTLSGVQPEDEAEYYCALWYSNLWVFGGGTKLTVL | 70 |
| | VL5 | QTVVTQEPSLTVSPGGTVTLTCRSSTGAVTTSNYANWVQQKPGQAPRGLIGGTNKRAPGVPARFSGSLLGGKAALTLSGVQPEDEAEYYCALWYSNLWVFGGGTKVEIK | 71 |

TABLE 2-continued

Sequences of the variable regions of the new humanized CD3 antibody

| Domian | Code | Amino acid sequences of the variable regions of the humanized CD3 antibody (those in bold and underlined being CDR regions) | Sequence No. |
|---|---|---|---|
| | VL5a | QTVVTQEPSLTVSPGGTVTLTCRSSTGAVTTSNYANWFQQKPGQAPRGLIGGTNKRAPGVPARFSGSLLGGKAALTLSGVQPEDEAEYYCALWYSNLWVFGGGTKVEIK | 72 |
| | VL5b | QTVVTQEPSLTVSPGGTVTLTCRSSTGAVTTSNYANWQQKPGQAPRALIGGTNKRAPGVPARFSGSLLGGKAALTLSGVQPEDEAEYYCALWYSNLWVFGGGTKVEIK | 73 |

Note:
VHs and VLs may be paired up arbitrarily.

Antibody Sequence Information
(1) Antibodies of Targeted Immune Cell Antigens

TABLE 3

Sequences of the variable regions of existing anti-CD3 antibodies

| Antibody code (sequence source) | VHs, VHs1 or VHs2 | Sequence No. | VLs, VLs1 or VLs2 | Sequence No. |
|---|---|---|---|---|
| SP34 (WO2007042261 A2) | EVQLVESGGGLVQPKGSLKLSCAASGFTFNTYAMNWVRQAPGKGLEWVARIRSKYNNYATYYADSVKDRFTISRDDSQSILYLQMNNLKTEDTAMYYCVRHGNFGNSYVSWFAYWGQGTLVTVSS | 74 | QAVVTQESALTTSPGETVTLTCRSSTGAVTTSNYANWVQEKPDHLFTGLIGGTNKRAPGVPARFSGSLIGDKAALTITGAQTEDEAIYFCALWYSNLWVFGGGTKLTVL | 75 |
| L2K (U.S. Pat. No. 7,112,324) | DIKLQQSGAELARPGASVKMSCKTSGYTFTRYTMHWVKQRPGQGLEWIGYINPSRGYTNYNQKFKDKATLTTDKSSSTAYMQLSSLTSEDSAVYYCARYYDDHYCLDYWGQGTTLTVSS | 76 | DIQLTQSPAIMSASPGEKVTMTCRASSSVSYMNWYQQKSGTSPKRWIYDTSKVASGVPYRFSGSGSGTSYSLTISSMEAEDAATYYCQQWSSNPLTFGAGTKLELK | 77 |
| DiL2K (U.S. Pat. No. 8,076,459) | DVQLVQSGAEVKKPGASVKVSCKASGYTFTRYTMHWVRQAPGQGLEWIGYINPSRGYTNYADSVKGRFTITTTDKSTSTAYMELSSLRSEDTATYYCARYYDDHYCLDYWGQGTTVTVSS | 78 | DIVLTQSPATLSLSPGERATLSCRASQSVSYMNWYQQKPGKAPKRWIYDTSKVASGVPARFSGSGSGTDYSLTINSLEAEDAATYYCQQWSSNPLTFGGGTKVEIK | 79 |
| OKT3 | QVQLQQSGAELARPGASVKMSCKASGYTFTRYTMHWVKQRPGQGLEWIGYINPSRGYTNYNQKFKDKATLTTDKSSSTAYMQLSSLTSEDSAVYYCARYYDDHYCLDYWGQGTTLTVSS | 80 | QIVLTQSPAIMSASPGEKVTMTCSASSSVSYMNWYQQKSGTSPKRWIYDTSKLASGVPAHFRGSGSGTSYSLTISGMEAEDAATYYCQQWSSNPFTFGSGTKLEIN | 81 |
| AbII (U.S. Pat. No. 8,236,308) | QVQLQQSGAELARPGASVKMSCKASGYTFTRSTMHWVKQRPGQGLEWIGYINPSSAYTNYNQKFKDKATLTADKSSSTAYMQLSSLTSEDSAVYYCASPQVHYDYNGFPYWGQGTLVTVSA | 82 | QVVLTQSPAIMSAFPGEKVTMTCSASSSVSYMNWYQQKSGTSPKRWIYDSSKLASGVPARFSGSGSGTSYSLTISSMETEDAATYYCQQWSRNPPTFGGGTKLQIT | 83 |
| UCTH1 | EVQLQQSGPELVKPGASMKISCKASGYSFTGYTMNWVKQSHGKNLEWMGLINPYKGVSTYNQKFKDKATLTVDKSSSTAYMELLSLTSEDSAVYYCARSGYYGDSDWYFDVWGAGTTVTVSS | 84 | DIQMTQTTSSLSASLGDRVTISCRASQDIRNYLNWYQQKPDGTVKLLIYYTSRLHSGVPSKFSGSGSGTDYSLTISNLEQEDIATYFCQQGNTLPWTFAGGTKLEIK | 85 |
| CD3 antibody 1 (U.S. Pat. No. 8,846,042B2) | EVQLVESGGGLVQPGGSLRLSCAASGFTFSTYAMNWVRQAPGKGLEWVARIRSKYNNYATYYADSVKDRFTISRDDSKNTLYLQMNSLRAEDTAVYYCARHGNFGNSYVSWFAYWGQGTMVTVSS | 86 | QAVVTQEPSLTVSPGGTVTLTCRSSTGAVTTSNYANWVQQKPGQAPRGLIGGTNKRAPGTPARFSGSLLGGKAALTLSGVQPEDEAEYYCALWYSNLWVFGGGTKLTVL | 87 |
| CD3 antibody 2 (U.S. Pat. No. 9,650,446B2) | EVQLVESGGGLVQPGGSLRLSCAASGFTFNTYAMNWVRQAPGKGLEWVGRIRSKYNNYATYYADSVKGRFTISRDDSKNTLYLQMNSLRAEDTAVYYCARHGNFGNSYVSWFAYWGQGTLVTVSS | 88 | QAVVTQEPSLTVSPGGTVTLTCGSSTGAVTTSNYANWVQQKPGQAPRGLIGGTNKRAPGVPARFSGSLLGGKAALTLSGAQPEDEAEYYCALWYSNLWVFGGGTKLEIK | 89 |

(2) Antibodies Targeting Tumor Antigens or Other Antigens

TABLE 4

Sequences of the variable regions of anti-CD38 antibodies

| Antibody code (sequence source) | Amino acid sequences of the variable regions of anti-CD38 antibodies (those in bold and underlined being CDR regions) | | | |
|---|---|---|---|---|
| | VHm | Sequence No. | VLm | Sequence No. |
| Dara (U.S. Pat. No. 9,040,050) | EVQLLESGGGLVQPGGSLRLSCAVSGFTFNSFAMSWVRQAPGKGLEWVSAISGSGGGTYYADSVKGRFTISRDNSKNTLYLQMNSLRAEDTAVYFCAKDKILWFGEPVFDYWGQGTLVTVSS | 90 | EIVLTQSPATLSLSPGERATLSCRASQSVSSYLAWYQQKPGQAPRLLIYDASNRATGIPARFSGSGSGTDFTLTISSLEPEDFAVYYCQQRSNWPPTFGQGTKVEIK | 91 |
| MOR (U.S. Pat. No. 8,088,896) | QVQLVESGGGLVQPGGSLRLSCAASGFTFSSYYMNWVRQAPGKGLEWVSGISGDPSNTYYADSVKGRFTISRDNSKNTLYLQMNSLRAEDTAVYYCARDLPLVYTGFAYWGQGTLVTVSS | 92 | DIELTQPPSVSVAPGQTARISCSGDNLRHYYVYWYQQKPGQAPVLVIYGDSKRPSGIPERFSGSNSGNTATLTISGTQAEDEADYYCQTYTGGASLVFGGGTKLTVL | 93 |
| SAR (U.S. Pat. No. 8,153,765) | QVQLVQSGAEVAKPGTSVKLSCKASGYTFTDYWMQWVKQRPGQGLEWIGTIYPGDGDTGYAQKFQGKATLTADKSSKTVYMHLSSLASEDSAVYYCARGDYYGSNSLDYWGQGTSVTVSS | 94 | DIVMTQSHLSMSTSLGDPVSITCKASQDVSTVVAWYQQKPGQSPRRLIYSASYRYIGVPDRFTGSGAGTDFTFTISSVQAEDLAVYYCQQHYSPPYTFGGGTKLEIK | 95 |
| 2F5 (U.S. Pat. No. 9,040,050) | QVQLVQSGAEVKKPGSSVKVSCKASGGTFSSYAFSWVRQAPGQGLEWMGRVIPFLGIANSAQKFQGRVTITADKSTSTAYMDLSSLRSEDTAVYYCARDDIAALGPFDYWGQGTLVTVSS | 96 | DIQMTQSPSSLSASVGDRVTITCRASQGISSWLAWYQQKPEKAPKSLIYAASSLQSGVPSRFSGSGSGTDFTLTISSLQPEDFATYYCQQYNSYPRTFGQGTKVEIK | 97 |

TABLE 5

Sequences of the variable regions of anti-BCMA antibodies

| Antibody code (sequence source) | Amino acid sequences of the variable regions of anti-BCMA antibodies (those in bold and underlined being CDR regions) | | | |
|---|---|---|---|---|
| | VHm | Sequence No. | VLm | Sequence No. |
| B50 (U.S. Pat. No. 9,598,500) | QVQLVQSGAEVKKPGASVKVSCKASGYSFPDYYINWVRQAPGQGLEWMGWIYFASGNSEYNQKFTGRVTMTRDTSINTAYMELSSLTSEDTAVYFCASLYDYDWYFDVWGQGTMVTVSS | 98 | DIVMTQTPLSLSVTPGQPASISCKSSQSLVHSNGNTYLHWYLQKPGQSPQLLIYKVSNRFSGVPDRFSGSGSGTDFTLKISRVEAEDVGIYYCSQSSIYPWTFGQGTKLEIK | 99 |
| B140153 (WO2016090320 A1) | QVQLVQSGAEVKKPGSSVKVSCKASGGTFSSYAISWVRQAPGQGLEWMGRIIPILGIANYAQKFQGRVTITADKSTSTAYMELSSLRSEDTAVYYCARGGYYSHDMWSEDWGQGTLVTVSS | 100 | LPVLTQPPSASGTPGQRVTISCSGRSSNIGSNSVNWYRQLPGAAPKLLIYSNNQRPPGVPVRFSGSKSGTSASLAISGLQSEDEATYYCATWDDNLNVHYVFGTGTKVTVLG | 101 |
| B140174 (WO2016090320 A1) | EVQLVQSGAEVKKPGESLKISCKGSGYSFTSYWIGWVRQMPGKGLEWMGIIYPGDSDTRYSPSFQGHVTISADKSISTAYLQWSSLKASDTAMYYCARYSGSFDNWGQGTLVTVSS | 102 | SYELTQPPSASGTPGQRVTMSCSGTSSNIGSHSVNWYQQLPGTAPKLLIYTNNQRPSGVPDRFSGSKSGTSASLAISGLQSEDEADYYCAAWDGSLNGLVFGGGTKLTVLG | 103 |
| B69 (U.S. Pat. No. 2,017,051,068 A1) | QLQLQESGPGLVKPSETLSLTCTVSGGSISSGSYFWGWIRQPPGKGLEWIGSIYYSGITYYNPSLKSRVTISVDTSKNQFSLKLSSVTAADTAVYYCARHDGAVAGLFDYWGQGTLVTVSSA | 104 | SYVLTQPPSVSVAPGQTARITCGGNNIGSKSVHWYQQPPGQAPVVVYDDSDRPSGIPERFSGNSNGNTATLTISRVEAGDEAVYYCQVWDSSSDHVVFGGGTKLTVL | 104 |

TABLE 6

Sequences of the variable regions of anti-PD-L1 antibodies

| Antibody code (sequence source) | Amino acid sequences of the variable regions of anti-PD-L1 antibodies (those in bold and underlined being CDR regions) | | | |
|---|---|---|---|---|
| | VHm | Sequence No. | VLm | Sequence No. |
| S70 (U.S. Pat. No. 7,943,743B2) | QVQLVQSGAEVKKPGSSVKVSCKTSGDTFSTYAISWVRQAPGQGLEWMGGIIPIFGKAHYAQKFQGRVTITADESTSTAYMELSSLRSEDTAVYFCARKFHFVSGSPFGMDVWGQGTTVTVSS | 106 | EIVLTQSPATLSLSPGERATLSCRASQSVSSYLAWYQQKPGQAPRLLIYDASNRATGIPARFSGSGSGTDFTLTISSLEPEDFAVYYCQQRSNWPTFGQGTKVEIK | 107 |
| Durvalumab (WO2010077634 A1) | EVQLVESGGGLVQPGGSLRLSCAASGFTFSDSWIHWVRQAPGKGLEWVAWISPYGGSTYYADSVKGRFTISADTSKNTAYLQMNSLRAEDTAVYYCARRHWPGGFDYWGQGTLVTVSS | 108 | DIQMTQSPSSLSASVGDRVTITCRASQDVSTAVAWYQQKPGKAPKLLIYSASFLYSGVPSRFSGSGSGTDFTLTISSLQPEDFATYYCQQYLYHPATFGQGTKVEIK | 109 |
| Avelumab (WO2011066389 A1) | EVQLVESGGGLVQPGGSLRLSCAASGFTFSRYWMSWVRQAPGKGLEWVANIKQDGSEKYYVDSVKGRFTISRDNAKNSLYLQMNSLRAEDTAVYYCAREGGWFGELAFDYWGQGTLVTVSS | 110 | EIVLTQSPGTLSLSPGERATLSCRASQRVSSSYLAWYQQKPGQAPRLLIYDASSRATGIPDRFSGSGSGTDFTLTISRLEPEDFAVYYCQQYGSLPWTFGQGTKVEIK | 111 |
| BMS-936559 (WO2013079174 A1) | EVQLLESGGGLVQPGGSLRLSCAASGFTFSSYIMMWVRQAPGKGLEWVSSIYPSGGITFYADTVKGRFTISRDNSKNTLYLQMNSLRAEDTAVYYCARIKLGTVTTVDYWGQGTLVTVSS | 112 | QSALTQPASVSGSPGQSITISCTGTSSDVGGYNYVSWYQQHPGKAPKLMIYDVSNRPSGVSNRFSGSKSGNTASLTISGLQAEDEADYYCSSYTSSSTRVFGTGTKVTVL | 113 |

TABLE 7

Sequences of the variable regions of anti-SLAMF7 antibodies

| Antibody code (sequence source) | Amino acid sequences of the variable regions of anti-SLAMF7 antibodies (those in bold and underlined being CDR regions) | | | |
|---|---|---|---|---|
| | VHm | Sequence No. | VLm | Sequence No. |
| Elotuzumab (WO2004100898 A2) | EVQLVESGGGLVQPGGSLRLSCAASGFDFSRYWMSWVRQAPGKGLEWIGEINPDSSTINYAPSLKDKFIISRDNAKNSLYLQMNSLRAEDTAVYYCARPDGNYWYFDVWGQGTLVTVSS | 114 | DIQMTQSPSSLSASVGDRVTITCKASQDVGIAVAWYQQKPGKVPKLLIYWASTRHTGVPDRFSGSGSGTDFTLTISSLQPEDVATYYCQQYSSYPYTFGQGTKVEIK | 115 |

TABLE 8

Sequences of the variable regions of anti-CEA antibodies

| Antibody code (sequence source) | Amino acid sequences of the variable regions of anti-CEA antibodies (those in bold and underlined being CDR regions) | | | |
|---|---|---|---|---|
| | VHm | Sequence No. | VLm | Sequence No. |
| hPR1A3 (Cancer Immunol Immunother (1999) 47: 299-306) | QVQLVQSGSELKKPGASVKVSCKASGYTFTVFGMNWVRQAPGQGLEWMGWINTKTGEATYVEEFKGRFVFSLDTSVSTAYLQISSLKADDTAVYYCARWDFYDYVEAMDYWGQGTTVTVSS | 116 | DIQMTQSPSSLSASVGDRVTITCKASQNVGTNVAWYQQKPGKAPKLLIYSASYRYSGVPSRFSGSGSGTDFTFTISSLQPEDIATYYCHQYYTYPLFTFGQGTKVEIKR | 117 |

TABLE 9

Sequences of the variable regions of anti-luciferase antibodies

| Antibody code (sequence source) | Amino acid sequences of the variable regions of anti-luciferase antibodies (those in bold and underlined being CDR regions) | | | |
|---|---|---|---|---|
| | VHm | Sequence No. | VLm | Sequence No. |
| 4420 | EVKLDETGGGLVQPGRPMKLSCVASGFTFSDYWM NWVRQSPEKGLEWVAQIRNKPYNYETYYSDSVK GRFTISRDDSKSSVYLQMNNLRVEDMGIYYCTGSY YGMDYWGQGTSVTVSS | 118 | DVVMTQTPLSLPVSLGDQASISCRSSQSLVH SNGNTYLRWYLQKPGQSPKVLIYKVSNRFS GVPDRFSGSGSGTDFTLKISRVEAEDLGVYF CSQSTHVPWTFGGGTKLEIK | 119 |

TABLE 35

Sequences of the variable regions of anti-Claudin 18.2 antibodies

| Antibody code (sequence source) | Amino acid sequences of the variable regions of anti-luciferase antibodies (those in bold and underlined being CDR regions) | | | |
|---|---|---|---|---|
| | VHm | Sequence No. | VLm | Sequence No. |
| IMAB362 (U.S. Pat. No. 20,090,169,547 A1) | QVQLQQPGAELVRPGASVKLSCKASGYTFTSYWIN WVKQRPGQGLEWIGNIYPSDSYTNYNQKFKDKAT LTVDKSSSTAYMQLSSPTSEDSAVYYCTRSWRGNS FDYWGQGTTLTVSS | 193 | DIVMTQSPSSLTVTAGEKVTMSCKSSQSLLN SGNQKNYLTWYQQKPGQPPKWYWASTR ESGVPDRFTGSGSGTDFTLTISSVQAEDLAVY YCQNDYSYPFTFGSGTKLEIK | 194 |

Sequences of Other Domains
(1) Amino Acid Sequences of Linker Domains

TABLE 10

Amino acid sequences of linkers

| Domain | Code | Amino acid sequence | Sequence No. |
|---|---|---|---|
| Linker | Lin1 | GGGGS | 120 |
| | Lin2 | GGGSAAA | 121 |
| | Lin3 | GGGGSAS | 122 |
| | Lin4 | GRPGSGRPGS | 123 |
| | Lin5 | GGGGSGGGGSAS | 124 |
| | Lin6 | GKSSGSGSESKS | 125 |
| | Lin7 | GSTSGSGKSSEGKG | 126 |
| | Lin8 | EPKSSDKTHTSPPS | 127 |
| | Lin9 | GGGGSDKTHTSPPS | 128 |
| | Lin10 | GGGGSGGGGSGGGGS | 129 |
| | Lin11 | GGGGSGGGGSGGGGSAS | 130 |
| | Lin12 | GSTSGSGKSSEGSGSTKG | 131 |
| | Lin13 | GSTSGSGKPGSGEGSTKG | 132 |
| | Lin14 | GGGGSGGGGSGGGGSGGGGS | 133 |
| | Lin15 | GGGGSGGGGSGGGGSGGGGSGGGGSAS | 134 |
| | Lin16 | GGGGSGGGGSGGGGSGGGGSGGGGSGG GGSAS | 135 |
| | Lin17 | AGGGSGGGGSGGGGSGGGGSGGGGSGG GGSGGGGSAS | 136 |
| | Lin18 | AGGGSGGGGSGGGGSGGGGSGGGGSGG GGSGGGGSGGGGSAS | 137 |
| | Lin19 | AGGGSGGGGSGGGGSGGGGSGGGGSGG GGSGGGGSGGGGSGGGGSAS | 138 |

(2) Amino Acid Sequences of Hinge Domains

TABLE 11

Amino acid sequences of hinges

| Domain | Code | Amino acid sequence | Sequence No. |
|---|---|---|---|
| Hinge 2/Hinge 4 | Hin1 | EPKSCDKTHTCP | 139 |
| Hinge 1/Hinge 3/ Hinge5/Hinge 6 | Hin2 | EPKSSDKTHTCP | 140 |
| | Hin3 | GGGGSDKTHTCP | 141 |
| | Hin4 | RGRGSDKTHTCP | 142 |
| | Hin5 | DGDGSDKTHTCP | 143 |
| | Hin6 | GRGRGSDKTHTCP | 144 |
| | Hin7 | GDGDGSDKTHTCP | 145 |
| | Hin8 | RGRGSSDKTHTCP | 146 |
| | Hin9 | DGDGSSDKTHTCP | 147 |

(3) Amino Acid Sequences of CL Domains of Light Chain Constant Regions

TABLE 12

Amino acid sequences of CL

| Domain | Code | Amino acid sequence | Sequence No. |
|---|---|---|---|
| CL | Lc1 | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 148 |
| | Lc2 | GQPKANPTVTLFPPSSEELQANKATLVCLISDFYPGAVTVAWKADGSPVKAGVETTKPSKQSNNKYAASSYLSLTPEQWKSHRSYSCQVTHEGSTVEKTVAPTECS | 149 |
| | Lc3 | GQPKAAPSVTLFPPSSEELQANKATLVCLISDFYPGAVTVAWKADSSPVKAGVETTTPSKQSNNKYAASSYLSLTPEQWKSHRSYSCQVTHEGSTVEKTVAPTECS | 150 |
| | Lc4 | GQPKAAPSVTLFPPSSEELQANKATLVCLISDFYPGAVTVAWKADSSPAKAGVETTTPSKQSNNKYAASSYLSLTPEQWKSHKSYSCQVTHEGSTVEKTVAPTECS | 151 |
| | Lc5 | GQPKAAPSVTLFPPSSEELQANKATLVCLISDFYPGAVKVAWKADGSPVNTGVETTTPSKQSNNKYAASSYLSLTPEQWKSHRSYSCQVTHEGSTVEKTVAPAECS | 152 |

TABLE 12-continued

Amino acid sequences of CL

| Domain | Code | Amino acid sequence | Sequence No. |
|---|---|---|---|
| | Lc6 | GQPKAAPTVTLFPPSSEELQANKATLVCLISDFYPGAVKVAWKADSSPAKAGVETTTPSKQSNNKYAASSYLSLTPEQWKSHKSYSCQVTHEGSTVEKTVAPTECS | 153 |

(4) Amino Acid Sequences of CH1 Domains of Heavy Chain Constant Regions

TABLE 13

Amino acid sequence of CH1

| Domain | Code | Amino acid sequence | Sequence No. |
|---|---|---|---|
| CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKV | 154 |

The Fc amino acid numbering follows the Kabat numbering. The "Kabat numbering" refers to a numbering system described by Kabat et al., which is set forth in the United States Department of Health and Human Services, "Sequence of Proteins of Immunological Interest" (1983). See the table below for specific numbering:

TABLE 14

Fc amino acid numbering based on the Kabat numbering scheme

| 216 | 217 | 218 | 219 | 220 | 221 | 222 | 223 | 224 | 225 | 226 | 227 | 228 | 229 | 230 | 231 | 232 | 233 | 234 | 235 | 236 | 237 | 238 | 239 | 240 | 241 |
|---|---|---|---|---|---|---|---|---|---|---|---|---|---|---|---|---|---|---|---|---|---|---|---|---|---|
| E | P | K | S | C | D | K | T | H | T | C | P | P | C | P | A | P | E | L | L | G | G | P | S | V | F |

| 242 | 243 | 244 | 245 | 246 | 247 | 248 | 249 | 250 | 251 | 252 | 253 | 254 | 255 | 256 | 257 | 258 | 259 | 260 | 261 | 262 | 263 | 264 | 265 | 266 | 267 |
|---|---|---|---|---|---|---|---|---|---|---|---|---|---|---|---|---|---|---|---|---|---|---|---|---|---|
| L | F | P | P | K | P | K | D | T | L | M | I | S | R | T | P | E | V | T | C | V | V | V | D | V | S |

| 268 | 269 | 270 | 271 | 272 | 273 | 274 | 275 | 276 | 277 | 278 | 279 | 280 | 281 | 282 | 283 | 284 | 285 | 286 | 287 | 288 | 289 | 290 | 291 | 292 | 293 |
|---|---|---|---|---|---|---|---|---|---|---|---|---|---|---|---|---|---|---|---|---|---|---|---|---|---|
| H | E | D | P | E | V | K | F | N | W | Y | V | D | G | V | E | V | H | N | A | K | T | K | P | R | E |

| 294 | 295 | 296 | 297 | 298 | 299 | 300 | 301 | 302 | 303 | 304 | 305 | 306 | 307 | 308 | 309 | 310 | 311 | 312 | 313 | 314 | 315 | 316 | 317 | 318 | 319 |
|---|---|---|---|---|---|---|---|---|---|---|---|---|---|---|---|---|---|---|---|---|---|---|---|---|---|
| E | Q | Y | N | S | T | Y | R | V | V | S | V | L | T | V | L | H | Q | D | W | L | N | G | K | E | Y |

| 320 | 321 | 322 | 323 | 324 | 325 | 326 | 327 | 328 | 329 | 330 | 331 | 332 | 333 | 334 | 335 | 336 | 337 | 338 | 339 | 340 | 341 | 342 | 343 | 344 | 345 |
|---|---|---|---|---|---|---|---|---|---|---|---|---|---|---|---|---|---|---|---|---|---|---|---|---|---|
| K | C | K | V | S | N | K | A | L | P | A | P | I | E | K | T | I | S | K | A | K | G | Q | P | R | E |

| 346 | 347 | 348 | 349 | 350 | 351 | 352 | 353 | 354 | 355 | 356 | 357 | 358 | 359 | 360 | 361 | 362 | 363 | 364 | 365 | 366 | 367 | 368 | 369 | 370 | 371 |
|---|---|---|---|---|---|---|---|---|---|---|---|---|---|---|---|---|---|---|---|---|---|---|---|---|---|
| P | Q | V | Y | T | L | P | P | S | R | D | E | L | T | K | N | Q | V | S | L | T | C | L | V | K | G |

| 372 | 373 | 374 | 375 | 376 | 377 | 378 | 379 | 380 | 381 | 382 | 383 | 384 | 385 | 386 | 387 | 388 | 389 | 390 | 391 | 392 | 393 | 394 | 395 | 396 | 397 |
|---|---|---|---|---|---|---|---|---|---|---|---|---|---|---|---|---|---|---|---|---|---|---|---|---|---|
| F | Y | P | S | D | I | A | V | E | W | E | S | N | G | Q | P | E | N | N | Y | K | T | T | P | P | V |

| 398 | 399 | 400 | 401 | 402 | 403 | 404 | 405 | 406 | 407 | 408 | 409 | 410 | 411 | 412 | 413 | 414 | 415 | 416 | 417 | 418 | 419 | 420 | 421 | 422 | 423 |
|---|---|---|---|---|---|---|---|---|---|---|---|---|---|---|---|---|---|---|---|---|---|---|---|---|---|
| L | D | S | D | G | S | F | F | L | Y | S | K | L | T | V | D | K | S | R | W | Q | Q | G | N | V | F |

| 424 | 425 | 426 | 427 | 428 | 429 | 430 | 431 | 432 | 433 | 434 | 435 | 436 | 437 | 438 | 439 | 440 | 441 | 442 | 443 | 444 | 445 | 446 | 447 | 448 | |
|---|---|---|---|---|---|---|---|---|---|---|---|---|---|---|---|---|---|---|---|---|---|---|---|---|---|
| S | C | S | V | M | H | E | A | L | H | N | H | Y | T | Q | K | S | L | S | L | S | P | G | K | — | | wherein,
amino acids at position 221-227 are the hinge domain,
amino acids at position 228-340 are the second constant region CH2 domain of heavy chains, and
amino acids at position 341-447 are the third constant region CH3 domain of heavy chains.

An antibody may be modified to improve the heterodimer pairing efficiency. For example, in some aspects, compared with wild-type antibody fragments, the Fc fragment of the monovalent unit heavy chain and/or the Fc fragment of the fusion peptide may comprise one or more substitutions, and knob-into-hole structural pairs are formed between these substitutions. The knob-into-hole configuration is known in the art. See, for example, Ridgway, et al., "'Knob-into-holes' engineering of antibody CH3 domains for heavy chain heterodimerization," Protein Engineering 9(7):617-21 (1996).

In one aspect, T366 on one CH3 domain is substituted by a larger amino acid residue, such as Tyrosine (Y) or Tryptophan (W). Then, Y407 on the other CH3 domain may be substituted by a smaller amino acid residue, such as Threonine (T), Alanine (A), or Valine (V).

TABLE 15

Fc amino acid substitution combinations form knob-into-hole structural pairs between monovalent units and single-chain units to improve the heterodimer pairing efficiency

| Combination No. | Substitution on one CH3 | Substitution on the other CH3 |
|---|---|---|
| 1 | T366W | Y407A |
| 2 | T366W | Y407V |
| 3 | T366Y | Y407A |
| 4 | T366Y | Y407V |
| 5 | T366W | T366S, L368A, Y407V |

In one aspect, one of the CH3 domains comprises one or more substitutions by amino acid residues having a positive charge under physiological conditions, while the other CH3 domain comprises one or more substitutions by one or more amino acid residues having a negative charge under physiological conditions. In one aspect, the amino acid residue having a positive charge may be Arginine (R), Histidine (H) or Lysine (K). In another aspect, the amino acid residue having a negative charge may be Aspartic acid (D) or Glutamic acid (E). Amino acid residues that may be substituted include, but are not limited to, D356, L368, K392, D399 and K409.

TABLE 16

CH3 amino acid substitution combinations form ionic bonds between monovalent units and single-chain units to improve the heterodimer pairing efficiency

| Combination No. | substitution(s) on one CH3 | substitution(s) on the other CH3 |
|---|---|---|
| 1 | D356K D399K | K392D K409D |
| 2 | L368R D399K | K392D K409D |
| 3 | L368K D399K | K392D K409D |
| 4 | L368R D399K | K409D |
| 5 | L368K D399K | K409D |
| 6 | L368R | K409D |
| 7 | L368K | K409D |

In one aspect, S354 on one of the CH3 domains is substituted by Cysteine, and Y349 on the other CH3 domain is also substituted by Cysteine. The residues on the two substitution positions form a disulfide bond.

TABLE 17

CH3 amino acid substitution combinations form disulfide bonds between monovalent units and single-chain units to improve the heterodimer pairing efficiency

| Combination No. | Substitution on one CH3 | Substitution on the other CH3 |
|---|---|---|
| 1 | S354C | Y349C |

In one aspect, H435 and Y436 on one of the CH3 domains are substituted by Arginine and Phenylalanine, respectively. This substitution leads to significantly weakened binding capability between Fc and protein A, such that the heterodimer and homodimer have different protein A binding activities, and it is easy to separate the two during affinity chromatography.

TABLE 18

One CH3 amino acid substitution leads to weakened binding capability with protein A

| Combination No. | Substitution on CH3 |
|---|---|
| 1 | H435R, Y436F |

TABLE 19

CH2 amino acid sequences of different Fc

| Combination Code | CH2 amino acid sequences | Sequence No. |
|---|---|---|
| WT | PCPAPELLGGPSVFLFPPKPKDTLMISRTPEVTCVVVDVSH EDPEVKFNWYVDGVEVHNAKTKPREEQYNSTYRVVSVLTVL HQDWLNGKEYKCKVSNKALPAPIEKTISKAK | 155 |
| AAG | PCPAPEAAGGPSVFLFPPKPKDTLMISRTPEVTCVVVDVSH EDPEVKFNWYVDGVEVHNAKTKPREEQYNSTYRVVSVLTVL HQDWLNGKEYKCKVSNKALGAPIEKTISKAK | 156 |
| FES | PCPAPEFEGGPSVFLFPPKPKDTLMISRTPEVTCVVVDVSH EDPEVKFNWYVDGVEVHNAKTKPREEQYNSTYRVVSVLTVL HQDWLNGKEYKCKVSNKALPASIEKTISKAK | 157 |
| N297A | PCPAPELLGGPSVFLFPPKPKDTLMISRTPEVTCVVVDVSH EDPEVKFNWYVDGVEVHNAKTKPREEQYASTYRVVSVLTVL HQDWLNGKEYKCKVSNKALPAPIEKTISKAK | 158 |

TABLE 19-continued

CH2 amino acid sequences of different Fc

| Combination Code | CH2 amino acid sequences | Sequence No. |
|---|---|---|
| N297Q | PCPAPELLGGPSVFLFPPKPKDTLMISRTPEVTCVVVDVSH EDPEVKFNWYVDGVEVHNAKTKPREEQYQSTYRVVSVLTVL HQDWLNGKEYKCKVSNKALPAPIEKTISKAK | 159 |
| LALA | PCPAPEAAGGPSVFLFPPKPKDTLMISRTPEVTCVVVDVSH EDPEVKFNWYVDGVEVHNAKTKPREEQYNSTYRVVSVLTVL HQDWLNGKEYKCKVSNKALPAPIEKTISKAK | 160 |
| SG2 | PSPAPPVAGPSVFLFPPKPKDTLMISRTPEVTCVVVDVSHE DPEVQFNWYVDGVEVHNAKTKPREEQFNSTFRVVSVLTVVH QDWLNGKEYKCKVSNKGLPAPIEKTISKTK | 161 |
| G2D | PCPAPPVAGPSVFLFPPKPKDTLMISRTPEVTCVVVDVSHE APEVQFNWYVDGVEVHNAKTKPREEQFNSTFRVVSVLTVVH QDWLNGKEYKCKVSNKGLPAPIEKTISKTK | 192 |

TABLE 20

CH3 amino acid sequences of Fc that form heterodimer

| Combination Code | CH3-a amino acid sequences | Sequence No. | CH3-b amino acid sequences | Sequence No. |
|---|---|---|---|---|
| WT | GQPREPQVYTLPPSRDELTKNQVSLTCLVKGFYPS DIAVEWESNGQPENNYKTTPPVLDSDGSFFLYSKL TVDKSRWQQGNVFSCSVMHEALHNHYTQKSLSL SPGK | 162 | GQPREPQVYTLPPSRDELTKNQVSLTCLVKGFYP SDIAVEWESNGQPENNYKTTPPVLDSDGSFFLYS KLTVDKSRWQQGNVFSCSVMHEALHNHYTQKS LSLSPGK | 163 |
| W: SAV | GQPREPQVYTLPPSRDELTKNQVSLWCLVKGFYPS DIAVEWESNGQPENNYKTTPPVLDSDGSFFLYSKL TVDKSRWQQGNVFSCSVMHEALHNHYTQKSLSL SPGK | 164 | GQPREPQVYTLPPSRDELTKNQVSLSCAVKGFYP SDIAVEWESNGQPENNYKTTPPVLDSDGSFFLVS KLTVDKSRWQQGNVFSCSVMHEALHNHYTQKS LSLSPGK | 165 |
| CW: CSAV | GQPREPQVYTLPPCRDELTKNQVSLWCLVKGFYP SDIAVEWESNGQPENNYKTTPPVLDSDGSFFLYSK LTVDKSRWQQGNVFSCSVMHEALHNHYTQKSLS LSPGK | 166 | GQPREPQVCTLPPSRDELTKNQVSLSCAVKGFYP SDIAVEWESNGQPENNYKTTPPVLDSDGSFFLVS KLTVDKSRWQQGNVFSCSVMHEALHNHYTQKS LSLSPGK | 167 |
| CW: CSAVRF | GQPREPQVYTLPPCRDELTKNQVSLWCLVKGFYP SDIAVEWESNGQPENNYKTTPPVLDSDGSFFLYSK LTVDKSRWQQGNVFSCSVMHEALHNHYTQKSLS LSPGK | 168 | GQPREPQVCTLPPSRDELTKNQVSLSCAVKGFYP SDIAVEWESNGQPENNYKTTPPVLDSDGSFFLVS KLTVDKSRWQQGNVFSCSVMHEALHNRFTQKS LSLSPGK | 169 |
| WDD: RKA | GQPREPQVYTLPPSRDELTKNQVSLWCLVKGFYPS DIAVEWESNGQPENNYDTTPPVLDSDGSFFLYSDL TVDKSRWQQGNVFSCSVMHEALHNHYTQKSLSL SPGK | 170 | GQPREPQVYTLPPSRDELTKNQVSLTCRVKGFYP SDIAVEWESNGQPENNYKTTPPVLKSDGSFFLAS KLTVDKSRWQQGNVFSCSVMHEALHNHYTQKS LSLSPGK | 171 |
| DD: KK | GQPREPQVYTLPPSRDELTKNQVSLTCLVKGFYPS DIAVEWESNGQPENNYDTTPPVLDSDGSFFLYSDL TVDKSRWQQGNVFSCSVMHEALHNHYTQKSL-SL SPGK | 172 | GQPREPQVYTLPPSKELTKNQVSLTCLVKGFYP SDIAVEWESNGQPENNYKTTPPVLKSDGSFFLYS KLTVDKSRWQQGNVFSCSVMHEALHNHYTQKS LSLSPGK | 173 |
| SAV: W | GQPREPQVYTLPPSRDELTKNQVSLSCAVKGFYPS DIAVEWESNGQPENNYKTTPPVLDSDGSFFLVSKL TVDKSRWQQGNVFSCSVMHEALHNHYTQKSLSL SPGK | 174 | GQPREPQVYTLPPSRDELTKNQVSLWCLVKGFYP SDIAVEWESNGQPENNYKTTPPVLDSDGSFFLYS KLTVDKSRWQQGNVFSCSVMHEALHNHYTQKS LSLSPGK | 175 |
| CSAV: CW | GQPREPQVCTLPPSRDELTKNQVSLSCAVKGFYPS DIAVEWESNGQPENNYKTTPPVLDSDGSFFLVSKL TVDKSRWQQGNVFSCSVMHEALHNHYTQKSLSL SPGK | 176 | GQPREPQVYTLPPCRDELTKNQVSLWCLVKGFY PSDIAVEWESNGQPENNYKTTPPVLDSDGSFFLY SKLTVDKSRWQQGNVFSCSVMHEALHNHYTQK SLSLSPGK | 177 |
| CSAVRF: CW | GQPREPQVCTLPPSRDELTKNQVSLSCAVKGFYPS DIAVEWESNGQPENNYKTTPPVLDSDGSFFLVSKL TVDKSRWQQGNVFSCSVMHEALHNRFTQKSLSL SPGK | 178 | GQPREPQVYTLPPCRDELTKNQVSLWCLVKGFY PSDIAVEWESNGQPENNYKTTPPVLDSDGSFFLY SKLTVDKSRWQQGNVFSCSVMHEALHNHYTQK SLSLSPGK | 179 |

TABLE 20-continued

CH3 amino acid sequences of Fc that form heterodimer

| Combination Code | CH3-a amino acid sequences | Sequence No. | CH3-b amino acid sequences | Sequence No. |
|---|---|---|---|---|
| RKA: WDD | GQPREPQVYTLPPSRDELTKNQVSLTCRVKGFYPSDIAVEWESNGQPENNYKTTPPVLKSDGSFFLASKLTVDKSRWQQGNVFSCSVMHEALHNHYTQKSLSLSPGK | 180 | GQPREPQVYTLPPSRDELTKNQVSLWCLVKGFYPSDIAVEWESNGQPENNYDTTPPVLDSDGSFFLYSDLTVDKSRWQQGNVFSCSVMHEALHNHYTQKSLSLSPGK | 181 |
| KK: DD | GQPREPQVYTLPPSRKELTKNQVSLTCLVKGFYPSDIAVEWESNGQPENNYKTTPPVLKSDGSFFLYSKLTVDKSRWQQGNVFSCSVMHEALHNHYTQKSLSLSPGK | 182 | GQPREPQVYTLPPSRDELTKNQVSLTCLVKGFYPSDIAVEWESNGQPENNYDTTPPVLDSDGSFFLYSDLTVDKSRWQQGNVFSCSVMHEALHNHYTQKSLSLSPGK | 183 |

Specific sequences of antigens

TABLE 21

Amino acid sequences of tumor antigens

| Name (source) of tumor antigen | Amino acid sequence | Sequence No. |
|---|---|---|
| Human CD38 (Source: UniProtKB - P28907) | VPRWRQQWSGPGTTKRFPETVLARCVKYTEIHPEMRHVDCQSVWDAFKGAFISKHPCNITEEDYQPLMKLGTQTVPCNKILLWSRIKDLAHQFTQVQRDMFTLEDTLLGYLADDLTWCGEFNTSKINYQSCPDWRKDCSNNPVSVFWKTVSRRFAEAACDVVHVMLNGSRSKIFDKNSTFGSVEVHNLQPEKVQTLEAWVIHGGREDSRDLCQDPTIKELESIISKRNIQFSCKNIYRPDKFLQCVKNPEDSSCTSEI | 184 |
| Human BCMA (Source: UniProtKB - Q02223) | MLQMAGQCSQNEYFDSLLHACIPCQLRCSSNTPPLTCQRYCNASVTNSVKGTNA | 185 |
| Human PD-L1 (Source: UniProtKB - Q9NZQ7) | FTVTVPKDLYVVEYGSNMTIECKFPVEKQLDLAALIVYWEMEDKNIIQFVHGEEDLKVQHSSYRQRARLLKDQLSLGNAALQITDVKLQDAGVYRCMISYGGADYKRITVKVNAPYNKINQRILVVDPVTSEHELTCQAEGYPKAEVIWTSSDHQVLSGKTTTTNSKREEKLFNVTSTLRINTTTNEIFYCTFRRLDPEENHTAELVIPELPLAHPPNER | 186 |
| Human SLAMF7 (Source: UniProtKB - Q9NQ25) | SGPVKELVGSVGGAVTFPLKSKVKQVDSIVWTFNTTPLVTIQPEGGTIIVTQNRNRERVDFPDGGYSLKLSKLKKNDSGIYYVGIYSSSLQQPSTQEYVLHVYEHLSKPKVTMGLQSNKNGTCVTNLTCCMEHGEEDVIYTWKALGQAANESHNGSILPISWRWGESDMTFICVARNPVSRNFSSPILARKLCEGAADDPDSSM | 187 |
| Human CEA (Source: UniProtKB - P06731) | KLTIESTPFNVAEGKEVLLLVHNLPQHLFGYSWYKGERVDGNRQIIGYVIGTQQATPGPAYSGREIIYPNASLLIQNIIQNDTGFYTLHVIKSDLVNEEATGQFRVYPELPKPSISSNNSKPVEDKDAVAFTCEPETQDATYLWWVNNQSLPVSPRLQLSNGNRTLTLFNVTRNDTASYKCETQNPVSARRSDSVILNVLYGPDAPTISPLNTSYRSGENLNLSCHAASNPPAQYSWFVNGTFQQSTQELFIPNITVNNSGSYTCQAHNSDTGLNRTTVTTITVYAEPPKPFITSNNSNPVEDEDAVALTCEPEIQNTTYLWWVNNQSLPVSPRLQLSNDNRTLTLLSVTRNDVGPYECGIQNKLSVDHSDPVILNVLYGPDDPTISPSYTYYRPGVNLSLSCHAASNPPAQYSWLIDGNIQQHTQELFISNITEKNSGLYTCQANNSASGHSRTTVKTITVSAELPKPSISSNNSKPVEDKDAVAFTCEPEAQNTTYLWWVNGQSLPVSPRLQLSNGNRTLTLFNVTRNDARAYVCGIQNSVSANRSDPVTLDVLYGPDTPIISPPDSSYLSGANLNLSCHSASNPSPQYSWRINGIPQQHTQVLFIAKITPNNNGTYACFVSNLATGRNNSIVKSITVSASGTSPGLSA | 188 |
| Human Claudin18.2 (Source: UniProtKB - P56856) | MAVTACQGLGFVVSLIGIAGIIAATCMDQWSTQDLYNNPVTAVFNYQGLWRSCVRESSGFTECRGYFTLLGLPAMLQAVRALMIVGIVLGAIGLLVSIFALKCIRIGSMEDSAKANMTLTSGIMFIVSGLCAIAGVSVFANMLVTNFWMSTANMYTGMGGMVQTVQTRYTFGAALFVGWVAGGLTLIGGVMMCIACRGLAPEETNYKAVSYHASGHSVAYKPGGFKASTGFGSNTKNKKIYDGGARTEDEVQSYPSKHDYV | 195 |

TABLE 22

Amino acid sequences of immune cell antigens

| Name (source) of immune cell antigen | Amino acid sequence | Sequence No. |
|---|---|---|
| Human CD3ε (Source: UniProtKB - P07766) | DGNEEMGGITQTPYKVSISGTTVILTCPQYP GSEILWQHNDKNIGGDEDDKNIGSDEDHLSL KEFSELEQSGYYVCYPRGSKPEDANFYLYLR ARVCENCMEMD | 189 |

Example 1: Humanized Modified SP34

(1) SP34 Sequence Analysis

The amino acid sequence of the variable region of SP34 heavy chain (SP34VH) is as follows, wherein those in bold and underlined are CDR regions and the others are FR regions:

```
SP34VH
1                             30                              60                              90
EVQLVESGGGLVQPKGSLKLSCAASGFTFNTYAMNWVRQAPGKGLEWVARIRSKYNNYATYYADSVKDRFTISRDDSQSILYLQMNNLKTEDTAMYYCVR
|←---------FR-H1---------→|CDR-H1|←--FR-H2-→|←-----CDR-H2-----→|←-----------FR-H3-----------→|

120   125
HGNFGNSYVSWFAYWGQGTLVTVSS
←---CDR-H3--→|←--FR-H4--→|
```

The amino acid sequence of the variable region of SP34 light chain (SP34VL) is as follows, wherein those in bold and underlined are CDR regions and the others are FR regions:

```
SP34VL
1                             30                              60                              90
QAVVTQESALTTSPGETVTLTCRSSTGAVTTSNYANWVQEKPDHLFTGLIGGTNKRAPGVPARFSGSLIGDKAALTITGAQTEDEAIYFCALWYSNLWV
|←------FR-L1------→|←--CDR-L1--→|←---FR-L2---→|CDR-L2|←------------FR-L3------------→|-CDR-L3-|

109
FGGGTKLTVL
←-FR-L4-→|
```

(2) Humanized Modification (2.1) Modification of the Heavy Chain Variable Region:

All full-human or humanized antibody sequences that have been on the market are analyzed and FR sequences of human heavy chain variable regions are selected as follows:

(i) The first group of FR (VHFR-1), . . . is expressed as CDR:

```
VHFR-1 (1)
EVQLVESGGGLVQPGGSLRLSCAASGFTFS . . WVRQAPGKGLEWV

S . . RFTISRDNAKNSLYLQMNSLRAEDTAVYYCAR . . . WGQ

GTLVTVSS
```

SP34VH and VHFR-1 are compared, the blocks are CDR regions, - indicates regions where the amino acids are identical, and * indicates that amino acids are different at the positions:

```
SP34VH         (1) EVQLVESGGGLVQPKGSLKLSCAASGFTFN TYAMN WVRQAPGKGLEWVA RIRSKYNNYATYYADSVKD RFTI
VHFR-1         (1) EVQLVESGGGLVQPGGSLRLSCAASGFTFS-----WVRQAPGKGLEWVS-------------------RFTI
Homology analysis (1) ---------------*---*---------- * TYAMN -------------* RIRSKYNNYATYYADSVKD ---

SRDDSQSILYLQMNNLKTEDTAMYYCVR HGNFGNSYVSWFAY WGQGTLVTVSS
                   SRDNAKNSLYLQMNSLRAEDTAVYYCAR--------------WGQGTLVTVSS
                   ---*****------*-**----*---*- HGNFGNSYVSWFAY -----------
```

According to the homology analysis and conservative substitution of amino acids, the first group of humanized antibody VHs sequences is obtained as follows:

| Code | Amino acid sequence of the heavy chain variable region of the humanized CD3 antibody (those in bold and underlined being CDR regions) | Sequence No. |
|---|---|---|
| VH1 | EVQLVESGGGLVQPGGSLRLSCAASGFTFSTYAMNWVRQAPGKGLEWVARIRSKYNNYATYYADSVKDRFTISRDNAKNSLYLQMNSLRAEDTAVYYCARHGNFGNSYVSWFAYWGQGTLVTVSS | 45 |
| VH1a | EVQLVESGGGLVQPGGSLRLSCAASGFTFSTYAMNWVRQAPGKGLEWVARIRSKYNNYATYYADSVKDRFTISRDDSKNSLYLQMNSLRAEDTAVYYCARHGNFGNSYVSWFAYWGQGTLVTVSS | 46 |
| VH1b | EVQLVESGGGLVQPGGSLRLSCAASGFTFSTYAMNWVRQAPGKGLEWVARIRSKYNNYATYYADSVKDRFTISRDDSKNSLYLQMNSLRAEDTAVYYCVRHGNFGNSYVSWFAYWGQGTLVTVSS | 47 |

(ii) The second group of FR (VHFR-2), ... is expressed as CDR:

VHFR-2 (1)
QVQLVESGGGVVQPGRSLRLSCAASGFTFS . . WVRQAPGKGLEWV

A . . . RFTISRDNSKNTLYLQMNSLRAEDTAVYYCAR . . . WGQ

GTLVTVSS

SP34VH and VHFR-2 are aligned, the blocks are CDR regions, - indicates regions where the amino acids are identical, and * indicates that amino acids are different at the positions:

```
SP34VH         (1) EVQLVESGGGLVQPKGSLKLSCAASGFTFN TYAMN WVRQAPGKGLEWVA RIRSKYNNYATYYADSVKD RFT
VHFR-2         (1) QVQLVESGGGVVQPGRSLRLSCAASGFTFS-----WVRQAPGKGLEWVA-------------------RFT
Homology analysis (1) *---------*---**--*---------- * TYAMN ------------- RIRSKYNNYATYYADSVKD ---

ISRDDSQSILYLQMNNLKTEDTAMYYCVR HGNFGNSYVSWFAY WGQGTLVTVSS
                   ISRDNSKNTLYLQMNSLRAEDTAVYYCAR--------------WGQGTLVTVSS
                   ----*-***------*-**----*---*- HGNFGNSYVSWFAY -----------
```

According to the homology analysis and conservative substitution of amino acids, the second group of humanized antibody VHs sequences is obtained as follows:

| Code | Amino acid sequence of the heavy chain variable region of the humanized CD3 antibody (those in bold and underlined being CDR regions) | Sequence No. |
|---|---|---|
| VH2 | QVQLVESGGGVVQPGRSLRLSCAASGFTFSTYAMNWVRQAPGKGLEWVARIRSKYNNYATYYADSVKDRFTISRDNSKNTLYLQMNSLRAEDTAVYYCARHGNFGNSYVSWFAYWGQGTLVTVSS | 48 |
| VH2a | QVQLVESGGGVVQPGRSLRLSCAASGFTFSTYAMNWVRQAPGKGLEWVARIRSKYNNYATYYADSVKDRFTISRDDSKNTLYLQMNSLRAEDTAVYYCARHGNFGNSYVSWFAYWGQGTLVTVSS | 49 |
| VH2b | QVQLVESGGGVVQPGRSLRLSCAASGFTFSTYAMNWVRQAPGKGLEWVARIRSKYNNYATYYADSVKDRFTISRDNSKNTLYLQMNSLRAEDTAVYYCVRHGNFGNSYVSWFAYWGQGTLVTVSS | 50 |
| VH2c | QVQLVESGGGVVQPGRSLRLSCAASGFTFSTYAMNWVRQAPGKGLEWVARIRSKYNNYATYYADSVKDRFTISRDDSKNTLYLQMNSLRAEDTAVYYCVRHGNFGNSYVSWFAYWGQGTLVTVSS | 51 |

| Code | Amino acid sequence of the heavy chain variable region of the humanized CD3 antibody (those in bold and underlined being CDR regions) | Sequence No. |
|---|---|---|
| VH2d | QVQLVESGGGVVQPGRSLRLSCAASGFTFSTYAMNWVRQAPGKGLEWVARIRSKYNNYATYYADSVKDRFTISRDDSKNTLYLQMNSLRAEDTAVYYCARHGNFGNSYVTWFAYWGQGTLVTVSS | 52 |
| VH2e | QVQLVESGGGVVQPGRSLRLSCAASGFTFSTYAMNWVRQAPGKGLEWVARIRSKYNNYATYYADSVKDRFTISRDDSKNTLYLQMNSLRAEDTAVYYCARHGNFGNSYVSYFAYWGQGTLVTVSS | 53 |
| VH2f | QVQLVESGGGVVQPGRSLRLSCAASGFTFSTYAMNWVRQAPGKGLEWVARIRSKYNNYATYYADSVKDRFTISRDDSKNTLYLQMNSLRAEDTAVYYCARHGNFGNSYVSFFAYWGQGTLVTVSS | 54 |
| VH2g | QVQLVESGGGVVQPGRSLRLSCAASGFTFSTYAMNWVRQAPGKGLEWVARIRSKYNNYATYYADSVKDRFTISRDDSKNTLYLQMNSLRAEDTAVYYCARHGNFGNSYVSWLAYWGQGTLVTVSS | 55 |
| VH2h | QVQLVESGGGVVQPGRSLRLSCAASGFTFSTYAMNWVRQAPGKGLEWVARIRSKYNNYATYYADSVKDRFTISRDDSKNTLYLQMNSLRAEDTAVYYCARHGNFGNSYVSWVAYWGQGTLVTVSS | 56 |
| VH2i | QVQLVESGGGVVQPGRSLRLSCAASGFTFSTYAMNWVRQAPGKGLEWVARIRSKYNNYATYYADSVKDRFTISRDDSKNTLYLQMNSLRAEDTAVYYCARHGNFGNSYVSWIAYWGQGTLVTVSS | 57 |
| VH2j | QVQLVESGGGVVQPGRSLRLSCAASGFTFSTYAMNWVRQAPGKGLEWVARIRSKYNNYATYYADSVKDRFTISRDDSKNTLYLQMNSLRAEDTAVYYCARHGNFGNSYVSWAAYWGQGTLVTVSS | 58 |
| VH2k | QVQLVESGGGVVQPGRSLRLSCAASGFTFSTYAMNWVRQAPGKGLEWVARIRSKYNNYATYYADSVKDRFTISRDDSKNTLYLQMNSLRAEDTAVYYCARHGNFGNSYVSWYAYWGQGTLVTVSS | 59 |
| VH2l | QVQLVESGGGVVQPGRSLRLSCAASGFTFSTYAMNWVRQAPGKGLEWVARIRSKYNNYATYYADSVKDRFTISRDDSKNTLYLQMNSLRAEDTAVYYCARHGNFGNSYVSWFVYWGQGTLVTVSS | 60 |
| VH2m | QVQLVESGGGVVQPGRSLRLSCAASGFTFSTYAMNWVRQAPGKGLEWVARIRSKYNNYATYYADSVKDRFTISRDDSKNTLYLQMNSLRAEDTAVYYCARHGNFGNSYVSWFLYWGQGTLVTVSS | 61 |
| VH2n | QVQLVESGGGVVQPGRSLRLSCAASGFTFSTYAMNWVRQAPGKGLEWVARIRSKYNNYATYYADSVKDRFTISRDDSKNTLYLQMNSLRAEDTAVYYCARHGNFGNSYVSWFIYWGQGTLVTVSS | 62 |

(2.2) Modification of the Light Chain Variable Region:

The selected human FR sequences are as follows:

(i) Light chain variable region sequences of all full-human or humanized antibody sequences that have been on the market are analyzed and the first group of FR (VLFR-1), . . . is expressed as CDR:

VLFR-1 (1)
EIVLTQSPGTLSLSPGERATLSC . . . WYQQKPGQAPRLLIY . .

. GIPDRFSGSGSGTDFTLTISRLEPEDFAVYYCQ . . . FGQGTKV

EIK

SP34VL and VLFR-1 are aligned, the blocks are CDR regions, - indicates regions where the amino acids are identical, and * indicates that amino acids are different at the positions:

```
SP34VL            (1)  QAVVTQESA-LTTSPGETVTLTC RSSTGAVTTSNYAN WVQEKPDHLFTGLIG GTNKRAP GVPARFSGSLIG
VLFR-1            (1)  EIVLTQSPGTLSLSPGERATLSC--------------WYQQKPGQAPRLLIY-------GIPDRFSGSGSG
Homology analysis (1)  **-*--****-**----**--* RSSTGAVTTSNYAN -*----*******-* GTNKRAP -*-*------**-

DKAALTITGAQTEDEAIYFC ALWYSNLWV FGGGTKLTVL
                       TDFTLTISRLEPEDFAVYYC---------FGQGTKVEIK
                       ****---*****---*-*-* ALWYSNLWV --*---****
```

According to the homology analysis and conservative substitution of amino acids, the first group of humanized antibody VLs sequences is obtained as follows:

| Code | Amino acid sequence of the light chain variable region of the humanized CD3 antibody (those in bold and underlined being CDR regions) | Sequence No. |
|---|---|---|
| VL3 | EIVLTQSPATLSLSPGERATLSCRSSTGAVTTSNYANWVQQKPGQAPRGLIGGTNKRAPGVPARFSGSLSGTDATLTISSLQPEDFAVYYCALWYSNWVFGGGTKVEIK | 63 |
| VL3a | EIVLTQSPATLSLSPGERATLSCRSSTGAVTTSNYANWVQQKPGQAPKGLIGGTNKRAPGVPARFSGSLSGTDATLTISSLQPEDFAVYYCALWYSNWVFGGGTKVEIK | 64 |
| VL3b | EIVLTQSPATLSLSPGERATLSCRSSTGAVTTSNYANWVQQKPGKAPKLLIGGTNKRAPGVPARFSGSLSGTDATLTISSLQPEDFAVYYCALWYSNWVFGGGTKVEIK | 65 |
| VL3c | EIVLTQSPATLSLSPGERATLSCRSSTGAVTTSNYANWVQQKPGKAPKSLIGGTNKRAPGVPARFSGSLSGTDATLTISSLQPEDFAVYYCALWYSNWVFGGGTKVEIK | 66 |
| VL3d | EIVMTQSPATLSLSPGERATLSCRSSTGAVTTSNYANWVQQKPGQAPKGLIGGTNKRAPGVPARFSGSLSGTDATLTISSLQPEDFAVYYCALWYSNWVFGGGTKVEIK | 67 |
| VL3e | EIVMTQSPATLSLSPGERATLSCRSSTGAVTTSNYANWVQQKPGKAPKLLIGGTNKRAPGVPARFSGSLSGTDATLTISSLQPEDFAVYYCALWYSNWVFGGGTKVEIK | 68 |
| VL3f | EIVMTQSPATLSLSPGERATLSCRSSTGAVTTSNYANWVQQKPGKAPKSLIGGTNKRAPGVPARFSGSLSGTDATLTISSLQPEDFAVYYCALWYSNWVFGGGTKVEIK | 69 |

(ii) NCBI-IgBlast is used to search for antibody light chain variable regions that are highly homologous with FR of SP34VL, and the second group of FR (VHFR-2), . . . is expressed as CDR:

VLFR-2 (1)
QTVVTQEPSLTVSPGGTVTLTC . . . WFQQKPGQAPRALIY . . . WTPARFSGSLLGGKAALTLSGVQPEDEAEYYC . . . FGGGTKVEIK

SP34VL and VLFR-2 are aligned, the blocks are CDR regions, - indicates regions where the amino acids are identical, and * indicates that amino acids are different at the positions:

```
SP34VL          (1) QAVVTQESALTTSPGETVTLTC RSSTGAVTTSNYAN WVQEKPDHLFTGLIG GTNKRAP GVPARFSGSLIGD
VLFR-2          (1) QTVVTQEPSLTVSPGGTVTLTC-------------- WFQQKPGQAPRALIY-------WTPARFSGSLLGG
Homology analysis (1) -*-----**--*---*------ RSSTGAVTTSNYAN -*-*--******--* GTNKRAP **--------*--

KAALTITGAQTEDEAIYFC ALWYSNLWV FGGGTKLTVL
                    KAALTLSGVQPEDEAEYYC---------FGGGTK VEIK
                    ------*-*-*------*- ALWYSNLWV -----****
```

According to the homology analysis and conservative substitution of amino acids, the second group of humanized antibody VLs sequences is obtained as follows:

Example 2: Humanized Antibody Preparation and Antibody Activity Detection

1. Method for construction of antibody expression plasmids. pcDNA3.1 is used as the vector.
(1) Amplify a target fragment DNA by Polymerase Chain Reaction (PCR), the polymerase being DNA polymerase (2× PrimeSTAR Max Premix, TaKaRa, Article No. R405A). Obtain the DNA sequence by performing reverse translation of the amino acid sequence No. 45-73. The obtained PCR product is the target fragment DNA.
(2) cleave the vector plasmid with a restriction endonuclease. The restriction endonuclease is, for example, NotI, NruI, BamHI-HF, or the like.

| Code | Amino acid sequence of the heavy chain variable region of the humanized CD3 antibody (those in bold and underlined being CDR regions) | Sequence No. |
|---|---|---|
| VL4 | QAVVTQEPSLTVFVSPGGTVTLTCRSSTGAVTTSNYANWFQQKPGQAPRALIYGTNKRAPWTPARFSGSLLGGKAALTLSGVQPEDEAEYYCALWYSNLWVFGGGTKLTVL | 70 |
| VL5 | QTVVTQEPSLTVFVSPGGTVTLTCRSSTGAVTTSNYANWVQQKPGQAPRGLIGGTNKRAPGVPARFSGSLLGGKAALTLSGVQPEDEAEYYCALWYSNLWVFGGGTKVEIK | 71 |
| VL5a | QTVVTQEPSLTVFVSPGGTVTLTCRSSTGAVTTSNYANWFQQKPGQAPRGLIGGTNKRAPGVPARFSGSLLGGKAALTLSGVQPEDEAEYYCALWYSNLWVFGGGTKVEIK | 72 |
| VL5b | QTVVTQEPSLTVFVSPGGTVTLTCRSSTGAVTTSNYANWVQQKPGQAPRALIGGTNKRAPGVPARFSGSLLGGKAALTLSGVQPEDEAEYYCALWYSNLWVFGGGTKVEIK | 73 |

The obtained cleavage product is the cleaved vector DNA.

There are two types of vectors: a heavy chain expression vector and a light chain expression vector, wherein the heavy chain expression vector comprises signal peptide and human IGG1 heavy chain constant region DNA sequences, including CH1, hinge, CH2 and CH3, and heavy chain variable region, and the cleavage site is between the 3' end of the signal peptide and the 5' end of CH1; and wherein the light chain expression vector comprises signal peptide and human kappa light chain constant region DNA sequences, as well as the light chain variable region, and the cleavage site is between the 3' end of the signal peptide and the 5' end of the light chain constant region.

(3) Purify the PCR product or digestion product with a DNA purification kit from Tiangen, and see the instructions included inside the kit from Tiangen for specific operation steps. The obtained purification product is the purified target fragment DNA and purified cleaved vector DNA.

(4) Recombination of the target fragment with a recombinase (Exnase II, Vazyme, Article No. C112-01).

Heavy chain fragments are recombined onto digested heavy chain expression vector DNA, and light chain fragments are recombined onto digested light chain expression vector DNA.

(5) Heat shock transformation

Take 10 μl recombination product and add the same into 100 μl Trans10 competent cells, gently mix well, place the same in an ice bath for 30 min, place the tube in 42° C. water bath for 60 s without shaking, quickly transfer to the ice bath for 2 min, add 600 μl LB liquid culture medium (containing antibiotics), culture on a shaker at 37° C. for 1 h, take a proper amount of the bacterial solution and coat the same on LB plates containing corresponding antibiotics, place the plates upside down in a 37° C. constant-temperature incubator for overnight culture. Pick single colonies, and send the samples to Wuhan Genecreate for sequencing. Select single colonies that are sequenced to be correct for expanded culture, and perform plasmid maxiprep for transfection experiments on mammal cells. Plasmids obtained from recombination of heavy chain fragments on digested heavy chain expression vector DNA are referred to as heavy chain expression plasmids, and plasmids obtained from recombination of light chain fragments on digested light chain expression vector DNA are referred to as light chain expression plasmids.

1. Antibody Expression Methods

There are two transient transfection expression systems, CHO—S and 293E, which are described in detail below:

(1) CHO-S transient transfection steps (taking a total transfection volume of 100 ml as an example)

a) Subculture on the day before cell transfection. For example, CD-CHO may be used for cell subculture, the suspension cell density is adjusted to $1 \times 10^6$ cells/ml, the volume is 90 ml, it is ensured that the cells are in the logarithmic growth phase, and the cell density can reach $2 \times 10^6$ cells/ml for transfection on the second day;

b) Overnight culture on a shaker at 37° C., 125 rpm, and 5% $CO_2$;

c) On the day of transfection, pre-heat FectoPRO transfection reagent to room temperature and gently mix well;

d) Take 10 ml serum-free culture medium, such as opti PRO-SFM, to dilute 50 μg DNA, gently mix well, add the mixture into 100 μl transfection reagent, mix well, and incubate at room temperature for 10 min to form a transfection complex;

e) Add the transfection complex into 90 ml of the prepared cells in the logarithmic growth phase, mix well immediately after the addition, and place on a shaker for culture at 37° C., 125 rpm, and 5% $CO_2$;

f) At 2 to 4 h after the transfection, add 75 μl transfection booster Fecto PRO® Booster;

g) At 18 to 24 h after the transfection, cool down to 32° C. for culture;

h) feed at 3, 5, and 7 days after the transfection, the volume of fed culture medium being 3.5% of the total cell volume;

i) Harvest the cells when the cell viability is lower than 70%, the expression time being 9 to 13 days.

(2) 293E transient transfection steps (taking a total transfection volume of 20 ml as an example)

a) Subculture on the day before cell transfection. For example, FreeStyle™ 293 may be used for cell subculture, the suspension cell density is adjusted to 0.6-$0.8 \times 10^6$ cells/ml, the volume is 20 ml, it is ensured that the cells are in the logarithmic growth phase, and the cell density can reach $1.2\text{-}1.6 \times 10^6$ cells/ml for transfection on the second day b) Overnight culture on a shaker at 37° C., 125 rpm, and 5% $CO_2$;

c) On the day of transfection, pre-heat LPEI to room temperature before use and gently mix well;

d) Use 0.67 ml serum-free culture medium, such as FreeStyle™ 293, to dilute 20 μg DNA, and mix well;

e) Use 0.67 ml serum-free culture medium, such as FreeStyle™ 293, to dilute 40 μg LPEI, and mix well;

f) Add the LPEI diluted in step 5 into DNA diluted in step 4, quickly mix well, and incubate at room temperature for 15 min to form a transfection complex;

g) Add the transfection complex in step 6 into 20 ml of the prepared cells in the logarithmic growth phase, mix well immediately after the addition, and place on a shaker for culture at 37° C., 125 rpm, and 5% $CO_2$;

h) feed at 1 and 3 days after the transfection, the volume of fed culture medium being 5% of the total cell volume;

i) Harvest on the $6^{th}$ day of expression.

Figure 2:
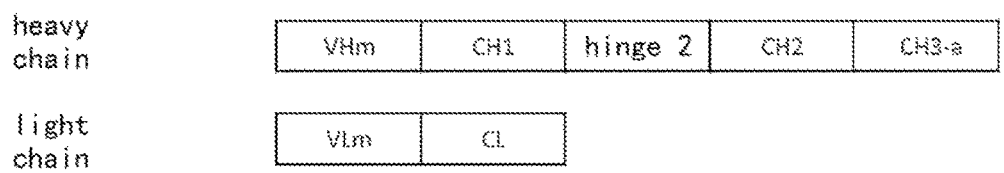
FIG. 2 is a schematic diagram of a primary structure of protein of each component of a monoclonal antibody.

(3) The transfection is co-transfection, which transfects any one kind of light chain expression plasmid and any one kind of heavy chain expression plasmid in equal ratio into the above-mentioned mammal cells, the antibody expressed is a monoclonal antibody having a bivalent symmetric Y-type structure that is consistent with that of natural antibodies. FIG. 2 is a schematic diagram of a primary structure of this structure.

(4) Codes and expression levels (in 293E cells) of monoclonal antibodies are as follows:

TABLE 23

Codes of humanized CD3 monoclonal antibodies

| Antibody code | Corresponding VHs code | Amino acid sequences of heavy chain variable regions (those in bold and underlined being CDR regions) | Sequence No. | Corresponding VLs code | Amino acid sequences of light chain variable regions (those in bold and underlined being CDR regions) | Sequence No. |
|---|---|---|---|---|---|---|
| B8 | VH1 | EVQLVESGGGLVQPGGSLRLSCAASGFTFSTY AMNWVRQAPGKGLEWVARIRSKYNNYATY YADSVKDRFTISRDNAKNSLYLQMNSLRAED TAVYYCARHGNFGNSYVSWFAYWGQGTLVT VSS | 45 | VL3 | EIVLTQSPATLSLSPGERATLSCRSSTG AVTTSNYANWVQQKPGQAPRGLIGGG TNKRAPGVPARFSGSLSGTDATLTISS LQPEDFAVYYCALWYSNLWVFGGGT KVEIK | 63 |
| B9 | VH2 | QVQLVESGGGVVQPGRSLRLSCAASGFTFSTY AMNWVRQAPGKGLEWVARIRSKYNNYATY YADSVKDRFTISRDNSKNTLYLQMNSLRAEDT AVYYCARHGNFGNSYVSWFAYWGQGTLVTV SS | 48 | VL3 | EIVLTQSPATLSLSPGERATLSCRSSTG AVTTSNYANWVQQKPGQAPRGLIGGG TNKRAPGVPARFSGSLSGTDATLTISS LQPEDFAVYYCALWYSNLWVFGGGT KVEIK | 63 |
| B10 | VH1 | EVQLVESGGGLVQPGGSLRLSCAASGFTFSTY AMNWVRQAPGKGLEWVARIRSKYNNYATY YADSVKDRFTISRDNAKNSLYLQMNSLRAED TAVYYCARHGNFGNSYVSWFAYWGQGTLVT VSS | 45 | VL3a | EIVLTQSPATLSLSPGERATLSCRSSTG AVTTSNYANWVQQKPGQAPKGLIGGG TNKRAPGVPARFSGSLSGTDATLTISS LQPEDFAVYYCALWYSNLWVFGGGT KVEIK | 64 |
| B11 | VH1 | EVQLVESGGGLVQPGGSLRLSCAASGFTFSTY AMNWVRQAPGKGLEWVARIRSKYNNYATY YADSVKDRFTISRDNAKNSLYLQMNSLRAED TAVYYCARHGNFGNSYVSWFAYWGQGTLVT VSS | 45 | VL3b | EIVLTQSPATLSLSPGERATLSCRSSTG AVTTSNYANWVQQKPGKAPKLLIGGG TNKRAPGVPARFSGSLSGTDATLTISS LQPEDFAVYYCALWYSNLWVFGGGT KVEIK | 65 |
| B12 | VH1 | EVQLVESGGGLVQPGGSLRLSCAASGFTFSTY AMNWVRQAPGKGLEWVARIRSKYNNYATY YADSVKDRFTISRDNAKNSLYLQMNSLRAED TAVYYCARHGNFGNSYVSWFAYWGQGTLVT VSS | 45 | VL3c | EIVLTQSPATLSLSPGERATLSCRSSTG AVTTSNYANWVQQKPGKAPKSLIGGG TNKRAPGVPARFSGSLSGTDATLTISS LQPEDFAVYYCALWYSNLWVFGGGT KVEIK | 66 |
| B13 | VH1 | EVQLVESGGGLVQPGGSLRLSCAASGFTFSTY AMNWVRQAPGKGLEWVARIRSKYNNYATY YADSVKDRFTISRDNAKNSLYLQMNSLRAED TAVYYCARHGNFGNSYVSWFAYWGQGTLVT VSS | 45 | VL3d | EIVMTQSPATLSLSPGERATLSCRSSTG AVTTSNYANWVQQKPGQAPKGLIGGG TNKRAPGVPARFSGSLSGTDATLTISS LQPEDFAVYYCALWYSNLWVFGGGT KVEIK | 67 |
| B14 | VH1 | EVQLVESGGGLVQPGGSLRLSCAASGFTFSTY AMNWVRQAPGKGLEWVARIRSKYNNYATY YADSVKDRFTISRDNAKNSLYLQMNSLRAED TAVYYCARHGNFGNSYVSWFAYWGQGTLVT VSS | 45 | VL3e | EIVMTQSPATLSLSPGERATLSCRSSTG AVTTSNYANWVQQKPGKAPKLLIGGG TNKRAPGVPARFSGSLSGTDATLTISS LQPEDFAVYYCALWYSNLWVFGGGT KVEIK | 68 |
| B15 | VH1 | EVQLVESGGGLVQPGGSLRLSCAASGFTFSTY AMNWVRQAPGKGLEWVARIRSKYNNYATY YADSVKDRFTISRDNAKNSLYLQMNSLRAED TAVYYCARHGNFGNSYVSWFAYWGQGTLVT VSS | 45 | VL3f | EIVMTQSPATLSLSPGERATLSCRSSTG AVTTSNYANWVQQKPGKAPKSLIGGG TNKRAPGVPARFSGSLSGTDATLTISS LQPEDFAVYYCALWYSNLWVFGGGT KVEIK | 69 |
| B16 | VH2 | QVQLVESGGGVVQPGRSLRLSCAASGFTFSTY AMNWVRQAPGKGLEWVARIRSKYNNYATY YADSVKDRFTISRDNSKNTLYLQMNSLRAEDT AVYYCARHGNFGNSYVSWFAYWGQGTLVTV SS | 48 | VL3a | EIVLTQSPATLSLSPGERATLSCRSSTG AVTTSNYANWVQQKPGQAPKGLIGGG TNKRAPGVPARFSGSLSGTDATLTISS LQPEDFAVYYCALWYSNLWVFGGGT KVEIK | 64 |
| B17 | VH2 | QVQLVESGGGVVQPGRSLRLSCAASGFTFSTY AMNWVRQAPGKGLEWVARIRSKYNNYATY YADSVKDRFTISRDNSKNTLYLQMNSLRAEDT AVYYCARHGNFGNSYVSWFAYWGQGTLVTV SS | 48 | VL3b | EIVLTQSPATLSLSPGERATLSCRSSTG AVTTSNYANWVQQKPGKAPKLLIGGG TNKRAPGVPARFSGSLSGTDATLTISS LQPEDFAVYYCALWYSNLWVFGGGT KVEIK | 65 |
| B18 | VH2 | QVQLVESGGGVVQPGRSLRLSCAASGFTFSTY AMNWVRQAPGKGLEWVARIRSKYNNYATY YADSVKDRFTISRDNSKNTLYLQMNSLRAEDT AVYYCARHGNFGNSYVSWFAYWGQGTLVTV SS | 48 | VL3c | EIVLTQSPATLSLSPGERATLSCRSSTG AVTTSNYANWVQQKPGKAPKSLIGGG TNKRAPGVPARFSGSLSGTDATLTISS LQPEDFAVYYCALWYSNLWVFGGGT KVEIK | 66 |
| B19 | VH2 | QVQLVESGGGVVQPGRSLRLSCAASGFTFSTY AMNWVRQAPGKGLEWVARIRSKYNNYATY YADSVKDRFTISRDNSKNTLYLQMNSLRAEDT AVYYCARHGNFGNSYVSWFAYWGQGTLVTV SS | 48 | VL3d | EIVMTQSPATLSLSPGERATLSCRSSTG AVTTSNYANWVQQKPGQAPKGLIGGG TNKRAPGVPARFSGSLSGTDATLTISS LQPEDFAVYYCALWYSNLWVFGGGT KVEIK | 67 |

TABLE 23-continued

Codes of humanized CD3 monoclonal antibodies

| Antibody code | Corresponding VHs code | Amino acid sequences of heavy chain variable regions (those in bold and underlined being CDR regions) | Sequence No. | Corresponding VLs code | Amino acid sequences of light chain variable regions (those in bold and underlined being CDR regions) | Sequence No. |
|---|---|---|---|---|---|---|
| B20 | VH2 | QVQLVESGGGVVQPGRSLRLSCAASGFTFSTYAMNWVRQAPGKGLEWVARIRSKYNNYATYYADSVKDRFTISRDNSKNTLYLQMNSLRAEDTAVYYCARHGNFGNSYVSWFAYWGQGTLVTVSS | 48 | VL3e | EIVMTQSPATLSLSPGERATLSCRSSTGAVTTSNYANWVQQKPGKAPKLLIGGTNKRAPGVPARFSGSLSGTDATLTISSLQPEDFAVYYCALWYSNLWVFGGGTKVEIK | 68 |
| B21 | VH2 | QVQLVESGGGVVQPGRSLRLSCAASGFTFSTYAMNWVRQAPGKGLEWVARIRSKYNNYATYYADSVKDRFTISRDNSKNTLYLQMNSLRAEDTAVYYCARHGNFGNSYVSWFAYWGQGTLVTVSS | 48 | VL3f | EIVMTQSPATLSLSPGERATLSCRSSTGAVTTSNYANWVQQKPGKAPKSLIGGTNKRAPGVPARFSGSLSGTDATLTISSLQPEDFAVYYCALWYSNLWVFGGGTKVEIK | 69 |
| B22 | VH1 | EVQLVESGGGLVQPGGSLRLSCAASGFTFSTYAMNWVRQAPGKGLEWVARIRSKYNNYATYYADSVKDRFTISRDNAKNSLYLQMNSLRAEDTAVYYCARHGNFGNSYVSWFAYWGQGTLVTVSS | 45 | VL4 | QAVVTQEPSLTVSPGGTVTLTCRSSTGAVTTSNYANWFQQKPGQAPRALIYGTNKRAPWTPARFSGSLLGGKAALTLSGVQPEDEAEYYCALWYSNLWVFGGGTKLTVL | 70 |
| B23 | VH2 | QVQLVESGGGVVQPGRSLRLSCAASGFTFSTYAMNWVRQAPGKGLEWVARIRSKYNNYATYYADSVKDRFTISRDNSKNTLYLQMNSLRAEDTAVYYCARHGNFGNSYVSWFAYWGQGTLVTVSS | 48 | VL4 | QAVVTQEPSLTVSPGGTVTLTCRSSTGAVTTSNYANWFQQKPGQAPRALIYGTNKRAPWTPARFSGSLLGGKAALTLSGVQPEDEAEYYCALWYSNLWVFGGGTKLTVL | 70 |
| B24 | VH1 | EVQLVESGGGLVQPGGSLRLSCAASGFTFSTYAMNWVRQAPGKGLEWVARIRSKYNNYATYYADSVKDRFTISRDNAKNSLYLQMNSLRAEDTAVYYCARHGNFGNSYVSWFAYWGQGTLVTVSS | 45 | VL5 | QTVVTQEPSLTVSPGGTVTLTCRSSTGAVTTSNYANWVQQKPGQAPRGLIGGTNKRAPGVPARFSGSLLGGKAALTLSGVQPEDEAEYYCALWYSNLWVFGGGTKVEIK | 71 |
| B25 | VH2 | QVQLVESGGGVVQPGRSLRLSCAASGFTFSTYAMNWVRQAPGKGLEWVARIRSKYNNYATYYADSVKDRFTISRDNSKNTLYLQMNSLRAEDTAVYYCARHGNFGNSYVSWFAYWGQGTLVTVSS | 48 | VL5 | QTVVTQEPSLTVSPGGTVTLTCRSSTGAVTTSNYANWVQQKPGQAPRGLIGGTNKRAPGVPARFSGSLLGGKAALTLSGVQPEDEAEYYCALWYSNLWVFGGGTKVEIK | 71 |
| B26 | VH1a | EVQLVESGGGLVQPGGSLRLSCAASGFTFSTYAMNWVRQAPGKGLEWVARIRSKYNNYATYYADSVKDRFTISRDDSKNSLYLQMNSLRAEDTAVYYCARHGNFGNSYVSWFAYWGQGTLVTVSS | 46 | VL3 | EIVLTQSPATLSLSPGERATLSCRSSTGAVTTSNYANWVQQKPGQAPRGLIGGTNKRAPGVPARFSGSLSGTDATLTISSLQPEDFAVYYCALWYSNLWVFGGGTKVEIK | 63 |
| B27 | VH1b | EVQLVESGGGLVQPGGSLRLSCAASGFTFSTYAMNWVRQAPGKGLEWVARIRSKYNNYATYYADSVKDRFTISRDDSKNSLYLQMNSLRAEDTAVYYCVRHGNFGNSYVSWFAYWGQGTLVTVSS | 47 | VL3 | EIVLTQSPATLSLSPGERATLSCRSSTGAVTTSNYANWVQQKPGQAPRGLIGGTNKRAPGVPARFSGSLSGTDATLTISSLQPEDFAVYYCALWYSNLWVFGGGTKVEIK | 63 |
| B28 | VH2a | QVQLVESGGGVVQPGRSLRLSCAASGFTFSTYAMNWVRQAPGKGLEWVARIRSKYNNYATYYADSVKDRFTISRDDSKNTLYLQMNSLRAEDTAVYYCARHGNFGNSYVSWFAYWGQGTLVTVSS | 49 | VL3 | EIVLTQSPATLSLSPGERATLSCRSSTGAVTTSNYANWVQQKPGQAPRGLIGGTNKRAPGVPARFSGSLSGTDATLTISSLQPEDFAVYYCALWYSNLWVFGGGTKVEIK | 63 |
| B29 | VH2b | QVQLVESGGGVVQPGRSLRLSCAASGFTFSTYAMNWVRQAPGKGLEWVARIRSKYNNYATYYADSVKDRFTISRDNSKNTLYLQMNSLRAEDTAVYYCVRHGNFGNSYVSWFAYWGQGTLVTVSS | 50 | VL3 | EIVLTQSPATLSLSPGERATLSCRSSTGAVTTSNYANWVQQKPGQAPRGLIGGTNKRAPGVPARFSGSLSGTDATLTISSLQPEDFAVYYCALWYSNLWVFGGGTKVEIK | 63 |
| B30 | VH2c | QVQLVESGGGVVQPGRSLRLSCAASGFTFSTYAMNWVRQAPGKGLEWVARIRSKYNNYATYYADSVKDRFTISRDDSKNTLYLQMNSLRAEDTAVYYCVRHGNFGNSYVSWFAYWGQGTLVTVSS | 51 | VL3 | EIVLTQSPATLSLSPGERATLSCRSSTGAVTTSNYANWVQQKPGQAPRGLIGGTNKRAPGVPARFSGSLSGTDATLTISSLQPEDFAVYYCALWYSNLWVFGGGTKVEIK | 63 |
| B31 | VH1a | EVQLVESGGGLVQPGGSLRLSCAASGFTFSTYAMNWVRQAPGKGLEWVARIRSKYNNYATYYADSVKDRFTISRDDSKNSLYLQMNSLRAEDTAVYYCARHGNFGNSYVSWFAYWGQGTLVTVSS | 46 | VL5 | QTVVTQEPSLTVSPGGTVTLTCRSSTGAVTTSNYANWVQQKPGQAPRGLIGGTNKRAPGVPARFSGSLLGGKAALTLSGVQPEDEAEYYCALWYSNLWVFGGGTKVEIK | 71 |

TABLE 23-continued

Codes of humanized CD3 monoclonal antibodies

| Antibody code | Corresponding VHs code | Amino acid sequences of heavy chain variable regions (those in bold and underlined being CDR regions) | Sequence No. | Corresponding VLs code | Amino acid sequences of light chain variable regions (those in bold and underlined being CDR regions) | Sequence No. |
|---|---|---|---|---|---|---|
| B32 | VH1b | EVQLVESGGGLVQPGGSLRLSCAASGFTFSTY AMNWVRQAPGKGLEWVARIRSKYNNYATY YADSVKDRFTISRDDSKNSLYLQMNSLRAEDT AVYYCVRHGNFGNSYVSWFAYWGQGTLVTV SS | 47 | VL5 | QTVVTQEPSLTVSPGGTVTLTCRSSTG AVTTSNYANWVQQKPGQAPRGLIGG TNKRAPGVPARFSGSLLGGKAALTLS GVQPEDEAEYYCALWYSNLWVFGG GTKVEIK | 71 |
| B33 | VH2a | QVQLVESGGGVVQPGRSLRLSCAASGFTFSTY AMNWVRQAPGKGLEWVARIRSKYNNYATY YADSVKDRFTISRDDSKNTLYLQMNSLRAEDT AVYYCARHGNFGNSYVSWFAYWGQGTLVTV SS | 49 | VL5 | QTVVTQEPSLTVSPGGTVTLTCRSSTG AVTTSNYANWVQQKPGQAPRGLIGG TNKRAPGVPARFSGSLLGGKAALTLS GVQPEDEAEYYCALWYSNLWVFGG GTKVEIK | 71 |
| B34 | VH2b | QVQLVESGGGVVQPGRSLRLSCAASGFTFSTY AMNWVRQAPGKGLEWVARIRSKYNNYATY YADSVKDRFTISRDNSKNTLYLQMNSLRAEDT AVYYCVRHGNFGNSYVSWFAYWGQGTLVTV SS | 50 | VL5 | QTVVTQEPSLTVSPGGTVTLTCRSSTG AVTTSNYANWVQQKPGQAPRGLIGG TNKRAPGVPARFSGSLLGGKAALTLS GVQPEDEAEYYCALWYSNLWVFGG GTKVEIK | 71 |
| B35 | VH2c | QVQLVESGGGVVQPGRSLRLSCAASGFTFSTY AMNWVRQAPGKGLEWVARIRSKYNNYATY YADSVKDRFTISRDDSKNTLYLQMNSLRAEDT AVYYCVRHGNFGNSYVSWFAYWGQGTLVTV SS | 51 | VL5 | QTVVTQEPSLTVSPGGTVTLTCRSSTG AVTTSNYANWVQQKPGQAPRGLIGG TNKRAPGVPARFSGSLLGGKAALTLS GVQPEDEAEYYCALWYSNLWVFGG GTKVEIK | 71 |
| B36 | VH2d | QVQLVESGGGVVQPGRSLRLSCAASGFTFSTY AMNWVRQAPGKGLEWVARIRSKYNNYATY YADSVKDRFTISRDDSKNTLYLQMNSLRAEDT AVYYCARHGNFGNSYVTWFAYWGQGTLVT VSS | 52 | VL5a | QTVVTQEPSLTVSPGGTVTLTCRSSTG AVTTSNYANWFQQKPGQAPRGLIGG TNKRAPGVPARFSGSLLGGKAALTLS GVQPEDEAEYYCALWYSNLWVFGG GTKVEIK | 72 |
| B37 | VH2e | QVQLVESGGGVVQPGRSLRLSCAASGFTFSTY AMNWVRQAPGKGLEWVARIRSKYNNYATY YADSVKDRFTISRDDSKNTLYLQMNSLRAEDT AVYYCARHGNFGNSYVSYFAYWGQGTLVTV SS | 53 | VL5a | QTVVTQEPSLTVSPGGTVTLTCRSSTG AVTTSNYANWFQQKPGQAPRGLIGG TNKRAPGVPARFSGSLLGGKAALTLS GVQPEDEAEYYCALWYSNLWVFGG GTKVEIK | 72 |
| B38 | VH2f | QVQLVESGGGVVQPGRSLRLSCAASGFTFSTY AMNWVRQAPGKGLEWVARIRSKYNNYATY YADSVKDRFTISRDDSKNTLYLQMNSLRAEDT AVYYCARHGNFGNSYVSFFAYWGQGTLVTV SS | 54 | VL5a | QTVVTQEPSLTVSPGGTVTLTCRSSTG AVTTSNYANWFQQKPGQAPRGLIGG TNKRAPGVPARFSGSLLGGKAALTLS GVQPEDEAEYYCALWYSNLWVFGG GTKVEIK | 72 |
| B39 | VH2g | QVQLVESGGGVVQPGRSLRLSCAASGFTFSTY AMNWVRQAPGKGLEWVARIRSKYNNYATY YADSVKDRFTISRDDSKNTLYLQMNSLRAEDT AVYYCARHGNFGNSYVSWLAYWGQGTLVT VSS | 55 | VL5a | QTVVTQEPSLTVSPGGTVTLTCRSSTG AVTTSNYANWFQQKPGQAPRGLIGG TNKRAPGVPARFSGSLLGGKAALTLS GVQPEDEAEYYCALWYSNLWVFGG GTKVEIK | 72 |
| B40 | VH2h | QVQLVESGGGVVQPGRSLRLSCAASGFTFSTY AMNWVRQAPGKGLEWVARIRSKYNNYATY YADSVKDRFTISRDDSKNTLYLQMNSLRAEDT AVYYCARHGNFGNSYVSWVAYWGQGTLVT VSS | 56 | VL5a | QTVVTQEPSLTVSPGGTVTLTCRSSTG AVTTSNYANWFQQKPGQAPRGLIGG TNKRAPGVPARFSGSLLGGKAALTLS GVQPEDEAEYYCALWYSNLWVFGG GTKVEIK | 72 |
| B41 | VH2i | QVQLVESGGGVVQPGRSLRLSCAASGFTFSTY AMNWVRQAPGKGLEWVARIRSKYNNYATY YADSVKDRFTISRDDSKNTLYLQMNSLRAEDT AVYYCARHGNFGNSYVSWIAYWGQGTLVTV SS | 57 | VL5a | QTVVTQEPSLTVSPGGTVTLTCRSSTG AVTTSNYANWFQQKPGQAPRGLIGG TNKRAPGVPARFSGSLLGGKAALTLS GVQPEDEAEYYCALWYSNLWVFGG GTKVEIK | 72 |
| B42 | VH2j | QVQLVESGGGVVQPGRSLRLSCAASGFTFSTY AMNWVRQAPGKGLEWVARIRSKYNNYATY YADSVKDRFTISRDDSKNTLYLQMNSLRAEDT AVYYCARHGNFGNSYVSWAAYWGQGTLVT VSS | 58 | VL5a | QTVVTQEPSLTVSPGGTVTLTCRSSTG AVTTSNYANWFQQKPGQAPRGLIGG TNKRAPGVPARFSGSLLGGKAALTLS GVQPEDEAEYYCALWYSNLWVFGG GTKVEIK | 72 |
| B43 | VH2k | QVQLVESGGGVVQPGRSLRLSCAASGFTFSTY AMNWVRQAPGKGLEWVARIRSKYNNYATY YADSVKDRFTISRDDSKNTLYLQMNSLRAEDT AVYYCARHGNFGNSYVSWYAYWGQGTLVT VSS | 59 | VL5a | QTVVTQEPSLTVSPGGTVTLTCRSSTG AVTTSNYANWFQQKPGQAPRGLIGG TNKRAPGVPARFSGSLLGGKAALTLS GVQPEDEAEYYCALWYSNLWVFGG GTKVEIK | 72 |

TABLE 23-continued

Codes of humanized CD3 monoclonal antibodies

| Antibody code | Corresponding VHs code | Amino acid sequences of heavy chain variable regions (those in bold and underlined being CDR regions) | Sequence No. | Corresponding VLs code | Amino acid sequences of light chain variable regions (those in bold and underlined being CDR regions) | Sequence No. |
|---|---|---|---|---|---|---|
| B44 | VH2l | QVQLVESGGGVVQPGRSLRLSCAASGFTFSTY AMNWVRQAPGKGLEWVARIRSKYNNYATY YADSVKDRFTISRDDSKNTLYLQMNSLRAEDT AVYYCARHGNFGNSYVSWFVYWGQGTLVT VSS | 60 | VL5a | QTVVTQEPSLTVSPGGTVTLTCRSSTG AVTTSNYANWFQQKPGQAPRGLIGGG TNKRAPGVPARFSGSLLGGKAALTLS GVQPEDEAEYYCALWYSNLWVFGG GTKVEIK | 72 |
| B45 | VH2m | QVQLVESGGGVVQPGRSLRLSCAASGFTFSTY AMNWVRQAPGKGLEWVARIRSKYNNYATY YADSVKDRFTISRDDSKNTLYLQMNSLRAEDT AVYYCARHGNFGNSYVSWFLYWGQGTLVT VSS | 61 | VL5a | QTVVTQEPSLTVSPGGTVTLTCRSSTG AVTTSNYANWFQQKPGQAPRGLIGGG TNKRAPGVPARFSGSLLGGKAALTLS GVQPEDEAEYYCALWYSNLWVFGG GTKVEIK | 72 |
| B46 | VH2n | QVQLVESGGGVVQPGRSLRLSCAASGFTFSTY AMNWVRQAPGKGLEWVARIRSKYNNYATY YADSVKDRFTISRDDSKNTLYLQMNSLRAEDT AVYYCARHGNFGNSYVSWFIYWGQGTLVTV SS | 62 | VL5a | QTVVTQEPSLTVSPGGTVTLTCRSSTG AVTTSNYANWFQQKPGQAPRGLIGGG TNKRAPGVPARFSGSLLGGKAALTLS GVQPEDEAEYYCALWYSNLWVFGG GTKVEIK | 72 |
| B47 | VH2d | QVQLVESGGGVVQPGRSLRLSCAASGFTFSTY AMNWVRQAPGKGLEWVARIRSKYNNYATY YADSVKDRFTISRDDSKNTLYLQMNSLRAEDT AVYYCARHGNFGNSYVTWFAYWGQGTLVT VSS | 52 | VL5b | QTVVTQEPSLTVSPGGTVTLTCRSSTG AVTTSNYANWVQQKPGQAPRALIGGG TNKRAPGVPARFSGSLLGGKAALTLS GVQPEDEAEYYCALWYSNLWVFGG GTKVEIK | 73 |
| B48 | VH2e | QVQLVESGGGVVQPGRSLRLSCAASGFTFSTY AMNWVRQAPGKGLEWVARIRSKYNNYATY YADSVKDRFTISRDDSKNTLYLQMNSLRAEDT AVYYCARHGNFGNSYVSYFAYWGQGTLVTV SS | 53 | VL5b | QTVVTQEPSLTVSPGGTVTLTCRSSTG AVTTSNYANWVQQKPGQAPRALIGGG TNKRAPGVPARFSGSLLGGKAALTLS GVQPEDEAEYYCALWYSNLWVFGG GTKVEIK | 73 |
| B49 | VH2f | QVQLVESGGGVVQPGRSLRLSCAASGFTFSTY AMNWVRQAPGKGLEWVARIRSKYNNYATY YADSVKDRFTISRDDSKNTLYLQMNSLRAEDT AVYYCARHGNFGNSYVSFFAYWGQGTLVTV SS | 54 | VL5b | QTVVTQEPSLTVSPGGTVTLTCRSSTG AVTTSNYANWVQQKPGQAPRALIGGG TNKRAPGVPARFSGSLLGGKAALTLS GVQPEDEAEYYCALWYSNLWVFGG GTKVEIK | 73 |
| B50 | VH2g | QVQLVESGGGVVQPGRSLRLSCAASGFTFSTY AMNWVRQAPGKGLEWVARIRSKYNNYATY YADSVKDRFTISRDDSKNTLYLQMNSLRAEDT AVYYCARHGNFGNSYVSWLAYWGQGTLVT VSS | 55 | VL5b | QTVVTQEPSLTVSPGGTVTLTCRSSTG AVTTSNYANWVQQKPGQAPRALIGGG TNKRAPGVPARFSGSLLGGKAALTLS GVQPEDEAEYYCALWYSNLWVFGG GTKVEIK | 73 |
| B51 | VH2h | QVQLVESGGGVVQPGRSLRLSCAASGFTFSTY AMNWVRQAPGKGLEWVARIRSKYNNYATY YADSVKDRFTISRDDSKNTLYLQMNSLRAEDT AVYYCARHGNFGNSYVSWVAYWGQGTLVT VSS | 56 | VL5b | QTVVTQEPSLTVSPGGTVTLTCRSSTG AVTTSNYANWVQQKPGQAPRALIGGG TNKRAPGVPARFSGSLLGGKAALTLS GVQPEDEAEYYCALWYSNLWVFGG GTKVEIK | 73 |
| B52 | VH2i | QVQLVESGGGVVQPGRSLRLSCAASGFTFSTY AMNWVRQAPGKGLEWVARIRSKYNNYATY YADSVKDRFTISRDDSKNTLYLQMNSLRAEDT AVYYCARHGNFGNSYVSWIAYWGQGTLVTV SS | 57 | VL5b | QTVVTQEPSLTVSPGGTVTLTCRSSTG AVTTSNYANWVQQKPGQAPRALIGGG TNKRAPGVPARFSGSLLGGKAALTLS GVQPEDEAEYYCALWYSNLWVFGG GTKVEIK | 73 |
| B53 | VH2j | QVQLVESGGGVVQPGRSLRLSCAASGFTFSTY AMNWVRQAPGKGLEWVARIRSKYNNYATY YADSVKDRFTISRDDSKNTLYLQMNSLRAEDT AVYYCARHGNFGNSYVSWAAYWGQGTLVT VSS | 58 | VL5b | QTVVTQEPSLTVSPGGTVTLTCRSSTG AVTTSNYANWVQQKPGQAPRALIGGG TNKRAPGVPARFSGSLLGGKAALTLS GVQPEDEAEYYCALWYSNLWVFGG GTKVEIK | 73 |
| B54 | VH2k | QVQLVESGGGVVQPGRSLRLSCAASGFTFSTY AMNWVRQAPGKGLEWVARIRSKYNNYATY YADSVKDRFTISRDDSKNTLYLQMNSLRAEDT AVYYCARHGNFGNSYVSWYAYWGQGTLVT VSS | 59 | VL5b | QTVVTQEPSLTVSPGGTVTLTCRSSTG AVTTSNYANWVQQKPGQAPRALIGGG TNKRAPGVPARFSGSLLGGKAALTLS GVQPEDEAEYYCALWYSNLWVFGG GTKVEIK | 73 |
| B55 | VH2l | QVQLVESGGGVVQPGRSLRLSCAASGFTFSTY AMNWVRQAPGKGLEWVARIRSKYNNYATY YADSVKDRFTISRDDSKNTLYLQMNSLRAEDT AVYYCARHGNFGNSYVSWFVYWGQGTLVT VSS | 60 | VL5b | QTVVTQEPSLTVSPGGTVTLTCRSSTG AVTTSNYANWVQQKPGQAPRALIGGG TNKRAPGVPARFSGSLLGGKAALTLS GVQPEDEAEYYCALWYSNLWVFGG GTKVEIK | 73 |

TABLE 23-continued

Codes of humanized CD3 monoclonal antibodies

| Antibody code | Corresponding VHs code | Amino acid sequences of heavy chain variable regions (those in bold and underlined being CDR regions) | Sequence No. | Corresponding VLs code | Amino acid sequences of light chain variable regions (those in bold and underlined being CDR regions) | Sequence No. |
|---|---|---|---|---|---|---|
| B56 | VH2m | QVQLVESGGGVVQPGRSLRLSCAASGFTFSTYAMNWVRQAPGKGLEWVARIRSKYNNYATYYADSVKDRFTISRDDSKNTLYLQMNSLRAEDTAVYYCARHGNFGNSYVSWFLYWGQGTLVTVSS | 61 | VL5b | QTVVTQEPSLTVSPGGTVTLTCRSSTGAVTTSNYANWVQQKPGQAPRALIGGTNKRAPGVPARFSGSLLGGKAALTLSGVQPEDEAEYYCALWYSNLWVFGGGTKVEIK | 73 |
| B57 | VH2n | QVQLVESGGGVVQPGRSLRLSCAASGFTFSTYAMNWVRQAPGKGLEWVARIRSKYNNYATYYADSVKDRFTISRDDSKNTLYLQMNSLRAEDTAVYYCARHGNFGNSYVSWFIYWGQGTLVTVSS | 62 | VL5b | QTVVTQEPSLTVSPGGTVTLTCRSSTGAVTTSNYANWVQQKPGQAPRALIGGTNKRAPGVPARFSGSLLGGKAALTLSGVQPEDEAEYYCALWYSNLWVFGGGTKVEIK | 73 |

Monoclonal antibodies of the above B8-B57 have the same heavy chain constant regions and light chain constant regions, and the specific sequences are as follows:

TABLE 24

Constant region sequences of monoclonal antibodies

| Constant region | Domain | Amino acid sequence | Sequence No. |
|---|---|---|---|
| Heavy chain constant regions | CH1 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKV | 154 |
| | Hinge | EPKSCDKTHTCP | 139 |
| | CH2 | PCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAK | 155 |
| | CH3 | GQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | 162 |
| Light chain constant regions | CL | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 148 |

The specific sequences of SP34 monoclonal antibody are as follows:

| SP34 monoclonal antibody | Domain | Specific sequences (those in bold and underlined being CDR regions) | Sequence No. |
|---|---|---|---|
| SP34 monoclonal antibody heavy chain | VH | EVQLVESGGGLVQPKGSLKLSCAASGFTFNTYAMNWVRQAPGKGLEWVARIRSKYNNYATYYADSVKDRFTISRDDSQSILYLQMNNLKTEDTAMYYCVRHGNFGNSYVSWFAYWGQGTLVTVSS | 74 |
| | CH1 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKV | 154 |
| | Hinge | EPKSCDKTHTCP | 139 |
| | CH2 | PCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAK | 155 |
| | CH3 | GQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | 162 |
| SP34 monoclonal antibody light chain | VL | QAVVTQESALTTSPGETVTLTCRSSTGAVTTSNYANWVQEKPDHLFTGLIGGTNKRAPGVPARFSGSLIGDKAALTITGAQTEDEAIYFCALWYSNLWVFGGGTKLTVL | 75 |
| | CL | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 148 |

Figure 3:
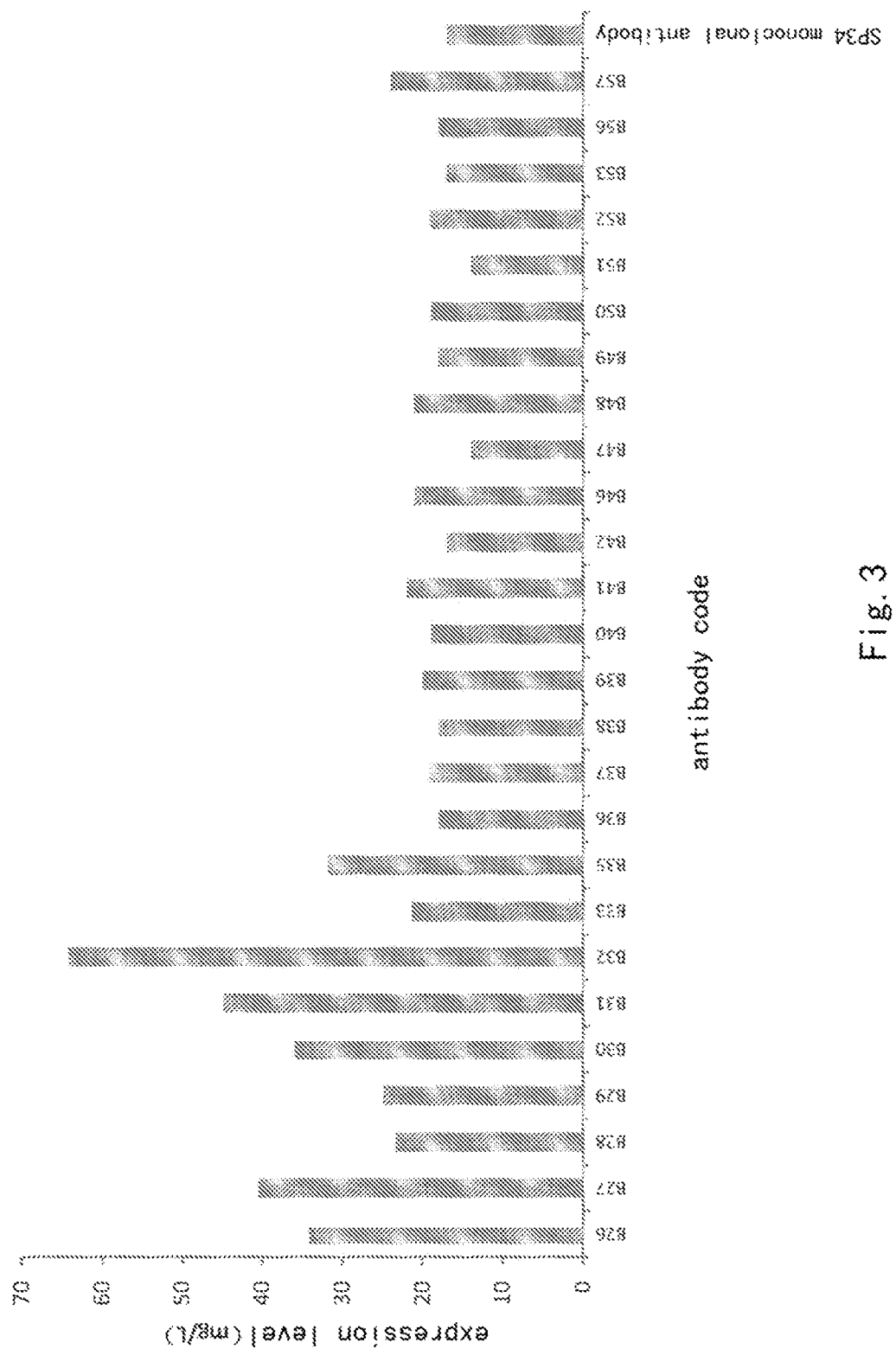
FIG. 3 illustrates expression levels of humanized CD3 monoclonal antibodies.

FIG. 3 illustrates expression levels of humanized CD3 monoclonal antibodies. From the antibody expression levels, it can be seen that monoclonal antibodies, such as B25-B33, B35-B42, B46-B53, B56-B57, and the like, have a transient transfection expression level of more than 15 mg/L.

2. Antibody Purification

Antibody purification is performed mainly through affinity chromatography, specifically:

(1) Harvest: centrifuge a cell culture broth for antibody expression at 3000×g for 10 mM, take the supernatant, filter it with a 0.22 μm filter, and store at 4° C. for later use;

(2) Affinity chromatography (MabSelect SuRe GE 17-5438-01, taking 18 ml column volume as an example)

a) Equilibrate: use the binding buffer (25 mM Tris, pH 7.0-7.4) to equilibrate the column until the UV detector and conductance value become stable or reach baseline, and equilibrate at least 5 column volumes;
   b) Load: load the filtered supernatant at a flow rate of 5 ml/min;
   c) wash to equilibrate: use the binding buffer to wash for 5 column volumes;
   d) Elute: use an elution buffer (50 mM citrate-citric acid, pH 3.4±0.1) to elute samples at a flow rate of 5 ml/min, elute for 5 column volumes, and collect eluting peaks;
   e) Neutralize: neutralize the eluate with 1 M Tris pH 8.0, and adjust pH of the sample to 6.0±0.1.

The antibody obtained through purification is a monoclonal antibody and has a bivalent symmetric Y-type structure that is consistent with that of natural antibodies.

3. Antibody Activity Detection

In this example, antibody activity detection mainly refers to detection of the binding activity between an antibody and CD3 positive cells.

1) Cell preparation: CD3 positive CIK cells from induced culture/T cells separated from human whole blood are used for CD3 end affinity detection. Take a sufficient amount of cells, centrifuge at 300 g for 5 mM, discard the supernatant, use 1% FBS-PBS to re-suspend the cells, adjust the density to $4 \times 10^6$/ml, take 50 μl for each well, and plate the cells at $2 \times 10^5$ per well. The centrifuge is at 4 degrees and 300×g, centrifuge for 5 min, discard the supernatant, and plating the cells on ice;

2) Antibody addition: according to the experiment design, subject the antibodies to gradient dilution, and perform the antibody dilution on ice. If the initial concentration of antibody dilution is 3000 nM, dilute 3×, and dilute by 11 concentration grades. Add the diluted antibody into the cell wells at 50 μl per well, gently pipette well, and incubate for 2 h at 4 degrees with shaking at 1100 rpm/min;

3) Wash: use 150 μl 1% FBS-PBS to resuspend the cells, centrifuge at 4 degrees and 300×g for 5 min, and discard the supernatant. Repeat the washing once;

4) Secondary antibody incubation: add diluted secondary antibody PE anti-human IgG FC (Biolegend, 409304), the final concentration of the secondary antibody is 8 μg/ml, and the volume is 50 μl/well. At the same time, provide wells only added with the cells and the secondary antibody as control, gently pipette the well, and incubate in dark for 1 h at 4 degrees with shaking at 1100 rpm/min;

5) Wash: use 150 μl 1% FBS-PBS to resuspend the cells, centrifuge at 4 degrees and 300×g for 5 min, and discard the supernatant. Repeat the washing once;

6) Fixation: add 200 μl 2% paraformaldehyde into each well to resuspend the cells and fix cells at room temperature for 20 min. Centrifuge at 300×g for 5 min, and discard the supernatant;

7) Cell re-suspension: use 200 μl 1% FBS-PBS to resuspend the cells, centrifuge at 300 g for 5 min, and discard the supernatant;

8) loading for flow cytometry: use 150 μl 1% FBS-PBS to resuspend the cells, and detect on a flow cytometer;

9) Data analysis: use software FlowJo 7.6 of the flow cytometer to analyze data, and use Graphpad Prism 5 to plot graphs to calculate EC50 values.

Figure 4:
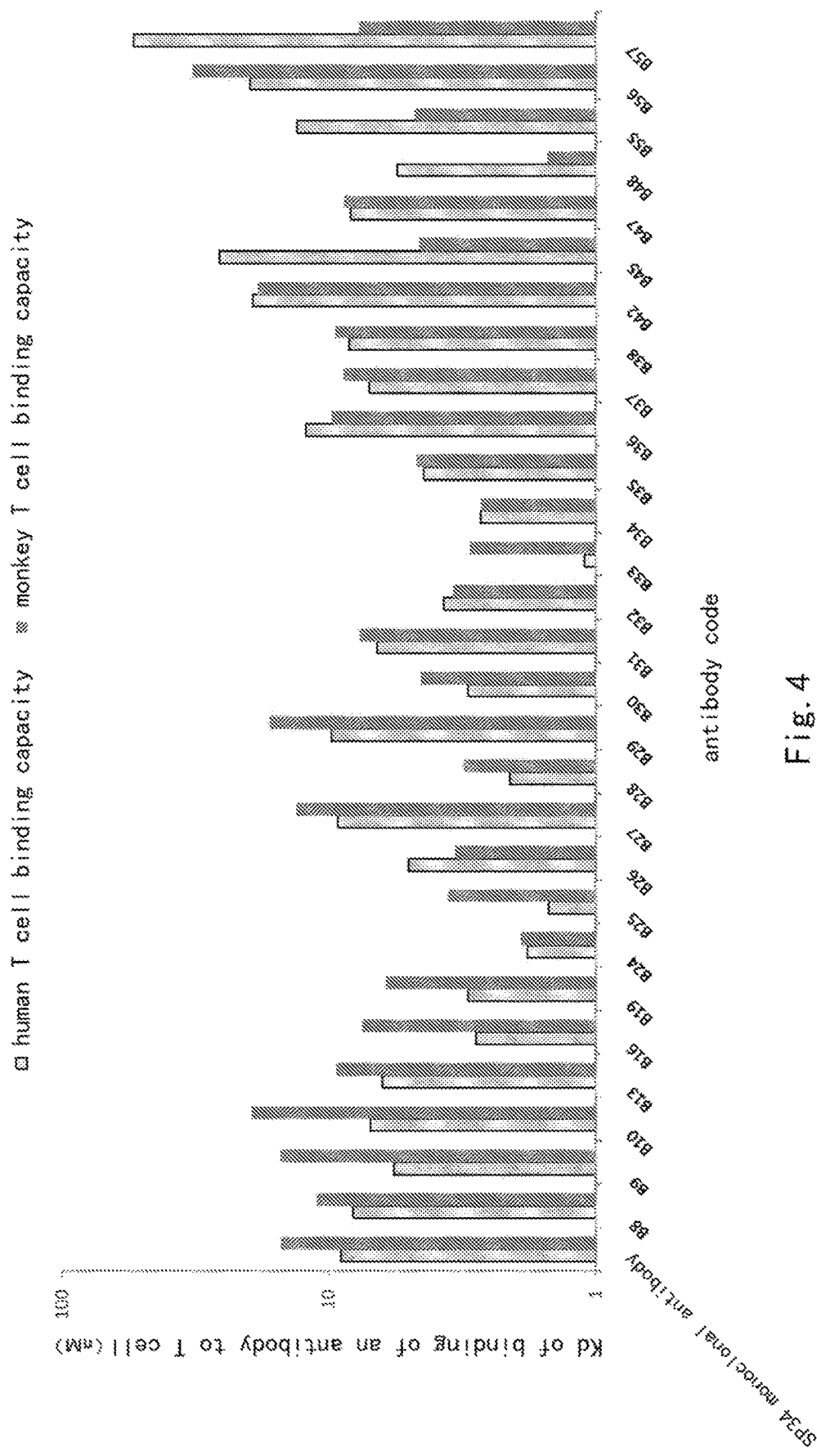
FIG. 4 illustrates binding capabilities of the monoclonal antibodies with the CD3+ T cells.

Detection results of binding activities between the antibodies and human and monkey T cells are shown in FIG. 4. FIG. 4 illustrates binding capabilities of the monoclonal antibodies with the CD3+T cells.

From the detection results of cell binding activities, it can be seen that, compared with sp34 monoclonal antibody, these antibodies all have higher affinity (EC50<100 nM) and can bind with both human and monkey CD3.

Example 3: Multi-Functional Antibody Preparation According to the Present Invention I. Plasmid Construction Method Operation steps are the same as those in "1. Method for construction of antibody expression plasmids" in Example 2 of the present application. Specifically, the construction of three plasmids is involved: light chain expression plasmid (pL), heavy chain expression plasmid (pH), and fusion peptide expression plasmid (pF1).

The multi-functional antibody expression method is the same as that in "2. Antibody expression methods" in Example 2 of the present application. During transfection, it is a co-transfection of three plasmids: to express the multi-functional antibody shown in FIG. 1, plasmids pL, pH and pF1 are needed for co-transfection to CHO-S or 293E cells for expression.

The multi-functional antibody according to the present invention consists of three polypeptides:

(1) Fusion peptide consisting of heavy chain variable region (VHs), linker1, light chain variable region (VLs), hinge 1, heavy chain constant region 2 (CH2), and heavy chain constant region 3 (CH3-b). See Table 10 for the linker1 sequence, the Hin2-9 sequence in Table 11 is the hinge 1, the CH2 sequence is in Table 19, and the CH3 sequence is the CH3-b sequence in Table 20. Sequences of VHs and VLs are all from the sequences of new humanized SP34 in the present application, and see Table 2 for details.

(2) Heavy chain consisting of heavy chain variable region (VHm), heavy chain constant region 2 (CH1), hinge, heavy chain constant region 2 (CH2), and heavy chain constant region 3 (CH3-a). See Table 13 for the CH1 sequence, the Hin1 sequence in Table 11 is the hinge sequence, the CH2 sequence is consistent with CH2 of the fusion peptide (see Table 19), and the CH3 sequence is the CH3-a sequence in Table 20; CH3-a corresponds, one to one, to CH3-b in Table 20.

(3) Light chain consisting of light chain variable region (VLm) and light chain constant region (CL). See Table 12 for the CL sequence;

See FIG. 1B for a schematic diagram of the composition of the multi-functional antibody.

II. Purification Method for the Multi-Functional Antibody:

Antibody purification is performed mainly through affinity chromatography, ion exchange chromatography, hydrophobic chromatography, and molecular sieve, specifically:

(1) Harvest: centrifuge a cell culture broth containing expressed antibody at 3000×g for 10 min, take the supernatant, filter with a 0.22 μm filter, and store at 4° C. for later use;

(2) Affinity chromatography (MabSelect SuRe GE 17-5438-01, taking 18 ml column volume as an example)
   a) Equilibrate: use the binding buffer (25 mM Tris, pH 7.0-7.4) to equilibrate the column until the UV detector and conductance value become stable or reach baseline, and equilibrate at least 5 column volumes;
   b) Load: load the filtered supernatant at a flow rate of 5 ml/min;
   c) wash to equilibrate: use the binding buffer to wash for 5 column volumes;
   d) Elute: use an elution buffer (50 mM citric acid, pH 3.4±0.1) to elute the samples at a flow rate of 5 ml/min for 5 column volumes, and collect fractions of elution peaks;
   e) Neutralize: neutralize the eluate with 1 M Tris pH 8.0, and adjust pH of the sample to 6.0±0.1.

(3) Ion exchange chromatography (taking cation exchange chromatography as an example, HiTrap SP-HP GE 17-1151-01, 5 ml column volume)
   a) Sample preparation: subject the sample for affinity chromatography to microfiltration, dilute the sample with ultra-pure water such that the conductance is lower than 5 mS/cm, and then adjust pH to 6.0±0.1;
   b) Equilibrate and load: use 5 column volumes of the buffer B (25 mM citric acid+1 M sodium chloride, the conductance should be 80 to 90 mS/cm, and pH is 6.0±0.1) to equilibrate, then further use at least 5 column volumes of the buffer A (25 mM citric acid, the conductance should be lower than 5 mS/cm, and pH is 6.0±0.1) to equilibrate the column until the baselines of conductance, pH, and UV become stable, and then load the sample at a flow rate of 3 ml/min;
   c) wash to equilibrate: use 5 column volumes of the buffer A to wash at a flow rate of 5 ml/min;
   d) Elute: 20 column volumes of 0-30% buffer B; 10 column volumes of 100% buffer B, at a flow rate of 3 ml/min throughout the process, collect the eluate in different tubes, and detect the collected eluate.

(4) Hydrophobic chromatography (Capto phenyl ImpRes filler GE XK16/20 11.5 cm/23 ml)
   a) Sample processing: use 5 M sodium chloride to adjust the sample to 1 M sodium chloride, and adjust pH to 6.0;
   b) Equilibrate and load: first, use 5 column volumes of the buffer A (25 mM Citrate+1 M sodium chloride, and pH is 6.0±0.1) to equilibrate at a flow rate of 5 ml/min; and then load the sample at a flow rate of 3.3 ml/min;
   c) Wash to equilibrate: use 5 column volumes of the buffer A to wash at a flow rate of 5 ml/min; use 5 column volumes of 10% buffer B (25 mM Citrate, and pH is 6.0±0.1) to wash at a flow rate of 5 ml/min;
   d) Elute: elute with 90% buffer B at a flow rate of 5 ml/min, collect the eluting peaks in different tubes, and detect the collected eluting peaks;

(5) Molecular sieve (HiLoad Superdex 200 pg GE 28989336 26/600)
   a) Equilibrate and load: use a buffer (20 mM histidine+0.15 M sodium chloride, and pH is 6.0±0.1) to equilibrate for 2 column volumes, and then load the sample at a flow rate of 3 ml/min;
   Elute: elute with a buffer B for 2 column volumes, collect the eluting peaks in different tubes, and detect the collected eluting peaks.

See the table below for codes of some antibodies that are specifically expressed and amino acid sequences of corresponding antibody variable regions:

TABLE 25

Codes of some multi-functional antibodies and amino acid sequences of variable regions according to the present invention

| Antibody code | Polypeptide | Domain | Code | Amino acid sequences (those in bold and underlined being CDR) | Sequence No. |
|---|---|---|---|---|---|
| Y101 | Fusion Peptide | VHs | VH1 | EVQLVESGGGLVQPGGSLRLSCAASGFTFSTYAMNWVRQAPGKGLEWVARIRSKYNNYATYYADS VKDRFTISRDNAKNSLYLQMNSLRAEDTAVYYCARHGNFGNSYVSWFAYWGQGTLVTVSS | 45 |
|  |  | Linker1 | Lin10 | GGGGSGGGGSGGGGS | 129 |
|  |  | VLs | VL3 | EIVLTQSPATLSLSPGERATLSCRSSTGAVTTSNYANWVQQKPGQAPRGLIGGTNKRAPGVPARFSG SLSGTDATLTISSLQPEDFAVYYCALWYSNLWVFGGGTKVEIK | 63 |
|  |  | Hinge 1 | Hin4 | RGRGSDKTHTCP | 142 |
|  |  | CH2 | N297Q | PCPAPELLGGPSVFLFPPKPKDTLMISRTPEVTCVVVDVSHEDPEVKFNWYVDGVEVHNAKTKPREE QYQSTYRVVSVLTVLHQDWLNGKEYKCKVSNKALPAPIEKTISKAK | 159 |
|  |  | CH3-b | CW: CSAV | GQPREPQVCTLPPSRDELTKNQVSLSCAVKGFYPSDIAVEWESNGQPENNYKTTPPVLDSDGSFFLVS KLTVDKSRWQQGNVFSCSVMHEALHNHYTQKSLSLSPGK | 167 |
|  | Heavy chain | VHm | S70 | QVQLVQSGAEVKKPGSSVKVSCKTSGDTFSTYAISWVRQAPGQGLEWMGGIIPIFGKAHYAQKFQ GRVTITADESTSTAYMELSSLRSEDTAVYFCARKFHFVSGSPFGMDVWGQGTTVTVSS | 106 |
|  |  | CH1 | CH1 | ASTKGPSVFPLAPSSKSTSGGTAALGCLVKDYFPEPVTVSWNSGALTSGVHTFPAVLQSSGLYSLSSV VTVPSSSLGTQTYICNVNHKPSNTKVDKKV | 154 |
|  |  | Hinge 2 | Hin1 | EPKSCDKTHTCP | 139 |
|  |  | CH2 | N297Q | PCPAPELLGGPSVFLFPPKPKDTLMISRTPEVTCVVVDVSHEDPEVKFNWYVDGVEVHNAKTKPREE QYQSTYRVVSVLTVLHQDWLNGKEYKCKVSNKALPAPIEKTISKAK | 159 |
|  |  | CH3-a | CW: CSAV | GQPREPQVYTLPPCRDELTKNQVSLWCLVKGFYPSDIAVEWESNGQPENNYKTTPPVLDSDGSFFLY SKLTVDKSRWQQGNVFSCSVMHEALHNHYTQKSLSLSPGK | 166 |

TABLE 25-continued

Codes of some multi-functional antibodies and amino acid sequences of variable regions according to the present invention

| Antibody code | Polypeptide | Domain | Code | Amino acid sequences (those in bold and underlined being CDR) | Sequence No. |
|---|---|---|---|---|---|
| | Light chain | VLm | S70 | EIVLTQSPATLSLSPGERATLSCRASQSVSSYLAWYQQKPGQAPRLLIYDASNRATGIPARFSGSGSGT DFTLTISSLEPEDFAVYYCQQRSNWPTFGQGTKVEIK | 107 |
| | | CL | Lc1 | RTVAAPSVFIFPPSDEQLKSGTASVVCLLNNFYPREAKVQWKVDNALQSGNSQESVTEQDSKDSTYS LSSTLTLSKADYEKHKVYACEVTHQGLSSPVTKSFNRGEC | 148 |
| Y102 | Fusion Peptide | VHs | VH2 | QVQLVESGGGVVQPGRSLRLSCAASGFTFSTYAMNWVRQAPGKGLEWVARIRSKYNNYATYYAD SVKDRFTISRDNSKNTLYLQMNSLRAEDTAVYYCARHGNFGNSYVSWFAYWGQGTLVTVSS | 48 |
| | | Linker1 | Lin10 | GGGGSGGGGSGGGGS | 129 |
| | | Vls | VL3 | EIVLTQSPATLSLSPGERATLSCRSSTGAVTTSNYANWVQQKPGQAPRGLIGGTNKRAPGVPARFSG SLSGTDATLTISSLQPEDFAVYYCALWYSNLWVFGGGTKVEIK | 63 |
| | | Hinge 1 | Hin4 | RGRGSDKTHTCP | 142 |
| | | CH2 | | N297QPCPAPELLGGPSVFLFPPKPKDTLMISRTPEVTCVVVDVSHEDPEVKFNWYVDGVEVHNAKTKPREE QYQSTYRVVSVLTVLHQDWLNGKEYKCKVSNKALPAPIEKTISKAK | 159 |
| | | CH3-b | CW: CSAV | GQPREPQVCTLPPSRDELTKNQVSLSCAVKGFYPSDIAVEWESNGQPENNYKTTPPVLDSDGSFFLVS KLTVDKSRWQQGNVFSCSVMHEALHNHYTQKSLSLSPGK | 167 |
| | Heavy chain | VHm | S70 | QVQLVQSGAEVKKPGSSVKVSCKTSGDTFSTYAISWVRQAPGQGLEWMGGIIPIFGKAHYAQKFQ GRVTITADESTSTAYMELSSLRSEDTAVYFCARKFHFVSGSPFGMDVWGQGTTVTVSS | 106 |
| | | CH1 | CH1 | ASTKGPSVFPLAPSSKSTSGGTAALGCLVKDYFPEPVTVSWNSGALTSGVHTFPAVLQSSGLYSLSSV VTVPSSSLGTQTYICNVNHKPSNTKVDKKV | 154 |
| | | Hinge 2 | Hin1 | EPKSCDKTHTCP | 139 |
| | | CH2 | | N297QPCPAPELLGGPSVFLFPPKPKDTLMISRTPEVTCVVVDVSHEDPEVKFNWYVDGVEVHNAKTKPREE QYQSTYRVVSVLTVLHQDWLNGKEYKCKVSNKALPAPIEKTISKAK | 159 |
| | | CH3-a | CW: CSAV | GQPREPQVYTLPPCRDELTKNQVSLWCLVKGFYPSDIAVEWESNGQPENNYKTTPPVLDSDGSFFLY SKLTVDKSRWQQGNVFSCSVMHEALHNHYTQKSLSLSPGK | 166 |
| | Light chain | VL | S70 | EIVLTQSPATLSLSPGERATLSCRASQSVSSYLAWYQQKPGQAPRLLIYDASNRATGIPARFSGSGSGT DFTLTISSLEPEDFAVYYCQQRRSNWPTFGQGTKVEIK | 107 |
| | | CL | Lc1 | RTVAAPSVFIFPPSDEQLKSGTASVVCLLNNFYPREAKVQWKVDNALQSGNSQESVTEQDSKDSTYS LSSTLTLSKADYEKHKVYACEVTHQGLSSPVTKSFNRGEC | 148 |
| Y103 | Fusion Peptide | VHs | VH2 | QVQLVESGGGVVQPGRSLRLSCAASGFTFSTYAMNWVRQAPGKGLEWVARIRSKYNNYATYVAD SVKDRFTISRDNSKNTLYLQMNSLRAEDTAVYYCARHGNFGNSYVSWFAYWGQGTLVTVSS | 48 |
| | | Linker1 | Lin10 | GGGGSGGGGSGGGGS | 129 |
| | | VLs | VL5 | QTVVTQEPSLTVSPGGTVTLTCRSSTGAVTTSNYANWVQQKPGQAPRGLIGGTNKRAPGVPARFSG SLLGGKAALTLSGVQPEDEAEYYCALWYSNLWVFGGGTKVEIK | 71 |
| | | Hinge 1 | Hin4 | RGRGSDKTHTCP | 142 |
| | | CH2 | | N297QPCPAPELLGGPSVFLFPPKPKDTLMISRTPEVTCVVVDVSHEDPEVKFNWYVDGVEVHNAKTKPREE QYQSTYRVVSVLTVLHQDWLNGKEYKCKVSNKALPAPIEKTISKAK | 159 |
| | | CH3-b | CW: CSAV | GQPREPQVCTLPPSRDELTKNQVSLSCAVKGFYPSDIAVEWESNGQPENNYKTTPPVLDSDGSFFLVS KLTVDKSRWQQGNVFSCSVMHEALHNHYTQKSLSLSPGK | 167 |
| | Heavy chain | VHm | S70 | QVQLVQSGAEVKKPGSSVKVSCKTSGDTFSTYAISWVRQAPGQGLEWMGGIIPIFGKAHYAQKFQ GRVTITADESTSTAYMELSSLRSEDTAVYFCARKFHFVSGSPFGMDVWGQGTTVTVSS | 106 |
| | | CH1 | CH1 | ASTKGPSVFPLAPSSKSTSGGTAALGCLVKDYFPEPVTVSWNSGALTSGVHTFPAVLQSSGLYSLSSV VTVPSSSLGTQTYICNVNHKPSNTKVDKKV | 154 |
| | | Hinge2 | Hin1 | EPKSCDKTHTCP | 139 |
| | | CH2 | | N297QPCPAPELLGGPSVFLFPPKPKDTLMISRTPEVTCVVVDVSHEDPEVKFNWYVDGVEVHNAKTKPREE QYQSTYRVVSVLTVLHQDWLNGKEYKCKVSNKALPAPIEKTISKAK | 159 |
| | | CH3-a | CW: CSAV | GQPREPQVYTLPPCRDELTKNQVSLWCLVKGFYPSDIAVEWESNGQPENNYKTTPPVLDSDGSFFLY SKLTVDKSRWQQGNVFSCSVMHEALHNHYTQKSLSLSPGK | 166 |
| | Light chain | VLm | S70 | EIVLTQSPATLSLSPGERATLSCRASQSVSSYLAWYQQKPGQAPRLLIYDASNRATGIPARFSGSGSGT DFTLTISSLEPEDFAVYYCQQRRSNWPTFGQGTKVEIK | 107 |
| | | CL | Lc1 | RTVAAPSVFIFPPSDEQLKSGTASVVCLLNNFYPREAKVQWKVDNALQSGNSQESVTEQDSKDSTYS LSSTLTLSKADYEKHKVYACEVTHQGLSSPVTKSFNRGEC | 148 |
| Y104 | Fusion Peptide | VHs | VH2a | QVQLVESGGGVVQPGRSLRLSCAASGFTFSTYAMNWVRQAPGKGLEWVARIRSKYNNYATYVAD SVKDRFTISRDDNSKNTLYLQMNSLRAEDTAVYYCARHGNFGNSYVSWFAYWGQGTLVTVSS | 49 |
| | | Linker1 | Lin10 | GGGGSGGGGSGGGGS | 129 |
| | | VLs | VL3 | EIVLTQSPATLSLSPGERATLSCRSSTGAVTTSNYANWVQQKPGQAPRGLIGGTNKRAPGVPARFSG SLSGTDATLTISSLQPEDFAVYYCALWYSNLWVFGGGTKVEIK | 63 |
| | | Hinge 1 | Hin4 | RGRGSDKTHTCP | 142 |
| | | CH2 | | N297QPCPAPELLGGPSVFLFPPKPKDTLMISRTPEVTCVVVDVSHEDPEVKFNWYVDGVEVHNAKTKPREE QYQSTYRVVSVLTVLHQDWLNGKEYKCKVSNKALPAPIEKTISKAK | 159 |
| | | CH3-b | CW: CSAV | GQPREPQVCTLPPSRDELTKNQVSLSCAVKGFYPSDIAVEWESNGQPENNYKTTPPVLDSDGSFFLVS KLTVDKSRWQQGNVFSCSVMHEALHNHYTQKSLSLSPGK | 167 |

TABLE 25-continued

Codes of some multi-functional antibodies and amino acid sequences of variable regions according to the present invention

| Antibody code | Polypeptide | Domain | Code | Amino acid sequences (those in bold and underlined being CDR) | Sequence No. |
|---|---|---|---|---|---|
| | Heavy chain | VHm | S70 | QVQLVQSGAEVKKPGSSVKVSCKTSGDTFSTYAISWVRQAPGQGLEWMGGIIPIFGKAHYAQKFQ GRVTITADESTSTAYMELSSLRSEDTAVYFCARKFHFVSGSPFGMDVWGQGTTVTVSS | 106 |
| | | CH1 | CH1 | ASTKGPSVFPLAPSSKSTSGGTAALGCLVKDYFPEPVTVSWNSGALTSGVHTFPAVLQSSGLYSLSSV VTVPSSSLGTQTYICNVNHKPSNTKVDKKV | 154 |
| | | HingE 2 | Hin1 | EPKSCDKTHTCP | 139 |
| | | CH2 | | N297QPCPAPELLGGPSVFLFPPKPKDTLMISRTPEVTCVVVDVSHEDPEVKFNWYVDGVEVHNAKTKPREE QYQSTYRVVSVLTVLHQDWLNGKEYKCKVSNKALPAPIEKTISKAK | 159 |
| | | CH3-a | CW: CSAV | GQPREPQVYTLPPCRDELTKNQVSLWCLVKGFYPSDIAVEWESNGQPENNYKTTPPVLDSDGSFFLY SKLTVDKSRWQQGNVFSCSVMHEALHNHYTQKSLSLSPGK | 166 |
| | Light chain | VLm | S70 | EIVLTQSPATLSLSPGERATLSCRASQSVSSYLAWYQQKPGQAPRLLIYDASNRATGIPARFSGSGSGT DFTLTISSLEPEDFAVYYCQQRSNWPTFGQGTKVEIK | 107 |
| | | CL | Lc1 | RTVAAPSVFIFPPSDEQLKSGTASVVCLLNNFYPREAKVQWKVDNALQSGNSQESVTEQDSKDSTYS LSSTLTLSKADYEKHKVYACEVTHQGLSSPVTKSFNRGEC | 148 |
| Y105 | Fusion peptide | VH2 | VH2a | QVQLVESGGGVVQPGRSLRLSCAASGFTFSTYAMNWVRQAPGKGLEWVARIRSKYNNYATYYAD SVKDRFTISRDDSKNTLYLQMNSLRAEDTAVYYCARHGNFGNSYVSWFAYWGQGTLVTVSS | 49 |
| | | Linker1 | Lin10 | GGGGSGGGGSGGGGS | 129 |
| | | VLs | VL5 | QTVVTQEPSLTVSPGGTVTLTCRSSTGAVTTSNYANWVQQKPGQAPRGLIGGTNKRAPGVPARFSG SLLGGKAALTLSGVQPEDEAEYYCALWYSNLWVFGGGTKVEIK | 71 |
| | | Hinge 1 | Hin4 | RGRGSDKTHTCP | 142 |
| | | CH2 | | N297QPCPAPELLGGPSVFLFPPKPKDTLMISRTPEVTCVVVDVSHEDPEVKFNWYVDGVEVHNAKTKPREE QYQSTYRVVSVLTVLHQDWLNGKEYKCKVSNKALPAPIEKTISKAK | 159 |
| | | CH3-b | CW: CSAV | GQPREPQVCTLPPSRDELTKNQVSLSCAVKGFYPSDIAVEWESNGQPENNYKTTPPVLDSDGSFFLVS KLTVDKSRWQQGNVFSCSVMHEALHNHYTQKSLSLSPGK | 167 |
| | Heavy chain | VHm | S70 | QVQLVQSGAEVKKPGSSVKVSCKTSGDTFSTYAISWVRQAPGQGLEWMGGIIPIFGKAHYAQKFQ GRVTITADESTSTAYMELSSLRSEDTAVYFCARKFHFVSGSPFGMDVWGQGTTVTVSS | 106 |
| | | CH1 | CH1 | ASTKGPSVFPLAPSSKSTSGGTAALGCLVKDYFPEPVTVSWNSGALTSGVHTFPAVLQSSGLYSLSSV VTVPSSSLGTQTYICNVNHKPSNTKVDKKV | 154 |
| | | Hinge 2 | Hin1 | EPKSCDKTHTCP | 139 |
| | | CH2 | | N297QPCPAPELLGGPSVFLFPPKPKDTLMISRTPEVTCVVVDVSHEDPEVKFNWYVDGVEVHNAKTKPREE QYQSTYRVVSVLTVLHQDWLNGKEYKCKVSNKALPAPIEKTISKAK | 159 |
| | | CH3-a | CW: CSAV | GQPREPQVYTLPPCRDELTKNQVSLWCLVKGFYPSDIAVEWESNGQPENNYKTTPPVLDSDGSFFLY SKLTVDKSRWQQGNVFSCSVMHEALHNHYTQKSLSLSPGK | 166 |
| | Light chain | VL | S70 | EIVLTQSPATLSLSPGERATLSCRASQSVSSYLAWYQQKPGQAPRLLIYDASNRATGIPARFSGSGSGT DFTLTISSLEPEDFAVYYCQQRSNWPTFGQGTKVEIK | 107 |
| | | CL | Lc1 | RTVAAPSVFIFPPSDEQLKSGTASVVCLLNNFYPREAKVQWKVDNALQSGNSQESVTEQDSKDSTYS LSSTLTLSKADYEKHKVYACEVTHQGLSSPVTKSFNRGEC | 148 |
| Y150-F8-3 | Fusion Peptide | VHs | VH1 | EVQLVESGGGLVQPGGSLRLSCAASGFTFSTYAMNWVRQAPGKGLEWVARIRSKYNNYATYVADS VKDRFTISRDNAKNSLYLQMNSLRAEDTAVYYCARHGNFGNSYVSWFAYWGQGTLVTVSS | 45 |
| | | Linker1 | Lin10 | GGGGSGGGGSGGGGS | 129 |
| | | VLs | VL3 | EIVLTQSPATLSLSPGERATLSCRSSTGAVTTSNYANWVQQKPGQAPRGLIGGTNKRAPGVPARFSG SLSGTDATLTISSLQPEDFAVYYCALWYSNLWVFGGGTKVEIK | 63 |
| | | Hinge1 | Hin3 | GGGGSDKTHTCP | 141 |
| | | CH2 | FES | PCPAPEFEGGPSVFLFPPKPKDTLMISRTPEVTCVVVDVSHEDPEVKFNWYVDGVEVHNAKTKPREE QYNSTYRVVSVLTVLHQDWLNGKEYKCKVSNKALPASIEKTISKAK | 157 |
| | | CH3-b | CW: CSAV | GQPREPQVCTLPPSRDELTKNQVSLSCAVKGFYPSDIAVEWESNGQPENNYKTTPPVLDSDGSFFLVS KLTVDKSRWQQGNVFSCSVMHEALHNHYTQKSLSLSPGK | 167 |
| | Heavy chain | VHm | Dara | EVQLLESGGGLVQPGGSLRLSCAVSGFTFNSFAMSWVRQAPGKGLEWVSAISGSGGGTYYADSVK GRFTISRDNSKNTLYLQMNSLRAEDTAVYFCAKDKILWFGEPVFDYWGQGTLVTVSS | 90 |
| | | CH1 | CH1 | ASTKGPSVFPLAPSSKSTSGGTAALGCLVKDYFPEPVTVSWNSGALTSGVHTFPAVLQSSGLYSLSSV VTVPSSSLGTQTYICNVNHKPSNTKVDKKV | 154 |
| | | Hinge 2 | Hin1 | EPKSCDKTHTCP | 139 |
| | | CH2 | FES | PCPAPEFEGGPSVFLFPPKPKDTLMISRTPEVTCVVVDVSHEDPEVKFNWYVDGVEVHNAKTKPREE QYNSTYRVVSVLTVLHQDWLNGKEYKCKVSNKALPASIEKTISKAK | 157 |
| | | CH3-a | CW: CSAV | GQPREPQVYTLPPCRDELTKNQVSLWCLVKGFYPSDIAVEWESNGQPENNYKTTPPVLDSDGSFFLY SKLTVDKSRWQQGNVFSCSVMHEALHNHYTQKSLSLSPGK | 166 |
| | Light chain | VLm | Dara | EIVLTQSPATLSLSPGERATLSCRASQSVSSYLAWYQQKPGQAPRLLIYDASNRATGIPARFSGSGSGT DFTLTISSLEPEDFAVYYCQQRSNWPPTFGQGTKVEIK | 91 |
| | | CL | Lc1 | RTVAAPSVFIFPPSDEQLKSGTASVVCLLNNFYPREAKVQWKVDNALQSGNSQESVTEQDSKDSTYS LSSTLTLSKADYEKHKVYACEVTHQGLSSPVTKSFNRGEC | 148 |

TABLE 25-continued

Codes of some multi-functional antibodies and amino acid sequences of variable regions according to the present invention

| Antibody code | Polypeptide | Domain | Code | Amino acid sequences (those in bold and underlined being CDR) | Sequence No. |
|---|---|---|---|---|---|
| Y150-F8-4 | Fusion Peptide | VHs | VH2 | QVQLVESGGGVVQPGRSLRLSCAASGFTFSTYAMNWVRQAPGKGLEWVARIRSKYNNYATYVAD SVKDRFTISRDNSKNTLYLQMNSLRAEDTAVYYCARHGNFGNSYVSWFAYWGQGTLVTVSS | 48 |
|  |  | Linker1 | Lin10 | GGGGSGGGGSGGGGS | 129 |
|  |  | VLs | VL3 | EIVLTQSPATLSLSPGERATLSCRSSTGAVTTSNYANWVQQKPGQAPRGLIGGTNKRAPGVPARFSG SLSGTDATLTISSLQPEDFAVYYCALWYSNLWVFGGGTKVEIK | 63 |
|  |  | Hinge 1 | Hin3 | GGGGSDKTHTCP | 141 |
|  |  | CH2 | FES | PCPAPEFEGGPSVFLFPPKPKDTLMISRTPEVTCVVVDVSHEDPEVKFNWYVDGVEVHNAKTKPREE QYNSTYRVVSVLTVLHQDWLNGKEYKCKVSNKALPASIEKTISKAK | 157 |
|  |  | CH3-b | CW: CSAV | GQPREPQVCTLPPSRDELTKNQVSLSCAVKGFYPSDIAVEWESNGQPENNYKTTPPVLDSDGSFFLVS KLTVDKSRWQQGNVFSCSVMHEALHNHYTQKSLSLSPGK | 167 |
|  | Heavy chain | VHm | Dara | EVQLLESGGGLVQPGGSLRLSCAVSGFTFNSFAMSWVRQAPGKGLEWVSAISGSGGGTYYADSVK GRFTISRDNSKNTLYLQMNSLRAEDTAVYFCAKDKILWFGEPVFDYWGQGTLVTVSS | 90 |
|  |  | CH1 | CH1 | ASTKGPSVFPLAPSSKSTSGGTAALGCLVKDYFPEPVTVSWNSGALTSGVHTFPAVLQSSGLYSLSSV VTVPSSSLGTQTYICNVNHKPSNTKVDKKV | 154 |
|  |  | Hinge2 | Hin1 | EPKSCDKTHTCP | 139 |
|  |  | CH2 | FES | PCPAPEFEGGPSVFLFPPKPKDTLMISRTPEVTCVVVDVSHEDPEVKFNWYVDGVEVHNAKTKPREE QYNSTYRVVSVLTVLHQDWLNGKEYKCKVSNKALPASIEKTISKAK | 157 |
|  |  | CH3-a | CW: CSAV | GQPREPQVYTLPPCRDELTKNQVSLWCLVKGFYPSDIAVEWESNGQPENNYKTTPPVLDSDGSFFLY SKLTVDKSRWQQGNVFSCSVMHEALHNHYTQKSLSLSPGK | 166 |
|  | Light chain | VLm | Dara | EIVLTQSPATLSLSPGERATLSCRASQSVSSYLAWYQQKPGQAPRLLIYDASNRATGIPARFSGSGSGT DFTLTISSLEPEDFAVYYCQQRRSNWPPTFGQGTKVEIK | 91 |
|  |  | CL | Lc1 | RTVAAPSVFIFPPSDEQLKSGTASVVCLLNNFYPREAKVQWKVDNALQSGNSQESVTEQDSKDSTYS LSSTLTLSKADYEKHKVYACEVTHQGLSSPVTKSFNRGEC | 148 |
| Y150-F8-5 | Fusion Peptide | VHs | VH2a | QVQLVESGGGVVQPGRSLRLSCAASGFTFSTYAMNWVRQAPGKGLEWVARIRSKYNNYATYVAD SVKDRFTISRDDSKNTLYLQMNSLRAEDTAVYYCARHGNFGNSYVSWFAYWGQGTLVTVSS | 49 |
|  |  | Linker1 | Lin10 | GGGGSGGGGSGGGGS | 129 |
|  |  | VLs | VL5 | QTVVTQEPSLTVSPGGTVTLTCRSSTGAVTTSNYANWVQQKPGQAPRGLIGGTNKRAPGVPARFSG SLLGGKAALTLSGVQPEDEAEYYCALWYSNLWVFGGGTKVEIK | 71 |
|  |  | Hinge 1 | Hin3 | GGGGSDKTHTCP | 141 |
|  |  | CH2 | FEX | PCPAPEFEGGPSVFLFPPKPKDTLMISRTPEVTCVVVDVSHEDPEVKFNWYVDGVEVHNAKTKPREE QYNSTYRVVSVLTVLHQDWLNGKEYKCKVSNKALPASIEKTISKAK | 157 |
|  |  | CH3-b | CW: CSAV | GQPREPQVCTLPPSRDELTKNQVSLSCAVKGFYPSDIAVEWESNGQPENNYKTTPPVLDSDGSFFLVS KLTVDKSRWQQGNVFSCSVMHEALHNHYTQKSLSLSPGK | 167 |
|  | Heavy chain | VHm | Dara | EVQLLESGGGLVQPGGSLRLSCAVSGFTFNSFAMSWVRQAPGKGLEWVSAISGSGGGTYYADSVK GRFTISRDNSKNTLYLQMNSLRAEDTAVYFCAKDKILWFGEPVFDYWGQGTLVTVSS | 90 |
|  |  | CH1 | CH1 | ASTKGPSVFPLAPSSKSTSGGTAALGCLVKDYFPEPVTVSWNSGALTSGVHTFPAVLQSSGLYSLSSV VTVPSSSLGTQTYICNVNHKPSNTKVDKKV | 154 |
|  |  | Hinge 2 | Hin1 | EPKSCDKTHTCP | 139 |
|  |  | CH2 | FES | PCPAPEFEGGPSVFLFPPKPKDTLMISRTPEVTCVVVDVSHEDPEVKFNWYVDGVEVHNAKTKPREE QYNSTYRVVSVLTVLHQDWLNGKEYKCKVSNKALPASIEKTISKAK | 157 |
|  |  | CH3-a | CW: CSAV | GQPREPQVYTLPPCRDELTKNQVSLWCLVKGFYPSDIAVEWESNGQPENNYKTTPPVLDSDGSFFLY SKLTVDKSRWQQGNVFSCSVMHEALHNHYTQKSLSLSPGK | 166 |
|  | Light chain | VLm | Dara | EIVLTQSPATLSLSPGERATLSCRASQSVSSYLAWYQQKPGQAPRLLIYDASNRATGIPARFSGSGSGT DFTLTISSLEPEDFAVYYCQQRRSNWPPTFGQGTKVEIK | 91 |
|  |  | CL | Lc1 | RTVAAPSVFIFPPSDEQLKSGTASVVCLLNNFYPREAKVQWKVDNALQSGNSQESVTEQDSKDSTYS LSSTLTLSKADYEKHKVYACEVTHQGLSSPVTKSFNRGEC | 148 |
| Y150-F8-6 | Fusion Peptide | VHs | VH2c | QVQLVESGGGVVQPGRSLRLSCAASGFTFSTYAMNWVRQAPGKGLEWVARIRSKYNNYATYVAD SVKDRFTISRDDSKNTLYLQMNSLRAEDTAVYYCVRHGNFGNSYVSWFAYWGQGTLVTVSS | 51 |
|  |  | Linker1 | Lin10 | GGGGSGGGGSGGGGS | 129 |
|  |  | VLs | VL5 | QTVVTQEPSLTVSPGGTVTLTCRSSTGAVTTSNYANWVQQKPGQAPRGLIGGTNKRAPGVPARFSG SLLGGKAALTLSGVQPEDEAEYYCALWYSNLWVFGGGTKVEIK | 71 |
|  |  | Hinge 1 | Hin3 | GGGGSDKTHTCP | 141 |
|  |  | CH2 | FES | PCPAPEFEGGPSVFLFPPKPKDTLMISRTPEVTCVVVDVSHEDPEVKFNWYVDGVEVHNAKTKPREE QYNSTYRVVSVLTVLHQDWLNGKEYKCKVSNKALPASIEKTISKAK | 157 |
|  |  | CH3-b | CW: CSAV | GQPREPQVCTLPPSRDELTKNQVSLSCAVKGFYPSDIAVEWESNGQPENNYKTTPPVLDSDGSFFLVS KLTVDKSRWQQGNVFSCSVMHEALHNHYTQKSLSLSPGK | 167 |
|  | Heavy chain | VHm | Dara | EVQLLESGGGLVQPGGSLRLSCAVSGFTFNSFAMSWVRQAPGKGLEWVSAISGSGGGTYYADSVK GRFTISRDNSKNTLYLQMNSLRAEDTAVYFCAKDKILWFGEPVFDYWGQGTLVTVSS | 90 |
|  |  | CH1 | CH1 | ASTKGPSVFPLAPSSKSTSGGTAALGCLVKDYFPEPVTVSWNSGALTSGVHTFPAVLQSSGLYSLSSV VTVPSSSLGTQTYICNVNHKPSNTKVDKKV | 154 |
|  |  | Hinge 2 | Hin1 | EPKSCDKTHTCP | 139 |
|  |  | CH2 | FES | PCPAPEFEGGPSVFLFPPKPKDTLMISRTPEVTCVVVDVSHEDPEVKFNWYVDGVEVHNAKTKPREE QYNSTYRVVSVLTVLHQDWLNGKEYKCKVSNKALPASIEKTISKAK | 157 |

TABLE 25-continued

Codes of some multi-functional antibodies and amino acid sequences of variable regions according to the present invention

| Antibody code | Polypeptide | Domain | Code | Amino acid sequences (those in bold and underlined being CDR) | Sequence No. |
|---|---|---|---|---|---|
| | | CH3-a | CW: CSAV | GQPREPQVYTLPPCRDELTKNQVSLWCLVKGFYPSDIAVEWESNGQPENNYKTTPPVLDSDGSFFLY SKLTVDKSRWQQGNVFSCSVMHEALHNHYTQKSLSLSPGK | 166 |
| | Light chain | VLm | Dara | EIVLTQSPATLSLSPGERATLSCRASQSVSSYLAWYQQKPGQAPRLLIYDASNRATGIPARFSGSGSGT DFTLTISSLEPEDFAVYYCQQRSNWPPTFGQGTKVEIK | 91 |
| | | CL | Lc1 | RTVAAPSVFIFPPSDEQLKSGTASVVCLLNNFYPREAKVQWKVDNALQSGNSQESVTEQDSKDSTYS LSSTLTLSKADYEKHKVYACEVTHQGLSSPVTKSFNRGEC | 148 |
| Y150-F8-7 | Fusion Peptide | VH2 | Vh2a | QVQLVESGGGVVQPGRSLRLSCAASGFTFSTYAMNWVRQAPGKGLEWVARIRSKYNNYATYVAD SVKDRFTISRDDSKNTLYLQMNSLRAEDTAVYYCARHGNFGNSYVSWFAYWGQGTLVTVSS | 49 |
| | | Linker1 | Lin10 | GGGGSGGGGSGGGGS | 129 |
| | | VLs | VL5 | QTVVTQEPSLTVSPGGTVTLTCRSSTGAVTTSNYANWVQQKPGQAPRGLIGGTNKRAPGVPARFSG SLLGGKAALTLSGVQPEDEAEYYCALWYSNLWVFGGGTKVEIK | 71 |
| | | Hinge 1 | Hin6 | GRGRGSDKTHTCP | 144 |
| | | CH2 | N297A | PCPAPELLGGPSVFLFPPKPKDTLMISRTPEVTCVVVDVSHEDPEVKFNWYVDGVEVHNAKTKPREE QYASTYRVVSVLTVLHQDWLNGKEYKCKVSNKALPAPIEKTISKAK | 158 |
| | | CH3-b | CW: CSAV | GQPREPQVCTLPPSRDELTKNQVSLSCAVKGFYPSDIAVEWESNGQPENNYKTTPPVLDSDGSFFLVS KLTVDKSRWQQGNVFSCSVMHEALHNHYTQKSLSLSPGK | 167 |
| | Heavy chain | VHm | Dara | EVQLLESGGGLVQPGGSLRLSCAVSGFTFNSFAMSWVRQAPGKGLEWVSAISGSGGGTYYADSVK GRFTISRDNSKNTLYLQMNSLRAEDTAVYFCAKDKILWFGEPVFDYWGQGTLVTVSS | 90 |
| | | CH1 | CH1 | ASTKGPSVFPLAPSSKSTSGGTAALGCLVKDYFPEPVTVSWNSGALTSGVHTFPAVLQSSGLYSLSSV VTVPSSSLGTQTYICNVNHKPSNTKVDKKV | 154 |
| | | Hinge 2 | Hin1 | EPKSCDKTHTCP | 139 |
| | | CH2 | N297A | PCPAPELLGGPSVFLFPPKPKDTLMISRTPEVTCVVVDVSHEDPEVKFNWYVDGVEVHNAKTKPREE QYASTYRVVSVLTVLHQDWLNGKEYKCKVSNKALPAPIEKTISKAK | 158 |
| | | CH3-a | CW: CSAV | GQPREPQVYTLPPCRDELTKNQVSLWCLVKGFYPSDIAVEWESNGQPENNYKTTPPVLDSDGSFFLY SKLTVDKSRWQQGNVFSCSVMHEALHNHYTQKSLSLSPGK | 166 |
| | Light chain | VLm | Dara | EIVLTQSPATLSLSPGERATLSCRASQSVSSYLAWYQQKPGQAPRLLIYDASNRATGIPARFSGSGSGT DFTLTISSLEPEDFAVYYCQQRSNWPPTFGQGTKVEIK | 91 |
| | | CL | Lc1 | RTVAAPSVFIFPPSDEQLKSGTASVVCLLNNFYPREAKVQWKVDNALQSGNSQESVTEQDSKDSTYS LSSTLTLSKADYEKHKVYACEVTHQGLSSPVTKSFNRGEC | 148 |
| Y150-F8-8 | Fusion Peptide | VHs | VH2a | QVQLVESGGGVVQPGRSLRLSCAASGFTFSTYAMNWVRQAPGKGLEWVARIRSKYNNYATYVAD SVKDRFTISRDDSKNTLYLQMNSLRAEDTAVYYCARHGNFGNSYVSWFAYWGQGTLVTVSS | 49 |
| | | Linker1 | Lin10 | GGGGSGGGGSGGGGS | 129 |
| | | VLs | VL5 | QTVVTQEPSLTVSPGGTVTLTCRSSTGAVTTSNYANWVQQKPGQAPRGLIGGTNKRAPGVPARFSG SLLGGKAALTLSGVQPEDEAEYYCALWYSNLWVFGGGTKVEIK | 71 |
| | | Hinge 1 | Hin6 | GRGRGSDKTHTCP | 144 |
| | | CH2 | SG2 | PSPAPPVAGPSVFLFPPKPKDTLMISRTPEVTCVVVDVSHEDPEVQFNWYVDGVEVHNAKTKPREEQ FNSTFRVVSVLTVVHQDWLNGKEYKCKVSNKGLPAPIEKTISKTK | 161 |
| | | CH3-b | CW: CSAV | GQPREPQVCTLPPSRDELTKNQVSLSCAVKGFYPSDIAVEWESNGQPENNYKTTPPVLDSDGSFFLVS KLTVDKSRWQQGNVFSCSVMHEALHNHYTQKSLSLSPGK | 167 |
| | Heavy chain | VHm | Dara | EVQLLESGGGLVQPGGSLRLSCAVSGFTFNSFAMSWVRQAPGKGLEWVSAISGSGGGTYYADSVK GRFTISRDNSKNTLYLQMNSLRAEDTAVYFCAKDKILWFGEPVFDYWGQGTLVTVSS | 90 |
| | | CH1 | CH1 | ASTKGPSVFPLAPSSKSTSGGTAALGCLVKDYFPEPVTVSWNSGALTSGVHTFPAVLQSSGLYSLSSV VTVPSSSLGTQTYICNVNHKPSNTKVDKKV | 154 |
| | | Hinge 2 | Hin1 | EPKSCDKTHTCP | 139 |
| | | CH2 | SG2 | PSPAPPVAGPSVFLFPPKPKDTLMISRTPEVTCVVVDVSHEDPEVQFNWYVDGVEVHNAKTKPREEQ FNSTFRVVSVLTVVHQDWLNGKEYKCKVSNKGLPAPIEKTISKTK | 161 |
| | | CH3-a | CW: CSAV | GQPREPQVYTLPPCRDELTKNQVSLWCLVKGFYPSDIAVEWESNGQPENNYKTTPPVLDSDGSFFLY SKLTVDKSRWQQGNVFSCSVMHEALHNHYTQKSLSLSPGK | 166 |
| | Light chain | VLm | Dara | EIVLTQSPATLSLSPGERATLSCRASQSVSSYLAWYQQKPGQAPRLLIYDASNRATGIPARFSGSGSGT DFTLTISSLEPEDFAVYYCQQRSNWPPTFGQGTKVEIK | 91 |
| | | CL | Lc1 | RTVAAPSVFIFPPSDEQLKSGTASVVCLLNNFYPREAKVQWKVDNALQSGNSQESVTEQDSKDSTYS LSSTLTLSKADYEKHKVYACEVTHQGLSSPVTKSFNRGEC | 148 |
| Y150-F8-9 | Fusion Peptide | VHs | VH2a | QVQLVESGGGVVQPGRSLRLSCAASGFTFSTYAMNWVRQAPGKGLEWVARIRSKYNNYATYVAD SVKDRFTISRDDSKNTLYLQMNSLRAEDTAVYYCARHGNFGNSYVSWFAYWGQGTLVTVSS | 49 |
| | | Linker1 | Lin10 | GGGGSGGGGSGGGGS | 129 |
| | | VLs | VL5 | QTVVTQEPSLTVSPGGTVTLTCRSSTGAVTTSNYANWVQQKPGQAPRGLIGGTNKRAPGVPARFSG SLLGGKAALTLSGVQPEDEAEYYCALWYSNLWVFGGGTKVEIK | 71 |
| | | Hinge 1 | Hin6 | GRGRGSDKTHTCP | 144 |
| | | CH2 | SG2 | PSPAPPVAGPSVFLFPPKPKDTLMISRTPEVTCVVVDVSHEDPEVQFNWYVDGVEVHNAKTKPREEQ FNSTFRVVSVLTVVHQDWLNGKEYKCKVSNKGLPAPIEKTISKTK | 161 |
| | | CH3-b | CW: CSAV | GQPREPQVCTLPPSRDELTKNQVSLSCAVKGFYPSDIAVEWESNGQPENNYKTTPPVLDSDGSFFLVS KLTVDKSRWQQGNVFSCSVMHEALHNHYTQKSLSLSPGK | 167 |

TABLE 25-continued

Codes of some multi-functional antibodies and amino acid sequences of variable regions according to the present invention

| Antibody code | Polypeptide | Domain | Code | Amino acid sequences (those in bold and underlined being CDR) | Sequence No. |
|---|---|---|---|---|---|
| | Heavy chain | VHm | 2F5 | QVQLVQSGAEVKKPGSSVKVSCKASGGTFSSYAFSWVRQAPGQGLEWMGRVIPFLGIANSAQKFQGRVTITADKSTSTAYMDLSSLRSEDTAVYYCARDDIAALGPFDYWGQGTLVTVSS | 96 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKV | 154 |
| | | Hinge 2 | Hin1 | EPKSCDKTHTCP | 139 |
| | | CH2 | SG2 | PSPAPPVAGPSVFLFPPKPKDTLMISRTPEVTCVVVDVSHEDPEVQFNWYVDGVEVHNAKTKPREEQFNSTFRVVSVLTVVHQDWLNGKEYKCKVSNKGLPAPIEKTISKTK | 161 |
| | | CH3-a | CW:CSAV | GQPREPQVYTLPPCRDELTKNQVSLWCLVKGFYPSDIAVEWESNGQPENNYKTTPPVLDSDGSFFLYSKLTVDKSRWQQGNVFSCSVMHEALHNHYTQKSLSLSPGK | 166 |
| | Light chain | VLm | 2F5 | DIQMTQSPSSLSASVGDRVTITCRASQGISSWLAWYQQKPEKAPKSLIYAASSLQSGVPSRFSGSGSGTDFTLTISSLQPEDFATYYCQQYNSYPRTFGQGTKVEIK | 97 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 148 |
| Y150-F8-10 | Fusion Peptide | VHs | VH2j | QVQLVESGGGVVQPGRSLRLSCAASGFTFSTYAMNWVRQAPGKGLEWVARIRSKYNNYATYYADSVKDRFTISRDDSKNTLYLQMNSLRAEDTAVYYCARHGNFGNSYVSWAAYWGQGTLVTVSS | 58 |
| | | Linker1 | Lin10 | GGGGSGGGGSGGGGS | 129 |
| | | VLs | VL5a | QTVVTQEPSLTVSPGGTVTLTCRSSTGAVTTSNYANWFQQKPGQAPRGLIGGTNKRAPGVPARFGSSLLGGKAALTLSGVQPEDEAEYYCALWYSNLWVFGGGTKVEIK | 72 |
| | | Hinge1 | Hin6 | GRGRGSDKTHTCP | 144 |
| | | CH2 | G2D | PCPAPPVAGPSVFLFPPKPKDTLMISRTPEVTCVVVDVSHEAPEVQFNWYVDGVEVHNAKTKPREEQFNSTFRVVSVLTVVHQDWLNGKEYKCKVSNKGLPAPIEKTISKTK | 192 |
| | | CH3-b | CW:CSAV | GQPREPQVCTLPPSRDELTKNQVSLSCAVKGFYPSDIAVEWESNGQPENNYKTTPPVLDSDGSFFLVSKLTVDKSRWQQGNVFSCSVMHEALHNHYTQKSLSLSPGK | 167 |
| | Heavy chain | VHm | 2F5 | QVQLVQSGAEVKKPGSSVKVSCKASGGTFSSYAFSWVRQAPGQGLEWMGRVIPFLGIANSAQKFQGRVTITADKSTSTAYMDLSSLRSEDTAVYYCARDDIAALGPFDYWGQGTLVTVSS | 96 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKV | 154 |
| | | Hinge 2 | Hin1 | EPKSCDKTHTCP | 139 |
| | | CH2 | G2D | PCPAPPVAGPSVFLFPPKPKDTLMISRTPEVTCVVVDVSHEAPEVQFNWYVDGVEVHNAKTKPREEQFNSTFRVVSVLTVVHQDWLNGKEYKCKVSNKGLPAPIEKTISKTK | 192 |
| | | CH3-a | CW:CSAV | GQPREPQVYTLPPCRDELTKNQVSLWCLVKGFYPSDIAVEWESNGQPENNYKTTPPVLDSDGSFFLYSKLTVDKSRWQQGNVFSCSVMHEALHNHYTQKSLSLSPGK | 166 |
| | Light chain | VL | 2F5 | DIQMTQSPSSLSASVGDRVTITCRASQGISSWLAWYQQKPEKAPKSLIYAASSLQSGVPSRFSGSGSGTDFTLTISSLQPEDFATYYCQQYNSYPRTFGQGTKVEIK | 97 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 148 |
| Y150-F8-11 | Fusion Peptide | VHs | VH21 | QVQLVESGGGVVQPGRSLRLSCAASGFTFSTYAMNWVRQAPGKGLEWVARIRSKYNNYATYYADSVKDRFTISRDDSKNTLYLQMNSLRAEDTAVYYCARHGNFGNSYVSWFVYWGQGTLVTVSS | 60 |
| | | Linker1 | Lin10 | GGGGSGGGGSGGGGS | 129 |
| | | VLs | VL5a | QTVVTQEPSLTVSPGGTVTLTCRSSTGAVTTSNYANWFQQKPGQAPRGLIGGTNKRAPGVPARFGSSLLGGKAALTLSGVQPEDEAEYYCALWYSNLWVFGGGTKVEIK | 72 |
| | | Hinge 1 | Hin6 | GRGRGSDKTHTCP | 144 |
| | | CH2 | SG2 | PSPAPPVAGPSVFLFPPKPKDTLMISRTPEVTCVVVDVSHEDPEVQFNWYVDGVEVHNAKTKPREEQFNSTFRVVSVLTVVHQDWLNGKEYKCKVSNKGLPAPIEKTISKTK | 161 |
| | | CH3-b | CW:CSAV | GQPREPQVCTLPPSRDELTKNQVSLSCAVKGFYPSDIAVEWESNGQPENNYKTTPPVLDSDGSFFLVSKLTVDKSRWQQGNVFSCSVMHEALHNHYTQKSLSLSPGK | 167 |
| | Heavy chain | VHm | 2F5 | QVQLVQSGAEVKKPGSSVKVSCKASGGTFSSYAFSWVRQAPGQGLEWMGRVIPFLGIANSAQKFQGRVTITADKSTSTAYMDLSSLRSEDTAVYYCARDDIAALGPFDYWGQGTLVTVSS | 96 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKV | 154 |
| | | Hinge 2 | Hin1 | EPKSCDKTHTCP | 139 |
| | | CH2 | SG2 | PSPAPPVAGPSVFLFPPKPKDTLMISRTPEVTCVVVDVSHEDPEVQFNWYVDGVEVHNAKTKPREEQFNSTFRVVSVLTVVHQDWLNGKEYKCKVSNKGLPAPIEKTISKTK | 161 |
| | | CH3-a | CW:CSAV | GQPREPQVYTLPPCRDELTKNQVSLWCLVKGFYPSDIAVEWESNGQPENNYKTTPPVLDSDGSFFLYSKLTVDKSRWQQGNVFSCSVMHEALHNHYTQKSLSLSPGK | 166 |
| | Light chain | VLm | 2F5 | DIQMTQSPSSLSASVGDRVTITCRASQGISSWLAWYQQKPEKAPKSLIYAASSLQSGVPSRFSGSGSGTDFTLTISSLQPEDFATYYCQQYNSYPRTFGQGTKVEIK | 97 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 148 |

TABLE 25-continued

Codes of some multi-functional antibodies and amino acid sequences of variable regions according to the present invention

| Antibody code | Polypeptide | Domain | Code | Amino acid sequences (those in bold and underlined being CDR) | Sequence No. |
|---|---|---|---|---|---|
| Y150-F8-12 | Fusion Peptide | VH2 | VH21 | QVQLVESGGGVVQPGRSLRLSCAASGFTFSTYAMNWVRQAPGKGLEWVARIRSKYNNYATYVAD SVKDRFTISRDDSKNTLYLQMNSLRAEDTAVYYCARHGNFGNSYVSWFVYWGQGTLVTVSS | 60 |
| | | Linker1 | Lin10 | GGGGSGGGGSGGGGS | 129 |
| | | VLs | VL5b | QTVVTQEPSLTVSPGGTVTLTCRSSTGAVTTSNYANWVQQKPGQAPRALIGGTNKRAPGVPARFSG SLLGGKAALTLSGVQPEDEAEYYCALWYSNLWVFGGGTKVEIK | 73 |
| | | Hinge1 | Hin6 | GRGRGSDKTHTCP | 144 |
| | | CH2 | SG2 | PSPAPPVAGPSVFLFPPKPKDTLMISRTPEVTCVVVDVSHEDPEVQFNWYVDGVEVHNAKTKPREEQ FNSTFRVVSVLTVVHQDWLNGKEYKCKVSNKGLPAPIEKTISKTK | 161 |
| | | CH3-b | CW:CSAV | GQPREPQVCTLPPSRDELTKNQVSLSCAVKGFYPSDIAVEWESNGQPENNYKTTPPVLDSDGSFFLVS KLTVDKSRWQQGNVFSCSVMHEALHNHYTQKSLSLSPGK | 167 |
| | Heavy chain | VHm | 2F5 | QVQLVQSGAEVKKPGSSVKVSCKASGGTFSSYAFSWVRQAPGQGLEWMGRVIPFLGIANSAQKFQ GRVTITADKSTSTAYMDLSSLRSEDTAVYYCARDDIAALGPFDYWGQGTLVTVSS | 96 |
| | | CH1 | CH1 | ASTKGPSVFPLAPSSKSTSGGTAALGCLVKDYFPEPVTVSWNSGALTSGVHTFPAVLQSSGLYSLSSV VTVPSSSLGTQTYICNVNHKPSNTKVDKKV | 154 |
| | | Hinge 2 | Hin1 | EPKSCDKTHTCP | 139 |
| | | CH2 | SG2 | PSPAPPVAGPSVFLFPPKPKDTLMISRTPEVTCVVVDVSHEDPEVQFNWYVDGVEVHNAKTKPREEQ FNSTFRVVSVLTVVHQDWLNGKEYKCKVSNKGLPAPIEKTISKTK | 161 |
| | | CH3-a | CW:CSAV | GQPREPQVYTLPPCRDELTKNQVSLWCLVKGFYPSDIAVEWESNGQPENNYKTTPPVLDSDGSFFLY SKLTVDKSRWQQGNVFSCSVMHEALHNHYTQKSLSLSPGK | 166 |
| | Light Chain | VLm | 2F5 | DIQMTQSPSSLSASVGDRVTITCRASQGISSWLAWYQQKPEKAPKSLIYAASSLQSGVPSRFSGSGS GTDFTLTISSLQPEDFATYYCQQYNSYPRTFGQGTKVEIK | 97 |
| | | CL | Lc1 | RTVAAPSVFIFPPSDEQLKSGTASVVCLLNNFYPREAKVQWKVDNALQSGNSQESVTEQDSKDSTYS LSSTLTLSKADYEKHKVYACEVTHQGLSSPVTKSFNRGEC | 148 |
| Y150-F8-13 | Fusion Peptide | VHs | VH2k | QVQLVESGGGVVQPGRSLRLSCAASGFTFSTYAMNWVRQAPGKGLEWVARIRSKYNNYATYYAD SVKDRFTISRDDSKNTLYLQMNSLRAEDTAVYYCARHGNFGNSYVSWYAYWGQGTLVTVSS | 59 |
| | | Linker1 | Lin10 | GGGGSGGGGSGGGGS | 129 |
| | | VLs | VL5a | QTVVTQEPSLTVSPGGTVTLTCRSSTGAVTTSNYANWFQQKPGQAPRGLIGGTNKRAPGVPARFSG SLLGGKAALTLSGVQPEDEAEYYCALWYSNLWVFGGGTKVEIK | 72 |
| | | Hinge 1 | Hin6 | GRGRGSDKTHTCP | 144 |
| | | CH2 | SG2 | PSPAPPVAGPSVFLFPPKPKDTLMISRTPEVTCVVVDVSHEDPEVQFNWYVDGVEVHNAKTKPREEQ FNSTFRVVSVLTVVHQDWLNGKEYKCKVSNKGLPAPIEKTISKTK | 161 |
| | | CH3-b | CW:CSAV | GQPREPQVCTLPPSRDELTKNQVSLSCAVKGFYPSDIAVEWESNGQPENNYKTTPPVLDSDGSFFLVS KLTVDKSRWQQGNVFSCSVMHEALHNHYTQKSLSLSPGK | 167 |
| | Heavy chain | VHm | 2F5 | QVQLVQSGAEVKKPGSSVKVSCKASGGTFSSYAFSWVRQAPGQGLEWMGRVIPFLGIANSAQKFQ GRVTITADKSTSTAYMDLSSLRSEDTAVYYCARDDIAALGPFDYWGQGTLVTVSS | 96 |
| | | CH1 | CH1 | ASTKGPSVFPLAPSSKSTSGGTAALGCLVKDYFPEPVTVSWNSGALTSGVHTFPAVLQSSGLYSLSSV VTVPSSSLGTQTYICNVNHKPSNTKVDKKV | 154 |
| | | Hinge 2 | Hin1 | EPKSCDKTHTCP | 139 |
| | | CH2 | SG2 | PSPAPPVAGPSVFLFPPKPKDTLMISRTPEVTCVVVDVSHEDPEVQFNWYVDGVEVHNAKTKPREEQ FNSTFRVVSVLTVVHQDWLNGKEYKCKVSNKGLPAPIEKTISKTK | 161 |
| | | CH3-a | CW:CSAV | GQPREPQVYTLPPCRDELTKNQVSLWCLVKGFYPSDIAVEWESNGQPENNYKTTPPVLDSDGSFFLY SKLTVDKSRWQQGNVFSCSVMHEALHNHYTQKSLSLSPGK | 166 |
| | Light chain | VLm | 2F5 | DIQMTQSPSSLSASVGDRVTITCRASQGISSWLAWYQQKPEKAPKSLIYAASSLQSGVPSRFSGSGS GTDFTLTISSLQPEDFATYYCQQYNSYPRTFGQGTKVEIK | 97 |
| | | CL | Lc1 | RTVAAPSVFIFPPSDEQLKSGTASVVCLLNNFYPREAKVQWKVDNALQSGNSQESVTEQDSKDSTYS LSSTLTLSKADYEKHKVYACEVTHQGLSSPVTKSFNRGEC | 148 |
| Y150-F8-14 | Fusion Peptide | VHs | VH2m | QVQLVESGGGVVQPGRSLRLSCAASGFTFSTYAMNWVRQAPGKGLEWVARIRSKYNNYATYYAD SVKDRFTISRDDSKNTLYLQMNSLRAEDTAVYYCARHGNFGNSYVSWFLYWGQGTLVTVSS | 61 |
| | | Linker1 | Lin10 | GGGGSGGGGSGGGGS | 129 |
| | | VLs | VL5b | QTVVTQEPSLTVSPGGTVTLTCRSSTGAVTTSNYANWVQQKPGQAPRALIGGTNKRAPGVPARFSG SLLGGKAALTLSGVQPEDEAEYYCALWYSNLWVFGGGTKVEIK | 73 |
| | | Hinge 1 | Hin6 | GRGRGSDKTHTCP | 144 |
| | | CH2 | SG2 | PSPAPPVAGPSVFLFPPKPKDTLMISRTPEVTCVVVDVSHEDPEVQFNWYVDGVEVHNAKTKPREEQ FNSTFRVVSVLTVVHQDWLNGKEYKCKVSNKGLPAPIEKTISKTK | 161 |
| | | CH3-b | CW:CSAV | GQPREPQVCTLPPSRDELTKNQVSLSCAVKGFYPSDIAVEWESNGQPENNYKTTPPVLDSDGSFFLVS KLTVDKSRWQQGNVFSCSVMHEALHNHYTQKSLSLSPGK | 167 |
| | Heavy chain | VHm | 2F5 | QVQLVQSGAEVKKPGSSVKVSCKASGGTFSSYAFSWVRQAPGQGLEWMGRVIPFLGIANSAQKFQ GRVTITADKSTSTAYMDLSSLRSEDTAVYYCARDDIAALGPFDYWGQGTLVTVSS | 96 |
| | | CH1 | CH1 | ASTKGPSVFPLAPSSKSTSGGTAALGCLVKDYFPEPVTVSWNSGALTSGVHTFPAVLQSSGLYSLSSV VTVPSSSLGTQTYICNVNHKPSNTKVDKKV | 154 |
| | | Hinge 2 | Hin1 | EPKSCDKTHTCP | 139 |
| | | CH2 | SG2 | PSPAPPVAGPSVFLFPPKPKDTLMISRTPEVTCVVVDVSHEDPEVQFNWYVDGVEVHNAKTKPREEQ FNSTFRVVSVLTVVHQDWLNGKEYKCKVSNKGLPAPIEKTISKTK | 161 |
| | | CH3-a | CW:CSAV | GQPREPQVYTLPPCRDELTKNQVSLWCLVKGFYPSDIAVEWESNGQPENNYKTTPPVLDSDGSFFLY SKLTVDKSRWQQGNVFSCSVMHEALHNHYTQKSLSLSPGK | 166 |

TABLE 25-continued

Codes of some multi-functional antibodies and amino acid sequences of variable regions according to the present invention

| Antibody code | Polypeptide | Domain | Code | Amino acid sequences (those in bold and underlined being CDR) | Sequence No. |
|---|---|---|---|---|---|
| | Light chain | VLm | 2F5 | DIQMTQSPSSLSASVGDRVTITCRASQGISSWLAWYQQKPEKAPKSLIYAASSLQSGVPSRFSGSGSGTDFTLTISSLQPEDFATYYCQQYNSYPRTFGQGTKVEIK | 97 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 148 |
| Y150-F8-15 | Fusion Peptide | VHs | VH2n | QVQLVESGGGVVQPGRSLRLSCAASGFTFSTYAMNWVRQAPGKGLEWVARIRSKYNNYATYVADSVKDRFTISRDDSKNTLYLQMNSLRAEDTAVYYCARHGNFGNSYVSWFIYWGQGTLVTVSS | 62 |
| | | Linker1 | Lin10 | GGGGSGGGGSGGGGS | 129 |
| | | VLs | VL5b | QTVVTQEPSLTVSPGGTVTLTCRSSTGAVTTSNYANWVQQKPGQAPRALIGGTNKRAPGVPARFSGSLLGGKAALTLSGVQPEDEAEYYCALWYSNLWVFGGGTKVEIK | 73 |
| | | Hinge1 | Hin6 | GRGRGSDKTHTCP | 144 |
| | | CH2 | SG2 | PSPAPPVAGPSVFLFPPKPKDTLMISRTPEVTCVVVDVSHEDPEVQFNWYVDGVEVHNAKTKPREEQFNSTFRVVSVLTVVHQDWLNGKEYKCKVSNKGLPAPIEKTISKTK | 161 |
| | | CH3-b | CW:CAV | GQPREPQVCTLPPSRDELTKNQVSLSCAVKGFYPSDIAVEWESNGQPENNYKTTPPVLDSDGSFFLVSKLTVDKSRWQQGNVFSCSVMHEALHNHYTQKSLSLSPGK | 167 |
| | Heavy chain | VHm | 2F5 | QVQLVQSGAEVKKPGSSVKVSCKASGGTFSSYAFSWVRQAPGQGLEWMGRVIPFLGIANSAQKFQGRVTITADKSTSTAYMDLSSLRSEDTAVYYCARDDIAALGPFDYWGQGTLVTVSS | 96 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKV | 154 |
| | | Hinge 2 | Hin1 | EPKSCDKTHTCP | 139 |
| | | CH2 | SG2 | PSPAPPVAGPSVFLFPPKPKDTLMISRTPEVTCVVVDVSHEDPEVQFNWYVDGVEVHNAKTKPREEQFNSTFRVVSVLTVVHQDWLNGKEYKCKVSNKGLPAPIEKTISKTK | 161 |
| | | CH3-a | CW:CSAV | GQPREPQVYTLPPCRDELTKNQVSLWCAVKGFYPSDIAVEWESNGQPENNYKTTPPVLDSDGSFFLYSKLTVDKSRWQQGNVFSCSVMHEALHNHYTQKSLSLSPGK | 166 |
| | Light chain | VLm | 2F5 | DIQMTQSPSSLSASVGDRVTITCRASQGISSWLAWYQQKPEKAPKSLIYAASSLQSGVPSRFSGSGSGTDFTLTISSLQPEDFATYYCQQYNSYPRTFGQGTKVEIK | 97 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 148 |
| Y150-F9-7 | Fusion Peptide | VHs | VH2a | QVQLVESGGGVVQPGRSLRLSCAASGFTFSTYAMNWVRQAPGKGLEWVARIRSKYNNYATYVADSVKDRFTISRDDSKNTLYLQMNSLRAEDTAVYYCARHGNFGNSYVSWFAYWGQGTLVTVSS | 49 |
| | | Linker1 | Lin10 | GGGGSGGGGSGGGGS | 129 |
| | | VLs | VL5 | QTVVTQEPSLTVSPGGTVTLTCRSSTGAVTTSNYANWVQQKPGQAPRGLIGGTNKRAPGVPARFSGSLLGGKAALTLSGVQPEDEAEYYCALWYSNLWVFGGGTKVEIK | 71 |
| | | Hinge 1 | Hin3 | GGGGSDKTHTCP | 141 |
| | | CH2 | FES | PCPAPEFEGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPASIEKTISKAK | 157 |
| | | CH3-b | CW:CSAV | GQPREPQVCTLPPSRDELTKNQVSLSCAVKGFYPSDIAVEWESNGQPENNYKTTPPVLDSDGSFFLVSKLTVDKSRWQQGNVFSCSVMHEALHNHYTQKSLSLSPGK | 167 |
| | Heavy chain | VHm | MOR | QVQLVESGGGLVQPGGSLRLSCAASGFTFSSYYMNWVRQAPGKGLEWVSGISGDPSNTYYADSVKGRFTISRDNSKNTLYLQMNSLRAEDTAVYYCARDLPLVYTGFAYWGQGTLVTVSS | 92 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKV | 154 |
| | | Hinge 2 | Hin1 | EPKSCDKTHTCP | 139 |
| | | CH2 | FES | PCPAPEFEGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPASIEKTISKAK | 157 |
| | | CH3-a | CW:CSAV | GQPREPQVYTLPPCRDELTKNQVSLWCAVKGFYPSDIAVEWESNGQPENNYKTTPPVLDSDGSFFLYSKLTVDKSRWQQGNVFSCSVMHEALHNHYTQKSLSLSPGK | 166 |
| | Light chain | VLm | MOR | DIELTQPPSVSVAPGQTARISCSGDNLRHYYVYWYQQKPGQAPVLVIYGDSKRPSGIPERFSGSNSGNTATLTISGTQAEDEADYYCQTYTGGASLVFGGGTKLTVL | 93 |
| | | CL | Lc3 | GQPKAAPSVTLFPPSSEELQANKATLVCLISDFYPGAVTVAWKADSSPVKAGVETTTPSKQSNNKYAASSYLSLTPEQWKSHRSYSCQVTHEGSTVEKTVAPTECS | 150 |
| Y150-F9-11 | Fusion Peptide | VHs | VH2a | QVQLVESGGGVVQPGRSLRLSCAASGFTFSTYAMNWVRQAPGKGLEWVARIRSKYNNYATYVADSVKDRFTISRDDSKNTLYLQMNSLRAEDTAVYYCARHGNFGNSYVSWFAYWGQGTLVTVSS | 49 |
| | | Linker1 | Lin10 | GGGGSGGGGSGGGGS | 129 |
| | | VLs | VL5 | QTVVTQEPSLTVSPGGTVTLTCRSSTGAVTTSNYANWVQQKPGQAPRGLIGGTNKRAPGVPARFSGSLLGGKAALTLSGVQPEDEAEYYCALWYSNLWVFGGGTKVEIK | 71 |
| | | Hinge 1 | Hin6 | GRGRGSDKTHTCP | 144 |
| | | CH2 | SG2 | PSPAPPVAGPSVFLFPPKPKDTLMISRTPEVTCVVVDVSHEDPEVQFNWYVDGVEVHNAKTKPREEQFNSTFRVVSVLTVVHQDWLNGKEYKCKVSNKGLPAPIEKTISKTK | 161 |
| | | CH3-b | CW:CSAV | GQPREPQVCTLPPSRDELTKNQVSLSCAVKGFYPSDIAVEWESNGQPENNYKTTPPVLDSDGSFFLVSKLTVDKSRWQQGNVFSCSVMHEALHNHYTQKSLSLSPGK | 167 |

TABLE 25-continued

Codes of some multi-functional antibodies and amino acid sequences of variable regions according to the present invention

| Antibody code | Polypeptide | Domain | Code | Amino acid sequences (those in bold and underlined being CDR) | Sequence No. |
|---|---|---|---|---|---|
| | Heavy chain | VHm | MOR | QVQLVESGGGLVQPGGSLRLSCAASGFTFSSYYMNWVRQAPGKGLEWVSGISGDPSNTYYADSV KGRFTISRDNSKNTLYLQMNSLRAEDTAVYYCARDLPLVYTGFAYWGQGTLVTVSS | 92 |
| | | CH1 | CH1 | ASTKGPSVFPLAPSSKSTSGGTAALGCLVKDYFPEPVTVSWNSGALTSGVHTFPAVLQSSGLYSLSSV VTVPSSSLGTQTYICNVNHKPSNTKVDKKV | 154 |
| | | Hinge 2 | Hin1 | EPKSCDKTHTCP | 139 |
| | | CH2 | SG2 | PSPAPPVAGPSVFLFPPKPKDTLMISRTPEVTCVVVDVSHEDPEVQFNWYVDGVEVHNAKTKPREEQ FNSTFRVVSVLTVVHQDWLNGKEYKCKVSNKGLPAPIEKTISKTK | 161 |
| | | CH3-a | CW: CSAV | GQPREPQVYTLPPCRDELTKNQVSLWCLVKGFYPSDIAVEWESNGQPENNYKTTPPVLDSDGSFFLY SKLTVDKSRWQQGNVFSCSVMHEALHNHYTQKSLSLSPGK | 166 |
| | Light chain | VLm | MOR | DIELTQPPSVSVAPGQTARISCSGDNLRHYYVYWYQQKPGQAPVLIYGDSKRPSGIPERFSGSNSG NTATLTISGTQAEDEADYYCQTYTGGASLVFGGGTKLTVL | 93 |
| | | CL | Lc1 | RTVAAPSVFIFPPSDEQLKSGTASVVCLLNNFYPREAKVQWKVDNALQSGNSQESVTEQDSKDSTYS LSSTLTLSKADYEKHKVYACEVTHQGLSSPVTKSFNRGEC | 148 |
| Y150-F9-12 | Fusion Peptide | VHs | VH2a | QVQLVESGGGVVQPGRSLRLSCAASGFTFSTYAMNWVRQAPGKGLEWVARIRSKYNNYATYVAD SVKDRFTISRDDSKNTLYLQMNSLRAEDTAVYYCARHGNFGNSYVSWFAYWGQGTLVTVSS | 49 |
| | | Linker1 | Lin10 | GGGGSGGGGSGGGGS | 129 |
| | | VLs | VL5 | QTVVTQEPSLTVSPGGTVTLTCRSSTGAVTTSNYANWVQQKPGQAPRGLIGGTNKRAPGVPARFSG SLLGGKAALTLSGVQPEDEAEYYCALWYSNLWVFGGGTKVEIK | 71 |
| | | Hinge 1 | Hin6 | GRGRGSDKTHTCP | 144 |
| | | CH2 | G2D | PCPAPPVAGPSVFLFPPKPKDTLMISRTPEVTCVVVDVSHEAPEVQFNWYVDGVEVHNAKTKPREEQ FNSTFRVVSVLTVVHQDWLNGKEYKCKVSNKGLPAPIEKTISKTK | 192 |
| | | CH3-b | CW: SAV | GQPREPQVCTLPPSRDELTKNQVSLSCAVKGFYPSDIAVEWESNGQPENNYKTTPPVLDSDGSFFLVS KLTVDKSRWQQGNVFSCSVMHEALHNHYTQKSLSLSPGK | 167 |
| | Heavy chain | VHm | MOR | QVQLVESGGGLVQPGGSLRLSCAASGFTFSSYYMNWVRQAPGKGLEWVSGISGDPSNTYYADSV KGRFTISRDNSKNTLYLQMNSLRAEDTAVYYCARDLPLVYTGFAYWGQGTLVTVSS | 92 |
| | | CH1 | CH1 | ASTKGPSVFPLAPSSKSTSGGTAALGCLVKDYFPEPVTVSWNSGALTSGVHTFPAVLQSSGLYSLSSV VTVPSSSLGTQTYICNVNHKPSNTKVDKKV | 154 |
| | | Hinge 2 | Hin1 | EPKSCDKTHTCP | 139 |
| | | CH2 | G2D | PCPAPPVAGPSVFLFPPKPKDTLMISRTPEVTCVVVDVSHEAPEVQFNWYVDGVEVHNAKTKPREEQ FNSTFRVVSVLTVVHQDWLNGKEYKCKVSNKGLPAPIEKTISKTK | 192 |
| | | CH3-a | CW: CSAV | GQPREPQVYTLPPCRDELTKNQVSLWCLVKGFYPSDIAVEWESNGQPENNYKTTPPVLDSDGSFFLY SKLTVDKSRWQQGNVFSCSVMHEALHNHYTQKSLSLSPGK | 166 |
| | Light chain | VL | MOR | DIELTQPPSVSVAPGQTARISCSGDNLRHYYVYWYQQKPGQAPVLIYGDSKRPSGIPERFSGSNSG NTATLTISGTQAEDEADYYCQTYTGGASLVFGGGTKLTVL | 93 |
| | | CL | Lc1 | RTVAAPSVFIFPPSDEQLKSGTASVVCLLNNFYPREAKVQWKVDNALQSGNSQESVTEQDSKDSTYS LSSTLTLSKADYEKHKVYACEVTHQGLSSPVTKSFNRGEC | 148 |
| MS-hCD3-IC15 | Fusion Peptide | VHs | VH2a | QVQLVESGGGVVQPGRSLRLSCAASGFTFSTYAMNWVRQAPGKGLEWVARIRSKYNNYATYYAD SVKDRFTISRDDSKNTLYLQMNSLRAEDTAVYYCARHGNFGNSYVSWFAYWGQGTLVTVSS | 49 |
| | | Linker1 | Lin10 | GGGGSGGGGSGGGGS | 129 |
| | | VLs | VL5 | QTVVTQEPSLTVSPGGTVTLTCRSSTGAVTTSNYANWVQQKPGQAPRGLIGGTNKRAPGVPARFSG SLLGGKAALTLSGVQPEDEAEYYCALWYSNLWVFGGGTKVEIK | 71 |
| | | Hinge 1 | Hin3 | GGGGSDKTHTCP | 141 |
| | | CH2 | N297Q | PCPAPELLGGPSVFLFPPKPKDTLMISRTPEVTCVVVDVSHEDPEVKFNWYVDGVEVHNAKTKPREE QYQSTYRVVSVLTVLHQDWLNGKEYKCKVSNKALPAPIEKTISKAK | 159 |
| | | CH3-b | CW: CSAV | GQPREPQVCTLPPSRDELTKNQVSLSCAVKGFYPSDIAVEWESNGQPENNYKTTPPVLDSDGSFFLVS KLTVDKSRWQQGNVFSCSVMHEALHNHYTQKSLSLSPGK | 167 |
| | Heavy chain | VHm | 4420 | EVKLDETGGGLVQPGRPMKLSCVASGFTFSDYWMNWVRQSPEKGLEWVAQIRNKPYNYETYYSD SVKGRFTISRDDSKSSVYLQMNNLRVEDMGIYYCTGSYYGMDYWGQGTSVTVSS | 118 |
| | | CH1 | CH1 | ASTKGPSVFPLAPSSKSTSGGTAALGCLVKDYFPEPVTVSWNSGALTSGVHTFPAVLQSSGLYSLSSV VTVPSSSLGTQTYICNVNHKPSNTKVDKKV | 154 |
| | | Hinge 2 | Hin1 | EPKSCDKTHTCP | 139 |
| | | CH2 | N297Q | PCPAPELLGGPSVFLFPPKPKDTLMISRTPEVTCVVVDVSHEDPEVKFNWYVDGVEVHNAKTKPREE QYQSTYRVVSVLTVLHQDWLNGKEYKCKVSNKALPAPIEKTISKAK | 159 |
| | | CH3-a | CW: CSAV | GQPREPQVYTLPPCRDELTKNQVSLWCLVKGFYPSDIAVEWESNGQPENNYKTTPPVLDSDGSFFLY SKLTVDKSRWQQGNVFSCSVMHEALHNHYTQKSLSLSPGK | 166 |
| | Light chain | VLm | 4420 | DVVMTQTPLSLPVSLGDQASISCRSSQSLVHSNGNTYLRWYLQKPGQSPKVLIYKVSNRFSGVPDR FSGSGSGTDFTLKISRVEAEDLGVYFCSQSTHVPWTFGGGTKLEIK | 119 |
| | | CL | Lc1 | RTVAAPSVFIFPPSDEQLKSGTASVVCLLNNFYPREAKVQWKVDNALQSGNSQESVTEQDSKDSTYS LSSTLTLSKADYEKHKVYACEVTHQGLSSPVTKSFNRGEC | 148 |

TABLE 25-continued

Codes of some multi-functional antibodies and amino acid sequences of variable regions according to the present invention

| Antibody code | Polypeptide | Domain | Code | Amino acid sequences (those in bold and underlined being CDR) | Sequence No. |
|---|---|---|---|---|---|
| Ms-hCD3-IC16 | Fusion Peptide | VHs | VH2a | QVQLVESGGGVVQPGRSLRLSCAASGFTFSTYAMNWVRQAPGKGLEWVARIRSKYNNYATYVAD SVKDRFTISRDDSKNTLYLQMNSLRAEDTAVYYCARHGNFGNSYVSWFAYWGQGTLVTVSS | 49 |
| | | Linker1 | Lin10 | GGGGSGGGGSGGGGS | 129 |
| | | VLs | VL5 | QTVVTQEPSLTVSPGGTVTLTCRSSTGAVTTSNYANWVQQKPGQAPRGLIGGTNKRAPGVPARFSG SLLGGKAALTLSGVQPEDEAEYYCALWYSNLWVFGGGTKVEIK | 71 |
| | | Hinge 1 | Hin3 | GGGGSDKTHTCP | 141 |
| | | CH2 | FES | PCPAPEFEGGPSVFLFPPKPKDTLMISRTPEVTCVVVDVSHEDPEVKFNWYVDGVEVHNAKTKPREE QYNSTYRVVSVLTVLHQDWLNGKEYKCKVSNKALPASIEKTISKAK | 157 |
| | | CH3-b | CW: CSAV | GQPREPQVCTLPPSRDELTKNQVSLSCAVKGFYPSDIAVEWESNGQPENNYKTTPPVLDSDGSFFLVS KLTVDKSRWQQGNVFSCSVMHEALHNHYTQKSLSLSPGK | 167 |
| | Heavy chain | VHm | 4420 | EVKLDETGGGLVQPGRPMKLSCVASGFTFSDYWMNWVRQSPEKGLEWVAQIRNKPYNYETYYSD SVKGRFTISRDDSKSSVYLQMNNLRVEDMGIYYCTGSYYGMDYWGQGTSVTVSS | 118 |
| | | CH1 | CH1 | ASTKGPSVFPLAPSSKSTSGGTAALGCLVKDYFPEPVTVSWNSGALTSGVHTFPAVLQSSGLYSLSSV VTVPSSSLGTQTYICNVNHKPSNTKVDKKV | 154 |
| | | Hinge 2 | Hin1 | EPKSCDKTHTCP | 139 |
| | | CH2 | FES | PCPAPEFEGGPSVFLFPPKPKDTLMISRTPEVTCVVVDVSHEDPEVKFNWYVDGVEVHNAKTKPREE QYNSTYRVVSVLTVLHQDWLNGKEYKCKVSNKALPASIEKTISKAK | 157 |
| | | CH3-a | CW: CSAV | GQPREPQVYTLPPCRDELTKNQVSLWCLVKGFYPSDIAVEWESNGQPENNYKTTPPVLDSDGSFFLY SKLTVDKSRWQQGNVFSCSVMHEALHNHYTQKSLSLSPGK | 166 |
| | Light chain | VLm | 4420 | DVVMTQTPLSLPVSLGDQASISRSSQSLVHSNGNTYLRWYLQKPGQSPKVLIYKVSNRFSGVPDR FSGSGSGTDFTLKISRVEAEDLGVYFCSQSTHVPWTFGGGTKLEIK | 119 |
| | | CL | Lc1 | RTVAAPSVFIFPPSDEQLKSGTASVVCLLNNFYPREAKVQWKVDNALQSGNSQESVTEQDSKDSTYS LSSTLTLSKADYEKHKVYACEVTHQGLSSPVTKSFNRGEC | 148 |
| MS-hCD3-IC17 | Fusion Peptide | VHs | VH2a | QVQLVESGGGVVQPGRSLRLSCAASGFTFSTYAMNWVRQAPGKGLEWVARIRSKYNNYATYVAD SVKDRFTISRDDSKNTLYLQMNSLRAEDTAVYYCARHGNFGNSYVSWFAYWGQGTLVTVSS | 49 |
| | | Linker1 | Lin10 | GGGGSGGGGSGGGGS | 129 |
| | | VLs | VL5 | QTVVTQEPSLTVSPGGTVTLTCRSSTGAVTTSNYANWVQQKPGQAPRGLIGGTNKRAPGVPARFSG SLLGGKAALTLSGVQPEDEAEYYCALWYSNLWVFGGGTKVEIK | 71 |
| | | Hinge 1 | Hin3 | GGGGSDKTHTCP | 141 |
| | | CH2 | SG2 | PSPAPPVAGPSVFLFPPKPKDTLMISRTPEVTCVVVDVSHEDPEVQFNWYVDGVEVHNAKTKPREEQ FNSTFRVVSVLTVVHQDWLNGKEYKCKVSNKGLPAPIEKTISKTK | 161 |
| | | CH3-b | CW: CSAV | GQPREPQVCTLPPSRDELTKNQVSLSCAVKGFYPSDIAVEWESNGQPENNYKTTPPVLDSDGSFFLVS KLTVDKSRWQQGNVFSCSVMHEALHNHYTQKSLSLSPGK | 167 |
| | Heavy chain | VHm | 4420 | EVKLDETGGGLVQPGRPMKLSCVASGFTFSDYWMNWVRQSPEKGLEWVAQIRNKPYNYETYYSD SVKGRFTISRDDSKSSVYLQMNNLRVEDMGIYYCTGSYYGMDYWGQGTSVTVSS | 118 |
| | | CH1 | CH1 | ASTKGPSVFPLAPSSKSTSGGTAALGCLVKDYFPEPVTVSWNSGALTSGVHTFPAVLQSSGLYSLSSV VTVPSSSLGTQTYICNVNHKPSNTKVDKKV | 154 |
| | | Hinge 2 | Hin1 | EPKSCDKTHTCP | 139 |
| | | CH2 | SG2 | PSPAPPVAGPSVFLFPPKPKDTLMISRTPEVTCVVVDVSHEDPEVQFNWYVDGVEVHNAKTKPREEQ FNSTFRVVSVLTVVHQDWLNGKEYKCKVSNKGLPAPIEKTISKTK | 161 |
| | | CH3-a | CW: CSAV | GQPREPQVYTLPPCRDELTKNQVSLWCLVKGFYPSDIAVEWESNGQPENNYKTTPPVLDSDGSFFLY SKLTVDKSRWQQGNVFSCSVMHEALHNHYTQKSLSLSPGK | 166 |
| | Light chain | VLm | 4420 | DVVMTQTPLSLPVSLGDQASISRSSQSLVHSNGNTYLRWYLQKPGQSPKVLIYKVSNRFSGVPDR FSGSGSGTDFTLKISRVEAEDLGVYFCSQSTHVPWTFGGGTKLEIK | 119 |
| | | CL | Lc1 | RTVAAPSVFIFPPSDEQLKSGTASVVCLLNNFYPREAKVQWKVDNALQSGNSQESVTEQDSKDSTYS LSSTLTLSKADYEKHKVYACEVTHQGLSSPVTKSFNRGEC | 148 |
| Ms-hCD3-IC18 | Fusion Peptide | VHs | VH2j | QVQLVESGGGVVQPGRSLRLSCAASGFTFSTYAMNWVRQAPGKGLEWVARIRSKYNNYATYVAD SVKDRFTISRDDSKNTLYLQMNSLRAEDTAVYYCARHGNFGNSYVSWAAYWGQGTLVTVSS | 58 |
| | | Linker1 | Lin10 | GGGGSGGGGSGGGGS | 129 |
| | | VLs | VL5a | QTVVTQEPSLTVSPGGTVTLTCRSSTGAVTTSNYANWFQQKPGQAPRGLIGGTNKRAPGVPARFSG SLLGGKAALTLSGVQPEDEAEYYCALWYSNLWVFGGGTKVEIK | 72 |
| | | Hinge 1 | Hin3 | GGGGSDKTHTCP | 141 |
| | | CH2 | SG2 | PSPAPPVAGPSVFLFPPKPKDTLMISRTPEVTCVVVDVSHEDPEVQFNWYVDGVEVHNAKTKPREEQ FNSTFRVVSVLTVVHQDWLNGKEYKCKVSNKGLPAPIEKTISKTK | 161 |
| | | CH3-b | CW: CSAV | GQPREPQVCTLPPSRDELTKNQVSLSCAVKGFYPSDIAVEWESNGQPENNYKTTPPVLDSDGSFFLVS KLTVDKSRWQQGNVFSCSVMHEALHNHYTQKSLSLSPGK | 167 |
| | Heavy chain | VHm | 4420 | EVKLDETGGGLVQPGRPMKLSCVASGFTFSDYWMNWVRQSPEKGLEWVAQIRNKPYNYETYYSD SVKGRFTISRDDSKSSVYLQMNNLRVEDMGIYYCTGSYYGMDYWGQGTSVTVSS | 118 |
| | | CH1 | CH1 | ASTKGPSVFPLAPSSKSTSGGTAALGCLVKDYFPEPVTVSWNSGALTSGVHTFPAVLQSSGLYSLSSV VTVPSSSLGTQTYICNVNHKPSNTKVDKKV | 154 |
| | | Hinge 2 | Hin1 | EPKSCDKTHTCP | 139 |
| | | CH2 | SG2 | PSPAPPVAGPSVFLFPPKPKDTLMISRTPEVTCVVVDVSHEDPEVQFNWYVDGVEVHNAKTKPREEQ FNSTFRVVSVLTVVHQDWLNGKEYKCKVSNKGLPAPIEKTISKTK | 161 |
| | | CH3-a | CW: CSAV | GQPREPQVYTLPPCRDELTKNQVSLWCLVKGFYPSDIAVEWESNGQPENNYKTTPPVLDSDGSFFLY SKLTVDKSRWQQGNVFSCSVMHEALHNHYTQKSLSLSPGK | 166 |

TABLE 25-continued

Codes of some multi-functional antibodies and amino acid sequences of variable regions according to the present invention

| Antibody code | Polypeptide | Domain | Code | Amino acid sequences (those in bold and underlined being CDR) | Sequence No. |
|---|---|---|---|---|---|
| | Light chain | VLm | 4420 | DVVMTQTPLSLPVSLGDQASISCRSSQSLVHSNGNTYLRWYLQKPGQSPKVLIYKVSNRFSGVPDR FSGSGSGTDFTLKISRVEAEDLGVYFCSQSTHVPWTFGGGTKLEIK | 119 |
| | | CL | Lc1 | RTVAAPSVFIFPPSDEQLKSGTASVVCLLNNFYPREAKVQWKVDNALQSGNSQESVTEQDSKDSTYS LSSTLTLSKADYEKHKVYACEVTHQGLSSPVTKSFNRGEC | 148 |

Figure 5:
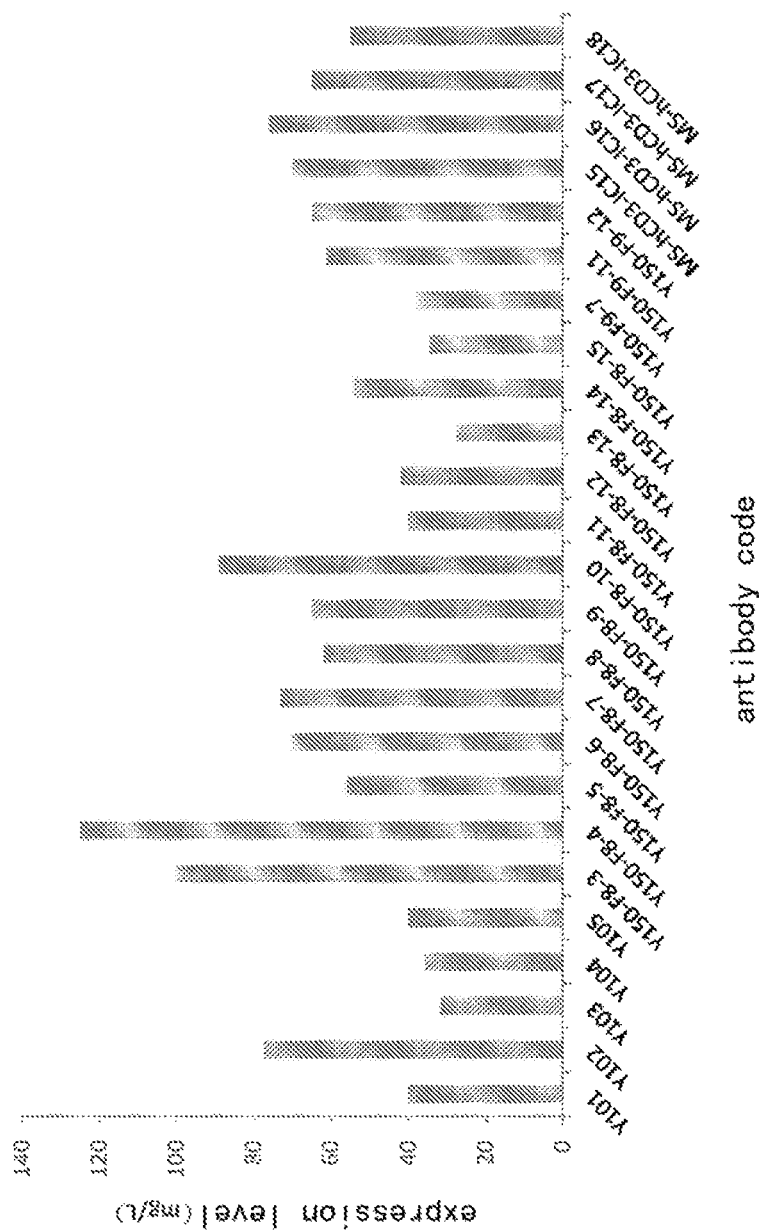
FIG. 5 illustrates a transient transfection expression level of a multi-functional antibody assembled from the humanized CD3 antibody in CHO cells.

See FIG. 5 for an expression level of the multi-functional antibody according to the present invention. FIG. 5 illustrates a transient transfection expression level of the multi-functional antibody assembled from the humanized CD3 antibody in CHO cells.

It can be seen from FIG. 5 that multi-functional antibodies assembled from different CD3 antibodies have different transient transfection expression levels in CHO cells. Y102, Y150-F8-3/F8-4/F8-6/F8-7/F8-8/F8-9/F8-10/F9-11/F9-12, and MS-hCD3-IC15/IC16/IC17 have significantly high expression levels, and the antibody expression level is not less than 40 mg/L.

Example 4: Biological Activity Detection of the Multi-Functional Antibody

1. Cell Affinity
1) Cell preparation: CD3 positive T cells separated from human whole blood are used for CD3 terminal affinity detection of multi-functional antibody molecules, and the affinity detection of tumor antigens is conducted on positive tumor cells of the corresponding antigens: for example, CD38 positive MM.1S cells (purchased from the Cell Resources Center of the Shanghai Institutes for Biological Sciences of the Chinese Academy of Sciences) or RPMI 8226 cells (purchased from the Cell Resources Center of the Shanghai Institutes for Biological Sciences of the Chinese Academy of Sciences) are used for CD38 antigen detection, H358 cells (purchased from the Cell Resources Center of the Shanghai Institutes for Biological Sciences of the Chinese Academy of Sciences) are used for PD-L1 antigen detection, and the like. Take a sufficient amount of cells, centrifuge at 300×g for 5 min, discard the supernatant, use 1% FBS-PBS to re-suspend the cells, adjust the density to 4×10$^6$/ml, take 50 µl for each well, and plate the cells at 2×10$^5$ per well. The centrifuge at 4 degrees and 300×g for 5 min, discard the supernatant, and plate the cells on ice;
2) Antibody addition: according to the experiment design, subject the antibodies to gradient dilution, and perform the antibody dilution on ice. If the initial concentration of antibody dilution is 3000 nM, dilute 3×, and dilute by 11 concentration grades. Add the diluted antibody into the cell wells at 50 µl per well, gently pipette well, and incubate for 2 h at 4 degrees with shaking at 1100 rpm/min;
3) Wash: use 150 µl 1% FBS-PBS to resuspend the cells, centrifuge at 4 degrees and 300×g for 5 min, and discard the supernatant. Repeat the washing once;
4) Secondary antibody incubation: add diluted secondary antibody PE anti-human IgG FC (Biolegend, 409304), the final concentration of the secondary antibody is 8 ug/ml, and the volume is 50 µl/well. At the same time, provide wells only added with the cells and the secondary antibody as control, gently pipette well, and incubate in dark for 1 h at 4 degrees with shaking at 1100 rpm/min;
5) Wash: use 150 µl 1% FBS-PBS to resuspend the cells, centrifuge at 4 degrees and 300 g for 5 min, and discard the supernatant. Repeat the washing once;
6) Fixation: add 200 µl 2% paraformaldehyde into each well to resuspend the cells and fix cells at room temperature for 20 min. Centrifuge at 300×g for 5 min, and discard the supernatant;
7) Cell re-suspension: use 200 µl 1% FBS-PBS to resuspend the cells, centrifuge at 300×g for 5 min, and discard the supernatant;
8) loading for flow cytometry: use 150 µl 1% FBS-PBS to resuspend the cells, and detect on a flow cytometer;
9) Data analysis: use analysis software FlowJo 7.6 of the flow cytometer to analyze data, and use Graphpad Prism 5 to plot graphs and calculate Kd values.

2. T Cell Activation
1) Take tumor cells in good culture states (non-small cell lung cancer cell H358 purchased from the Cell Resources Center of the Shanghai Institutes for Biological Sciences of the Chinese Academy of Sciences; myeloma cells MC/CAR purchased from ATCC), prepare single cell suspension, and plate the single cell suspension according to 2E4/well cell number into a 96-well plate
2) Isolate PBMC from whole blood of healthy volunteers by density gradient centrifugation, and add PBMC into the tumor cell plate according to an effect/target ratio (E:T) designed in the experiment
3) Perform a series of concentration gradient dilution on the antibodies according to the experimental design, add antibodies of various concentrations
4) Place the 96-well plate in a 37° C. and 5% CO$_2$ incubator for incubation until the detection time. Collect suspended PBMC cells, add corresponding CD3, CD69 detecting antibodies, after 1 h of incubation, wash off excess antibodies, resuspend the cells, determine CD3 and CD69 dual positive cell percent by flow cytometry, i.e., a percent of activated T cells in PBMC induced by the antibodies. Specifically, the calculation is as follows:

$$CD3 \text{ and } CD69 \text{ dual positive cell percent (\%)} = \frac{CD3 \text{ and } CD69 \text{ dual positive cell number}}{\text{total number of } CD3 \text{ positive cells}} \times 100\%$$

Use the GraphPad Prism 5 software to perform non-linear fitting with the double antibody concentration as the X axis, the CD3&CD69)% value as the Y axis (log(agonist) vs. response—Variable slope), and calculate to obtain the T cell activation curve and EC50 value.

3. In Vitro Killing

1) Take a sufficient amount of tumor cells (e.g., H358 cells and MC/CAR cells), and prepare single cell suspensions;
2) CFSE stained tumor cells: centrifuge a certain amount of cell suspension (300×g, 5 min), and discard the supernatant; add 2 ml CFSE solution prepared with PBS, which has a final CFSE concentration of 5 μM; place the cells in a 5% $CO_2$, 37° C. incubator, and incubate for 15 min; take out the cells, wash with PBS, centrifuge (300×g, 5 min), discard the supernatant, repeat washing for three times, use a complete medium to resuspend the cells, and take the suspension for cell count;
3) plating the tumor cells: use the complete medium to resuspend the cell to a density of $2\times10^5$/ml, and add the same into a 96-well plate according to $2\times10^4$ cells/well, i.e., 100 μl/well;
4) Add effector cell PBMC (isolated from human whole blood): resuspend the effector cells using the complete medium used by tumor cells in the experiment system, add a corresponding number of the effector cells that is converted according to the effect/target ratio in the experiment design, and add according to 50 μl volume/well;
5) Add the diluted antibody: according to the experiment design, the highest antibody concentration is 10 μg/ml. Since 50 μl of the antibody is added, which is ¼ of the total volume of 200 μl, all the antibodies must be prepared at 4× concentration for addition. Therefore, the antibodies are first diluted to 40 μg/ml, 10× dilution is performed starting from 40 μg/ml with 9 grades, and the volume is 50 μl/well;
6) Observe the 96-well plate under a microscope, ensuring that the cells are evenly distributed in the culture wells, place the plate in a 5% $CO_2$, 37° C. cell incubator for incubation, and leave it for detection;
7) When the detection time arrives, adherent cells are processed: pipette out the cell supernatant, wash with 30 μl/well PBS, pipette out the washing solution and combine the washing solution with the supernatant that was pipetted out previously; add 30 μl Trypsin/well into the cell wells, and place the plate in the 5% $CO_2$, 37° C. cell incubator for 3-5 min of digestion, add the previously collected supernatant, and pipette cells in each well to form a single cell suspension; suspended cells are processed: pipette for multiple times to mix well;
8) Add PI into each sample at 10-15 min before detection by the flow cytometer (the final concentration is 10 μg/ml), 10 ul/well;
9) Perform detection on the flow cytometer; use the FlowJo software to analyze detection results from the flow cytometer, output the data analysis to Microsoft Excel, use GraphPad for table preparation and analysis, and the cell killing calculation formula is: the percent of CFSE, PI dual positive cells in CFSE positive cells is the mortality rate of target cells.

The calculation formula is as follows:

$$\text{mortality rate of target cells (\%)} = \frac{pI \text{ and } CFSE \text{ dual positive cell number}}{CFES \text{ positive cell number}} \times 100$$

10) Calculation of killing of an antibody to tumor cells: according to the calculation formula for the mortality rate of target cells, calculate the mortality rate of target cells under each antibody concentration, plot with the antibody concentration as the X axis and the mortality rate of target cells as the Y axis, and obtain EC50 values using Graphpad Prism 5 as the data analysis software, which is the killing capacity of this antibody.

See Table 28 for specific binding activities of some multi-functional antibodies.

Figure 7:
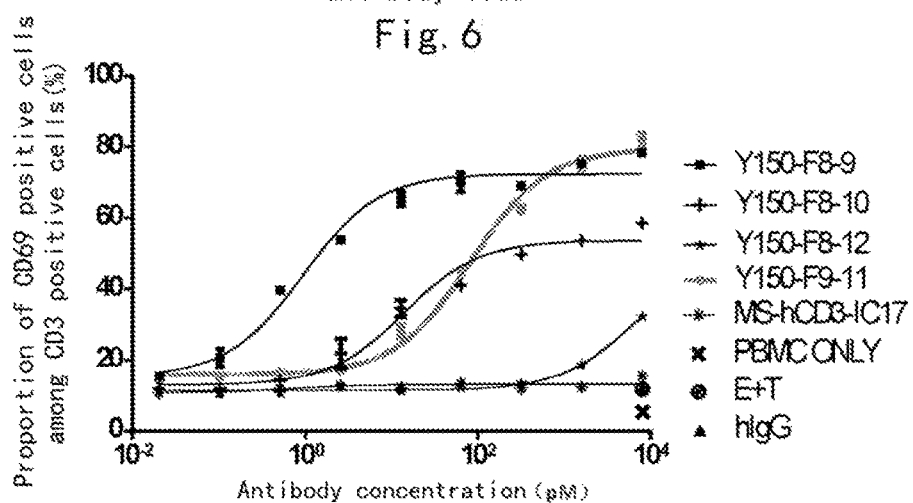
FIG. 7 illustrates in vitro T-cell activation capabilities of different multi-functional antibodies according to the present invention.

See FIG. 7 and Table 29 for specific T-cell activation capabilities of some multi-functional antibodies.

Figure 8:
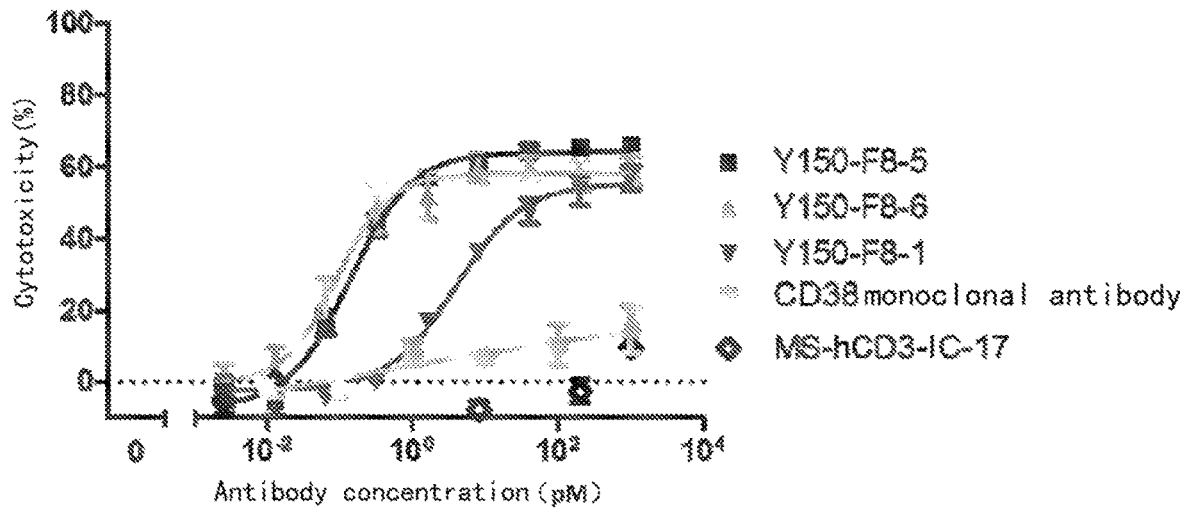
FIG. 8 illustrates in vitro killig capability of different multi-functional antibodies against multiple myeloma cells MC/CAR.
Figure 9:
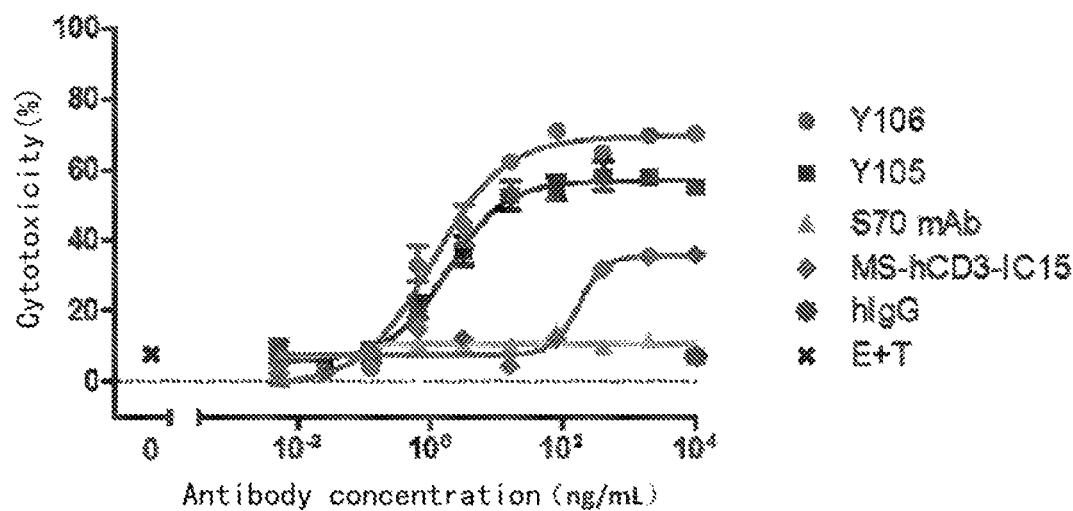
FIG. 9 illustrates in vitro killig capability of different multi-functional antibodies against lung cancer cells H358.

See FIGS. 8 and 9 and Table 30 and Table 31 for cytotoxicity of some multi-functional antibodies.

Comparative Example 1

I. Alignment of Sequences of Humanized Antibodies and Existing CD3 Antibodies:

The variable region sequence of CD3 antibody 1 is from U.S. Pat. No. 8,846,042B2, wherein the sequence number of the heavy chain variable region in this patent is 44, and the sequence number of the light chain variable region in this patent is 56;

The variable region sequence of CD3 antibody 2 is from U.S. Pat. No. 9,650,446B2, wherein the sequence number of the heavy chain variable region in this patent is 85, and the sequence number of the light chain variable region in this patent is 194.

(1) Alignment of Heavy Chain Variable Regions:

```
                            1                                                      50
VH2a              (1)  QVQLVESGGGVVQPGRSLRLSCAASGFTFSTYAMNWVRQAPGKGLEWVARIRSKYNNYATYYADSVKDRFT
CD3 antibody 1 VH (1)  EVQLVESGGGLVQPGGSLRLSCAASGFTFSTYAMNWVRQAPGKGLEWVARIRSKYNNYATYYADSVKDRFT
CD3 antibody 2 VH (1)  EVQLVESGGGLVQPGGSLRLSCAASGFTFNTYAMNWVRQAPGKGLEWVERIRSKYNNYATYYADSVKGRFT Homology analysis (1)  *---------*----*-------------*TYAMN-------------*RIRSKYNNYATYYADSVK*---
                       |<----------FR-H1---------->|CDR-H1|<-FR-H2->|<-----CDR-H2---H->|<---

100                    125
                       ISRDDSKNTLYLQMNSLRAEDTAVYYCARHGNFGNSYVSWFAYWGQGTLVTVSS
                       ISRDDSKNTLYLQMNSLRAEDTAVYYCARHGNFGNSYVSWFAYWGQGTMVTVSS
                       ISRDDSKNTLYLQMNSLRAEDTAVYYCARHGNFGNSYVSWFAYWGQGTLVTVSS

----------------------------HGNFGNSYVSYNAY-----*-----
                       -----------FR-H3---------->|<---CDR-H3--->|<--FR-H4->|
```

Between VH2a and CD3 antibody 1 VH, the amino acid sequence similarity is 96.8%, and the difference appears at FR-H1 and FR-H4;

Between VH2a and CD3 antibody 2 VH, the amino acid sequence similarity is 95.2%, and the difference appears at FR-H1, FR-H2 and CDR-H2;

(2) Alignment of Light Chain Variable Regions:

```
                        1                                                50
VL5               (1)  QIVVTQEPSLTVSPGGTVTLTCRSSTGAVTTSNYANWVQQKPGQAPRGLIGGTNKRAPGVPARFSGSLLG
CD3 antibody 1 VL (1)  QAVVTQEPSLTVSPGGTVTLTCRSSTGAVTTSNYANWVQQKPGQAPRGLIGGTNKRAPGTPARFSGSLLG
CD3 antibody 2 VL (1)  QAVVTQEPSLTVSPGGTVTLTCGSSTGAVTTSNYANWVQQKPGQAPRGLIGGTNKRAPGVPARFSGSLLG
Homology analysis (1)  -*-------------------*SSTGAVTTSNYAN---------------GTNKRAP-*---------
                       |←------FR-L1-------→|←--CDR-L1--→|←----FR-L2---→|CDR-L2|←---------

100      109
                       GKAALTLSGVQPEDEAEYYCALWYSNLWVFGGGTKVEIK
                       GKAALTLSGVQPEDEAEYYCALWYSNLWVFGGGTKLTVL
                       GKAALTLSGAQPEDEAEYYCALWYSNLWVFGGGTKLEIK
                       ---------*----------ALWYSNLWV------****
                       ----FR-L3--------→|-CDR-L3--|←-FR-H4→|
```

Between VL5 and CD3 antibody 1 VL, the amino acid sequence similarity is 94.5%, and the difference appears at FR-L1, FR-L3 and FR-L4;

Between VL5 and CD3 antibody 2 VL, the amino acid sequence similarity is 96.3%, and the difference appears at FR-L1, CDR-L1, FR-L3 and FR-L4;

II. Comparison of Biological Activity Between Humanized Antibodies and Monoclonal Antibodies of Existing CD3 Antibodies:

(1) Affinity Detection of Existing CD3 Antibodies

TABLE 26

| Code of comparative antibody | Poly-peptide | Domain | Amino acid sequences (those in bold and underlined being CDR) | Sequence No. |
|---|---|---|---|---|
| SP34 monoclonal antibody | Heavy chain | VH | EVQLVESGGGLVQPKGSLKLSCAASGFTFNTYAMNWVRQAPGKGLEWVARIRSKYNNYATY YADSVKDRFTISRDDSQSILYLQMNNLKTEDTAMYYCVRHGNFGNSYVSVVFAYWGQGTLVT VSS | 74 |
| | | CH1 | ASTKGPSVFPLAPSSKSTSGGTAALGCLVKDYFPEPVTVSWNSGALTSGVHTFPAVLQSSGLYS LSSVVTVPSSSLGTQTYICNVNHKPSNTKVDKKV | 154 |
| | | Hinge | EPKSCDKTHTCP | 139 |
| | | CH2 | PCPAPELLGGPSVFLFPPKPKDTLMISRTPEVTCVVVDVSHEDPEVKFNWYVDGVEVHNAKTK PREEQYNSTYRVVSVLTVLHQDWLNGKEYKCKVSNKALPAPIEKTISKAK | 155 |
| | | CH3 | GQPREPQVYTLPPSRDELTKNQVSLTCLVKGFYPSDIAVEWESNGQPENNYKTTPPVLDSDGSF FLYSKLTVDKSRWQQGNVFSCSVMHEALHNHYTQKSLSLSPGK | 162 |
| | Light chain | VL | QAVVTQESALTTSPGETVTLTCRSSTGAVTTSNYANWVQEKPDHLFTGLIGGTNKRAPGVPA RFSGSLIGDKAALITGAQTEDEAIYFCALWYSNLWVFGGGTKLTVL | 75 |
| | | CL | RTVAAPSVFIFPPSDEQLKSGTASVVCLLNNFYPREAKVQWKVDNALQSGNSQESVTEQDSKD STYSLSSTLTLSKADYEKHKVYACEVTHQGLSSPVTKSFNRGEC | 148 |
| CD3Ab1 | Heavy chain | VH | EVQLVESGGGLVQPGGSLRLSCAASGFTFSTYAMNWVRQAPGKGLEWVARIRSKYNNYATY YADSVKDRFTISRDDSKNTLYLQMNSLRAEDTAVYYCARHGNFGNSYVS WFAYWGQGTMVTVSS | 86 |
| | | CH1 | ASTKGPSVFPLAPSSKSTSGGTAALGCLVKDYFPEPVTVSWNSGALTSGVHTFPAVLQSSGLYS LSSVVTVPSSSLGTQTYICNVNHKPSNTKVDKKV | 154 |
| | | Hinge | EPKSCDKTHTCP | 139 |
| | | CH2 | PCPAPELLGGPSVFLFPPKPKDTLMISRTPEVTCVVVDVSHEDPEVKFNWYVDGVEVHNAKTK PREEQYNSTYRVVSVLTVLHQDWLNGKEYKCKVSNKALPAPIEKTISKAK | 155 |
| | | CH3 | GQPREPQVYTLPPSRDELTKNQVSLTCLVKGFYPSDIAVEWESNGQPENNYKTTPPVLDSDGSF FLYSKLTVDKSRWQQGNVFSCSVMHEALHNHYTQKSLSLSPGK | 162 |
| | Light chain | VL | QAVVTQEPSLTVSPGGTVTLTCGSSTGAVTTSNYANWVQQKPGQAPRGLIGGTNKRAPGTPA RFSGSLLGGKAALTLSGVQPEDEAEYYCALWYSNLWVFGGGTKLTVL | 87 |
| | | CL | RTVAAPSVFIFPPSDEQLKSGTASVVCLLNNFYPREAKVQWKVDNALQSGNSQESVTEQDSKD STYSLSSTLTLSKADYEKHKVYACEVTHQGLSSPVTKSFNRGEC | 148 |
| CD3Ab2 | Heavy chain | VH | EVQLVESGGGLVQPGGSLRLSCAASGFTFNTYAMNWVRQAPGKGLEWVGRIRSKYNNYATY YADSVKGRFTISRDDSKNTLYLQMNSLRAEDTAVYYCARHGNFGNSYVSWFAYWGQGTLVT VSS | 88 |
| | | CH1 | ASTKGPSVFPLAPSSKSTSGGTAALGCLVKDYFPEPVTVSWNSGALTSGVHTFPAVLQSSGLYS LSSVVTVPSSSLGTQTYICNVNHKPSNTKVDKKV | 154 |
| | | Hinge | EPKSCDKTHTCP | 139 |
| | | CH2 | PCPAPELLGGPSVFLFPPKPKDTLMISRTPEVTCVVVDVSHEDPEVKFNWYVDGVEVHNAKTK PREEQYNSTYRVVSVLTVLHQDWLNGKEYKCKVSNKALPAPIEKTISKAK | 155 |
| | | CH3 | GQPREPQVYTLPPSRDELTKNQVSLTCLVKGFYPSDIAVEWESNGQPENNYKTTPPVLDSDGSF FLYSKLTVDKSRWQQGNVFSCSVMHEALHNHYTQKSLSLSPGK | 162 |
| | Light chain | VL | QAVVTQEPSLTVSPGGTVLTLCGSSTGAVTTSNYANWVQQKPGQAPRGLIGGTNKRAPGVPA RFSGSLLGGKAALTLSGAQPEDEAEYYCALWYSNLWYFGGGTKLEIK | 89 |
| | | CL | RTVAAPSVFIFPPSDEQLKSGTASVVCLLNNFYPREAKVQWKVDNALQSGNSQESVTEQDSKD STYSLSSTLTLSKADYEKHKVYACEVTHQGLSSPVTKSFNRGEC | 148 |

TABLE 26-continued

Codes and amino acid sequences of existing CD3 antibodies

| Code of comparative antibody | Poly-peptide | Domain | Amino acid sequences (those in bold and underlined being CDR) | Sequence No. |
|---|---|---|---|---|
| CD3Ab3 | Heavy chain | VH | EVQLVESGGGLVQPGGSLRLSCAASGFTFSTYAMNWVRQAPGKGLEWVARIRSKYNNYATY YADSVKDRFTISRDDSKNTLYLQMNSLRAEDTAVYYCARHGNFGNSYVS WFAYWGQGTMVTVSS | 86 |
| | | CH1 | ASTKGPSVFPLAPSSKSTSGGTAALGCLVKDYFPEPVTVSWNSGALTSGVHTFPAVLQSSGLYS LSSVVTVPSSSLGTQTYICNVNHKPSNTKVDKKV | 154 |
| | | Hinge | EPKSCDKTHTCP | 139 |
| | | CH2 | PCPAPELLGGPSVFLFPPKPKDTLMISRTPEVTCVVVDVSHEDPEVKFNWYVDGVEVHNAKTK PREEQYNSTYRVVSVLTVLHQDWLNGKEYKCKVSNKALPAPIEKTISKAK | 155 |
| | | CH3 | GQPREPQVYTLPPSRDELTKNQVSLTCLVKGFYPSDIAVEWESNGQPENNYKTTPPVLDSDGSF FLYSKLTVDKSRWQQGNVFSCSVMHEALHNHYTQKSLSLSPGK | 162 |
| | Light chain | VL | QAVVTQEPSLTVSPGGTVTLTCGSSTGAVTTSNYANWVQQKPGQAPRGLIGGTNKRAPGVPA RFSGSLLGGKAALTLSGAQPEDEAEYYCALWYSNLWVFGGGTKLEIK | 89 |
| | | CL | RTVAAPSVFIFPPSDEQLKSGTASVVCLLNNFYPREAKVQWKVDNALQSGNSQESVTEQDSKD STYSLSSTLTLSKADYEKHKVYACEVTHQGLSSPVTKSFNRGEC | 148 |

Figure 6:
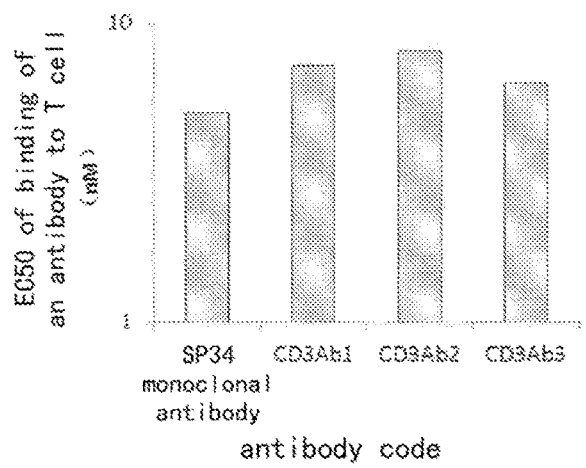
FIG. 6 illustrates the cell affinity of monoclonal antibodies of existing CD3 antibodies.

The preparation method for existing monoclonal antibodies is the same as the antibody preparation method in Examples 2 and 3. See FIG. 6 for detection data regarding cell binding activities. FIG. 6 illustrates the cell affinity of monoclonal antibodies of existing CD3 antibodies.

Comparative Example 2

(4) Codes and Variable Region Amino Acid Sequences of Some Comparative Multi-Functional Antibodies See the Table Below for Details:

TABLE 27

Codes and variable region amino acid sequences of comparative multi-functional antibodies

| Code of comparative antibody | Poly-peptide | Domain | Code | Amino acid sequences (those in bold and underlined being CDR) | Sequence No. |
|---|---|---|---|---|---|
| Y106 | Fusion Peptide | VHs | SP34 | EVQLVESGGGLVQPKGSLKLSCAASGFTFNTYAMNWVRQAPGKGLEWVARIRSKYNNYATYYAD SVKDRFTISRDDSQSILYLQMNNLKTEDTAMYYCVRHGNFGNSYVSWFAYWGQGTLVTVSS | 91 |
| | | Linker1 | Lin10 | GGGGSGGGGSGGGGS | 129 |
| | | VLs | SP34 | QAVVTQESALTTSPGETVTLTCRSSTGAVTTSNYANWVQEKPDHLFTGLIGGTNKRAPGVPARFSGS LIGDKAALTITGAQTEDEAIYFCALWYSNLWVFGGGTKLTVL | 75 |
| | | Hinge 1 Hin4 | | RGRGSDKTHTCP | 142 |
| | | CH2 | N297Q | PCPAPELLGGPSVFLFPPKPKDTLMISRTPEVTCVVVDVSHEDPEVKFNWYVDGVEVHNAKTPREE QYQSTYRVVSVLTVLHQDWLNGKEYKCKVSNKALPAPIEKTISKAK | 159 |
| | | CH3-b | CW: CSAV | GQPREPQVCTLPPSRDELTKNQVSLSCAVKGFYPSDIAVEWESNGQPENNYKTTPPVLDSDGSFFLVS KLTVDKSRWQQGNVFSCSVMHEALHNHYTQKSLSLSPGK | 167 |
| | Heavy Chain | VHm | S70 | QVQLVQSGAEVKKPGSSVKVSCKTSGDTFSTYAISWVRQAPGQGLEWMGGIIPIFGKAHYAQKFQ GRVTITADESTSTAYMELSSLRSEDTAVYFCARKFHFVSGSPFGMDVWGQGTTVTVSS | 106 |
| | | CH1 | CH1 | ASTKGPSVFPLAPSSKSTSGGTAALGCLVKDYFPEPVTVSWNSGALTSGVHTFPAVLQSSGLYSLSSV VTVPSSSLGTQTYICNVNHKPSNTKVDKKV | 154 |
| | | Hinge 2 CH2 | Hin1 N297Q | EPKSCDKTHTCP PCPAPELLGGPSVFLFPPKPKDTLMISRTPEVTCVVVDVSHEDPEVKFNWYVDGVEVHNAKTPREE QYASTYRVVSVLTVLHQDWLNGKEYKCKVSNKALPAPIEKTISKAK | 139 159 |
| | | CH3-a | CW: CSAV | GQPREPQVYTLPPCRDELTKNQVSLWCLVKGFYPSDIAVEWESNGQPENNYKTTPPVLDSDGSFFLY SKLTVDKSRWQQGNVFSCSVMHEALHNHYTQKSLSLSPGK | 166 |
| | Light chain | VLm | S70 | EIVLTQSPATLSLSPGERATLSCRASQSVSSYLAWYQQKPGQAPRLLIYDASNRATGIPARFSGSGSGT DFTLTISSLEPEDFAVYYCQQRSNWPTFGQGTKVEIK | 107 |
| | | CL | Lc1 | RTVAAPSVFIFPPSDEQLKSGTASVVCLLNNFYPREAKVQWKVDNALQSGNSQESVTEQDSKDSTYS LSSTLTLSKADYEKHKVYACEVTHQGLSSPVTKSFNRGEC | 148 |
| Y150-F 8-1 | Fusion Peptide | VHs | SP34 | EVQLVESGGGLVQPKGSLKLSCAASGFTFNTYAMNWVRQAPGKGLEWVARIRSKYNNYATYYAD SVKDRFTISRDDSQSILYLQMNNLKTEDTAMYYCVRHGNFGNSYVSWFAYWGQGTLVTVSS | 74 |
| | | Linker1 | Lin10 | GGGGSGGGGSGGGGS | 129 |
| | | VLs | SP34 | QAVVTQESALTTSPGETVTLTCRSSTGAVTTSNYANWVQEKPDHLFTGLIGGTNKRAPGVPARFSGS LIGDKAALTITGAQTEDEAIYFCALWYSNLWVFGGGTKLTVL | 75 |
| | | Hinge 1 | Hin7 | GDGDGSDKTHTCP | 145 |
| | | CH2 | FES | PCPAPEFEGGPSVFLFPPKPKDTLMISRTPEVTCVVVDVSHEDPEVKFNWYVDGVEVHNAKTPREE QYNSTYRVVSVLTVLHQDWLNGKEYKCKVSNKALPASIEKTISKAK | 157 |
| | | CH3-b | CW: CSAV | GQPREPQVCTLPPSRDELTKNQVSLSCAVKGFYPSDIAVEWESNGQPENNYKTTPPVLDSDGSFFLVS KLTVDKSRWQQGNVFSCSVMHEALHNHYTQKSLSLSPGK | 167 |
| | Heavy Chain | VHm | Dara | EVQLLESGGGLVQPGGSLRLSCAVSGFTFNSFAMSWVRQAPGKGLEWVSAISGSGGGTYYADSVK GRFTISRDNSKNTLYLQMNSLRAEDTAVYFCAKDKILWEGEPVEDYWGQGTLVTVSS | 90 |
| | | CH1 | CH1 | ASTKGPSVFPLAPSSKSTSGGTAALGCLVKDYFPEPVTVSWNSGALTSGVHTFPAVLQSSGLYSLSSV VTVPSSSLGTQTYICNVNHKPSNTKVDKKV | 154 |
| | | Hinge 2 CH2 | Hin1 FES | EPKSCDKTHTCP PCPAPEFEGGPSVFLFPPKPKDTLMISRTPEVTCVVVDVSHEDPEVKFNWYVDGVEVHNAKTPREE QYNSTYRVVSVLTVLHQDWLNGKEYKCKVSNKALPASIEKTISKAK | 139 157 |
| | | CH3-a | CW: CSAV | GQPREPQVYTLPPCRDELTKNQVSLWCLVKGFYPSDIAVEWESNGQPENNYKTTPPVLDSDGSFFLY SKLTVDKSRWQQGNVFSCSVMHEALHNHYTQKSLSLSPGK | 166 |

TABLE 27-continued

Codes and variable region amino acid sequences of comparative multi-functional antibodies

| Code of comparative antibody | Poly-peptide | Domain | Code | Amino acid sequences (those in bold and underlined being CDR) | Sequence No. |
|---|---|---|---|---|---|
| | Light chain | VLm | Dara | EIVLTQSPATLSLSPGERATLSCRASQSVSSYLAWYQQKPGQAPRLLIYDASNRATGIPARFSGSGSGT DFTLTISSLEPEDFAVYYCQQRSNWPPTFGQGTKVEIK | 91 |
| | | CL | Lc1 | RTVAAPSVFIFPPSDEQLKSGTASVVCLLNNFYPREAKVQWKVDNALQSGNSQESVTEQDSKDSTYS LSSTLTLSKADYEKHKVYACEVTHQGLSSPVTKSFNRGEC | 148 |
| Y150-F 8-2 | Fusion Peptide | VHs | SP34 | EVQLVESGGGLVQPKGSLKLSCAASGFTFNTYAMNWVRQAPGKGLEWVARIRSKYNNYATYYAD SVKDRFTISRDDSQSILYLQMNNLKTEDTAMYYCVRHGNFGNSYYSWFAYWGQGTLVTVSS | 74 |
| | | Linker1 VLs | Lin10 SP34 | GGGGSGGGGSGGGGS | 129 |
| | | | | QAVVTQESALTTSPGETVTLTCRSSTGAVTTSNYANWVQEKPDHLFTGLIGGTNKRAPGVPARFSGS LIGDKAALTITGAQTEDEAIYFCALWYSNLWVFGGGTKLTVL | 75 |
| | | Hinge 1 CH2 | Hin7 N297Q | GDGDGSDKTHTCP | 145 |
| | | | | PCPAPELLGGPSVFLFPPKPKDTLMISRTPEVTCVVVDVSHEDPEVKFNWYVDGVEVHNAKTKPREE QYQSTYRVVSVLTVLHQDWLNGKEYKCKVSNKALPAPIEKTISKAK | 159 |
| | | CH3-b | CW: CSAV | GQPREPQVCTLPPSRDELTKNQVSLSCAVKGFYPSDIAVEWESNGQPENNYKTTPPVLDSDGSFFLVS KLTVDKSRWQQGNVFSCSVMHEALHNHYTQKSLSLSPGK | 167 |
| | Heavy Chain | VHm | Dara | EVQLLESGGGLVQPGGSLRLSCAVSGFTFNSFAMSWVRQAPGKGLEWVSAISGSGGGTYYADSVK GRFTISRDNSKNTLYLQMNSLRAEDTAVYFCAKDKILLWEGEPVEDYWGQGTLVTVSS | 90 |
| | | CH1 | CH1 | ASTKGPSVFPLAPSSKSTSGGTAALGCLVKDYFPEPVTVSWNSGALTSGVHTFPAVLQSSGLYSLSSV VTVPSSSLGTQTYICNVNHKPSNTKVDKKV | 154 |
| | | Hinge 2 CH2 | Hin1 N297Q | EPKSCDKTHTCP | 139 |
| | | | | PCPAPELLGGPSVFLFPPKPKDTLMISRTPEVTCVVVDVSHEDPEVKFNWYVDGVEVHNAKTKPREE QYQSTYRVVSVLTVLHQDWLNGKEYKCKVSNKALPAPIEKTISKAK | 159 |
| | | CH3-a | CW: CSAV | GQPREPQVYTLPPCRDELTKNQVSLWCLVKGFYPSDIAVEWESNGQPENNYKTTPPVLDSDGSFFLY SKLTVDKSRWQQGNVFSCSVMHEALHNHYTQKSLSLSPGK | 166 |
| | Light chain | VLm | Dara | EIVLTQSPATLSLSPGERATLSCRASQSVSSYLAWYQQKPGQAPRLLIYDASNRATGIPARFSGSGSGT DFTLTISSLEPEDFAVYYCQQRSNWPPTFGQGTKVEIK | 91 |
| | | CL | Lc1 | RTVAAPSVFIFPPSDEQLKSGTASVVCLLNNFYPREAKVQWKVDNALQSGNSQESVTEQDSKDSTYS LSSTLTLSKADYEKHKVYACEVTHQGLSSPVTKSFNRGEC | 148 |
| Y150-F 9-6 | Fusion Peptide | VHs | SP34 | EVQLVESGGGLVQPKGSLKLSCAASGFTFNTYAMNWVRQAPGKGLEWVARIRSKYNNYATYYAD SVKDRFTISRDDSQSILYLQMNNLKTEDTAMYYCVRHGNFGNSYYSWFAYWGQGTLVTVSS | 74 |
| | | Linker1 VLs | Lin10 SP34 | GGGGSGGGGSGGGGS | 129 |
| | | | | QAVVTQESALTTSPGETVTLTCRSSTGAVTTSNYANWVQEKPDHLFTGLIGGTNKRAPGVPARFSGS LIGDKAALTITGAQTEDEAIYFCALWYSNLWVFGGGTKLTVL | 75 |
| | | Hinge 1 CH2 | Hin7 FES | GDGDGSDKTHTCP | 145 |
| | | | | PCPAPEFEGGPSVFLFPPKPKDTLMISRTPEVTCVVVDVSHEDPEVKFNWYVDGVEVHNAKTKPREE QYNSTYRVVSVLTVLHQDWLNGKEYKCKVSNKALPASIEKTISKAK | 157 |
| | | CH3-b | CW: CSAV | GQPREPQVCTLPPSRDELTKNQVSLSCAVKGFYPSDIAVEWESNGQPENNYKTTPPVLDSDGSFFLVS KLTVDKSRWQQGNVFSCSVMHEALHNHYTQKSLSLSPGK | 167 |
| | Heavy Chain | VHm | MOR | QVQLVESGGGLVQPGGSLRLSCAASGFTFSSYYMNWVRQAPGKGLEWVSGISGDPSNTYYADSV KGRFTISRDNSKNTLYLQMNSLRAEDTAVYYCARDLPLVYTGFAYWGQGTLVTVSS | 92 |
| | | CH1 | CH1 | ASTKGPSVFPLAPSSKSTSGGTAALGCLVKDYFPEPVTVSWNSGALTSGVHTFPAVLQSSGLYSLSSV VTVPSSSLGTQTYICNVNHKPSNTKVDKKV | 154 |
| | | Hinge 2 CH2 | Hin1 FES | EPKSCDKTHTCP | 139 |
| | | | | PCPAPEFEGGPSVFLFPPKPKDTLMISRTPEVTCVVVDVSHEDPEVKFNWYVDGVEVHNAKTKPREE QYNSTYRVVSVLTVLHQDWLNGKEYKCKVSNKALPASIEKTISKAK | 157 |

TABLE 27-continued

Codes and variable region amino acid sequences of comparative multi-functional antibodies

| Code of comparative antibody | Poly-peptide | Domain | Code | Amino acid sequences (those in bold and underlined being CDR) | Sequence No. |
|---|---|---|---|---|---|
| | | CH3-a | CW: CSAV | GQPREPQVYTLPPCRDELTKNQVSLMWCLVKGFYPSDIAVEWESNGQPENNYKTTPVLDSDGSFFLY SKLTVDKSRWQQGNVFSCSVMHEALHNHYTQKSLSLSPGK | 166 |
| | Light chain | VLm | MOR | DIELTQPPSVSVAPGQTARISCSGDNLRHYVYWYQQKPGQAPVLVIYGDSKRPSGIPERFSGSNSG NTATLTISGTQAEDEADYYCQTYTGGASLVFGGGTKLTVL | 93 |
| | | CL | Lc1 | GQPKAAPSVTLFPPSSEELQANKATLVCLISDFYPGAVTVAWKADSSPVKAGVETTTPSKQSNNKYA ASSYLSLTPEQWKSHRSYCQVTHEGSTVEKTVAPTECS | 150 |
| CT-F1 | Fusion Peptide | VHs | CD3 antibody 1 | EQLVESGGGLVQPGGSLRLSCAASGF TABLE 27-continued Codes and variable region amino acid sequences of comparative multi-functional antibodies

| Code of comparative antibody | Poly-peptide | Domain | Code | Amino acid sequences (those in bold and underlined being CDR) | Sequence No. |
|---|---|---|---|---|---|
| | | Hinge 2 CH2 | Hin1 FES | EPKSCDKTHTCP PCPAPEFEGGPSVFLFPPKPKDTLMISRTPEVTCVVVDSHEDPEVKFNWYVDGVEVHNAKTKPREE QYNSTYRVVSVLTVLHQDWLNGKEYKCKVSNKALPASIEKTISKAK | 139 157 |
| | | CH3-a | CW: CSAV | GQPREPQVYTLPPCRDELTKNQVSLWCLVKGFYPSDIAVEWESNGQPENNYKTTPPVLDSDGSFFLY SKLTVDKSRWQQGNVFSCSVMHEALHNHYTQKSLSLSPGK | 166 |
| | Light chain | VLm | Dara | EIVLTQSPATLSLSPGERATLSCRASQSVSSYLAWYQQKPGQAPRLLIYDASNRATGIPARFSGSGSGT DFTLTISSLEPEDFAVYYCQQRSNWPPTFGQGTKVEIK | 91 |
| | | CL | Lc1 | RTVAAPSVFIFPPSDEQLKSGTASVVCLLNNFYPREAKVQWKVDNALQSGNSQESVTEQDSKDSTYS LSSTLTLSKADYEKHKVYACEVTHQGLSSPVTKSFNRGEC | 148 |
| CT-F3 | Fusion Peptide | VHs | CD3 antibody 1 | EQLVESGGGLVQPGGSLRLSCAASGFTFSTYAMNWVRQAPGKGLEWVARIRSKYNNYATYVADS VKDRFTISRDDSKNTLYLQMNSLRAEDTAVYYCARHGNFGNSYVSWFAYWGQGTMVTVSS | 86 |
| | | Linker1 VLs | Lin10 CD3 antibody 2 | GGGGSGGGGSGGGGS QAVVTQEPSLTVSPGGTVTLTCGSSTGAVTTSNYANWVQQKPGQAPRGLIGGTNKRAPGVPARFSG SLLGGKAALTLSGAQPEDEAEYYCALWYSNLWVFGGGTKLEIK | 129 89 |
| | | Hinge 1 CH2 | Hin3 FES | GGGGSDKTHTCP PCPAPEFEGGPSVFLFPPKPKDTLMISRTPEVTCVVVDSHEDPEVKFNWYVDGVEVHNAKTKPREE QYNSTYRVVSVLTVLHQDWLNGKEYKCKVSNKALPASIEKTISKAK | 141 157 |
| | | CH3-b | CW: CSAV | GQPREPQVCTLPPSRDELTKNQVSLSCAVKGFYPSDIAVEWESNGQPENNYKTTPPVLDSDGSFFLVS KLTVDKSRWQQGNVFSCSVMHEALHNHYTQKSLSLSPGK | 167 |
| | Heavy chain | VHm | Dara | EVQLLESGGGLVQPGGSLRLSCAVSGFTFNSFAMSWVRQAPGKGLEWVSAISGSGGSTYYADSVK GRFTISRDNSKNTLYLQMNSLRAEDTAVYFCAKDKILWEGEPVEDYWGQGTLVTVSS | 90 |
| | | CH1 | CH1 | ASTKGPSVFPLAPSSKSTSGGTAALGCLVKDYFPEPVTVSWNSGALTSGVHTFPAVLQSSGLYSLSSV VTVPSSSLGTQTYICNVNHKPSNTKVDKKV | 154 |
| | | Hinge 2 CH2 | Hin1 FES | EPKSCDKTHTCP PCPAPEFEGGPSVFLFPPKPKDTLMISRTPEVTCVVVDSHEDPEVKFNWYVDGVEVHNAKTKPREE QYNSTYRVVSVLTVLHQDWLNGKEYKCKVSNKALPASIEKTISKAK | 139 157 |
| | | CH3-a | CW: CSAV | GQPREPQVYTLPPCRDELTKNQVSLWCLVKGFYPSDIAVEWESNGQPENNYKTTPPVLDSDGSFFLY SKLTVDKSRWQQGNVFSCSVMHEALHNHYTQKSLSLSPGK | 166 |
| | Light chain | VLm | Dara | EIVLTQSPATLSLSPGERATLSCRASQSVSSYLAWYQQKPGQAPRLLIYDASNRATGIPARFSGSGSGT DFTLTISSLEPEDFAVYYCQQRSNWPPTFGQGTKVEIK | 91 |
| | | CL | Lc1 | RTVAAPSVFIFPPSDEQLKSGTASVVCLLNNFYPREAKVQWKVDNALQSGNSQESVTEQDSKDSTYS LSSTLTLSKADYEKHKVYACEVTHQGLSSPVTKSFNRGEC | 148 |
| CT-F4 | Fusion Peptide | VHs | CD3 antibody 1 | EQLVESGGGLVQPGGSLRLSCAASGFTFSTYAMNWVRQAPGKGLEWVARIRSKYNNYATYVADS VKDRFTISRDDSKNTLYLQMNSLRAEDTAVYYCARHGNFGNSYVSWFAYWGQGTMVTVSS | 86 |
| | | Linker1 VLs | Lin10 CD3 antibody 1 | GGGGSGGGGSGGGGS QVVTQEPSLTVSPGGTVTLTCRSSTGAVTTSNYANWVQQKPGQAPRGLIGGTNKRAPGTPARFSG SLLGGKAALTLSGVQPEDEAEYYCALWYSNLWVFGGGTKLTVL | 129 87 |
| | | Hinge 1 CH2 | Hin3 N297Q | GGGGSDKTHTCP PCPAPELLGGPSVFLFPPKPKDTLMISRTPEVTCVVVDSHEDPEVKFNWYVDGVEVHNAKTKPREE QYQSTYRVVSVLTVLHQDWLNGKEYKCKVSNKALPAPIEKTISKAK | 141 159 |
| | | CH3-b | CW: CSAV | GQPREPQVCTLPPSRDELTKNQVSLSCAVKGFYPSDIAVEWESNGQPENNYKTTPPVLDSDGSFFLVS KLTVDKSRWQQGNVFSCSVMHEALHNHYTQKSLSLSPGK | 167 |

TABLE 27-continued

Codes and variable region amino acid sequences of comparative multi-functional antibodies

| Code of comparative antibody | Poly-peptide | Domain | Code | Amino acid sequences (those in bold and underlined being CDR) | Sequence No. |
|---|---|---|---|---|---|
| | Heavy Chain | VHm | S70 | QVQLVQSGAEVKKPGSSVKVSCKTSGDTFSTYAISWRQAPGQGLEWMGGIIPIFGKAHYAQKFQ GRVTITADESTSTAYMELSSLRSEDTAVYFCARKFHFVSGSPFGMDV**WGQGTTVTVSS | 106 |
| | | CH1 | CH1 | ASTKGPSVFPLAPSSKSTSGGTAALGCLVKDYFPEPVTVSWNSGALTSGVHTFPAVLQSSGLYSLSSV VTVPSSSLGTQTYICNVNHKPSNTKVDKKV | 154 |
| | | Hinge 2 CH2 | Hin1 N297Q | EPKSCDKTHTCP PCPAPELLGGPSVFLFPPKPKDTLMISRTPEVTCVVVDVSHEDPEVKFNWYVDGVEVHNAKTKPREE QYQSTYRVVSVLTVLHQDWLNGKEYKCKVSNKALPAPIEKTISKAK | 139 159 |
| | | CH3-a | CW: CSAV | GQPREPQVYTLPPCRDELTKNQVSLWCLVKGFYPSDIAVEWESNGQPENNYKTTPPVLDSDGSFFLY SKLTVDKSRWQQGNVFSCSVMHEALHNHYTQKSLSLSPGK | 166 |
| | Light chain | VLm | S70 | EIVLTQSPATLSLSPGERATLSCRASQSVSSYLAWYQQKPGQAPRLLIYDASNRATGIPARFSGSGSGT DFTLTISSLEPEDFAVYYCQQRSNWPTFGQGTKVEIK | 107 |
| | | CL | Lc1 | RTVAAPSVFIFPPSDEQLKSGTASVVCLLNNFYPREAKVQWKVDNALQSGNSQESVTEQDSKDSTYS LSSTLTLSKADYEKHKVYACEVTHQGLSSPVTKSFNRGEC | 148 |
| CT-F5 | Fusion Peptide | VHs | CD3 antibody 2 | EQLVESGGGLVQPGGSLRLSCAASGFTFNTYAMNWVRQAPGKGLEWVGRIRSKYNNYATYYAD SVKGRFTISRDDSKNTLYLQMNSLRAEDTAVYYCARHGNFGNSYVSWFAYWGQGTLVTVSS | 88 |
| | | Linker1 VLs | Lin10 CD3 antibody 2 | GGGGSGGGGSGGGGS QAVVTQEPSLTVSPGGTVLTCGSSTGAVTTSNYANWVQQKPGQAPRGLIGGTNKRAPGVPARFSG SLLGGKAALTLSGAQPEDEAEYYCALWYSNLWVFGGGTKLEIK | 129 89 |
| | | H TABLE 27-continued Codes and variable region amino acid sequences of comparative multi-functional antibodies

| Code of comparative antibody | Poly-peptide | Domain | Code | Amino acid sequences (those in bold and underlined being CDR) | Sequence No. |
|---|---|---|---|---|---|
| | | CH3-b | CW: CSAV | GQPREPQVCTLPPSRDELTKNQVSLSCAVKGFYPSDIAVEWESNGQPENNYKTTPPVLDSDGSFFLVS KLTVDKSRWQQGNVFSCCSVMHEALHNHYTQKSLSLSPGK | 167 |
| | Heavy Chain | VHm | N297Q | QVQLVQSGAEVKKPGSSVKVSCKTSGDTFSTYAISWVRQAPGQGLEWMGGIIPIFGKAHYAQKFQ GRVTITADESTSTAYMELSSLRSEDTAVYFCARKFHFVSGSPFGMDVWGQGTTVTVSS | 106 |
| | | CH1 | CH1 | ASTKGPSVFPLAPSSKSTSGGTAALGCLVKDYFPEPVTVSWNSGALTSGVHTFPAVLQSSGLYSLSSV VTVPSSSLGTQTYICNVNHKPSNTKVDKKV | 154 |
| | | Hinge2 CH2 | Hin1 | EPKSCDKTHTCP PCPAPELLGGPSVFLFPPKPKDTLMISRTPEVTCVVVDVSHEDPEVKFNWYVDGVEVHNAKTKPREE QYQSTYRVVSVLTVLHQDWLNGKEYKCKVSNKALPAPIEKTISKAK | 139 159 |
| | | CH3-a | CW: CSAV S70 | GQPREPQVYTLPPCRDELTKNQVSLWCLVKGFYPSDIAVEWESNGQPENNYKTTPPVLDSDGSFFLY SKLTVDKSRWQQGNVFSCSVMHEALHNHYTQKSLSLSPGK | 166 |
| | Light chain | VLm | S70 | EIVLTQSPATLSLSPGERATLSCRASQSVSSYLAWYQQKPGQAPRLLIYDASNRATGIPARFSGSGSGT DFTLTISSLEPEDFAVYYCQQRSNWPTFGQGTKVEIK | 107 |
| | | CL | Lc1 | RTVAAPSVFIFPPSDEQLKSGTASVVCLLNNFYPREAKVQWKVDNALQSGNSQESVTEQDSKDSTYS LSSTLTLSKADYEKHKVYACEVTHQGLSSPVTKSFNRGEC | 148 |
| IC-2 | Fusion Peptide | VHs | SP34 | EVQLVESGGGLVQPKGSLKLSCAASGFTFNTYAMNWVRQAPGKGLEWVARIRSKYNNYATYYAD SVKDRFTISRDDSQSILYLQMNNLKTEDTAMYYCVRHGNFGNSYVSWFAYWGQGTLVTVSS GGGGSGGGGSGGGGS | 74 |
| | | Linker1 VLs | Lin10 SP34 | QAVVTQESALTTSPGETVTLTCRSSTGAVTTSNYANWVQEKPDHLFTGLIGGTNKRAPGVPARFSGS LIGDKAALTITGAQTEDEAIYFCALWYSNLWVFGGGTKLTVL | 129 75 |
| | Heavy Chain | Hinge1 CH2 | Hin7 FES | GDGDGSDKTHTCP PCPAPEFEGGPSVFLFPPKPKDTLMISRTPEVTCVVVDVSHEDPEVKFNWYVDGVEVHNAKTKPREE QYNSTYRVVSVLTVLHQDWLNGKEYKCKVSNKALPASIEKTISKAK | 145 157 |
| | | CH3-b | CW: CSAV | GQPREPQVCTLPPSRDELTKNQVSLSCAVKGFYPSDIAVEWESNGQPENNYKTTPPVLDSDGSFFLVS KLTVDKSRWQQGNVFSCCSVMHEALHNHYTQKSLSLSPGK | 167 |
| | | VHm | 4420 | EVKLDETGGGLVQGRPMKLLSCVASGFTSDYWMNWVRQSPEKGLEWVAQIRNKPYNYETYYSD SVKGRFTISRDDSKSSVYLQMNNLRVEDMGIYYCTGSYYGMDYWGQGTSVTVSS | 118 |
| | | CH1 | CH1 | ASTKGPSVFPLAPSSKSTSGGTAALGCLVKDYFPEPVTVSWNSGALTSGVHTFPAVLQSSGLYSLSSV VTVPSSSLGTQTYICNVNHKPSNTKVDKKV | 154 |
| | | Hinge2 CH2 | Hin1 FES | EPKSCDKTHTCP PCPAPEFEGGPSVFLFPPKPKDTLMISRTPEVTCVVVDVSHEDPEVKFNWYVDGVEVHNAKTKPREE QYNSTYRVVSVLTVLHQDWLNGKEYKCKVSNKALPASIEKTISKAK | 139 157 |
| | | CH3-a | CW: CSAV | GQPREPQVYTLPPCRDELTKNQVSLWCLVKGFYPSDIAVEWESNGQPENNYKTTPPVLDSDGSFFLY SKLTVDKSRWQQGNVFSCSVMHEALHNHYTQKSLSLSPGK | 166 |
| | Light chain | VLm | 4420 | DVVMTQTPLSLPVSLGDQASISCRSSQSLVHSNGNTYLRWYLQKPGQSPKVLIIYKVSNRFSGVPDR FSGSGSGTDFTLKISRVEAEDLGVYFCSQSTHVPWTFGGGTKLEIK | 119 |
| | | CL | Lc1 | RTVAAPSVFIFPPSDEQLKSGTASVVCLLNNFYPREAKVQWKVDNALQSGNSQESVTEQDSKDSTYS LSSTLTLSKADYEKHKVYACEVTHQGLSSPVTKSFNRGEC | 148 |
| IC-3 | Fusion Peptide | VHs | SP34 | EVQLVESGGGLVQPKGSLKLSCAASGFTFNTYAMNWVRQAPGKGLEWVARIRSKYNNYATYYAD SVKDRFTISRDDSQSILYLQMNNLKTEDTAMYYCVRHGNFGNSYVSWFAYWGQGTLVTVSS GGGGSGGGGSGGGGS | 74 |
| | | Linker1 VLs | Lin10 SP34 | QAVVTQESALTTSPGETVTLTCRSSTGAVTTSNYANWVQEKPDHLFTGLIGGTNKRAPGVPARFSGS LIGDKAALTITGAQTEDEAIYFCALWYSNLWVFGGGTKLTVL | 129 75 |

TABLE 27-continued

Codes and variable region amino acid sequences of comparative multi-functional antibodies

| Code of comparative antibody | Polypeptide | Domain | Code | Amino acid sequences (those in bold and underlined being CDR) | Sequence No. |
|---|---|---|---|---|---|
| | | Hinge 1 CH2 | Hin7 N297Q | GDGDGSDKTHTCP PCPAPELLGGPSVFLFPPKPKDTLMISRTPEVTCVVVDVSHEDPEVKFNWYVDGVEVHNAKTKPREE QYQSTYRVVSVLTVLHQDWLNGKEYKCKVSNKALPAPIEKTISKAK | 145 159 |
| | | CH3-b | CW: CSAV | GQPREPQVCTLPPSRDELTKNQVSLSCAVKGFYPSDIAVEWESNGQPENNYKTTPPVLDSDGSFFLvS KLTVDKSRWQQGNVFSCSVMHEALHNHYTQKSLSLSPGK | 167 |
| | Heavy Chain | VHm 4420 | | EVKLDETGGGLVQPGRPMKLSCVASGFTFSDYWMNWVRQSPEKGLEWVAQIRNKPYNYETYYSD SVKGRFTISRDDSKSSVYLQMNNLRVEDMGIYYCTGSYYGMDYWGQGTSVTVSS | 118 |
| | | CH1 | CH1 | ASTKGPSVFPLAPSSKSTSGGTAALGCLVKDYFPEPVTVSWNSGALTSGVHTFPAVLQSSGLYSLSSV VTVPSSSLGTQTYICNVNHKPSNTKVDKKV | 154 |
| | | Hinge 2 CH2 | Hin1 N297Q | EPKSCDKTHTCP PCPAPELLGGPSVFLFPPKPKDTLMISRTPEVTCVVVDVSHEDPEVKFNWYVDGVEVHNAKTKPREE QYQSTYRVVSVLTVLHQDWLNGKEYKCKVSNKALPAPIEKTISKAK | 139 159 |
| | | CH3-a | CW: CSAV | GQPREPQVYTLPPCRDELTKNQVSLWCLVKGFYPSDIAVEWESNGQPENNYKTTPPVLDSDGSFFLY SKLTVDKSRWQQGNVFSCSVMHEALHNHYTQKSLSLSPGK | 166 |
| | Light chain | VLm 4420 | | DVVMTQTPLSLPVSLGDQASISCRSSQSLVHSNGNTYLRWYLQKPGQSPKVLIYKVSNRFSGVPDR FSGSGSGTDFTLKISRVEAEDLGVFPCSQSTHVPWTFGGGTKLEIK | 119 |
| | | CL | Lc1 | RTVAAPSVFIFPPSDEQLKSGTASVVCLLNNFYPREAKVQWKVDNALQSGNSQESVTEQDSKDSTYS LSSTLTLSKADYEKHKVYACEVTHQGLSSPVTKSFNRGEC | 148 |
| IC-4 | Fusion Peptide | VHs | CD3 antibody 1 | EQLVESGGGLVQPGGSLRLSCAASGFTFSTYAMNWVRQAPGKGLEWVARIRSKYNNYATVVADS VKDRFTISRDDSKNTLYLQMNSLRAEDTAVYYCARHGNFGNSYVSWFAYWGQGTMVTVSS | 86 |
| | | Linker1 VLs | Lin10 CD3 antibody 1 | GGGGSGGGGSGGGGS QAVVTQEPSLTVSPGGTVTLTCRSSTGAVTTSNYANWVQQKPGQAPRGLIGGTNKRAPGTPARFSG SLLGGKAALTLSGVQPEDEAEYYCALWYSNLWVFGGGTKLTVL | 129 87 |
| | Heavy Chain | Hinge 1 CH2 | Hin3 FES | GGGSDKTHTCP PCPAPEFEGGPSVFLFPPKPKDTLMISRTPEVTCVVVDVSHEDPEVKFNWYVDGVEVHNAKTKPREE QYNSTYRVVSVLTVLHQDWLNGKEYKCKVSNKALPASIEKTISKAK | 141 157 |
| | | CH3-b | CW: CSAV | GQPREPQVCTLPPSRDELTKNQVSLSCAVKGFYPSDIAVEWESNGQPENNYKTTPPVLDSDGSFFLvS KLTVDKSRWQQGNVFSCSVMHEALHNHYTQKSLSLSPGK | 167 |
| | | VHm 4420 | | EVKLDETGGGLVQPGRPMKLSCVASGFTFSDYWMNWVRQSPEKGLEWVAQIRNKPYNYETYYSD SVKGRFTISRDDSKSSVYLQMNNLRVEDMGIYYCTGSYYGMDYWGQGTSVTVSS | 118 |
| | | CH1 | CH1 | ASTKGPSVFPLAPSSKSTSGGTAALGCLVKDYFPEPVTVSWNSGALTSGVHTFPAVLQSSGLYSLSSV VTVPSSSLGTQTYICNVNHKPSNTKVDKKV | 154 |
| | | Hinge 2 CH2 | Hin1 FES | EPKSCDKTHTCP PCPAPEFEGGPSVFLFPPKPKDTLMISRTPEVTCVVVDVSHEDPEVKFNWYVDGVEVHNAKTKPREE QYNSTYRVVSVLTVLHQDWLNGKEYKCKVSNKALPASIEKTISKAK | 139 157 |
| | | CH3-a | CW: CSAV | GQPREPQVYTLPPCRDELTKNQVSLWCLVKGFYPSDIAVEWESNGQPENNYKTTPPVLDSDGSFFLY SKLTVDKSRWQQGNVFSCSVMHEALHNHYTQKSLSLSPGK | 166 |
| | Light chain | VLm 4420 | | DVVMTQTPLSLPVSLGDQASISCRSSQSLVHSNGNTYLRWYLQKPGQSPKVLIYKVSNRFSGVPDR FSGSGSGTDFTLKISRVEAEDLGVFPCSQSTHVPWTFGGGTKLEIK | 119 |
| | | CL | Lc1 | RTVAAPSVFIFPPSDEQLKSGTASVVCLLNNFYPREAKVQWKVDNALQSGNSQESVTEQDSKDSTYS LSSTLTLSKADYEKHKVYACEVTHQGLSSPVTKSFNRGEC | 148 |

TABLE 27-continued

Codes and variable region amino acid sequences of comparative multi-functional antibodies

| Code of comparative antibody | Poly-peptide | Domain | Code | Amino acid sequences (those in bold and underlined being CDR) | Sequence No. |
|---|---|---|---|---|---|
| IC-5 | Fusion Peptide | VHs | CD3 antibody 2 | EVQLVESGGGLVQPGGSLRLSCAASGFTFNTYAMNWVRQAPGKGLEWVGRIRSKYNNYATTYAD SVKGRFTISRDDSKNTLYLQMNSLRAEDTAVYYCARHGNFGNSYVSWFAYWGQGTLVTVSS | 88 |
| | | Linker1 | Lin10 | GGGGSGGGGSGGGGS | 129 |
| | | VLs | CD3 antibody 2 | QAVVTQEPSLTVSPGGTVTLTCGSSTGAVTTSNYANWVQQKPGQAPRGLIGGTNKRAPGVPARFSG SLLGGKAALTLSGAQPEDEAEYYCALWYSNLWVFGGGTKLEIK | 89 |
| | | Hinge 1 | Hin3 | GGGGSDKTHTCP | 141 |
| | | CH2 | FES | PCPAPEFEGGPSVFLFPPKPKDTLMISRTPEVTCVVVDVSHEDPEVKFNWYVDGVEVHNAKTKPREE QYNSTYRVVSVLTVLHQDWLNGKEYKCKVSNKALPASIEKTISKAK | 157 |
| | | CH3-b | CW: CSAV | GQPREPQVCTLPPSRDELTKNQVSLSCAVKGFYPSDIAVEWESNGQPENNYKTTPPVLDSDGSFFLVS KLTVDKSRWQQGNVFSCSVMHEALHNHYTQKSLSLSPGK | 167 |
| | Heavy Chain | VHm | 4420 | EVKLDETGGGLVQPGRPMKLSCVASGFTFSDYWMNWVRQSPEKGLEWVAQIRNKPYNYETYYSD SVKGRFTISRDDSKSSVYLQMNNLRVEDMGIYYCTGSYYGMDYWGQGTSVTVSS | 118 |
| | | CH1 | CH1 | ASTKGPSVFPLAPSSKSTSGGTAALGCLVKDYFPEPVTVSWNSGALTSGVHTFPAVLQSSGLYSLSSV VTVPSSSLGTQTYICNVNHKPSNTKVDKKV | 154 |
| | | Hinge 2 | Hin1 | EPKSCDKTHTCP | 139 |
| | | CH2 | FES | PCPAPEFEGGPSVFLFPPKPKDTLMISRTPEVTCVVVDVSHEDPEVKFNWYVDGVEVHNAKTKPREE QYNSTYRVVSVLTVLHQDWLNGKEYKCKVSNKALPASIEKTISKAK | 157 |
| | | CH3-a | CW: CSAV | GQPREPQVYTLPPCRDELTKNQVSLWCLVKGFYPSDIAVEWESNGQPENNYKTTPPVLDSDGSFFLY SKLTVDKSRWQQGNVFSCSVMHEALHNHYTQKSLSLPGK | 166 |
| | Light chain | VLm | 4420 | DVVMTQTPLSLPVSLGDQASISCRSSQSLVHSNGNTYLRWYLQKPGQSPKVLIYKVSNRFSGVPDR FSGSGSGTDFTLKISRVEAEDLGVFYCSQSTHVPWTFGGGTKLEIK | 119 |
| | | CL | Lc1 | RTVAAPSVFIFPPSDEQLKSGTASVVCLLNNFYPREAKVQWKVDNALQSGNSQESVTEQDSKDSTYS LSSTLTLSKADYEKHKVYACEVTHQGLSSPVTKSFNRGEC | 148 |
| IC-6 | Fusion Peptide | VHs | CD3 antibody 1 | EVQLVESGGGLVQPGGSLRLSCAASGFTFSTYAMNWVRQAPGKGLEWVARIRSKYNNYATTYADS VKDRFTISRDDSKNTLYLQMNSLRAEDTAVYYCARGNFGNSYVSWFAYWGQGTMVTVSS | 86 |
| | | Linker1 | Lin10 | GGGGSGGGGSGGGGS | 129 |
| | | VLs | CD3 antibody 2 | QAVVTQEPSLTVSPGGTVTLTCGSSTGAVTTSNYANWVQQKPGQAPRGLIGGTNKRAPGVPARFSG SLLGGKAALTLSGAQPEDEAEYYCALWYSNLWVFGGGTKLEIK | 89 |
| | | Hinge 1 | Hin3 | GGGGSDKTHTCP | 141 |
| | | CH2 | FES | PCPAPEFEGGPSVFLFPPKPKDTLMISRTPEVTCVVVDVSHEDPEVKFNWYVDGVEVHNAKTKPREE QYNSTYRVVSVLTVLHQDWLNGKEYKCKVSNKALPASIEKTISKAK | 157 |
| | | CH3-b | CW: CSAV | GQPREPQVCTLPPSRDELTKNQVSLSCAVKGFYPSDIAVEWESNGQPENNYKTTPPVLDSDGSFFLVS KLTVDKSRWQQGNVFSCSVMHEALHNHYTQKSLSLSPGK | 167 |
| | Heavy Chain | VHm | 4420 | EVKLDETGGGLVQPGRPMKLSCVASGFTFSDYWMNWVRQSPEKGLEWVAQIRNKPYNYETYYSD SVKGRFTISRDDSKSSVYLQMNNLRVEDMGIYYCTGSYYGMDYWGQGTSVTVSS | 118 |
| | | CH1 | CH1 | ASTKGPSVFPLAPSSKSTSGGTAALGCLVKDYFPEPVTVSWNSGALTSGVHTFPAVLQSSGLYSLSSV VTVPSSSLGTQTYICNVNHKPSNTKVDKKV | 154 |
| | | Hinge 2 | Hin1 | EPKSCDKTHTCP | 139 |
| | | CH2 | FES | PCPAPEFEGGPSVFLFPPKPKDTLMISRTPEVTCVVVDVSHEDPEVKFNWYVDGVEVHNAKTKPREE QYNSTYRVVSVLTVLHQDWLNGKEYKCKVSNKALPASIEKTISKAK | 157 |
| | | CH3-a | CW: CSAV | GQPREPQVYTLPPCRDELTKNQVSLWCLVKGFYPSDIAVEWESNGQPENNYKTTPPVLDSDGSFFLY SKLTVDKSRWQQGNVFSCSVMHEALHNHYTQKSLSLPGK | 166 |

TABLE 27-continued

Codes and variable region amino acid sequences of comparative multi-functional antibodies

| Code of comparative antibody | Poly-peptide | Domain | Code | Amino acid sequences (those in bold and underlined being CDR) | Sequence No. |
|---|---|---|---|---|---|
| | Light chain | VLm | 4420 | DVVMTQTPLSLPVSLGDQASISCRSSQSLVHSNGNTYLRWYLQKPGQSPKVLIIYKVSNRFSGVPDR FSGSGSGTDFTLKISRVEAEDLGVYFCSQSTHVPWTFGGGTKLEIK | 157 |
| | | CL | Lc1 | RTVAAPSVFIFPPSDEQLKSGTASVVCLLNNFYPREAKVQWKVDNALQSGNSQESVTEQDSKDSTYS LSSTLTLSKADYEKHKVYACEVTHQGLSSPVTKSFNRGEC | 166 |
| IC-7 | Fusion Peptide | VHs | CD3 antibody 1 | EVQLVESGGGLVQPGGSLRLSCAASGFTFSTYAMNWVRQAPGKGLEWVARIRSKYNNYATYYADS VKDRFTISRDDSKNTLYLQMNSLRAEDTAVYYCARHGNFGNSYVSWFAYWGQGTMVTVSS | 86 |
| | | Linker1 | Lin10 | GGGGSGGGGSGGGGS | 129 |
| | | VLs | CD3 antibody 2 | QAVVTQEPSLTVSPGGTVTLTCGSSTGAVTTSNYANWVQQKPGQAPRGLIGGTNKRAPGVPARFSG SLLGGKAALTLSGAQPEDEAEYYCALWYSNLWVFGGGTKLEIK | 89 |
| | | Hinge 1 | Hin3 | GGGGSDKTHTCP | 141 |
| | | CH2 | N297Q | PCPAPELLGGPSVFLFPPKPKDTLMISRTPEVTCVVVDVSHEDPEVKFNWYVDGVEVHNAKTKPREE QYQSTYRVVSVLTVLHQDWLNGKEYKCKVSNKALPAPIEKTISKAK | 159 |
| | | CH3-b | CW: CSAV | GQPREPQVCTLPPSRDELTKNQVSLSCAVKGFYPSDIAVEWESNGQPENNYKTTPPVLDSDGSFFLVS KLTVDKSRWQQGNVFSCSVMHEALHNHYTQKSLSLSPGK | 167 |
| | Heavy Chain | VHm | 4420 | EVKLDETGGGLVQPGRPMKLSCVASGFTFSDYWMNWVRQSPEKGLEWVAQIRNKPYNYETYYSD SVKGRFTISRDDSKSSVYLQMNNLRVEDMGIYYCTGSYYGMDYWGQGTSVTVSS | 118 |
| | | CH1 | CH1 | ASTKGPSVFPLAPSSKSTSGGTAALGCLVKDYFPEPVTVSWNSGALTSGVHTFPAVLQSSGLYSLSSV VTVPSSSLGTQTYICNVNHKPSNTKVDKKV | 154 |
| | | Hinge 2 | Hin1 | EPKSCDKTHTCP | 139 |
| | | CH2 | N297Q | PCPAPELLGGPSVFLFPPKPKDTLMISRTPEVTCVVVDVSHEDPEVKFNWYVDGVEVHNAKTKPREE QYQSTYRVVSVLTVLHQDWLNGKEYKCKVSNKALPAPIEKTISKAK | 159 |
| | | CH3-a | CW: CSAV | GQPREPQVYTLPPCRDELTKNQVSLWCLVKGFYPSDIAVEWESNGQPENNYKTTPPVLDSDGSFFLY SKLTVDKSRWQQGNVFSCSVMHEALHNHYTQKSLSLSPGK | 166 |
| | Light chain | VLm | 4420 | DVVMTQTPLSLPVSLGDQASISCRSSQSLVHSNGNTYLRWYLQKPGQSPKVLIIYKVSNRFSGVPDR FSGSGSGTDFTLKISRVEAEDLGVYFCSQSTHVPWTFGGGTKLEIK | 119 |
| | | CL | Lc1 | RTVAAPSVFIFPPSDEQLKSGTASVVCLLNNFYPREAKVQWKVDNALQSGNSQESVTEQDSKDSTYS LSSTLTLSKADYEKHKVYACEVTHQGLSSPVTKSFNRGEC | 148 |

(2) Cell Affinity Detection for the Multi-Functional Antibodies According to the Present Invention and Comparative Multi-Functional Antibodies See the table below for affinity detection results for multi-functional antibodies:

TABLE 28

Cell affinity of different multi-functional antibodies

| Notes | Antibody code | Tumor cell binding EC50 value (nM) | Human CD3 positive T cell binding EC50 value (nM) | Monkey CD3 positive T cell binding EC50 value (nM) |
|---|---|---|---|---|
| Multi-functional antibodies according to the present invention | Y102 | 1.43 | 453.60 | 723.37 |
| | Y103 | 1.33 | 1135.00 | NA |
| | Y104 | 1.20 | 107.30 | 203.99 |
| | Y105 | 0.95 | 144.60 | 168.39 |
| | Y150-F8-5 | 1.53 | 192.32 | 290.55 |
| | Y150-F8-6 | 1.24 | 24.04 | 29.19 |
| | Y150-F8-7 | 2.69 | 91.90 | 142.06 |
| | Y150-F8-8 | 1.76 | 107.14 | 158.92 |
| | Y150-F8-9 | 51.86 | 88.10 | 94.13 |
| | Y150-F8-10 | 42.71 | 416.24 | 439.95 |
| | Y150-F8-12 | 47.88 | 561.44 | 606.87 |
| | Y150-F8-14 | 49.85 | 564.74 | 597.69 |
| | Y150-F9-7 | 103.16 | 426.46 | 422.11 |
| | Y150-F9-11 | 105.60 | 437.18 | 461.05 |
| | MS-hCD3-IC15 | NA | 193.76 | 377.81 |
| | MS-hCD3-IC16 | NA | 170.02 | 294.63 |
| | MS-hCD3-IC17 | NA | 121.89 | 221.79 |
| | MS-hCD3-IC18 | NA | 581.70 | 680.27 |
| Comparative multi-functional antibodies | Y106 | 1.48 | 3.60 | 6.89 |
| | Y150-F8-1 | 2.91 | 101.40 | 151.79 |
| | Y150-F8-2 | 2.39 | 85.50 | 101.88 |
| | Y150-F9-6 | 27.1 | 111.33 | 130.5 |
| | CT-F1 | 3.47 | 176.64 | 346.56 |
| | CT-F2 | 3.21 | 125.54 | 173.53 |
| | CT-F3 | 2.17 | 170.88 | 229.03 |
| | CT-F4 | 1.48 | 187.18 | 326.21 |
| | CT-F5 | 1.38 | 148.45 | 189.52 |
| | CT-F6 | 1.33 | 156.42 | 240.32 |
| | IC-2 | NA | 171.91 | 311.81 |
| | IC-3 | NA | 155.22 | 285.07 |
| | IC-4 | NA | 197.27 | 296.13 |
| | IC-5 | NA | 122.13 | 160.60 |
| | IC-6 | NA | 118.00 | 153.82 |

Table 28 shows that, after the CD3 humanized antibodies according to the present invention are combined into multi-functional antibodies with various CD38 monoclonal antibodies, the affinity at two ends is affected to various degrees.

(3) Detection of T-Cell Activation Level of the Multi-Functional Antibodies According to the Present Invention See FIG. 7 for detection of human T-cell activation level of the multi-functional antibodies according to the present invention, Y150-F8-9, Y150-F8-10, Y150-F8-12, Y150-F9-11, and MS-hCD3-IC-17 (wherein the amount ratio of effector cells, human PBMC, to the target cells MC/CAR is 5:1, and the processing time is 48 h). FIG. 7 illustrates in vitro T-cell activation capabilities of different multi-functional antibodies according to the present invention.

TABLE 29

EC50 values of in vitro T-cell activation by different multi-functional antibodies

| | Antibody code | EC50 values of T-cell activation (pM) |
|---|---|---|
| Multi-functional antibodies according to the present invention | Y150-F8-9 | 0.96 |
| | Y150-F8-10 | 14.11 |
| | Y150-F8-12 | 6531* |
| | Y150-F9-11 | 83.55 |

*indicates that plateau has not been reached and the curve fitting is not accurate. The actual EC50 value may be higher than the number in the table.

In FIG. 7, Y150-F8-9 has the strongest T-cell activation capability, and the binding capability of this antibody with two antigens (CD38 and CD3) are both the strongest in the antibodies in the figure; Y150-F8-8 has the T-cell activation capability at a similar level as that of Y150-F8-9 (data not shown); for the antibodies of Y150-F8-9, Y150-F8-10 and Y150-F8-12, the anti-CD38 antibody sequences are completely the same, and the affinities with CD38 are also the same, but the anti-CD3 antibody sequences are not completely consistent, there is a difference of 1 to 3 amino acid point mutations in the affinity with CD3, and there is also significant difference in T-cell activation capability: Y150-F8-9 has the strongest T-cell activation capability, followed by Y150-F8-10, while Y150-F8-12 has a weak T-cell activation capability. Y150-F9-11 has significant T-cell activation capability.

(4) Cytotoxicity Detection for the Multi-Functional Antibodies According to the Present Invention and Comparative Multi-Functional Antibodies See FIG. 8 for detection results of cytotoxicity of the multi-functional antibodies according to the present invention, Y150-F8-5 and Y150-F8-6, and the comparative multi-functional antibody Y150-F8-1 against multiple myeloma cells MC/CAR (wherein the amount ratio of effector cells, human PBMC, to the target cells MC/CAR is 5:1, and the processing time is 72 h):

FIG. 8 illustrates in vitro cytotoxicity of different multi-functional antibodies against multiple myeloma cells MC/CAR.

TABLE 30

EC50 values of cytotoxicity against tumor cells MC/CAR by different multi-functional antibodies

| | Antibody code | Cytotoxicity EC50 (ng/ml) |
|---|---|---|
| Multi-functional antibodies according to the present invention | Y150-F8-5 | 0.1 |
| | Y150-F8-6 | 0.1 |
| Comparative multi-functional antibody | Y150-F8-1 | 3.8 |
| Control antibodies | CD38 monoclonal antibody | Too weak to be calculated |
| | MS-hCD3-IC17 | No cytotoxicity |

In FIG. 8, the anti-CD3 scFv sequences of Y150-8-5 and Y150-8-6 are both new humanized CD3 antibody sequences. In addition, sequences of other parts of the antibodies (including Fab and Fc) are completely the same as those of Y150-F8-1. The anti-CD3 scFv sequence of Y150-F8-1 is the sequence of a known antibody SP34. It can be seen from the above data that the multi-functional antibodies according to the present invention have similar to or even stronger cytotoxicity against tumor cells. The control antibodies do not have cytotoxicity, indicating that the cytotoxicity of the multi-functional antibodies is generated from bispecific and targeted binding to tumor and immune cells, thereby inducing the immune cells to attack the tumor cells. The CD38 monoclonal antibody is the CD38 antibody drug DARZALEX® that has been marketed.

See FIG. 9 for detection results of cytotoxicity of the multi-functional antibody Y105 according to the present invention against lung cancer cells H358 (wherein the amount ratio of effector cells, human PBMC, to the target cells MC/CAR is 10:1, and the processing time is 48 h).

FIG. 9 illustrates in vitro cytotoxicity of different multi-functional antibodies against lung cancer cells H358.

TABLE 31

EC50 values of cytotoxicity against tumor cells H358 by different multi-functional antibodies

|  | Antibody code | Cytotoxicity EC50 (ng/ml) |
|---|---|---|
| Multi-functional antibodies according to the present invention | Y105 | 1.8 |
| Comparative multi-functional antibody | Y106 | 1.1 |
| Control antibodies | S70 monoclonal antibody | No cytotoxicity |
|  | MS-hCD3-IC15 | 171.8 |

In FIG. 9, the anti-CD3 scFv sequence of Y105 is a new humanized CD3 antibody sequence. In addition, sequences of other parts of the antibody (including Fab and Fc) are completely the same as those of Y106. The sequence of anti-CD3 scFv sequence of Y106 is the sequence of a known antibody SP34. It can be seen from the above data that the multi-functional antibodies according to the present invention have similar to or even stronger cytotoxicity against tumor cells. The control antibodies have very weak cytotoxicity, indicating that the cytotoxicity of the multi-functional antibodies is generated from bispecific and targeted binding to tumor and immune cells, thereby inducing the immune cells to attack the tumor cells. S70 mAb is the PD-L1 antibody drug Tecentriq® that has been marketed.

(5) Stability Detection for the Multi-Functional Antibodies According to the Present Invention and Comparative Multi-Functional Antibodies Experiment I: Detection of Accelerated Thermal Stability at 40° C. with the Following Specific Operation Steps 1. Place a sample in a specific buffer, and the buffer has the following composition: (a) citric acid buffer: 20 mM citric acid, pH 5.5, or (b) histidine buffer: 50 mM histidine, pH 5.5, and adjust the sample concentration to 1 mg/mL;
2. Add the sample to tubes at 500 μL per tube, seal and place the tubes in a 40° C. water bath, and take samples at every 24 h for HPLC-SEC detection. The water batch time is 14 days in total.

See FIGS. 10-16 for detection results.

Figure 10:
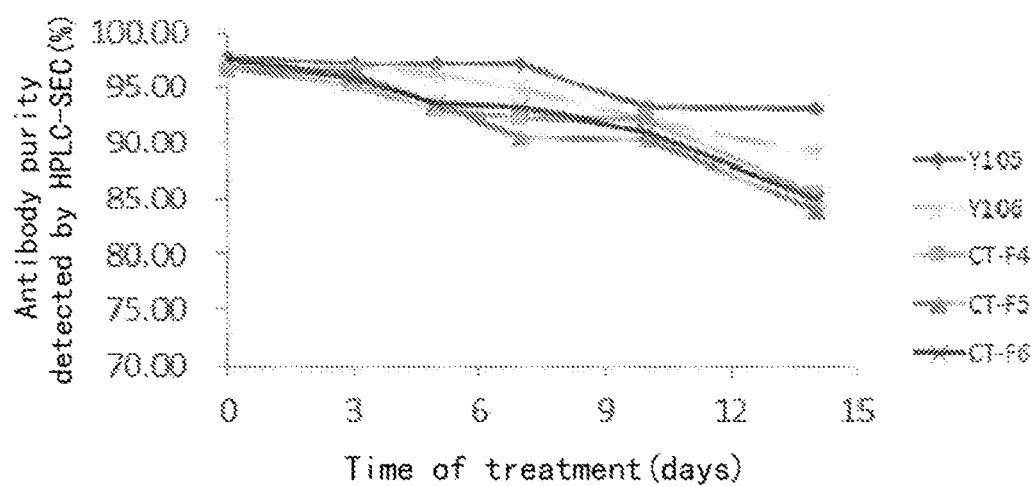
FIG. 10 illustrates accelerated thermal stability detection at 40° C. of a multi-functional antibody Y105 according to the present invention and reference antibodies Y106, CT-F4, CT-F5 and CT-F6 in a citric acid buffer system.

FIG. 10 illustrates accelerated thermal stability detection at 40° C. of a multi-functional antibody Y105 according to the present invention and comparative antibodies Y106, CT-F4, CT-F5 and CT-F6 in a citric acid buffer system. It can be seen from FIG. 10 that the multi-functional antibody according to the present invention has excellent thermal stability, the antibody does not experience significant changes after 14 days of treatment at 40° C., which is similar to the comparative antibody Y100, but is significantly superior to CT-F4, CT-F5 and CT-F6, wherein Y105 has the same Fab and Fc sequences as all the comparative antibodies, but a different ScFv. Y105 is the CD3 antibody VH2a and VL5 sequences according to the present invention, Y106 is the SP34 antibody sequence, CT-F4 is the CD3 antibody 1 sequence, CT-F5 is the CD3 antibody 2 sequence, and CT-F6 is the CD3 antibody 1VH and CD3 antibody 2VL sequences.

Figure 11:
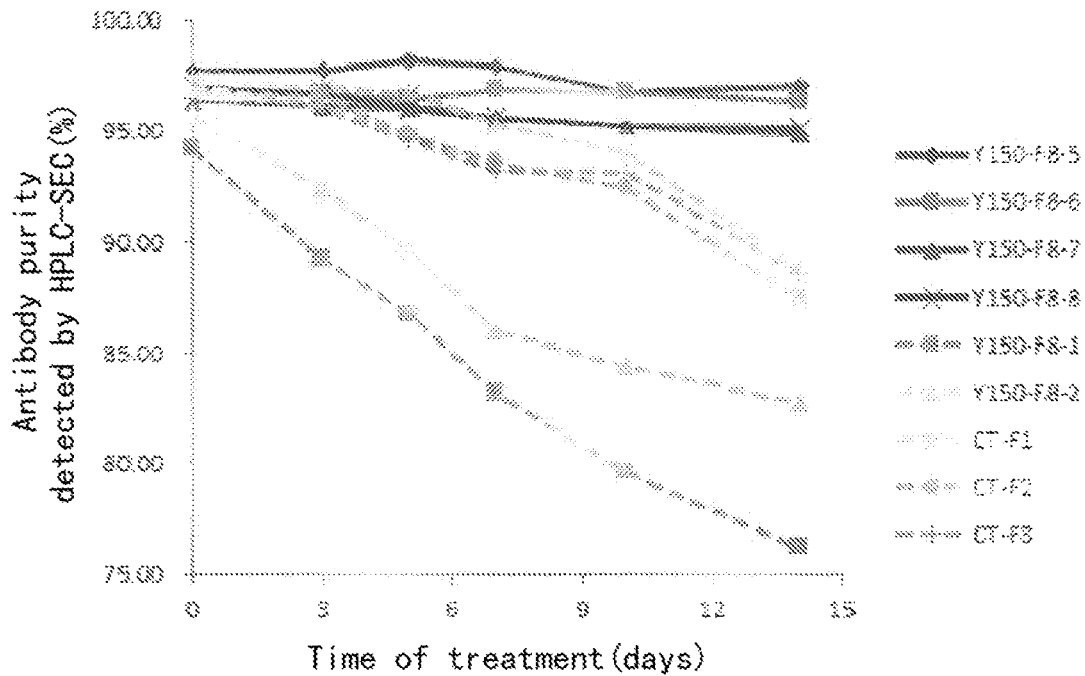
FIG. 11 illustrates accelerated thermal stability detection at 40° C. of multi-functional antibodies Y150-F8-5, Y150-F8-6, Y150-F8-7 and Y150-F8-8 according to the present invention and comparative antibodies Y150-F8-1, Y150-F8-2, CT-F1, CT-F2 and CT-F3 in a citric acid buffer system.

FIG. 11 illustrates accelerated thermal stability detection at 40° C. of multi-functional antibodies Y150-F8-5, Y150-F8-6, Y150-F8-7 and Y150-F8-8 according to the present invention and comparative antibodies Y150-F8-1, Y150-F8-2, CT-F1, CT-F2 and CT-F3 in a citric acid buffer system. In FIG. 11, all the multi-functional antibodies have the same Fab sequence, and Y150-F8-5, Y150-F8-6, Y150-F8-1, CT-F1, CT-F2 and CT-F3 have the same Fc sequence; the CD3 antibody sequences of Y150-F8-5, Y150-F8-6, Y150-F8-7 and Y150-F8-8 are VH2a and VL5; the CD3 antibody sequences of Y150-F8-1 and Y150-F8-2 are SP34, the CD3 antibody sequence of CT-F1 is the CD3 antibody 1, the CD3 antibody sequence of CT-F2 is the CD3 antibody 2, and the CD3 antibody sequences of CT-F3 are the CD3 antibody 1VH and CD3 antibody 2VL. It can be seen from the data in the figure that the multi-functional antibodies according to the present invention have thermal stability significantly superior to the thermal stability of the comparative antibodies.

Figure 12:
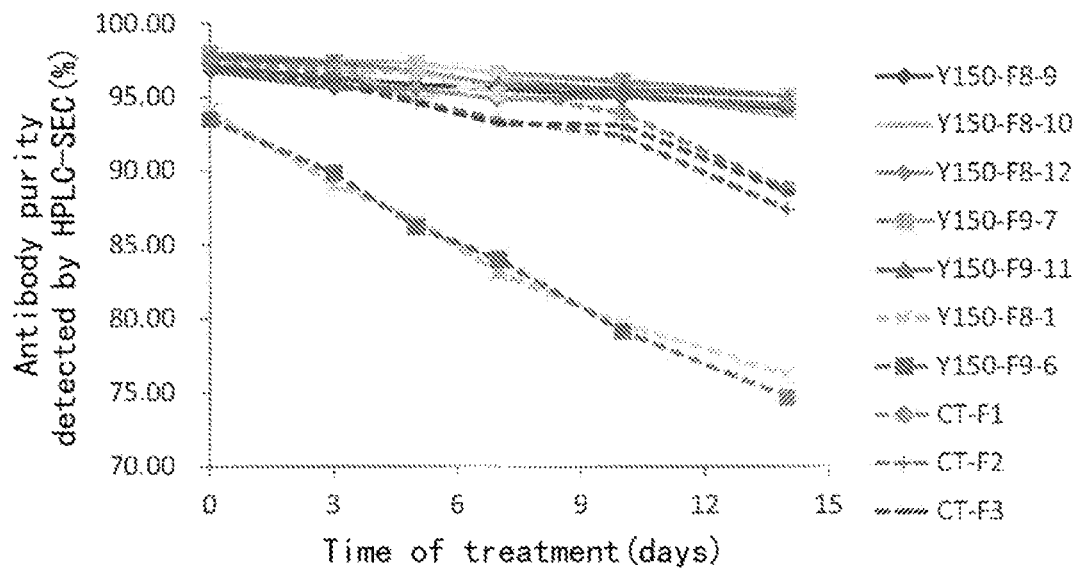
FIG. 12 illustrates accelerated thermal stability detection at 40° C. of multi-functional antibodies Y150-F8-9, F8-10, F8-12, F9-7 and F9-11 according to the present invention and comparative antibodies Y150-F8-1, Y150-F9-6, CT-F1, CT-F2 and CT-F3 in a citric acid buffer system.

FIG. 12 illustrates accelerated thermal stability detection at 40° C. of multi-functional antibodies Y150-F8-9, F8-10, F8-12, F9-7 and F9-11 according to the present invention and comparative antibodies Y150-F8-1, Y150-F9-6, CT-F1, CT-F2 and CT-F3 in a citric acid buffer system. In FIG. 12, Y150-F8-9, F8-10, F8-12, F9-7 and F9-11 are multi-functional antibodies according to the present invention, and the CD3 antibody sequences are VH2a and VL5, or VH2j and VL5a (F8-10), or VH21 and VL5b (F8-12); Y150-F8-1, Y150-F9-6, CT-F1, CT-F2 and CT-F3 are comparative multi-functional antibodies, and the CD3 antibody sequences are SP34 (Y150-F8-1, Y150-F9-6), CD3 antibody 1 (CT-F1), CD3 antibody 2 (CT-F2), and CD3 antibody 1VH and CD3 antibody 2VL (CT-F3), respectively. It can be seen from the data in FIG. 12 that the multi-functional antibodies according to the present invention have thermal stability significantly superior to the thermal stability of the comparative antibodies.

Figure 13:
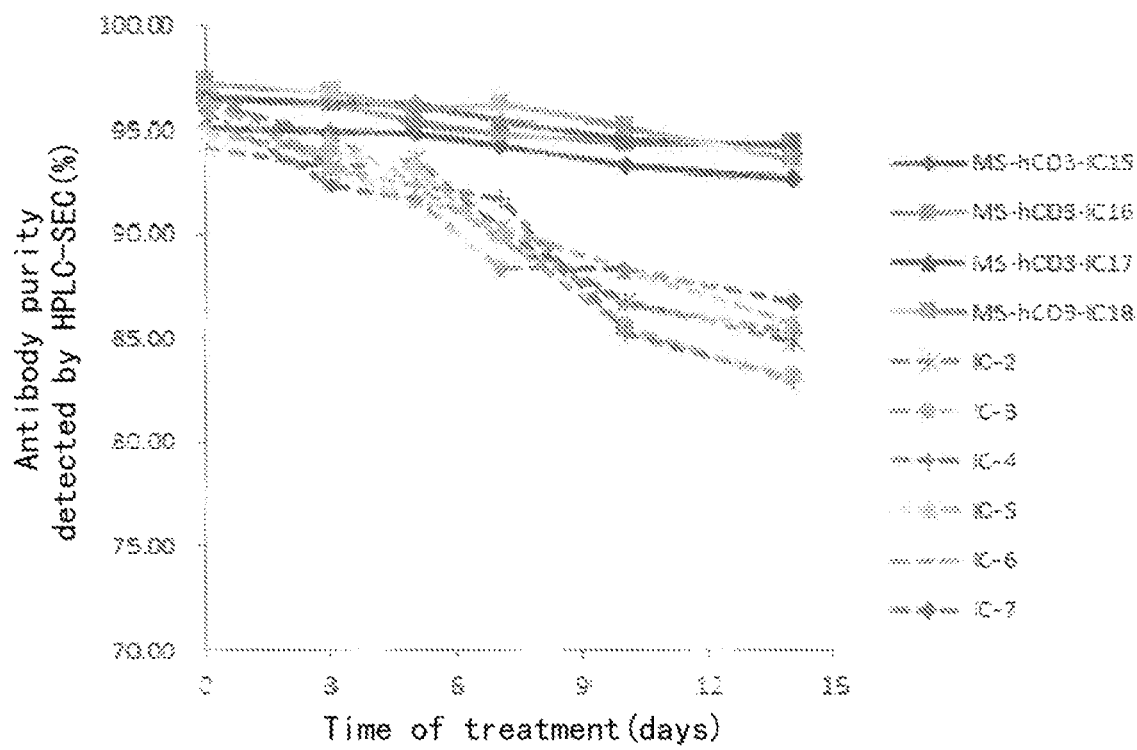
FIG. 13 illustrates accelerated thermal stability detection at 40° C. of multi-functional antibodies MS-hCD3-IC15, IC16, IC17 and IC18 according to the present invention and comparative antibodies IC-2 to IC-7 in a citric acid buffer system.

FIG. 13 illustrates accelerated thermal stability detection at 40° C. of multi-functional antibodies MS-hCD3-IC15, IC16, IC17 and IC18 according to the present invention and comparative antibodies IC-2 to IC-7 in a citric acid buffer system. In FIG. 13, all antibodies have exactly the same Fab sequence, wherein MS-hCD3-IC15, IC16, IC17 and IC18 are multi-functional antibodies according to the present invention, and the CD3 antibody sequences are VH2a and VL5, or VH2j and VL5a (IC18). IC-2 to IC-7 are comparative multi-functional antibodies, and the CD3 antibody sequences are SP34 (IC-2 and IC-3), CD3 antibody 1 (IC-4), CD3 antibody 2 (IC-5), and CD3 antibody 1VH and CD3 antibody 2VL (IC-6 and IC-7), respectively. It can be seen from the data in the figure that the multi-functional antibodies according to the present invention have thermal stability significantly superior to the thermal stability of the comparative antibodies.

Figure 14:
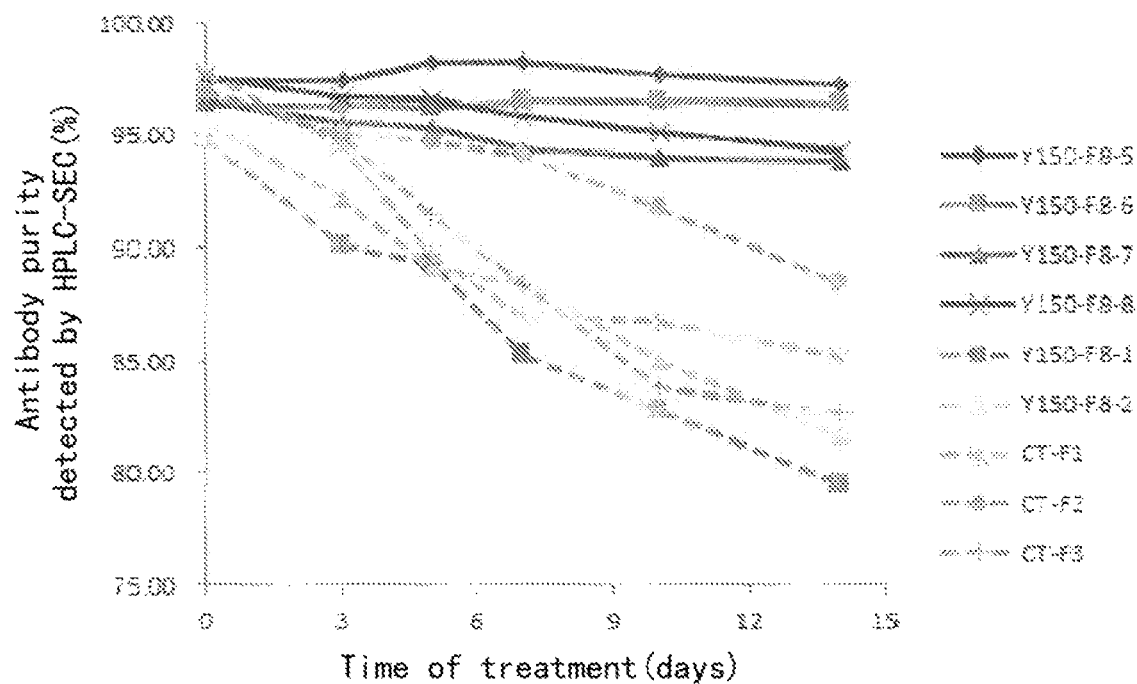
FIG. 14 illustrates accelerated thermal stability detection at 40° C. of multi-functional antibodies Y150-F8-5, Y150-F8-6, Y150-F8-7 and Y150-F8-8 according to the present invention and comparative antibodies Y150-F8-1, Y150-F8-2, CT-F1, CT-F2 and CT-F3 in a histidine buffer system.

FIG. 14 illustrates accelerated thermal stability detection at 40° C. of multi-functional antibodies Y150-F8-5, Y150-F8-6, Y150-F8-7 and Y150-F8-8 according to the present invention and comparative antibodies Y150-F8-1, Y150-F8-2, CT-F1, CT-F2 and CT-F3 in a histidine buffer system. In FIG. 14, all multi-functional antibodies have the same Fab sequence, and Y150-F8-5, Y150-F8-6, Y150-F8-1, CT-F1, CT-F2 and CT-F3 have the same Fc sequence; the CD3 antibody sequences of Y150-F8-5, Y150-F8-6, Y150-F8-7 and Y150-F8-8 are VH2a and VL5; the CD3 antibody sequences of Y150-F8-1 and Y150-F8-2 are SP34, the CD3 antibody sequence of CT-F1 is the CD3 antibody 1, the CD3 antibody sequence of CT-F2 is the CD3 antibody 2, and the CD3 antibody sequences of CT-F3 are the CD3 antibody 1VH and CD3 antibody 2VL. It can be seen from the data in the figure that the multi-functional antibodies according to the present invention all have excellent thermal stability, while the thermal stability of the comparative antibodies Y150-F8-1, Y150-F8-2, CT-F1, CT-F2 and CT-F3 is significantly weaker than those of the multi-functional antibodies according to the present invention.

Figure 15:
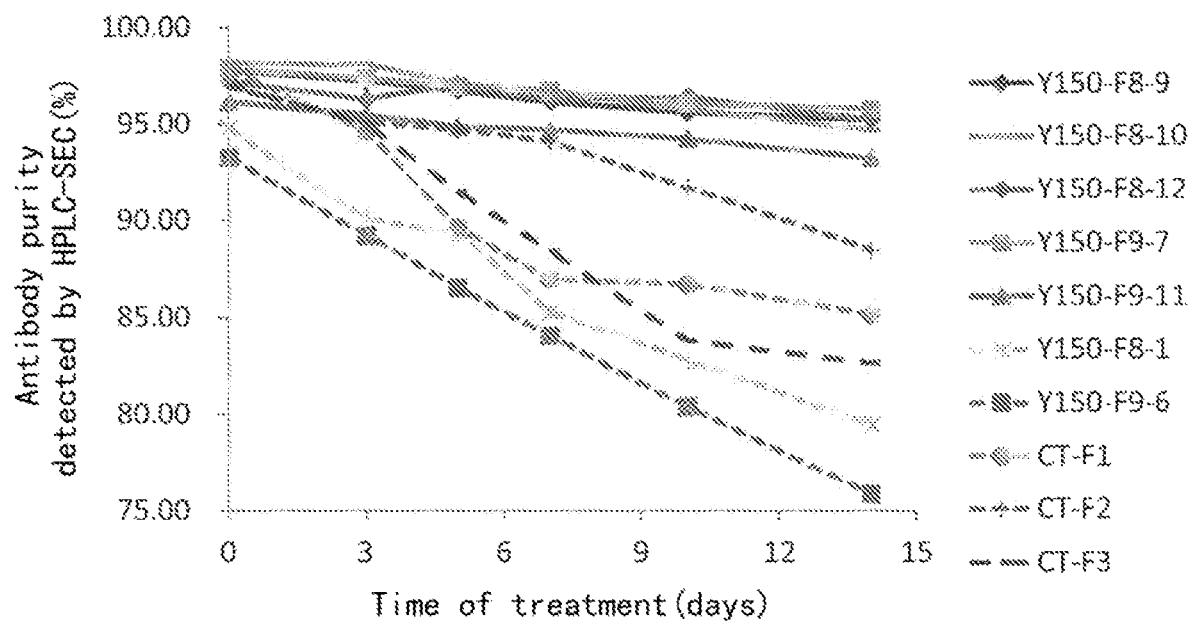
FIG. 15 illustrates accelerated thermal stability detection at 40° C. of multi-functional antibodies Y150-F8-9, F8-10, F8-12, F9-7 and F9-11 according to the present invention and comparative antibodies Y150-F8-1, Y150-F9-6, CT-F1, CT-F2 and CT-F3 in a histidine buffer system.

FIG. 15 illustrates accelerated thermal stability detection at 40° C. of multi-functional antibodies Y150-F8-9, F8-10, F8-12, F9-7 and F9-11 according to the present invention and comparative antibodies Y150-F8-1, Y150-F9-6, CT-F1, CT-F2 and CT-F3 in a histidine buffer system. In FIG. 15, Y150-F8-9, F8-10, F8-12, F9-7 and F9-11 are multi-functional antibodies according to the present invention, and the CD3 antibody sequences are VH2a and VL5, or VH2j and VL5a (F8-10), or VH21 and VL5b (F8-12); Y150-F8-1, Y150-F9-6, CT-F1, CT-F2 and CT-F3 are comparative multi-functional antibodies, and the CD3 antibody sequences are SP34 (Y150-F8-1 and Y150-F9-6), CD3 antibody 1 (CT-F1), CD3 antibody 2 (CT-F2), and CD3 antibody 1VH and CD3 antibody 2VL (CT-F3), respectively. It can be seen from the data in FIG. 15 that the multi-functional antibodies according to the present invention have thermal stability significantly superior to the thermal stability of the comparative antibodies.

Figure 16:
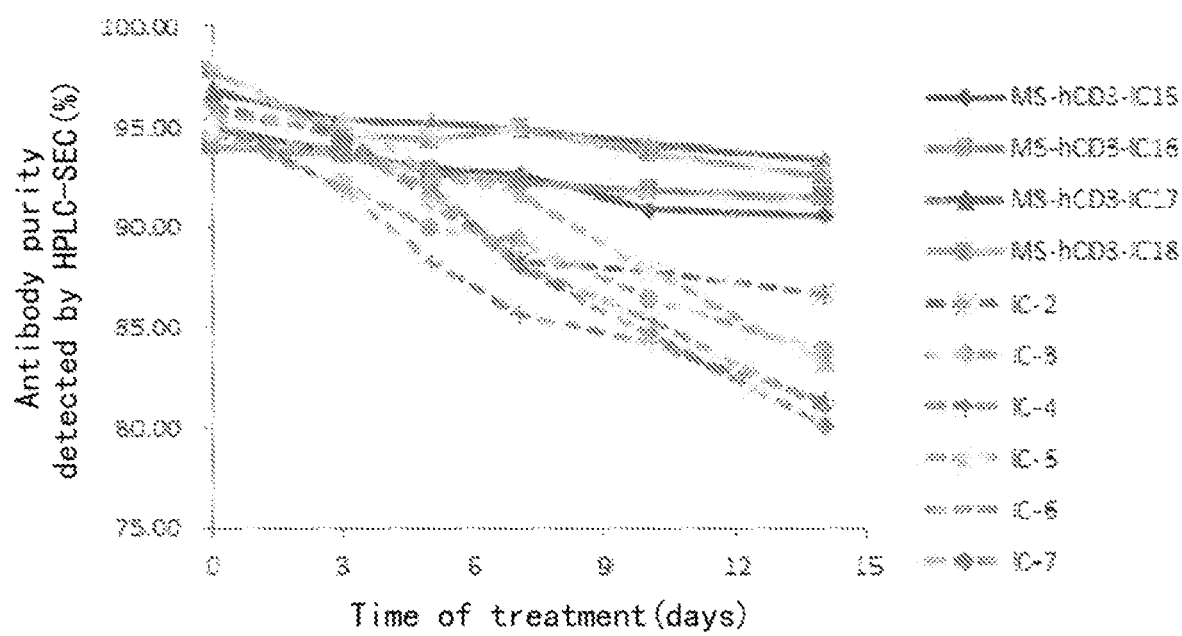
FIG. 16 illustrates accelerated thermal stability detection at 40° C. of multi-functional antibodies MS-hCD3-IC15, IC16, IC17 and IC18 according to the present invention and comparative antibodies IC-2 to IC-7 in a histidine buffer system.

FIG. 16 illustrates accelerated thermal stability detection at 40° C. of multi-functional antibodies MS-hCD3-IC15, IC16, IC17 and IC18 according to the present invention and comparative antibodies IC-2 to IC-7 in a histidine buffer system. In FIG. 16, all antibodies have exactly the same Fab sequence, wherein MS-hCD3-IC15, IC16, IC17 and IC18 are multi-functional antibodies according to the present invention, and the CD3 antibody sequences are VH2a and VL5, or VH2j and VL5a (IC18). IC-2 to IC-7 are comparative multi-functional antibodies, and the CD3 antibody sequences are SP34 (IC-2 and IC-3), CD3 antibody 1 (IC-4), CD3 antibody 2 (IC-5), and CD3 antibody 1VH and CD3 antibody 2VL (IC-6 and IC-7), respectively. It can be seen from the data in the figure that the multi-functional antibodies according to the present invention have thermal stability significantly superior to the thermal stability of the comparative antibodies.

Experiment II: Low-pH Stability Detection

Low-pH stability is also referred to as acid resistance, which investigates whether an antibody molecule can maintain its original state after being treated in an acidic environment for a period of time and then neutralized to physiological conditions. The specific method is as follows: when protein A affinity chromatography is performed on an antibody molecule, the antibody solution eluted from the acid eluting step (using pH 3.5 citric acid buffer) is not neutralized; after staying in the buffer for a period of time, samples are taken at 30 min and 60 min, added ⅒ volume of 1M Tris-HCl (pH8.0) for neutralization, and HPLC-SEC detection is performed on the samples.

Figure 17:
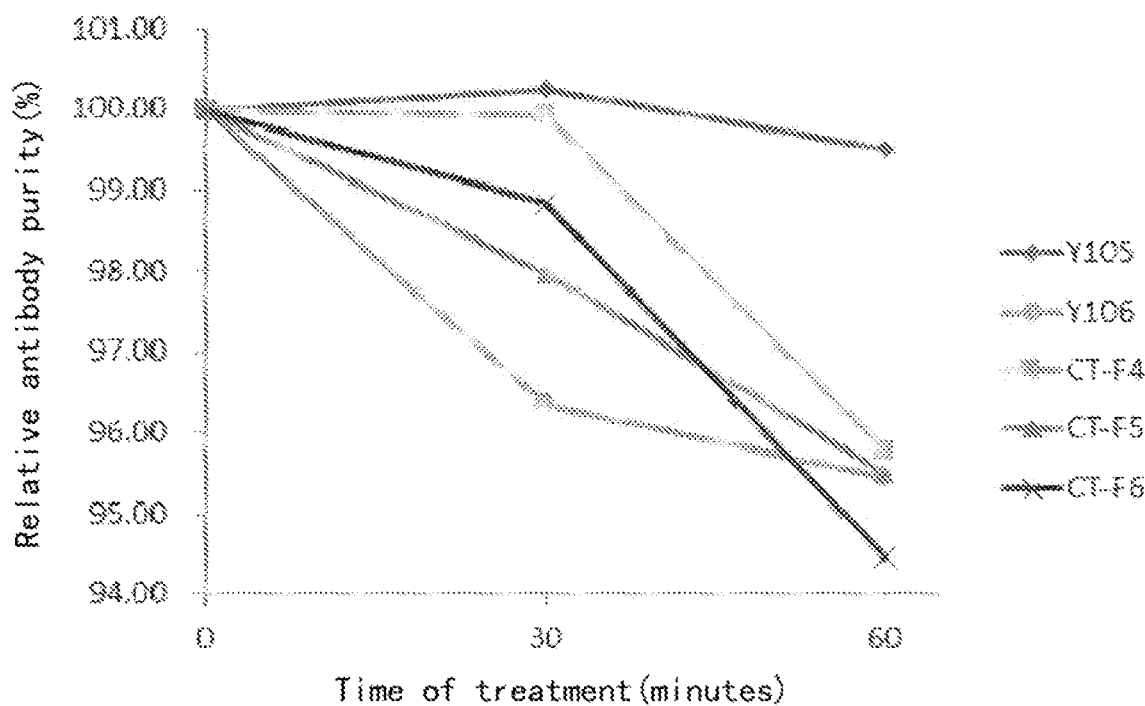
FIG. 17 illustrates acid-resistant stability detection of a multi-functional antibody Y105 according to the present invention and comparative antibodies Y106, CT-F4, CT-F5 and CT-F6 in a citric acid buffer system with pH 3.5.

FIG. 17 illustrates acid-resistant stability detection of a multi-functional antibody Y105 according to the present invention and comparative antibodies Y106, CT-F4, CT-F5 and CT-F6 in a citric acid buffer system with pH 3.5. It can be seen from FIG. 17 that the multi-functional antibody Y105 according to the present invention has excellent acid resistance, the antibody does not experience significant changes after 60 min treatment at low pH, and its acid resistance is significantly superior to that of Y106, CT-F4, CT-F5 and CT-F6.

Figure 18:
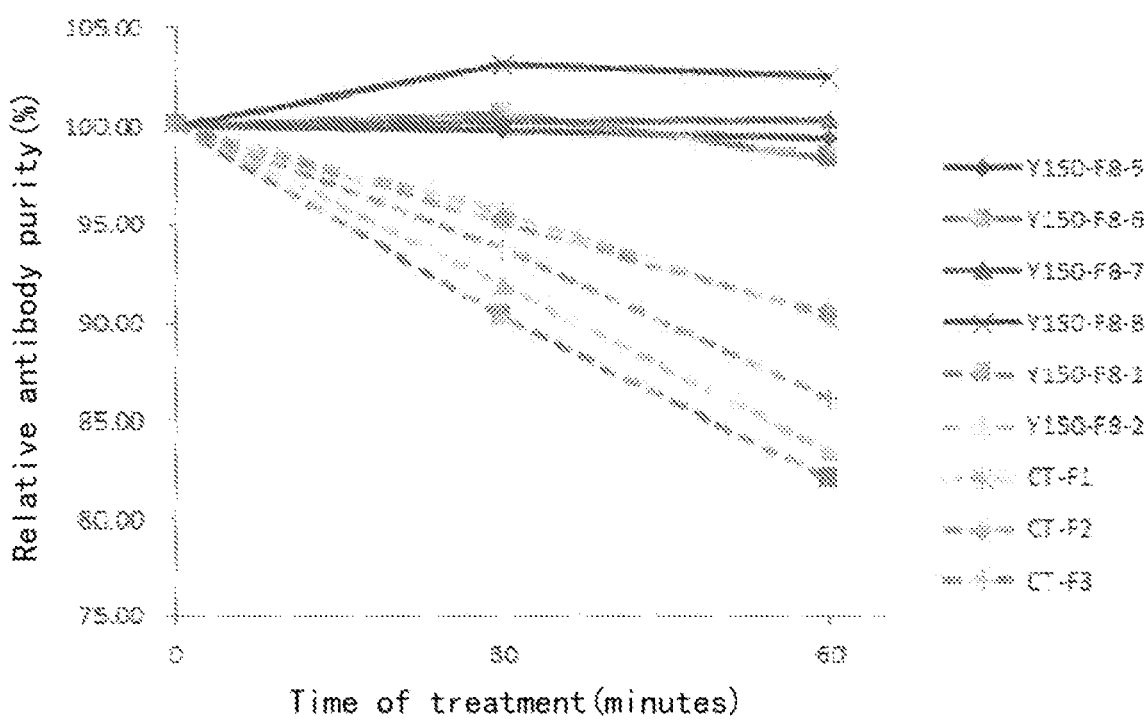
FIG. 18 illustrates acid-resistant stability detection of multi-functional antibodies Y150-F8-5, Y150-F8-6, Y150-F8-7 and Y150-F8-8 according to the present invention and comparative antibodies Y150-F8-1, Y150-F8-2, CT-F1, CT-F2 and CT-F3 in a citric acid buffer system with pH 3.5.

FIG. 18 illustrates acid-resistant stability detection of multi-functional antibodies Y150-F8-5, Y150-F8-6, Y150-F8-7 and Y150-F8-8 according to the present invention and comparative antibodies Y150-F8-1, Y150-F8-2, CT-F1, CT-F2 and CT-F3 in a citric acid buffer system with pH 3.5. In FIG. 18, all multi-functional antibodies have the same Fab sequence, and Y150-F8-5, Y150-F8-6, Y150-F8-1, CT-F1, CT-F2 and CT-F3 have the same Fc sequence; the CD3 antibody sequences of Y150-F8-5, Y150-F8-6, Y150-F8-7 and Y150-F8-8 are VH2a and VL5; the CD3 antibody sequences of Y150-F8-1 and Y150-F8-2 are SP34, the CD3 antibody sequence of CT-PI is the CD3 antibody 1, the CD3 antibody sequence of CT-F2 is the CD3 antibody 2, and the CD3 antibody sequences of CT-F3 are the CD3 antibody 1VH and CD3 antibody 2VL. It can be seen from the data in the figure that the multi-functional antibodies according to the present invention have acid resistance significantly superior to that of the comparative antibodies.

Figure 19:
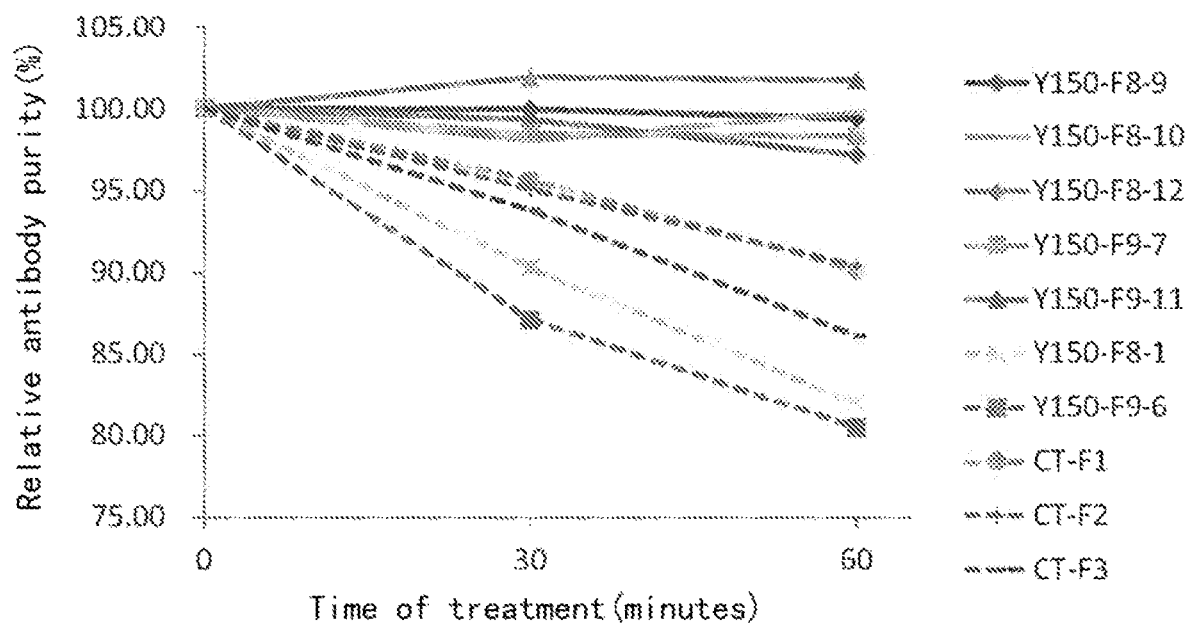
FIG. 19 illustrates acid-resistant stability detection of multi-functional antibodies Y150-F8-9, F8-10, F8-12, F9-7 and F9-11 according to the present invention and comparative antibodies Y150-F8-1, Y150-F9-6, CT-F1, CT-F2 and CT-F3 in a citric acid buffer system with pH 3.5.

FIG. 19 illustrates acid-resistant stability detection of multi-functional antibodies Y150-F8-9, F8-10, F8-12, F9-7 and F9-11 according to the present invention and comparative antibodies Y150-F8-1, Y150-F9-6, CT-F1, CT-F2 and CT-F3 in a citric acid buffer system with pH 3.5. In FIG. 19, Y150-F8-9, Y150-F9-7 and Y150-F9-11 are multi-functional antibodies according to the present invention, and the CD3 antibody sequences are VH2a and VL5, or VH2j and VL5a (F8-10), or VH21 and VL5b (F8-12); Y150-F8-1, CT-F1, CT-F2 and CT-F3 are comparative multi-functional antibodies, and the CD3 antibody sequences are SP34 (Y150-F8-1 and Y150-F9-6), CD3 antibody 1 (CT-F1), CD3 antibody 2 (CT-F2), and CD3 antibody 1VH and CD3 antibody 2VL (CT-F3), respectively. It can be seen from the data in FIG. 19 that the multi-functional antibodies according to the present invention have acid resistance significantly superior to that of the comparative antibodies.

Figure 20:
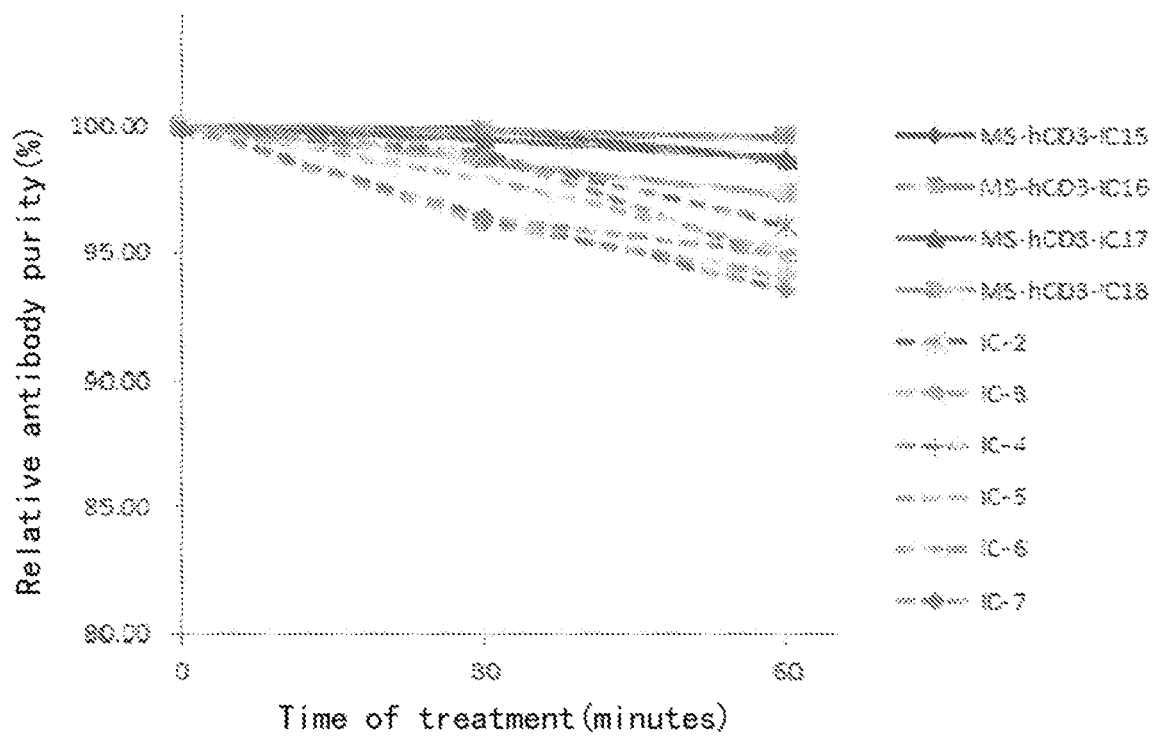
FIG. 20 illustrates acid-resistant stability detection of multi-functional antibodies MS-hCD3-IC15, IC16, IC17 and IC18 according to the present invention and comparative antibodies IC-2 to IC-7 in a citric acid buffer system with pH 3.5.

FIG. 20 illustrates acid-resistant stability detection of multi-functional antibodies MS-hCD3-IC15, IC16, IC17 and IC18 according to the present invention and comparative antibodies IC-2 to IC-7 in a citric acid buffer system with pH 3.5. In FIG. 20, all antibodies have exactly the same Fab sequence, wherein MS-hCD3-IC15, IC16, IC17 and IC18 are multi-functional antibodies according to the present invention, and the CD3 antibody sequences are VH2a and VL5, or VH2j and VL5a (IC18). IC-2 to IC-7 are comparative multi-functional antibodies, and the CD3 antibody sequences are SP34 (IC-2 and IC-3), CD3 antibody 1 (IC-4), CD3 antibody 2 (IC-5), and CD3 antibody 1VH and CD3 antibody 2VL (IC-6 and IC-7), respectively. It can be seen from the data in the figure that the multi-functional antibodies according to the present invention have acid resistance significantly superior to that of the comparative antibodies.

(6) In Vivo Efficacy Experiment Using Multi-Functional Antibodies According to the Present Invention and Comparative Multi-Functional Antibodies I. Experimental Materials Cells: Daudi (human multiple myeloma cell line purchased from ATCC), human PBMC;
Mice: NOD/SCID 5-week old, female, Beijing Vital River Laboratory Animal Technology Co., Ltd.
Inoculation method: Daudi cells—Subcutaneously on right back; human PBMC—tail vein, inoculated with Daudi and PBMC cells on D0;
drugs to be tested: (B) Y150-F8-8, (C) Y150-F8-9, (D) Y150-F9-11; Negative control: (A) blank control; (H) MS-hCD3-IC-17; Positive control: (G) CD38mAb (CD38 monoclonal antibody, Darzalex®);
Administration mode: (1) Y150-F8-8, Y150-F8-9, Y150-F9-11 and MS-hCD3-17, administered via tail vein at different doses, respectively, start administration on D0, TIWx2; (2) CD38mAb, administered on D0 and D7, the dose on D0 is 5 mg/kg, the dose on D7 is 15 mg/kg; 6 animals per group;
Weight: measure weight 3 times per week during drug administration and 2 times per week thereafter
Tumor volume: for 9-20 days of the tumor latency period and when the average tumor volume reaches 30 mm$^3$, measure the length and width of the tumor 2 times per week with a monitoring period of about 30 days, or when the average tumor volume of the negative control group reaches 2000 mm$^3$, take photos of all remaining tumor-bearing mice. When the tumor volume of a group gets close to 2000 mm$^3$ or the tumor volume of an individual mice reaches 3000 mm$^3$, end this group.

II. Experimental Results

Figure 21A:
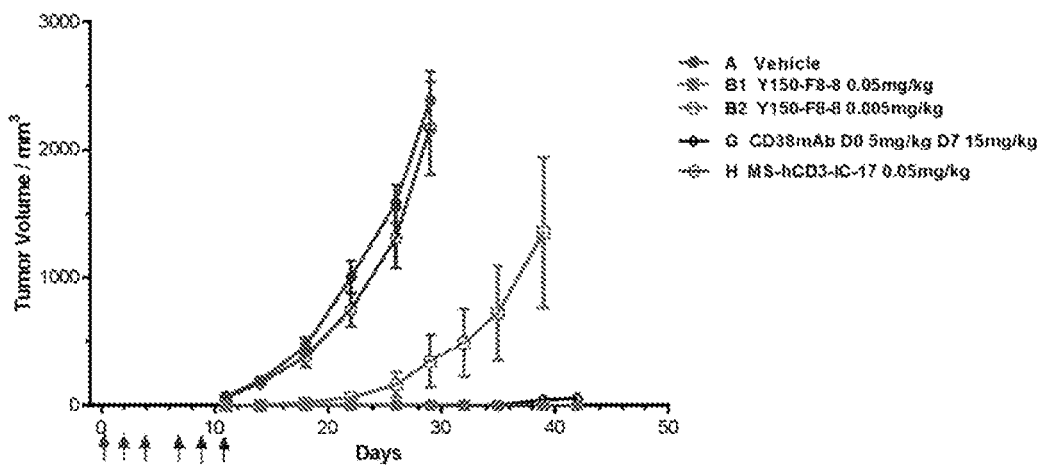
FIG. 21 illustrates in vivo efficacy and tumor volume monitoring of different multi-functional antibodies in a mouse tumor model, wherein a multi-functional antibody Y150-F8-8 according to the present invention is used in FIG. 21A; a multi-functional antibody F8-9 according to the present invention is used in FIG. 21B; a multi-functional antibody F9-11 according to the present invention is used in FIG. 21C; the anti-CD3 antibody sequences are all VH2a and VL5, and the anti-CD38 antibody sequences are all different.
Figure 21B:
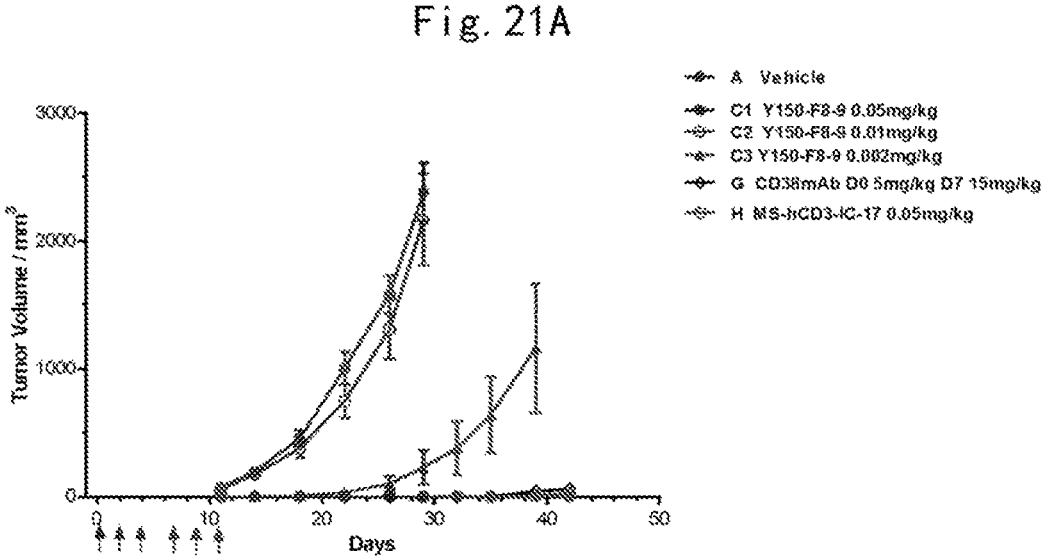
Figure 21C:
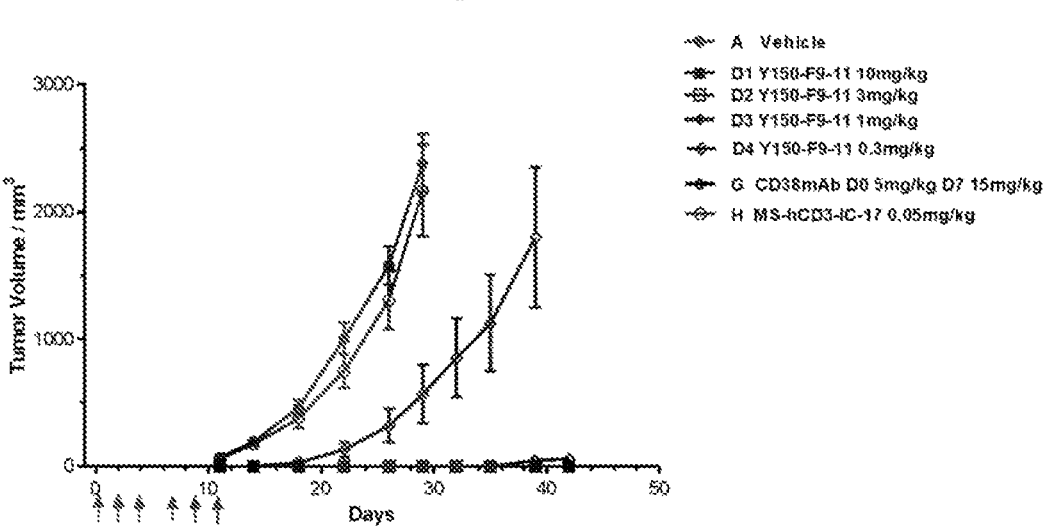

Experimental results of Y150-F8-8 are shown in FIG. 21A, experimental results of Y150-F8-9 are shown in FIG. 21B, and experimental results of Y150-F9-11 are shown in FIG. 21C.

FIG. 21 illustrates in vivo efficacy and tumor volume monitoring of different multi-functional antibodies in a mouse tumor model, wherein Y150-F8-8 (A), F8-9 (B) and F9-11 (C) are all multi-functional antibodies according to the present invention, the anti-CD3 antibody sequences are all VH2a and VL5, and the anti-CD38 antibody sequences are all different.

TABLE 32

In vivo efficacy of different multi-functional antibodies (29 days after drug administration)

| Antibody | Group | Dose (mg/kg) | TV (mm$^3$) | T/C (%) |
|---|---|---|---|---|
| Blank control | A | 0 | 2382 | 100.00 |
| Y150-F8-8 | B1 | 0.05 | 0 | 0.00 |
|  | B2 | 0.005 | 344.8 | 14.48 |
| Y150-F8-9 | C1 | 0.05 | 0 | 0.00 |
|  | C2 | 0.01 | 0 | 0.00 |
|  | C3 | 0.002 | 229.9 | 9.65 |
| Y150-F9-11 | D1 | 10 | 0 | 0.00 |
|  | D2 | 3 | 0 | 0.00 |
|  | D3 | 1 | 0 | 0.00 |
|  | D4 | 0.3 | 567.5 | 23.82 |
| CD38mAb | G | 5(D0), 15(D7) | 0 | 0.00 |
| MS-hCD3-IC17 | H | 0.05 | 2167 | 90.99 |

From FIG. 21, it can be seen that the multi-functional antibodies Y150-F8-8, F8-9 and F9-11 according to the present invention have significant tumor-inhibiting effect, and there is no significant difference when compared with the control monoclonal antibody, all of which can completely inhibit tumors at an effective dose, and the animals do not show significant toxic side effect.

(7) Monkey Toxicity Experiment by Using Multi-Functional Antibodies According to the Present Invention 2F5mAb is an anti-CD38 monoclonal antibody, which can cross bind to human and monkey CD38s, and the specific sequences are:

TABLE 33

2F5 monoclonal antibody sequences

| Code of comparative antibody | Polypeptide | Domain | Amino acid sequences (those in bold and underlied being CDR) | Sequence No. |
|---|---|---|---|---|
| 2F5mAb | Heavy chain | VH | QVQLVQSGAEVKKPGSSVKVSCKASGGTFSSYAFSWVRQA PGQGLEWMGRVIPFLGIANSAQKFQGRVTITADKSTSTAYM DLSSLRSEDTAVYYCARDDIAALGPFDYWGQGTLVTVSS | 96 |
|  |  | CH1 | ASTKGPSVFPLAPSSKSTSGGTAALGCLVKDYFPEPVTVSW NSGALTSGVHTFPAVLQSSGLYSLSSVVTVPSSSLGTQTYIC NVNHKPSNTKVDKKV | 154 |
|  |  | Hinge | EPKSCDKTHTCP | 139 |
|  |  | CH2 | PCPAPELLGGPSVFLFPPKPKDTLMISRTPEVTCVVVDVSHE DPEVKFNWYVDGVEVHNAKTKPREEQYNSTYRVVSVLTV LHQDWLNGKEYKCKVSNKALPAPIEKTISKAK | 155 |
|  |  | CH3 | GQPREPQVYTLPPSRDELTKNQVSLTCLVKGFYPSDIAVEW ESNGQPENNYKTTPPVLDSDGSFFLYSKLTVDKSRWQQGN VFSCSVMHEALHNHYTQKSLSLSPGK | 162 |
|  | Light chain | VL | DIQMTQSPSSLSASVGDRVTITCRASQGISSWLAWYQQKPE KAPKSLIYAASSLQSGVPSRFSGSGSGTDFTLTISSLQPEDFA TYYCQQYNSYPRTFGQGTKVEIK | 97 |

TABLE 33-continued

2F5 monoclonal antibody sequences

| Code of comparative antibody | Polypeptide | Domain | Amino acid sequences (those in bold and underlied being CDR) | Sequence No. |
|---|---|---|---|---|
| | | CL | RTVAAPSVFIFPPSDEQLKSGTASVVCLLNNFYPREAKVQW KVDNALQSGNSQESVTEQDSKDSTYSLSSTLTLSKADYEK HKVYACEVTHQGLSSPVTKSFNRGEC | 148 |

Monkey toxicity experiments are conducted on multi-functional antibodies Y150-F8-10, F9-11, and F9-12, as well as comparative antibody Y150-F9-6 and monoclonal antibody 2F5mAb, respectively, the drugs are administered once via intravenous infusion, and the doses are listed in the table below:

TABLE 34

Drug doses administered in the monkey toxicity experiments

| Antibody | Amount | Dose (mg/kg) | Toxic response |
|---|---|---|---|
| Y150-F9-6 | 2 | 0.5 | Mortality rate 100% |
| Y150-F8-10 | 2 | 1.0 | No death |
| Y150-F9-11 | 2 | 1.0 | No death |
| Y150-F9-12 | 2 | 1.0 | No death |

For the Y150-F8-10, F9-11, and F9-12 groups, cell numbers in the lymphocyte subpopulation CD38+CD20+ in monkeys all decrease significantly within 24 h after the drug administration, while for the 2F5mAb group (the dose is 20 mg/kg), the number of cells in the subpopulation decrease to around 30% of the number prior to the drug administration, and the cells are not completely eliminated. These data show that Y150-F8-10, F9-11, and F9-12 molecules have the effect of significantly eliminating CD38+ cells. From Table 34, it can be seen that Y150-F8-10, Y150-F9-11, and Y150-F9-12 have weaker toxicity than that of Y150-F9-6.

The invention claimed is:

1. An antibody or an antigen binding fragment thereof specifically binding to human CD3, wherein the antibody or the antigen binding fragment comprises a heavy chain variable region and a light chain variable region, and the heavy chain variable region comprises
   an amino acid sequence selected from the group consisting of SEQ ID NOs: 45-62;
and
   the light chain variable region comprises
   an amino acid sequence selected from the group consisting of SEQ ID NOs: 63-73.

2. The antibody or antigen binding fragment thereof of claim 1, wherein the heavy chain variable region and the light chain variable region respectively comprise the amino acid sequences of:
   SEQ ID NOs: 46 and 63;
   SEQ ID NOs: 47 and 63;
   SEQ ID NOs: 49 and 63;
   SEQ ID NOs: 50 and 63;
   SEQ ID NOs: 51 and 63;
   SEQ ID NOs: 46 and 71;
   SEQ ID NOs: 47 and 71;
   SEQ ID NOs: 49 and 71;
   SEQ ID NOs: 51 and 71;
   SEQ ID NOs: 52 and 72;
   SEQ ID NOs: 53 and 72;
   SEQ ID NOs: 54 and 72;
   SEQ ID NOs: 55 and 72;
   SEQ ID NOs: 56 and 72;
   SEQ ID NOs: 57 and 72;
   SEQ ID NOs: 58 and 72;
   SEQ ID NOs: 62 and 72;
   SEQ ID NOs: 52 and 73;
   SEQ ID NOs: 53 and 73;
   SEQ ID NOs: 54 and 73;
   SEQ ID NOs: 55 and 73;
   SEQ ID NOs: 56 and 73;
   SEQ ID NOs: 57 and 73;
   SEQ ID NOs: 58 and 73;
   SEQ ID NOs: 61 and 73;
   SEQ ID NOs: 62 and 73;
   SEQ ID NOs: 45 and 63;
   SEQ ID NOs: 48 and 63;
   SEQ ID NOs: 45 and 64;
   SEQ ID NOs: 45 and 67;
   SEQ ID NOs: 48 and 64;
   SEQ ID NOs: 48 and 67;
   SEQ ID NOs: 45 and 71;
   SEQ ID NOs: 48 and 71;
   SEQ ID NOs: 50 and 71;
   SEQ ID NOs: 61 and 72;
   SEQ ID NOs: 60 and 73;
   SEQ ID NOs: 60 and 72; or
   SEQ ID NOs: 59 and 72.

3. A polynucleotide, which encodes the antibody or antigen binding fragment thereof according to claim 1.

4. A pharmaceutical composition, comprising the antibody or antigen binding fragment thereof according to claim 1 and a pharmaceutically acceptable carrier or excipient.

5. The antibody or antigen binding fragment thereof of claim 1, wherein the heavy chain variable region comprises the amino acid sequence of SEQ ID NO: 49 and the light chain variable region comprises amino acid sequences of SEQ ID NO: 71.

* * * * *

SEQUENCE LISTING

```
<160> NUMBER OF SEQ ID NOS: 195

<210> SEQ ID NO 1
<211> LENGTH: 5
<212> TYPE: PRT
<213> ORGANISM: Artificial Sequence
<220> FEATURE:
<223> OTHER INFORMATION: Synthetic

<400> SEQUENCE: 1

Thr Tyr Ala Met Asn
1               5

<210> SEQ ID NO 2
<211> LENGTH: 19
<212> TYPE: PRT
<213> ORGANISM: Artificial Sequence
<220> FEATURE:
<223> OTHER INFORMATION: Synthetic

<400> SEQUENCE: 2

Arg Ile Arg Ser Lys Tyr Asn Asn Tyr Ala Thr Tyr Tyr Ala Asp Ser
1               5                   10                  15

Val Lys Asp

<210> SEQ ID NO 3
<211> LENGTH: 14
<212> TYPE: PRT
<213> ORGANISM: Artificial Sequence
<220> FEATURE:
<223> OTHER INFORMATION: Synthetic

<400> SEQUENCE: 3
```

His Gly Asn Phe Gly Asn Ser Tyr Val Ser Trp Phe Ala Tyr
1               5                   10

<210> SEQ ID NO 4
<211> LENGTH: 14
<212> TYPE: PRT
<213> ORGANISM: Artificial Sequence
<220> FEATURE:
<223> OTHER INFORMATION: Synthetic

<400> SEQUENCE: 4

His Gly Asn Phe Gly Asn Ser Tyr Val Thr Trp Phe Ala Tyr
1               5                   10

<210> SEQ ID NO 5
<211> LENGTH: 14
<212> TYPE: PRT
<213> ORGANISM: Artificial Sequence
<220> FEATURE:
<223> OTHER INFORMATION: Synthetic

<400> SEQUENCE: 5

His Gly Asn Phe Gly Asn Ser Tyr Val Ser Tyr Phe Ala Tyr
1               5                   10

<210> SEQ ID NO 6
<211> LENGTH: 14
<212> TYPE: PRT
<213> ORGANISM: Artificial Sequence
<220> FEATURE:
<223> OTHER INFORMATION: Synthetic

<400> SEQUENCE: 6

His Gly Asn Phe Gly Asn Ser Tyr Val Ser Phe Phe Ala Tyr
1               5                   10

<210> SEQ ID NO 7
<211> LENGTH: 14
<212> TYPE: PRT
<213> ORGANISM: Artificial Sequence
<220> FEATURE:
<223> OTHER INFORMATION: Synthetic

<400> SEQUENCE: 7

His Gly Asn Phe Gly Asn Ser Tyr Val Ser Trp Leu Ala Tyr
1               5                   10

<210> SEQ ID NO 8
<211> LENGTH: 14
<212> TYPE: PRT
<213> ORGANISM: Artificial Sequence
<220> FEATURE:
<223> OTHER INFORMATION: Synthetic

<400> SEQUENCE: 8

His Gly Asn Phe Gly Asn Ser Tyr Val Ser Trp Val Ala Tyr
1               5                   10

<210> SEQ ID NO 9
<211> LENGTH: 14
<212> TYPE: PRT
<213> ORGANISM: Artificial Sequence
<220> FEATURE:
<223> OTHER INFORMATION: Synthetic

<400> SEQUENCE: 9

His Gly Asn Phe Gly Asn Ser Tyr Val Ser Trp Ile Ala Tyr

```
<210> SEQ ID NO 10
<211> LENGTH: 14
<212> TYPE: PRT
<213> ORGANISM: Artificial Sequence
<220> FEATURE:
<223> OTHER INFORMATION: Synthetic

<400> SEQUENCE: 10

His Gly Asn Phe Gly Asn Ser Tyr Val Ser Trp Ala Ala Tyr
1               5                   10

<210> SEQ ID NO 11
<211> LENGTH: 14
<212> TYPE: PRT
<213> ORGANISM: Artificial Sequence
<220> FEATURE:
<223> OTHER INFORMATION: Synthetic

<400> SEQUENCE: 11

His Gly Asn Phe Gly Asn Ser Tyr Val Ser Trp Tyr Ala Tyr
1               5                   10

<210> SEQ ID NO 12
<211> LENGTH: 14
<212> TYPE: PRT
<213> ORGANISM: Artificial Sequence
<220> FEATURE:
<223> OTHER INFORMATION: Synthetic

<400> SEQUENCE: 12

His Gly Asn Phe Gly Asn Ser Tyr Val Ser Trp Phe Val Tyr
1               5                   10

<210> SEQ ID NO 13
<211> LENGTH: 14
<212> TYPE: PRT
<213> ORGANISM: Artificial Sequence
<220> FEATURE:
<223> OTHER INFORMATION: Synthetic

<400> SEQUENCE: 13

His Gly Asn Phe Gly Asn Ser Tyr Val Ser Trp Phe Leu Tyr
1               5                   10

<210> SEQ ID NO 14
<211> LENGTH: 14
<212> TYPE: PRT
<213> ORGANISM: Artificial Sequence
<220> FEATURE:
<223> OTHER INFORMATION: Synthetic

<400> SEQUENCE: 14

His Gly Asn Phe Gly Asn Ser Tyr Val Ser Trp Phe Ile Tyr
1               5                   10

<210> SEQ ID NO 15
<211> LENGTH: 30
<212> TYPE: PRT
<213> ORGANISM: Artificial Sequence
<220> FEATURE:
<223> OTHER INFORMATION: Synthetic

<400> SEQUENCE: 15

Glu Val Gln Leu Val Glu Ser Gly Gly Gly Leu Val Gln Pro Gly Gly
1               5                   10                  15
```

Ser Leu Arg Leu Ser Cys Ala Ala Ser Gly Phe Thr Phe Ser
            20                  25                  30

<210> SEQ ID NO 16
<211> LENGTH: 30
<212> TYPE: PRT
<213> ORGANISM: Artificial Sequence
<220> FEATURE:
<223> OTHER INFORMATION: Synthetic

<400> SEQUENCE: 16

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser
            20                  25                  30

<210> SEQ ID NO 17
<211> LENGTH: 14
<212> TYPE: PRT
<213> ORGANISM: Artificial Sequence
<220> FEATURE:
<223> OTHER INFORMATION: Synthetic

<400> SEQUENCE: 17

Trp Val Arg Gln Ala Pro Gly Lys Gly Leu Glu Trp Val Ala
1               5                   10

<210> SEQ ID NO 18
<211> LENGTH: 32
<212> TYPE: PRT
<213> ORGANISM: Artificial Sequence
<220> FEATURE:
<223> OTHER INFORMATION: Synthetic

<400> SEQUENCE: 18

Arg Phe Thr Ile Ser Arg Asp Asn Ala Lys Asn Ser Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 19
<211> LENGTH: 32
<212> TYPE: PRT
<213> ORGANISM: Artificial Sequence
<220> FEATURE:
<223> OTHER INFORMATION: Synthetic

<400> SEQUENCE: 19

Arg Phe Thr Ile Ser Arg Asp Asp Ser Lys Asn Ser Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 20
<211> LENGTH: 32
<212> TYPE: PRT
<213> ORGANISM: Artificial Sequence
<220> FEATURE:
<223> OTHER INFORMATION: Synthetic

<400> SEQUENCE: 20

Arg Phe Thr Ile Ser Arg Asp Asp Ser Lys Asn Ser Leu Tyr Leu Gln
1               5                   10                  15

Met Asn Ser Leu Arg Ala Glu Asp Thr Ala Val Tyr Tyr Cys Val Arg 20                  25                  30

<210> SEQ ID NO 21
<211> LENGTH: 32
<212> TYPE: PRT
<213> ORGANISM: Artificial Sequence
<220> FEATURE:
<223> OTHER INFORMATION: Synthetic

<400> SEQUENCE: 21

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 22
<211> LENGTH: 32
<212> TYPE: PRT
<213> ORGANISM: Artificial Sequence
<220> FEATURE:
<223> OTHER INFORMATION: Synthetic

<400> SEQUENCE: 22

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Val Arg
            20                  25                  30

<210> SEQ ID NO 23
<211> LENGTH: 32
<212> TYPE: PRT
<213> ORGANISM: Artificial Sequence
<220> FEATURE:
<223> OTHER INFORMATION: Synthetic

<400> SEQUENCE: 23

Arg Phe Thr Ile Ser Arg Asp Asp Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 24
<211> LENGTH: 32
<212> TYPE: PRT
<213> ORGANISM: Artificial Sequence
<220> FEATURE:
<223> OTHER INFORMATION: Synthetic

<400> SEQUENCE: 24

Arg Phe Thr Ile Ser Arg Asp Asp Ser Lys Asn Thr Leu Tyr Leu Gln
1               5                   10                  15

Met Asn Ser Leu Arg Ala Glu Asp Thr Ala Val Tyr Tyr Cys Val Arg
            20                  25                  30

<210> SEQ ID NO 25
<211> LENGTH: 11
<212> TYPE: PRT
<213> ORGANISM: Artificial Sequence
<220> FEATURE:
<223> OTHER INFORMATION: Synthetic

<400> SEQUENCE: 25

Trp Gly Gln Gly Thr Leu Val Thr Val Ser Ser
1               5                   10

<210> SEQ ID NO 26
<211> LENGTH: 14
<212> TYPE: PRT
<213> ORGANISM: Artificial Sequence
<220> FEATURE:
<223> OTHER INFORMATION: Synthetic

<400> SEQUENCE: 26

Arg Ser Ser Thr Gly Ala Val Thr Thr Ser Asn Tyr Ala Asn
1               5                   10

<210> SEQ ID NO 27
<211> LENGTH: 7
<212> TYPE: PRT
<213> ORGANISM: Artificial Sequence
<220> FEATURE:
<223> OTHER INFORMATION: Synthetic

<400> SEQUENCE: 27

Gly Thr Asn Lys Arg Ala Pro
1               5

<210> SEQ ID NO 28
<211> LENGTH: 9
<212> TYPE: PRT
<213> ORGANISM: Artificial Sequence
<220> FEATURE:
<223> OTHER INFORMATION: Synthetic

<400> SEQUENCE: 28

Ala Leu Trp Tyr Ser Asn Leu Trp Val
1               5

<210> SEQ ID NO 29
<211> LENGTH: 23
<212> TYPE: PRT
<213> ORGANISM: Artificial Sequence
<220> FEATURE:
<223> OTHER INFORMATION: Synthetic

<400> SEQUENCE: 29

Glu Ile Val Leu Thr Gln Ser Pro Ala Thr Leu Ser Leu Ser Pro Gly
1               5                   10                  15

Glu Arg Ala Thr Leu Ser Cys
            20

<210> SEQ ID NO 30
<211> LENGTH: 23
<212> TYPE: PRT
<213> ORGANISM: Artificial Sequence
<220> FEATURE:
<223> OTHER INFORMATION: Synthetic

<400> SEQUENCE: 30

Glu Ile Val Met Thr Gln Ser Pro Ala Thr Leu Ser Leu Ser Pro Gly
1               5                   10                  15

Glu Arg Ala Thr Leu Ser Cys
            20

<210> SEQ ID NO 31
<211> LENGTH: 22
<212> TYPE: PRT
<213> ORGANISM: Artificial Sequence
<220> FEATURE:
<223> OTHER INFORMATION: Synthetic

```
<400> SEQUENCE: 31

Gln Thr Val Val Thr Gln Glu Pro Ser Leu Thr Val Ser Pro Gly Gly
1               5                   10                  15

Thr Val Thr Leu Thr Cys
            20

<210> SEQ ID NO 32
<211> LENGTH: 15
<212> TYPE: PRT
<213> ORGANISM: Artificial Sequence
<220> FEATURE:
<223> OTHER INFORMATION: Synthetic

<400> SEQUENCE: 32

Trp Phe Gln Gln Lys Pro Gly Gln Ala Pro Arg Ala Leu Ile Tyr
1               5                   10                  15

<210> SEQ ID NO 33
<211> LENGTH: 15
<212> TYPE: PRT
<213> ORGANISM: Artificial Sequence
<220> FEATURE:
<223> OTHER INFORMATION: Synthetic

<400> SEQUENCE: 33

Trp Phe Gln Gln Lys Pro Gly Gln Ala Pro Arg Gly Leu Ile Gly
1               5                   10                  15

<210> SEQ ID NO 34
<211> LENGTH: 15
<212> TYPE: PRT
<213> ORGANISM: Artificial Sequence
<220> FEATURE:
<223> OTHER INFORMATION: Synthetic

<400> SEQUENCE: 34

Trp Val Gln Gln Lys Pro Gly Gln Ala Pro Arg Ala Leu Ile Gly
1               5                   10                  15

<210> SEQ ID NO 35
<211> LENGTH: 15
<212> TYPE: PRT
<213> ORGANISM: Artificial Sequence
<220> FEATURE:
<223> OTHER INFORMATION: Synthetic

<400> SEQUENCE: 35

Trp Tyr Gln Gln Lys Pro Gly Gln Ala Pro Arg Ala Leu Ile Tyr
1               5                   10                  15

<210> SEQ ID NO 36
<211> LENGTH: 15
<212> TYPE: PRT
<213> ORGANISM: Artificial Sequence
<220> FEATURE:
<223> OTHER INFORMATION: Synthetic

<400> SEQUENCE: 36

Trp Val Gln Gln Lys Pro Gly Gln Ala Pro Arg Gly Leu Ile Gly
1               5                   10                  15

<210> SEQ ID NO 37
<211> LENGTH: 15
<212> TYPE: PRT
<213> ORGANISM: Artificial Sequence
<220> FEATURE:
```

-continued

<223> OTHER INFORMATION: Synthetic

<400> SEQUENCE: 37

Trp Val Gln Gln Lys Pro Gly Gln Ala Pro Lys Gly Leu Ile Gly
1               5                   10                  15

<210> SEQ ID NO 38
<211> LENGTH: 15
<212> TYPE: PRT
<213> ORGANISM: Artificial Sequence
<220> FEATURE:
<223> OTHER INFORMATION: Synthetic

<400> SEQUENCE: 38

Trp Val Gln Gln Lys Pro Gly Lys Ala Pro Lys Leu Leu Ile Gly
1               5                   10                  15

<210> SEQ ID NO 39
<211> LENGTH: 32
<212> TYPE: PRT
<213> ORGANISM: Artificial Sequence
<220> FEATURE:
<223> OTHER INFORMATION: Synthetic

<400> SEQUENCE: 39

Gly Val Pro Ala Arg Phe Ser Gly Ser Leu Ser Gly Thr Asp Ala Thr
1               5                   10                  15

Leu Thr Ile Ser Ser Leu Gln Pro Glu Asp Phe Ala Val Tyr Tyr Cys
            20                  25                  30

<210> SEQ ID NO 40
<211> LENGTH: 32
<212> TYPE: PRT
<213> ORGANISM: Artificial Sequence
<220> FEATURE:
<223> OTHER INFORMATION: Synthetic

<400> SEQUENCE: 40

Trp Thr Pro Ala Arg Phe Ser Gly Ser Leu Leu Gly Gly Lys Ala Ala
1               5                   10                  15

Leu Thr Leu Ser Gly Val Gln Pro Glu Asp Glu Ala Glu Tyr Tyr Cys
            20                  25                  30

<210> SEQ ID NO 41
<211> LENGTH: 32
<212> TYPE: PRT
<213> ORGANISM: Artificial Sequence
<220> FEATURE:
<223> OTHER INFORMATION: Synthetic

<400> SEQUENCE: 41

Gly Val Pro Ala Arg Phe Ser Gly Ser Leu Leu Gly Gly Lys Ala Ala
1               5                   10                  15

Leu Thr Leu Ser Gly Val Gln Pro Glu Asp Glu Ala Glu Tyr Tyr Cys
            20                  25                  30

<210> SEQ ID NO 42
<211> LENGTH: 32
<212> TYPE: PRT
<213> ORGANISM: Artificial Sequence
<220> FEATURE:
<223> OTHER INFORMATION: Synthetic

<400> SEQUENCE: 42

Gly Thr Pro Ala Arg Phe Ser Gly Ser Leu Leu Gly Gly Lys Ala Ala

```
                1               5                  10                 15
Leu Thr Leu Ser Gly Val Gln Pro Glu Asp Glu Ala Glu Tyr Tyr Cys
            20              25              30
```

<210> SEQ ID NO 43
<211> LENGTH: 10
<212> TYPE: PRT
<213> ORGANISM: Artificial Sequence
<220> FEATURE:
<223> OTHER INFORMATION: Synthetic

<400> SEQUENCE: 43

```
Phe Gly Gly Gly Thr Lys Val Glu Ile Lys
1               5                  10
```

<210> SEQ ID NO 44
<211> LENGTH: 10
<212> TYPE: PRT
<213> ORGANISM: Artificial Sequence
<220> FEATURE:
<223> OTHER INFORMATION: Synthetic

<400> SEQUENCE: 44

```
Phe Gly Gly Gly Thr Lys Leu Thr Val Leu
1               5                  10
```

<210> SEQ ID NO 45
<211> LENGTH: 125
<212> TYPE: PRT
<213> ORGANISM: Artificial Sequence
<220> FEATURE:
<223> OTHER INFORMATION: Synthetic

<400> SEQUENCE: 45

```
Glu Val Gln Leu Val Glu Ser Gly Gly Gly Leu Val Gln Pro Gly Gly
1               5                  10                 15

Ser Leu Arg Leu Ser Cys Ala Ala Ser Gly Phe Thr Phe Ser Thr Tyr
            20              25              30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125
```

<210> SEQ ID NO 46
<211> LENGTH: 125
<212> TYPE: PRT
<213> ORGANISM: Artificial Sequence
<220> FEATURE:
<223> OTHER INFORMATION: Synthetic

<400> SEQUENCE: 46

```
Glu Val Gln Leu Val Glu Ser Gly Gly Gly Leu Val Gln Pro Gly Gly
1               5                  10                 15

Ser Leu Arg Leu Ser Cys Ala Ala Ser Gly Phe Thr Phe Ser Thr Tyr
```

```
                    20                  25                  30
Ala Met Asn Trp Val Arg Gln Ala Pro Gly Lys Gly Leu Glu Trp Val
                35                  40                  45

Ala Arg Ile Arg Ser Lys Tyr Asn Asn Tyr Ala Thr Tyr Tyr Ala Asp
            50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Arg Ala Glu Asp Thr Ala Val Tyr
                    85                  90                  95

Tyr Cys Ala Arg His Gly Asn Phe Gly Asn Ser Tyr Val Ser Trp Phe
                100                 105                 110

Ala Tyr Trp Gly Gln Gly Thr Leu Val Thr Val Ser Ser
            115                 120                 125

<210> SEQ ID NO 47
<211> LENGTH: 125
<212> TYPE: PRT
<213> ORGANISM: Artificial Sequence
<220> FEATURE:
<223> OTHER INFORMATION: Synthetic

<400> SEQUENCE: 47

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
                20                  25                  30

Ala Met Asn Trp Val Arg Gln Ala Pro Gly Lys Gly Leu Glu Trp Val
                35                  40                  45

Ala Arg Ile Arg Ser Lys Tyr Asn Asn Tyr Ala Thr Tyr Tyr Ala Asp
            50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Arg Ala Glu Asp Thr Ala Val Tyr
                    85                  90                  95

Tyr Cys Val Arg His Gly Asn Phe Gly Asn Ser Tyr Val Ser Trp Phe
                100                 105                 110

Ala Tyr Trp Gly Gln Gly Thr Leu Val Thr Val Ser Ser
            115                 120                 125

<210> SEQ ID NO 48
<211> LENGTH: 125
<212> TYPE: PRT
<213> ORGANISM: Artificial Sequence
<220> FEATURE:
<223> OTHER INFORMATION: Synthetic

<400> SEQUENCE: 48

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Thr Tyr
                20                  25                  30

Ala Met Asn Trp Val Arg Gln Ala Pro Gly Lys Gly Leu Glu Trp Val
                35                  40                  45

Ala Arg Ile Arg Ser Lys Tyr Asn Asn Tyr Ala Thr Tyr Tyr Ala Asp
            50                  55                  60

Ser Val Lys Asp Arg Phe Thr Ile Ser Arg Asp Asn Ser Lys Asn Thr
65                  70                  75                  80
```

```
Leu Tyr Leu Gln Met Asn Ser Leu Arg Ala Glu Asp Thr Ala Val Tyr
                85                  90                  95

Tyr Cys Ala Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 49
<211> LENGTH: 125
<212> TYPE: PRT
<213> ORGANISM: Artificial Sequence
<220> FEATURE:
<223> OTHER INFORMATION: Synthetic

<400> SEQUENCE: 49

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 50
<211> LENGTH: 125
<212> TYPE: PRT
<213> ORGANISM: Artificial Sequence
<220> FEATURE:
<223> OTHER INFORMATION: Synthetic

<400> SEQUENCE: 50

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 51
```

```
<211> LENGTH: 125
<212> TYPE: PRT
<213> ORGANISM: Artificial Sequence
<220> FEATURE:
<223> OTHER INFORMATION: Synthetic

<400> SEQUENCE: 51

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 52
<211> LENGTH: 125
<212> TYPE: PRT
<213> ORGANISM: Artificial Sequence
<220> FEATURE:
<223> OTHER INFORMATION: Synthetic

<400> SEQUENCE: 52

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg His Gly Asn Phe Gly Asn Ser Tyr Val Thr Trp Phe
            100                 105                 110

Ala Tyr Trp Gly Gln Gly Thr Leu Val Thr Val Ser Ser
        115                 120                 125

<210> SEQ ID NO 53
<211> LENGTH: 125
<212> TYPE: PRT
<213> ORGANISM: Artificial Sequence
<220> FEATURE:
<223> OTHER INFORMATION: Synthetic

<400> SEQUENCE: 53

Gln Val Gln Leu Val Glu Ser Gly Gly Gly Val Val Gln Pro Gly Arg
1               5                   10                  15
```

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg His Gly Asn Phe Gly Asn Ser Tyr Val Ser Tyr Phe
            100                 105                 110

Ala Tyr Trp Gly Gln Gly Thr Leu Val Thr Val Ser Ser
        115                 120                 125

<210> SEQ ID NO 54
<211> LENGTH: 125
<212> TYPE: PRT
<213> ORGANISM: Artificial Sequence
<220> FEATURE:
<223> OTHER INFORMATION: Synthetic

<400> SEQUENCE: 54

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg His Gly Asn Phe Gly Asn Ser Tyr Val Ser Phe Phe
            100                 105                 110

Ala Tyr Trp Gly Gln Gly Thr Leu Val Thr Val Ser Ser
        115                 120                 125

<210> SEQ ID NO 55
<211> LENGTH: 125
<212> TYPE: PRT
<213> ORGANISM: Artificial Sequence
<220> FEATURE:
<223> OTHER INFORMATION: Synthetic

<400> SEQUENCE: 55

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

```
Leu Tyr Leu Gln Met Asn Ser Leu Arg Ala Glu Asp Thr Ala Val Tyr
                85                  90                  95

Tyr Cys Ala Arg His Gly Asn Phe Gly Asn Ser Tyr Val Ser Trp Leu
            100                 105                 110

Ala Tyr Trp Gly Gln Gly Thr Leu Val Thr Val Ser Ser
        115                 120                 125

<210> SEQ ID NO 56
<211> LENGTH: 125
<212> TYPE: PRT
<213> ORGANISM: Artificial Sequence
<220> FEATURE:
<223> OTHER INFORMATION: Synthetic

<400> SEQUENCE: 56

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg His Gly Asn Phe Gly Asn Ser Tyr Val Ser Trp Val
            100                 105                 110

Ala Tyr Trp Gly Gln Gly Thr Leu Val Thr Val Ser Ser
        115                 120                 125

<210> SEQ ID NO 57
<211> LENGTH: 125
<212> TYPE: PRT
<213> ORGANISM: Artificial Sequence
<220> FEATURE:
<223> OTHER INFORMATION: Synthetic

<400> SEQUENCE: 57

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg His Gly Asn Phe Gly Asn Ser Tyr Val Ser Trp Ile
            100                 105                 110

Ala Tyr Trp Gly Gln Gly Thr Leu Val Thr Val Ser Ser
        115                 120                 125
```

<210> SEQ ID NO 58
<211> LENGTH: 125
<212> TYPE: PRT
<213> ORGANISM: Artificial Sequence
<220> FEATURE:
<223> OTHER INFORMATION: Synthetic

<400> SEQUENCE: 58

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg His Gly Asn Phe Gly Asn Ser Tyr Val Ser Trp Ala
            100                 105                 110

Ala Tyr Trp Gly Gln Gly Thr Leu Val Thr Val Ser Ser
        115                 120                 125
```

<210> SEQ ID NO 59
<211> LENGTH: 125
<212> TYPE: PRT
<213> ORGANISM: Artificial Sequence
<220> FEATURE:
<223> OTHER INFORMATION: Synthetic

<400> SEQUENCE: 59

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg His Gly Asn Phe Gly Asn Ser Tyr Val Ser Trp Tyr
            100                 105                 110

Ala Tyr Trp Gly Gln Gly Thr Leu Val Thr Val Ser Ser
        115                 120                 125
```

<210> SEQ ID NO 60
<211> LENGTH: 125
<212> TYPE: PRT
<213> ORGANISM: Artificial Sequence
<220> FEATURE:
<223> OTHER INFORMATION: Synthetic

<400> SEQUENCE: 60

```
Gln Val Gln Leu Val Glu Ser Gly Gly Gly Val Val Gln Pro Gly Arg
1               5                   10                  15
```

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp
        50                  55                  60

Ser Val Lys Asp Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg His Gly Asn Phe Gly Asn Ser Tyr Val Ser Trp Phe
            100                 105                 110

Val Tyr Trp Gly Gln Gly Thr Leu Val Thr Val Ser Ser
        115                 120                 125

<210> SEQ ID NO 61
<211> LENGTH: 125
<212> TYPE: PRT
<213> ORGANISM: Artificial Sequence
<220> FEATURE:
<223> OTHER INFORMATION: Synthetic

<400> SEQUENCE: 61

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp
        50                  55                  60

Ser Val Lys Asp Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg His Gly Asn Phe Gly Asn Ser Tyr Val Ser Trp Phe
            100                 105                 110

Leu Tyr Trp Gly Gln Gly Thr Leu Val Thr Val Ser Ser
        115                 120                 125

<210> SEQ ID NO 62
<211> LENGTH: 125
<212> TYPE: PRT
<213> ORGANISM: Artificial Sequence
<220> FEATURE:
<223> OTHER INFORMATION: Synthetic

<400> SEQUENCE: 62

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp
        50                  55                  60

Ser Val Lys Asp Arg Phe Thr Ile Ser Arg Asp Asp Ser Lys Asn Thr

```
                65                  70                  75                  80
Leu Tyr Leu Gln Met Asn Ser Leu Arg Ala Glu Asp Thr Ala Val Tyr
                    85                  90                  95

Tyr Cys Ala Arg His Gly Asn Phe Gly Asn Ser Tyr Val Ser Trp Phe
                    100                 105                 110

Ile Tyr Trp Gly Gln Gly Thr Leu Val Thr Val Ser Ser
                    115                 120                 125

<210> SEQ ID NO 63
<211> LENGTH: 110
<212> TYPE: PRT
<213> ORGANISM: Artificial Sequence
<220> FEATURE:
<223> OTHER INFORMATION: Synthetic

<400> SEQUENCE: 63

Glu Ile Val Leu Thr Gln Ser Pro Ala Thr Leu Ser Leu Ser Pro Gly
1               5                   10                  15

Glu Arg Ala Thr Leu Ser Cys Arg Ser Ser Thr Gly Ala Val Thr Thr
                20                  25                  30

Ser Asn Tyr Ala Asn Trp Val Gln Gln Lys Pro Gly Gln Ala Pro Arg
            35                  40                  45

Gly Leu Ile Gly Gly Thr Asn Lys Arg Ala Pro Gly Val Pro Ala Arg
        50                  55                  60

Phe Ser Gly Ser Leu Ser Gly Thr Asp Ala Thr Leu Thr Ile Ser Ser
65                  70                  75                  80

Leu Gln Pro Glu Asp Phe Ala Val Tyr Tyr Cys Ala Leu Trp Tyr Ser
                85                  90                  95

Asn Leu Trp Val Phe Gly Gly Gly Thr Lys Val Glu Ile Lys
                100                 105                 110

<210> SEQ ID NO 64
<211> LENGTH: 110
<212> TYPE: PRT
<213> ORGANISM: Artificial Sequence
<220> FEATURE:
<223> OTHER INFORMATION: Synthetic

<400> SEQUENCE: 64

Glu Ile Val Leu Thr Gln Ser Pro Ala Thr Leu Ser Leu Ser Pro Gly
1               5                   10                  15

Glu Arg Ala Thr Leu Ser Cys Arg Ser Ser Thr Gly Ala Val Thr Thr
                20                  25                  30

Ser Asn Tyr Ala Asn Trp Val Gln Gln Lys Pro Gly Gln Ala Pro Lys
            35                  40                  45

Gly Leu Ile Gly Gly Thr Asn Lys Arg Ala Pro Gly Val Pro Ala Arg
        50                  55                  60

Phe Ser Gly Ser Leu Ser Gly Thr Asp Ala Thr Leu Thr Ile Ser Ser
65                  70                  75                  80

Leu Gln Pro Glu Asp Phe Ala Val Tyr Tyr Cys Ala Leu Trp Tyr Ser
                85                  90                  95

Asn Leu Trp Val Phe Gly Gly Gly Thr Lys Val Glu Ile Lys
                100                 105                 110

<210> SEQ ID NO 65
<211> LENGTH: 110
<212> TYPE: PRT
<213> ORGANISM: Artificial Sequence
<220> FEATURE:
```

<223> OTHER INFORMATION: Synthetic

<400> SEQUENCE: 65

Glu Ile Val Leu Thr Gln Ser Pro Ala Thr Leu Ser Leu Ser Pro Gly
1               5                   10                  15

Glu Arg Ala Thr Leu Ser Cys Arg Ser Ser Thr Gly Ala Val Thr Thr
            20                  25                  30

Ser Asn Tyr Ala Asn Trp Val Gln Gln Lys Pro Gly Lys Ala Pro Lys
        35                  40                  45

Leu Leu Ile Gly Gly Thr Asn Lys Arg Ala Pro Gly Val Pro Ala Arg
    50                  55                  60

Phe Ser Gly Ser Leu Ser Gly Thr Asp Ala Thr Leu Thr Ile Ser Ser
65                  70                  75                  80

Leu Gln Pro Glu Asp Phe Ala Val Tyr Tyr Cys Ala Leu Trp Tyr Ser
                85                  90                  95

Asn Leu Trp Val Phe Gly Gly Gly Thr Lys Val Glu Ile Lys
            100                 105                 110

<210> SEQ ID NO 66
<211> LENGTH: 110
<212> TYPE: PRT
<213> ORGANISM: Artificial Sequence
<220> FEATURE:
<223> OTHER INFORMATION: Synthetic

<400> SEQUENCE: 66

Glu Ile Val Leu Thr Gln Ser Pro Ala Thr Leu Ser Leu Ser Pro Gly
1               5                   10                  15

Glu Arg Ala Thr Leu Ser Cys Arg Ser Ser Thr Gly Ala Val Thr Thr
            20                  25                  30

Ser Asn Tyr Ala Asn Trp Val Gln Gln Lys Pro Gly Lys Ala Pro Lys
        35                  40                  45

Ser Leu Ile Gly Gly Thr Asn Lys Arg Ala Pro Gly Val Pro Ala Arg
    50                  55                  60

Phe Ser Gly Ser Leu Ser Gly Thr Asp Ala Thr Leu Thr Ile Ser Ser
65                  70                  75                  80

Leu Gln Pro Glu Asp Phe Ala Val Tyr Tyr Cys Ala Leu Trp Tyr Ser
                85                  90                  95

Asn Leu Trp Val Phe Gly Gly Gly Thr Lys Val Glu Ile Lys
            100                 105                 110

<210> SEQ ID NO 67
<211> LENGTH: 110
<212> TYPE: PRT
<213> ORGANISM: Artificial Sequence
<220> FEATURE:
<223> OTHER INFORMATION: Synthetic

<400> SEQUENCE: 67

Glu Ile Val Met Thr Gln Ser Pro Ala Thr Leu Ser Leu Ser Pro Gly
1               5                   10                  15

Glu Arg Ala Thr Leu Ser Cys Arg Ser Ser Thr Gly Ala Val Thr Thr
            20                  25                  30

Ser Asn Tyr Ala Asn Trp Val Gln Gln Lys Pro Gly Gln Ala Pro Lys
        35                  40                  45

Gly Leu Ile Gly Gly Thr Asn Lys Arg Ala Pro Gly Val Pro Ala Arg
    50                  55                  60

Phe Ser Gly Ser Leu Ser Gly Thr Asp Ala Thr Leu Thr Ile Ser Ser

```
                65                  70                  75                  80
Leu Gln Pro Glu Asp Phe Ala Val Tyr Tyr Cys Ala Leu Trp Tyr Ser
                    85                  90                  95

Asn Leu Trp Val Phe Gly Gly Gly Thr Lys Val Glu Ile Lys
                100                 105                 110

<210> SEQ ID NO 68
<211> LENGTH: 110
<212> TYPE: PRT
<213> ORGANISM: Artificial Sequence
<220> FEATURE:
<223> OTHER INFORMATION: Synthetic

<400> SEQUENCE: 68

Glu Ile Val Met Thr Gln Ser Pro Ala Thr Leu Ser Leu Ser Pro Gly
1               5                   10                  15

Glu Arg Ala Thr Leu Ser Cys Arg Ser Ser Thr Gly Ala Val Thr Thr
                20                  25                  30

Ser Asn Tyr Ala Asn Trp Val Gln Gln Lys Pro Gly Lys Ala Pro Lys
            35                  40                  45

Leu Leu Ile Gly Gly Thr Asn Lys Arg Ala Pro Gly Val Pro Ala Arg
        50                  55                  60

Phe Ser Gly Ser Leu Ser Gly Thr Asp Ala Thr Leu Thr Ile Ser Ser
65                  70                  75                  80

Leu Gln Pro Glu Asp Phe Ala Val Tyr Tyr Cys Ala Leu Trp Tyr Ser
                    85                  90                  95

Asn Leu Trp Val Phe Gly Gly Gly Thr Lys Val Glu Ile Lys
                100                 105                 110

<210> SEQ ID NO 69
<211> LENGTH: 110
<212> TYPE: PRT
<213> ORGANISM: Artificial Sequence
<220> FEATURE:
<223> OTHER INFORMATION: Synthetic

<400> SEQUENCE: 69

Glu Ile Val Met Thr Gln Ser Pro Ala Thr Leu Ser Leu Ser Pro Gly
1               5                   10                  15

Glu Arg Ala Thr Leu Ser Cys Arg Ser Ser Thr Gly Ala Val Thr Thr
                20                  25                  30

Ser Asn Tyr Ala Asn Trp Val Gln Gln Lys Pro Gly Lys Ala Pro Lys
            35                  40                  45

Ser Leu Ile Gly Gly Thr Asn Lys Arg Ala Pro Gly Val Pro Ala Arg
        50                  55                  60

Phe Ser Gly Ser Leu Ser Gly Thr Asp Ala Thr Leu Thr Ile Ser Ser
65                  70                  75                  80

Leu Gln Pro Glu Asp Phe Ala Val Tyr Tyr Cys Ala Leu Trp Tyr Ser
                    85                  90                  95

Asn Leu Trp Val Phe Gly Gly Gly Thr Lys Val Glu Ile Lys
                100                 105                 110

<210> SEQ ID NO 70
<211> LENGTH: 109
<212> TYPE: PRT
<213> ORGANISM: Artificial Sequence
<220> FEATURE:
<223> OTHER INFORMATION: Synthetic

<400> SEQUENCE: 70
```

-continued

```
Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Phe Gln Gln Lys Pro Gly Gln Ala Pro Arg Ala
        35                  40                  45

Leu Ile Tyr Gly Thr Asn Lys Arg Ala Pro Trp Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu
            100                 105
```

<210> SEQ ID NO 71
<211> LENGTH: 109
<212> TYPE: PRT
<213> ORGANISM: Artificial Sequence
<220> FEATURE:
<223> OTHER INFORMATION: Synthetic

<400> SEQUENCE: 71

```
Gln Thr Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Gly Val Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Val Glu Ile Lys
            100                 105
```

<210> SEQ ID NO 72
<211> LENGTH: 109
<212> TYPE: PRT
<213> ORGANISM: Artificial Sequence
<220> FEATURE:
<223> OTHER INFORMATION: Synthetic

<400> SEQUENCE: 72

```
Gln Thr Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Phe Gln Gln Lys Pro Gly Gln Ala Pro Arg Gly
        35                  40                  45

Leu Ile Gly Gly Thr Asn Lys Arg Ala Pro Gly Val Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
```

85                  90                  95

Leu Trp Val Phe Gly Gly Gly Thr Lys Val Glu Ile Lys
            100                 105

<210> SEQ ID NO 73
<211> LENGTH: 109
<212> TYPE: PRT
<213> ORGANISM: Artificial Sequence
<220> FEATURE:
<223> OTHER INFORMATION: Synthetic

<400> SEQUENCE: 73

Gln Thr Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Ala
        35                  40                  45

Leu Ile Gly Gly Thr Asn Lys Arg Ala Pro Gly Val Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Val Glu Ile Lys
            100                 105

<210> SEQ ID NO 74
<211> LENGTH: 125
<212> TYPE: PRT
<213> ORGANISM: Artificial Sequence
<220> FEATURE:
<223> OTHER INFORMATION: Synthetic

<400> SEQUENCE: 74

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Gln Ser Ile
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 75
<211> LENGTH: 109
<212> TYPE: PRT
<213> ORGANISM: Artificial Sequence
<220> FEATURE:
<223> OTHER INFORMATION: Synthetic

<400> SEQUENCE: 75

-continued

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

Leu Trp Val Phe Gly Gly Gly Thr Lys Leu Thr Val Leu
            100                 105

<210> SEQ ID NO 76
<211> LENGTH: 119
<212> TYPE: PRT
<213> ORGANISM: Artificial Sequence
<220> FEATURE:
<223> OTHER INFORMATION: Synthetic

<400> SEQUENCE: 76

Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser
        115

<210> SEQ ID NO 77
<211> LENGTH: 106
<212> TYPE: PRT
<213> ORGANISM: Artificial Sequence
<220> FEATURE:
<223> OTHER INFORMATION: Synthetic

<400> SEQUENCE: 77

Asp Ile Gln Leu Thr Gln Ser Pro Ala Ile Met Ser Ala Ser Pro Gly
1               5                   10                  15

Glu Lys Val Thr Met Thr Cys Arg Ala Ser Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Val Ala Ser Gly Val Pro Tyr Arg Phe Ser Gly Ser
    50                  55                  60

Gly Ser Gly Thr Ser Tyr Ser Leu Thr Ile Ser Ser Met Glu Ala Glu

```
                65                  70                  75                  80
Asp Ala Ala Thr Tyr Tyr Cys Gln Gln Trp Ser Ser Asn Pro Leu Thr
                    85                  90                  95

Phe Gly Ala Gly Thr Lys Leu Glu Leu Lys
                100                 105

<210> SEQ ID NO 78
<211> LENGTH: 119
<212> TYPE: PRT
<213> ORGANISM: Artificial Sequence
<220> FEATURE:
<223> OTHER INFORMATION: Synthetic

<400> SEQUENCE: 78

Asp Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
                20                  25                  30

Thr Met His Trp Val Arg Gln Ala Pro Gly Gln Gly Leu Glu Trp Ile
            35                  40                  45

Gly Tyr Ile Asn Pro Ser Arg Gly Tyr Thr Asn Tyr Ala Asp Ser Val
    50                  55                  60

Lys Gly Arg Phe Thr Ile Thr Thr Asp Lys Ser Thr Ser Thr Ala Tyr
65                  70                  75                  80

Met Glu Leu Ser Ser Leu Arg Ser Glu Asp Thr Ala Thr Tyr Tyr Cys
                85                  90                  95

Ala Arg Tyr Tyr Asp Asp His Tyr Cys Leu Asp Tyr Trp Gly Gln Gly
                100                 105                 110

Thr Thr Val Thr Val Ser Ser
        115

<210> SEQ ID NO 79
<211> LENGTH: 106
<212> TYPE: PRT
<213> ORGANISM: Artificial Sequence
<220> FEATURE:
<223> OTHER INFORMATION: Synthetic

<400> SEQUENCE: 79

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Tyr Met
                20                  25                  30

Asn Trp Tyr Gln Gln Lys Pro Gly Lys Ala Pro Lys Arg Trp Ile Tyr
            35                  40                  45

Asp Thr Ser Lys Val Ala Ser Gly Val Pro Ala Arg Phe Ser Gly Ser
    50                  55                  60

Gly Ser Gly Thr Asp Tyr Ser Leu Thr Ile Asn Ser Leu Glu Ala Glu
65                  70                  75                  80

Asp Ala Ala Thr Tyr Tyr Cys Gln Gln Trp Ser Ser Asn Pro Leu Thr
                85                  90                  95

Phe Gly Gly Gly Thr Lys Val Glu Ile Lys
                100                 105

<210> SEQ ID NO 80
<211> LENGTH: 119
<212> TYPE: PRT
<213> ORGANISM: Artificial Sequence
<220> FEATURE:
```

-continued

<223> OTHER INFORMATION: Synthetic

<400> SEQUENCE: 80

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Thr Ala Tyr
65                  70                  75                  80

Met Gln Leu Ser Ser Leu Thr Ser Glu Asp Ser Ala Val Tyr Tyr Cys
            85                  90                  95

Ala Arg Tyr Tyr Asp Asp His Tyr Cys Leu Asp Tyr Trp Gly Gln Gly
            100                 105                 110

Thr Thr Leu Thr Val Ser Ser
        115

<210> SEQ ID NO 81
<211> LENGTH: 106
<212> TYPE: PRT
<213> ORGANISM: Artificial Sequence
<220> FEATURE:
<223> OTHER INFORMATION: Synthetic

<400> SEQUENCE: 81

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Leu Ala Ser Gly Val Pro Ala His Phe Arg Gly Ser
    50                  55                  60

Gly Ser Gly Thr Ser Tyr Ser Leu Thr Ile Ser Gly Met Glu Ala Glu
65                  70                  75                  80

Asp Ala Ala Thr Tyr Tyr Cys Gln Gln Trp Ser Ser Asn Pro Phe Thr
            85                  90                  95

Phe Gly Ser Gly Thr Lys Leu Glu Ile Asn
            100                 105

<210> SEQ ID NO 82
<211> LENGTH: 121
<212> TYPE: PRT
<213> ORGANISM: Artificial Sequence
<220> FEATURE:
<223> OTHER INFORMATION: Synthetic

<400> SEQUENCE: 82

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Ser
            20                  25                  30

Thr Met His Trp Val Lys Gln Arg Pro Gly Gln Gly Leu Glu Trp Ile
        35                  40                  45

Gly Tyr Ile Asn Pro Ser Ser Ala Tyr Thr Asn Tyr Asn Gln Lys Phe

```
                50                  55                  60
Lys Asp Lys Ala Thr Leu Thr Ala Asp Lys Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Ser Pro Gln Val His Tyr Asp Tyr Asn Gly Phe Pro Tyr Trp Gly
                100                 105                 110

Gln Gly Thr Leu Val Thr Val Ser Ala
            115                 120

<210> SEQ ID NO 83
<211> LENGTH: 106
<212> TYPE: PRT
<213> ORGANISM: Artificial Sequence
<220> FEATURE:
<223> OTHER INFORMATION: Synthetic

<400> SEQUENCE: 83

Gln Val Val Leu Thr Gln Ser Pro Ala Ile Met Ser Ala Phe Pro Gly
 1               5                  10                  15

Glu Lys Val Thr Met Thr Cys Ser Ala Ser Ser Val Ser Tyr Met
                 20                  25                  30

Asn Trp Tyr Gln Gln Lys Ser Gly Thr Ser Pro Lys Arg Trp Ile Tyr
             35                  40                  45

Asp Ser Ser Lys Leu Ala Ser Gly Val Pro Ala Arg Phe Ser Gly Ser
         50                  55                  60

Gly Ser Gly Thr Ser Tyr Ser Leu Thr Ile Ser Ser Met Glu Thr Glu
 65                  70                  75                  80

Asp Ala Ala Thr Tyr Tyr Cys Gln Gln Trp Ser Arg Asn Pro Pro Thr
                 85                  90                  95

Phe Gly Gly Gly Thr Lys Leu Gln Ile Thr
            100                 105

<210> SEQ ID NO 84
<211> LENGTH: 122
<212> TYPE: PRT
<213> ORGANISM: Artificial Sequence
<220> FEATURE:
<223> OTHER INFORMATION: Synthetic

<400> SEQUENCE: 84

Glu Val Gln Leu Gln Gln Ser Gly Pro Glu Leu Val Lys Pro Gly Ala
 1               5                  10                  15

Ser Met Lys Ile Ser Cys Lys Ala Ser Gly Tyr Ser Phe Thr Gly Tyr
                 20                  25                  30

Thr Met Asn Trp Val Lys Gln Ser His Gly Lys Asn Leu Glu Trp Met
             35                  40                  45

Gly Leu Ile Asn Pro Tyr Lys Gly Val Ser Thr Tyr Asn Gln Lys Phe
         50                  55                  60

Lys Asp Lys Ala Thr Leu Thr Val Asp Lys Ser Ser Thr Ala Tyr
 65                  70                  75                  80

Met Glu Leu Leu Ser Leu Thr Ser Glu Asp Ser Ala Val Tyr Tyr Cys
                 85                  90                  95

Ala Arg Ser Gly Tyr Tyr Gly Asp Ser Asp Trp Tyr Phe Asp Val Trp
                100                 105                 110

Gly Ala Gly Thr Thr Val Thr Val Ser Ser
            115                 120
```

<210> SEQ ID NO 85
<211> LENGTH: 107
<212> TYPE: PRT
<213> ORGANISM: Artificial Sequence
<220> FEATURE:
<223> OTHER INFORMATION: Synthetic

<400> SEQUENCE: 85

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Arg Asn Tyr
                20                  25                  30

Leu Asn Trp Tyr Gln Gln Lys Pro Asp Gly Thr Val Lys Leu Leu Ile
            35                  40                  45

Tyr Tyr Thr Ser Arg Leu His Ser Gly Val Pro Ser Lys Phe Ser Gly
50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Trp
                85                  90                  95

Thr Phe Ala Gly Gly Thr Lys Leu Glu Ile Lys
            100                 105

<210> SEQ ID NO 86
<211> LENGTH: 125
<212> TYPE: PRT
<213> ORGANISM: Artificial Sequence
<220> FEATURE:
<223> OTHER INFORMATION: Synthetic

<400> SEQUENCE: 86

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
                20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp
50                  55                  60

Ser Val Lys Asp Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg His Gly Asn Phe Gly Asn Ser Tyr Val Ser Trp Phe
            100                 105                 110

Ala Tyr Trp Gly Gln Gly Thr Met Val Thr Val Ser Ser
        115                 120                 125

<210> SEQ ID NO 87
<211> LENGTH: 109
<212> TYPE: PRT
<213> ORGANISM: Artificial Sequence
<220> FEATURE:
<223> OTHER INFORMATION: Synthetic

<400> SEQUENCE: 87

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser

```
                20                  25                  30

Asn Tyr Ala Asn Trp Val Gln Gln Lys Pro Gly Gln Ala Pro Arg Gly
            35                  40                  45

Leu Ile Gly Gly Thr Asn Lys Arg Ala Pro Gly Thr Pro Ala Arg Phe
        50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu
            100                 105

<210> SEQ ID NO 88
<211> LENGTH: 125
<212> TYPE: PRT
<213> ORGANISM: Artificial Sequence
<220> FEATURE:
<223> OTHER INFORMATION: Synthetic

<400> SEQUENCE: 88

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 89
<211> LENGTH: 109
<212> TYPE: PRT
<213> ORGANISM: Artificial Sequence
<220> FEATURE:
<223> OTHER INFORMATION: Synthetic

<400> SEQUENCE: 89

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Gly Val Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95
```

```
Leu Trp Val Phe Gly Gly Gly Thr Lys Leu Glu Ile Lys
            100                 105
```

<210> SEQ ID NO 90
<211> LENGTH: 122
<212> TYPE: PRT
<213> ORGANISM: Artificial Sequence
<220> FEATURE:
<223> OTHER INFORMATION: Synthetic

<400> SEQUENCE: 90

```
Glu Val Gln Leu Leu Glu Ser Gly Gly Gly Leu Val Gln Pro Gly Gly
1               5                   10                  15

Ser Leu Arg Leu Ser Cys Ala Val Ser Gly Phe Thr Phe Asn Ser Phe
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Lys Asp Lys Ile Leu Trp Phe Gly Glu Pro Val Phe Asp Tyr Trp
            100                 105                 110

Gly Gln Gly Thr Leu Val Thr Val Ser Ser
            115                 120
```

<210> SEQ ID NO 91
<211> LENGTH: 107
<212> TYPE: PRT
<213> ORGANISM: Artificial Sequence
<220> FEATURE:
<223> OTHER INFORMATION: Synthetic

<400> SEQUENCE: 91

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Thr Phe Gly Gln Gly Thr Lys Val Glu Ile Lys
            100                 105
```

<210> SEQ ID NO 92
<211> LENGTH: 120
<212> TYPE: PRT
<213> ORGANISM: Artificial Sequence
<220> FEATURE:
<223> OTHER INFORMATION: Synthetic

<400> SEQUENCE: 92

```
Gln Val Gln Leu Val Glu Ser Gly Gly Gly Leu Val Gln Pro Gly Gly
```

```
            1               5                  10                 15
Ser Leu Arg Leu Ser Cys Ala Ala Ser Gly Phe Thr Phe Ser Ser Tyr
                20                  25                 30

Tyr Met Asn Trp Val Arg Gln Ala Pro Gly Lys Gly Leu Glu Trp Val
            35                  40                 45

Ser Gly Ile Ser Gly Asp Pro Ser Asn Thr Tyr Tyr Ala Asp Ser Val
    50                  55                 60

Lys Gly Arg Phe Thr Ile Ser Arg Asp Asn Ser Lys Asn Thr Leu Tyr
65                  70                  75                 80

Leu Gln Met Asn Ser Leu Arg Ala Glu Asp Thr Ala Val Tyr Tyr Cys
                85                  90                 95

Ala Arg Asp Leu Pro Leu Val Tyr Thr Gly Phe Ala Tyr Trp Gly Gln
            100                 105                110

Gly Thr Leu Val Thr Val Ser Ser
            115                 120
```

<210> SEQ ID NO 93
<211> LENGTH: 107
<212> TYPE: PRT
<213> ORGANISM: Artificial Sequence
<220> FEATURE:
<223> OTHER INFORMATION: Synthetic

<400> SEQUENCE: 93

```
            1               5                  10                 15
Asp Ile Glu Leu Thr Gln Pro Pro Ser Val Ser Val Ala Pro Gly Gln
1               5                  10                 15

Thr Ala Arg Ile Ser Cys Ser Gly Asp Asn Leu Arg His Tyr Tyr Val
            20                  25                 30

Tyr Trp Tyr Gln Gln Lys Pro Gly Gln Ala Pro Val Leu Val Ile Tyr
            35                  40                 45

Gly Asp Ser Lys Arg Pro Ser Gly Ile Pro Glu Arg Phe Ser Gly Ser
    50                  55                 60

Asn Ser Gly Asn Thr Ala Thr Leu Thr Ile Ser Gly Thr Gln Ala Glu
65                  70                  75                 80

Asp Glu Ala Asp Tyr Tyr Cys Gln Thr Tyr Thr Gly Gly Ala Ser Leu
                85                  90                 95

Val Phe Gly Gly Gly Thr Lys Leu Thr Val Leu
            100                 105
```

<210> SEQ ID NO 94
<211> LENGTH: 120
<212> TYPE: PRT
<213> ORGANISM: Artificial Sequence
<220> FEATURE:
<223> OTHER INFORMATION: Synthetic

<400> SEQUENCE: 94

```
Gln Val Gln Leu Val Gln Ser Gly Ala Glu Val Ala Lys Pro Gly Thr
1               5                  10                 15

Ser Val Lys Leu Ser Cys Lys Ala Ser Gly Tyr Thr Phe Thr Asp Tyr
            20                  25                 30

Trp Met Gln Trp Val Lys Gln Arg Pro Gly Gln Gly Leu Glu Trp Ile
            35                  40                 45

Gly Thr Ile Tyr Pro Gly Asp Gly Asp Thr Gly Tyr Ala Gln Lys Phe
    50                  55                 60

Gln Gly Lys Ala Thr Leu Thr Ala Asp Lys Ser Ser Lys Thr Val Tyr
65                  70                  75                 80
```

```
Met His Leu Ser Ser Leu Ala Ser Glu Asp Ser Ala Val Tyr Tyr Cys
                85                  90                  95

Ala Arg Gly Asp Tyr Tyr Gly Ser Asn Ser Leu Asp Tyr Trp Gly Gln
            100                 105                 110

Gly Thr Ser Val Thr Val Ser Ser
        115                 120

<210> SEQ ID NO 95
<211> LENGTH: 107
<212> TYPE: PRT
<213> ORGANISM: Artificial Sequence
<220> FEATURE:
<223> OTHER INFORMATION: Synthetic

<400> SEQUENCE: 95

Asp Ile Val Met Thr Gln Ser His Leu Ser Met Ser Thr Ser Leu Gly
1               5                   10                  15

Asp Pro Val Ser Ile Thr Cys Lys Ala Ser Gln Asp Val Ser Thr Val
            20                  25                  30

Val Ala Trp Tyr Gln Gln Lys Pro Gly Gln Ser Pro Arg Arg Leu Ile
        35                  40                  45

Tyr Ser Ala Ser Tyr Arg Tyr Ile Gly Val Pro Asp Arg Phe Thr Gly
50                  55                  60

Ser Gly Ala Gly Thr Asp Phe Thr Phe Thr Ile Ser Ser Val Gln Ala
65                  70                  75                  80

Glu Asp Leu Ala Val Tyr Tyr Cys Gln His Tyr Ser Pro Pro Tyr
                85                  90                  95

Thr Phe Gly Gly Gly Thr Lys Leu Glu Ile Lys
            100                 105

<210> SEQ ID NO 96
<211> LENGTH: 120
<212> TYPE: PRT
<213> ORGANISM: Artificial Sequence
<220> FEATURE:
<223> OTHER INFORMATION: Synthetic

<400> SEQUENCE: 96

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Phe Ser Trp Val Arg Gln Ala Pro Gly Gln Gly Leu Glu Trp Met
        35                  40                  45

Gly Arg Val Ile Pro Phe Leu Gly Ile Ala Asn Ser Ala Gln Lys Phe
    50                  55                  60

Gln Gly Arg Val Thr Ile Thr Ala Asp Lys Ser Thr Ser Thr Ala Tyr
65                  70                  75                  80

Met Asp Leu Ser Ser Leu Arg Ser Glu Asp Thr Ala Val Tyr Tyr Cys
                85                  90                  95

Ala Arg Asp Asp Ile Ala Ala Leu Gly Pro Phe Asp Tyr Trp Gly Gln
            100                 105                 110

Gly Thr Leu Val Thr Val Ser Ser
        115                 120

<210> SEQ ID NO 97
<211> LENGTH: 107
<212> TYPE: PRT
<213> ORGANISM: Artificial Sequence
```

```
<220> FEATURE:
<223> OTHER INFORMATION: Synthetic

<400> SEQUENCE: 97

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Arg
                85                  90                  95

Thr Phe Gly Gln Gly Thr Lys Val Glu Ile Lys
            100                 105

<210> SEQ ID NO 98
<211> LENGTH: 119
<212> TYPE: PRT
<213> ORGANISM: Artificial Sequence
<220> FEATURE:
<223> OTHER INFORMATION: Synthetic

<400> SEQUENCE: 98

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Pro Asp Tyr
            20                  25                  30

Tyr Ile Asn Trp Val Arg Gln Ala Pro Gly Gln Gly Leu Glu Trp Met
        35                  40                  45

Gly Trp Ile Tyr Phe Ala Ser Gly Asn Ser Glu Tyr Asn Gln Lys Phe
    50                  55                  60

Thr Gly Arg Val Thr Met Thr Arg Asp Thr Ser Ile Asn Thr Ala Tyr
65                  70                  75                  80

Met Glu Leu Ser Ser Leu Thr Ser Glu Asp Thr Ala Val Tyr Phe Cys
                85                  90                  95

Ala Ser Leu Tyr Asp Tyr Asp Trp Tyr Phe Asp Val Trp Gly Gln Gly
            100                 105                 110

Thr Met Val Thr Val Ser Ser
        115

<210> SEQ ID NO 99
<211> LENGTH: 112
<212> TYPE: PRT
<213> ORGANISM: Artificial Sequence
<220> FEATURE:
<223> OTHER INFORMATION: Synthetic

<400> SEQUENCE: 99

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Val His Ser
            20                  25                  30

Asn Gly Asn Thr Tyr Leu His Trp Tyr Leu Gln Lys Pro Gly Gln Ser
        35                  40                  45
```

-continued

```
Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Ile Tyr Tyr Cys Ser Gln Ser
                85                  90                  95

Ser Ile Tyr Pro Trp Thr Phe Gly Gln Gly Thr Lys Leu Glu Ile Lys
            100                 105                 110
```

<210> SEQ ID NO 100
<211> LENGTH: 121
<212> TYPE: PRT
<213> ORGANISM: Artificial Sequence
<220> FEATURE:
<223> OTHER INFORMATION: Synthetic

<400> SEQUENCE: 100

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Tyr Ser His Asp Met Trp Ser Gly Asp Trp Gly
            100                 105                 110

Gln Gly Thr Leu Val Thr Val Ser Ser
        115                 120
```

<210> SEQ ID NO 101
<211> LENGTH: 112
<212> TYPE: PRT
<213> ORGANISM: Artificial Sequence
<220> FEATURE:
<223> OTHER INFORMATION: Synthetic

<400> SEQUENCE: 101

```
Leu Pro Val Leu Thr Gln Pro Ser Ala Ser Gly Thr Pro Gly Gln
1               5                   10                  15

Arg Val Thr Ile Ser Cys Ser Gly Arg Ser Ser Asn Ile Gly Ser Asn
                20                  25                  30

Ser Val Asn Trp Tyr Arg Gln Leu Pro Gly Ala Ala Pro Lys Leu Leu
            35                  40                  45

Ile Tyr Ser Asn Asn Gln Arg Pro Pro Gly Val Pro Val Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Thr Tyr Tyr Cys Ala Thr Trp Asp Asp Asn Leu
                85                  90                  95

Asn Val His Tyr Val Phe Gly Thr Gly Thr Lys Val Thr Val Leu Gly
            100                 105                 110
```

<210> SEQ ID NO 102

```
<211> LENGTH: 116
<212> TYPE: PRT
<213> ORGANISM: Artificial Sequence
<220> FEATURE:
<223> OTHER INFORMATION: Synthetic

<400> SEQUENCE: 102

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Tyr Ser Gly Ser Phe Asp Asn Trp Gly Gln Gly Thr Leu Val
            100                 105                 110

Thr Val Ser Ser
        115

<210> SEQ ID NO 103
<211> LENGTH: 111
<212> TYPE: PRT
<213> ORGANISM: Artificial Sequence
<220> FEATURE:
<223> OTHER INFORMATION: Synthetic

<400> SEQUENCE: 103

Ser Tyr Glu Leu Thr Gln Pro Pro Ser Ala Ser Gly Thr Pro Gly Gln
1               5                   10                  15

Arg Val Thr Met Ser Cys Ser Gly Thr Ser Ser Asn Ile Gly Ser His
            20                  25                  30

Ser Val Asn Trp Tyr Gln Gln Leu Pro Gly Thr Ala Pro Lys Leu Leu
        35                  40                  45

Ile Tyr Thr Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Gly Ser Leu
                85                  90                  95

Asn Gly Leu Val Phe Gly Gly Gly Thr Lys Leu Thr Val Leu Gly
            100                 105                 110

<210> SEQ ID NO 104
<211> LENGTH: 122
<212> TYPE: PRT
<213> ORGANISM: Artificial Sequence
<220> FEATURE:
<223> OTHER INFORMATION: Synthetic

<400> SEQUENCE: 104

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Gly
            20                  25                  30
```

```
Ser Tyr Phe Trp Gly Trp Ile Arg Gln Pro Pro Gly Lys Gly Leu Glu
            35                  40                  45

Trp Ile Gly Ser Ile Tyr Tyr Ser Gly Ile Thr Tyr Tyr Asn Pro Ser
 50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg His Asp Gly Ala Val Ala Gly Leu Phe Asp Tyr Trp Gly
                100                 105                 110

Gln Gly Thr Leu Val Thr Val Ser Ser Ala
            115                 120

<210> SEQ ID NO 105
<211> LENGTH: 108
<212> TYPE: PRT
<213> ORGANISM: Artificial Sequence
<220> FEATURE:
<223> OTHER INFORMATION: Synthetic

<400> SEQUENCE: 105

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Pro Pro Gly Gln Ala Pro Val Val Val Val Tyr
        35                  40                  45

Asp Asp Ser Asp Arg Pro Ser Gly Ile Pro Glu Arg Phe Ser Gly Asn
 50                 55                  60

Ser Asn Gly Asn Thr Ala Thr Leu Thr Ile Ser Arg Val Glu Ala Gly
65                  70                  75                  80

Asp Glu Ala Val Tyr Tyr Cys Gln Val Trp Asp Ser Ser Ser Asp His
                85                  90                  95

Val Val Phe Gly Gly Gly Thr Lys Leu Thr Val Leu
            100                 105

<210> SEQ ID NO 106
<211> LENGTH: 123
<212> TYPE: PRT
<213> ORGANISM: Artificial Sequence
<220> FEATURE:
<223> OTHER INFORMATION: Synthetic

<400> SEQUENCE: 106

Gln Val Gln Leu Val Gln Ser Gly Ala Glu Val Lys Lys Pro Gly Ser
1               5                   10                  15

Ser Val Lys Val Ser Cys Lys Thr Ser Gly Asp Thr Phe Ser Thr Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Lys Ala His Tyr Ala Gln Lys Phe
 50                 55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Lys Phe His Phe Val Ser Gly Ser Pro Phe Gly Met Asp Val
            100                 105                 110
```

```
Trp Gly Gln Gly Thr Thr Val Thr Val Ser Ser
        115                 120

<210> SEQ ID NO 107
<211> LENGTH: 106
<212> TYPE: PRT
<213> ORGANISM: Artificial Sequence
<220> FEATURE:
<223> OTHER INFORMATION: Synthetic

<400> SEQUENCE: 107

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Thr
                85                  90                  95

Phe Gly Gln Gly Thr Lys Val Glu Ile Lys
            100                 105

<210> SEQ ID NO 108
<211> LENGTH: 118
<212> TYPE: PRT
<213> ORGANISM: Artificial Sequence
<220> FEATURE:
<223> OTHER INFORMATION: Synthetic

<400> SEQUENCE: 108

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser
        115

<210> SEQ ID NO 109
<211> LENGTH: 107
<212> TYPE: PRT
<213> ORGANISM: Artificial Sequence
<220> FEATURE:
<223> OTHER INFORMATION: Synthetic

<400> SEQUENCE: 109
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
            85                  90                  95

Thr Phe Gly Gln Gly Thr Lys Val Glu Ile Lys
            100                 105

<210> SEQ ID NO 110
<211> LENGTH: 121
<212> TYPE: PRT
<213> ORGANISM: Artificial Sequence
<220> FEATURE:
<223> OTHER INFORMATION: Synthetic

<400> SEQUENCE: 110

Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Arg Glu Gly Gly Trp Phe Gly Glu Leu Ala Phe Asp Tyr Trp Gly
            100                 105                 110

Gln Gly Thr Leu Val Thr Val Ser Ser
        115                 120

<210> SEQ ID NO 111
<211> LENGTH: 108
<212> TYPE: PRT
<213> ORGANISM: Artificial Sequence
<220> FEATURE:
<223> OTHER INFORMATION: Synthetic

<400> SEQUENCE: 111

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Arg Val Ser Ser Ser
            20                  25                  30

Tyr Leu Ala Trp Tyr Gln Gln Lys Pro Gly Gln Ala Pro Arg Leu Leu
        35                  40                  45

Ile Tyr Asp Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Leu Pro
                85                  90                  95

Trp Thr Phe Gly Gln Gly Thr Lys Val Glu Ile Lys
            100                 105

<210> SEQ ID NO 112
<211> LENGTH: 120
<212> TYPE: PRT
<213> ORGANISM: Artificial Sequence
<220> FEATURE:
<223> OTHER INFORMATION: Synthetic

<400> SEQUENCE: 112

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ile Met Met Trp Val Arg Gln Ala Pro Gly Lys Gly Leu Glu Trp Val
        35                  40                  45

Ser Ser Ile Tyr Pro Ser Gly Gly Ile Thr Phe Tyr Ala Asp Thr Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Lys Leu Gly Thr Val Thr Val Asp Tyr Trp Gly Gln
            100                 105                 110

Gly Thr Leu Val Thr Val Ser Ser
        115                 120

<210> SEQ ID NO 113
<211> LENGTH: 110
<212> TYPE: PRT
<213> ORGANISM: Artificial Sequence
<220> FEATURE:
<223> OTHER INFORMATION: Synthetic

<400> SEQUENCE: 113

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Arg Val Phe Gly Thr Gly Thr Lys Val Thr Val Leu
            100                 105                 110

<210> SEQ ID NO 114
<211> LENGTH: 119
<212> TYPE: PRT
<213> ORGANISM: Artificial Sequence
<220> FEATURE:
<223> OTHER INFORMATION: Synthetic

<400> SEQUENCE: 114

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asp Phe Ser Arg Tyr
            20                  25                  30

Trp Met Ser Trp Val Arg Gln Ala Pro Gly Lys Gly Leu Glu Trp Ile
        35                  40                  45

Gly Glu Ile Asn Pro Asp Ser Ser Thr Ile Asn Tyr Ala Pro Ser Leu
    50                  55                  60

Lys Asp Lys Phe Ile Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Pro Asp Gly Asn Tyr Trp Tyr Phe Asp Val Trp Gly Gln Gly
            100                 105                 110

Thr Leu Val Thr Val Ser Ser
            115

<210> SEQ ID NO 115
<211> LENGTH: 107
<212> TYPE: PRT
<213> ORGANISM: Artificial Sequence
<220> FEATURE:
<223> OTHER INFORMATION: Synthetic

<400> SEQUENCE: 115

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Gly Ile Ala
            20                  25                  30

Val Ala Trp Tyr Gln Gln Lys Pro Gly Lys Val Pro Lys Leu Leu Ile
        35                  40                  45

Tyr Trp Ala Ser Thr Arg His Thr Gly Val Pro Asp Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln Tyr Ser Ser Tyr Pro Tyr
                85                  90                  95

Thr Phe Gly Gln Gly Thr Lys Val Glu Ile Lys
            100                 105

<210> SEQ ID NO 116
<211> LENGTH: 121
<212> TYPE: PRT
<213> ORGANISM: Artificial Sequence
<220> FEATURE:
<223> OTHER INFORMATION: Synthetic

<400> SEQUENCE: 116

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Val Phe
            20                  25                  30

Gly Met Asn Trp Val Arg Gln Ala Pro Gly Gln Gly Leu Glu Trp Met
        35                  40                  45

Gly Trp Ile Asn Thr Lys Thr Gly Glu Ala Thr Tyr Val Glu Glu Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Asp Asp Thr Ala Val Tyr Tyr Cys
                85                  90                  95

Ala Arg Trp Asp Phe Tyr Asp Tyr Val Glu Ala Met Asp Tyr Trp Gly
            100                 105                 110

Gln Gly Thr Thr Val Thr Val Ser Ser
        115                 120

<210> SEQ ID NO 117
<211> LENGTH: 109
<212> TYPE: PRT
<213> ORGANISM: Artificial Sequence
<220> FEATURE:
<223> OTHER INFORMATION: Synthetic

<400> SEQUENCE: 117

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Asn
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys His Gln Tyr Tyr Thr Tyr Pro Leu
                85                  90                  95

Phe Thr Phe Gly Gln Gly Thr Lys Val Glu Ile Lys Arg
            100                 105

<210> SEQ ID NO 118
<211> LENGTH: 118
<212> TYPE: PRT
<213> ORGANISM: Artificial Sequence
<220> FEATURE:
<223> OTHER INFORMATION: Synthetic

<400> SEQUENCE: 118

Glu Val Lys Leu Asp Glu Thr Gly Gly Gly Leu Val Gln Pro Gly Arg
1               5                   10                  15

Pro Met Lys Leu Ser Cys Val Ala Ser Gly Phe Thr Phe Ser Asp Tyr
            20                  25                  30

Trp Met Asn Trp Val Arg Gln Ser Pro Glu Lys Gly Leu Glu Trp Val
        35                  40                  45

Ala Gln Ile Arg Asn Lys Pro Tyr Asn Tyr Glu Thr Tyr Tyr Ser Asp
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Val Glu Asp Met Gly Ile Tyr
                85                  90                  95

Tyr Cys Thr Gly Ser Tyr Tyr Gly Met Asp Tyr Trp Gly Gln Gly Thr
            100                 105                 110

Ser Val Thr Val Ser Ser
        115

```
<210> SEQ ID NO 119
<211> LENGTH: 112
<212> TYPE: PRT
<213> ORGANISM: Artificial Sequence
<220> FEATURE:
<223> OTHER INFORMATION: Synthetic

<400> SEQUENCE: 119
```

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu Arg Trp Tyr Leu Gln Lys Pro Gly Gln Ser
        35                  40                  45

Pro Lys Val Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
            100                 105                 110

```
<210> SEQ ID NO 120
<211> LENGTH: 5
<212> TYPE: PRT
<213> ORGANISM: Artificial Sequence
<220> FEATURE:
<223> OTHER INFORMATION: Synthetic

<400> SEQUENCE: 120
```

Gly Gly Gly Gly Ser
1               5

```
<210> SEQ ID NO 121
<211> LENGTH: 7
<212> TYPE: PRT
<213> ORGANISM: Artificial Sequence
<220> FEATURE:
<223> OTHER INFORMATION: Synthetic

<400> SEQUENCE: 121
```

Gly Gly Gly Ser Ala Ala Ala
1               5

```
<210> SEQ ID NO 122
<211> LENGTH: 7
<212> TYPE: PRT
<213> ORGANISM: Artificial Sequence
<220> FEATURE:
<223> OTHER INFORMATION: Synthetic

<400> SEQUENCE: 122
```

Gly Gly Gly Gly Ser Ala Ser
1               5

```
<210> SEQ ID NO 123
<211> LENGTH: 10
<212> TYPE: PRT
<213> ORGANISM: Artificial Sequence
<220> FEATURE:
<223> OTHER INFORMATION: Synthetic

<400> SEQUENCE: 123
```

```
Gly Arg Pro Gly Ser Gly Arg Pro Gly Ser
1               5                   10

<210> SEQ ID NO 124
<211> LENGTH: 12
<212> TYPE: PRT
<213> ORGANISM: Artificial Sequence
<220> FEATURE:
<223> OTHER INFORMATION: Synthetic

<400> SEQUENCE: 124

Gly Gly Gly Gly Ser Gly Gly Gly Gly Ser Ala Ser
1               5                   10

<210> SEQ ID NO 125
<211> LENGTH: 12
<212> TYPE: PRT
<213> ORGANISM: Artificial Sequence
<220> FEATURE:
<223> OTHER INFORMATION: Synthetic

<400> SEQUENCE: 125

Gly Lys Ser Ser Gly Ser Gly Ser Glu Ser Lys Ser
1               5                   10

<210> SEQ ID NO 126
<211> LENGTH: 14
<212> TYPE: PRT
<213> ORGANISM: Artificial Sequence
<220> FEATURE:
<223> OTHER INFORMATION: Synthetic

<400> SEQUENCE: 126

Gly Ser Thr Ser Gly Ser Gly Lys Ser Ser Glu Gly Lys Gly
1               5                   10

<210> SEQ ID NO 127
<211> LENGTH: 14
<212> TYPE: PRT
<213> ORGANISM: Artificial Sequence
<220> FEATURE:
<223> OTHER INFORMATION: Synthetic

<400> SEQUENCE: 127

Glu Pro Lys Ser Ser Asp Lys Thr His Thr Ser Pro Pro Ser
1               5                   10

<210> SEQ ID NO 128
<211> LENGTH: 14
<212> TYPE: PRT
<213> ORGANISM: Artificial Sequence
<220> FEATURE:
<223> OTHER INFORMATION: Synthetic

<400> SEQUENCE: 128

Gly Gly Gly Gly Ser Asp Lys Thr His Thr Ser Pro Pro Ser
1               5                   10

<210> SEQ ID NO 129
<211> LENGTH: 15
<212> TYPE: PRT
<213> ORGANISM: Artificial Sequence
<220> FEATURE:
<223> OTHER INFORMATION: Synthetic

<400> SEQUENCE: 129

Gly Gly Gly Gly Ser Gly Gly Gly Gly Ser Gly Gly Gly Gly Ser
```

<210> SEQ ID NO 130
<211> LENGTH: 17
<212> TYPE: PRT
<213> ORGANISM: Artificial Sequence
<220> FEATURE:
<223> OTHER INFORMATION: Synthetic

<400> SEQUENCE: 130

Gly Gly Gly Gly Ser Gly Gly Gly Ser Gly Gly Gly Gly Ser Ala
1               5                   10                  15

Ser

<210> SEQ ID NO 131
<211> LENGTH: 18
<212> TYPE: PRT
<213> ORGANISM: Artificial Sequence
<220> FEATURE:
<223> OTHER INFORMATION: Synthetic

<400> SEQUENCE: 131

Gly Ser Thr Ser Gly Ser Gly Lys Ser Ser Glu Gly Ser Gly Ser Thr
1               5                   10                  15

Lys Gly

<210> SEQ ID NO 132
<211> LENGTH: 18
<212> TYPE: PRT
<213> ORGANISM: Artificial Sequence
<220> FEATURE:
<223> OTHER INFORMATION: Synthetic

<400> SEQUENCE: 132

Gly Ser Thr Ser Gly Ser Gly Lys Pro Gly Ser Gly Glu Gly Ser Thr
1               5                   10                  15

Lys Gly

<210> SEQ ID NO 133
<211> LENGTH: 20
<212> TYPE: PRT
<213> ORGANISM: Artificial Sequence
<220> FEATURE:
<223> OTHER INFORMATION: Synthetic

<400> SEQUENCE: 133

Gly Gly Gly Gly Ser Gly Gly Gly Ser Gly Gly Gly Gly Ser Gly
1               5                   10                  15

Gly Gly Gly Ser
            20

<210> SEQ ID NO 134
<211> LENGTH: 27
<212> TYPE: PRT
<213> ORGANISM: Artificial Sequence
<220> FEATURE:
<223> OTHER INFORMATION: Synthetic

<400> SEQUENCE: 134

Gly Gly Gly Gly Ser Gly Gly Gly Ser Gly Gly Gly Gly Ser Gly
1               5                   10                  15

Gly Gly Gly Ser Gly Gly Gly Gly Ser Ala Ser
            20                  25

<210> SEQ ID NO 135
<211> LENGTH: 32
<212> TYPE: PRT
<213> ORGANISM: Artificial Sequence
<220> FEATURE:
<223> OTHER INFORMATION: Synthetic

<400> SEQUENCE: 135

Gly Gly Gly Gly Ser Gly Gly Gly Ser Gly Gly Gly Gly Ser Gly
1               5                   10                  15

Gly Gly Gly Ser Gly Gly Gly Gly Ser Gly Gly Gly Ser Ala Ser
            20                  25                  30

<210> SEQ ID NO 136
<211> LENGTH: 37
<212> TYPE: PRT
<213> ORGANISM: Artificial Sequence
<220> FEATURE:
<223> OTHER INFORMATION: Synthetic

<400> SEQUENCE: 136

Ala Gly Gly Gly Ser Gly Gly Gly Ser Gly Gly Gly Gly Ser Gly
1               5                   10                  15

Gly Gly Gly Ser Gly Gly Gly Gly Ser Gly Gly Gly Ser Gly Gly
            20                  25                  30

Gly Gly Ser Ala Ser
        35

<210> SEQ ID NO 137
<211> LENGTH: 42
<212> TYPE: PRT
<213> ORGANISM: Artificial Sequence
<220> FEATURE:
<223> OTHER INFORMATION: Synthetic

<400> SEQUENCE: 137

Ala Gly Gly Gly Ser Gly Gly Gly Gly Ser Gly Gly Gly Ser Gly
1               5                   10                  15

Gly Gly Gly Ser Gly Gly Gly Gly Ser Gly Gly Gly Ser Gly Gly
            20                  25                  30

Gly Gly Ser Gly Gly Gly Gly Ser Ala Ser
        35                  40

<210> SEQ ID NO 138
<211> LENGTH: 47
<212> TYPE: PRT
<213> ORGANISM: Artificial Sequence
<220> FEATURE:
<223> OTHER INFORMATION: Synthetic

<400> SEQUENCE: 138

Ala Gly Gly Gly Ser Gly Gly Gly Gly Ser Gly Gly Gly Ser Gly
1               5                   10                  15

Gly Gly Gly Ser Gly Gly Gly Gly Ser Gly Gly Gly Ser Gly Gly
            20                  25                  30

Gly Gly Ser Gly Gly Gly Gly Ser Gly Gly Gly Ser Ala Ser
        35                  40                  45

<210> SEQ ID NO 139
<211> LENGTH: 12
<212> TYPE: PRT
<213> ORGANISM: Artificial Sequence
<220> FEATURE:

```
<223> OTHER INFORMATION: Synthetic

<400> SEQUENCE: 139

Glu Pro Lys Ser Cys Asp Lys Thr His Thr Cys Pro
1               5                   10

<210> SEQ ID NO 140
<211> LENGTH: 12
<212> TYPE: PRT
<213> ORGANISM: Artificial Sequence
<220> FEATURE:
<223> OTHER INFORMATION: Synthetic

<400> SEQUENCE: 140

Glu Pro Lys Ser Ser Asp Lys Thr His Thr Cys Pro
1               5                   10

<210> SEQ ID NO 141
<211> LENGTH: 12
<212> TYPE: PRT
<213> ORGANISM: Artificial Sequence
<220> FEATURE:
<223> OTHER INFORMATION: Synthetic

<400> SEQUENCE: 141

Gly Gly Gly Gly Ser Asp Lys Thr His Thr Cys Pro
1               5                   10

<210> SEQ ID NO 142
<211> LENGTH: 12
<212> TYPE: PRT
<213> ORGANISM: Artificial Sequence
<220> FEATURE:
<223> OTHER INFORMATION: Synthetic

<400> SEQUENCE: 142

Arg Gly Arg Gly Ser Asp Lys Thr His Thr Cys Pro
1               5                   10

<210> SEQ ID NO 143
<211> LENGTH: 12
<212> TYPE: PRT
<213> ORGANISM: Artificial Sequence
<220> FEATURE:
<223> OTHER INFORMATION: Synthetic

<400> SEQUENCE: 143

Asp Gly Asp Gly Ser Asp Lys Thr His Thr Cys Pro
1               5                   10

<210> SEQ ID NO 144
<211> LENGTH: 13
<212> TYPE: PRT
<213> ORGANISM: Artificial Sequence
<220> FEATURE:
<223> OTHER INFORMATION: Synthetic

<400> SEQUENCE: 144

Gly Arg Gly Arg Gly Ser Asp Lys Thr His Thr Cys Pro
1               5                   10

<210> SEQ ID NO 145
<211> LENGTH: 13
<212> TYPE: PRT
<213> ORGANISM: Artificial Sequence
<220> FEATURE:
<223> OTHER INFORMATION: Synthetic
```

<400> SEQUENCE: 145

Gly Asp Gly Asp Gly Ser Asp Lys Thr His Thr Cys Pro
1               5                   10

<210> SEQ ID NO 146
<211> LENGTH: 13
<212> TYPE: PRT
<213> ORGANISM: Artificial Sequence
<220> FEATURE:
<223> OTHER INFORMATION: Synthetic

<400> SEQUENCE: 146

Arg Gly Arg Gly Ser Ser Asp Lys Thr His Thr Cys Pro
1               5                   10

<210> SEQ ID NO 147
<211> LENGTH: 13
<212> TYPE: PRT
<213> ORGANISM: Artificial Sequence
<220> FEATURE:
<223> OTHER INFORMATION: Synthetic

<400> SEQUENCE: 147

Asp Gly Asp Gly Ser Ser Asp Lys Thr His Thr Cys Pro
1               5                   10

<210> SEQ ID NO 148
<211> LENGTH: 107
<212> TYPE: PRT
<213> ORGANISM: Artificial Sequence
<220> FEATURE:
<223> OTHER INFORMATION: Synthetic

<400> SEQUENCE: 148

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 149
<211> LENGTH: 106
<212> TYPE: PRT
<213> ORGANISM: Artificial Sequence
<220> FEATURE:
<223> OTHER INFORMATION: Synthetic

<400> SEQUENCE: 149

Gly Gln Pro Lys Ala Asn Pro Thr Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

```
Phe Tyr Pro Gly Ala Val Thr Val Ala Trp Lys Ala Asp Gly Ser Pro
        35                  40                  45

Val Lys Ala Gly Val Glu Thr Thr Lys Pro Ser Lys Gln Ser Asn Asn
 50                  55                  60

Lys Tyr Ala Ala Ser Ser Tyr Leu Ser Leu Thr Pro Glu Gln Trp Lys
 65                  70                  75                  80

Ser His Arg Ser Tyr Ser Cys Gln Val Thr His Glu Gly Ser Thr Val
                 85                  90                  95

Glu Lys Thr Val Ala Pro Thr Glu Cys Ser
                100                 105
```

<210> SEQ ID NO 150
<211> LENGTH: 106
<212> TYPE: PRT
<213> ORGANISM: Artificial Sequence
<220> FEATURE:
<223> OTHER INFORMATION: Synthetic

<400> SEQUENCE: 150

```
Gly Gln Pro Lys Ala Ala Pro Ser Val Thr Leu Phe Pro Pro Ser Ser
 1               5                  10                  15

Glu Glu Leu Gln Ala Asn Lys Ala Thr Leu Val Cys Leu Ile Ser Asp
                 20                  25                  30

Phe Tyr Pro Gly Ala Val Thr Val Ala Trp Lys Ala Asp Ser Ser Pro
        35                  40                  45

Val Lys Ala Gly Val Glu Thr Thr Pro Ser Lys Gln Ser Asn Asn
 50                  55                  60

Lys Tyr Ala Ala Ser Ser Tyr Leu Ser Leu Thr Pro Glu Gln Trp Lys
 65                  70                  75                  80

Ser His Arg Ser Tyr Ser Cys Gln Val Thr His Glu Gly Ser Thr Val
                 85                  90                  95

Glu Lys Thr Val Ala Pro Thr Glu Cys Ser
                100                 105
```

<210> SEQ ID NO 151
<211> LENGTH: 106
<212> TYPE: PRT
<213> ORGANISM: Artificial Sequence
<220> FEATURE:
<223> OTHER INFORMATION: Synthetic

<400> SEQUENCE: 151

```
Gly Gln Pro Lys Ala Ala Pro Ser Val Thr Leu Phe Pro Pro Ser Ser
 1               5                  10                  15

Glu Glu Leu Gln Ala Asn Lys Ala Thr Leu Val Cys Leu Ile Ser Asp
                 20                  25                  30

Phe Tyr Pro Gly Ala Val Thr Val Ala Trp Lys Ala Asp Ser Ser Pro
        35                  40                  45

Ala Lys Ala Gly Val Glu Thr Thr Thr Pro Ser Lys Gln Ser Asn Asn
 50                  55                  60

Lys Tyr Ala Ala Ser Ser Tyr Leu Ser Leu Thr Pro Glu Gln Trp Lys
 65                  70                  75                  80

Ser His Lys Ser Tyr Ser Cys Gln Val Thr His Glu Gly Ser Thr Val
                 85                  90                  95

Glu Lys Thr Val Ala Pro Thr Glu Cys Ser
                100                 105
```

<210> SEQ ID NO 152

<211> LENGTH: 106
<212> TYPE: PRT
<213> ORGANISM: Artificial Sequence
<220> FEATURE:
<223> OTHER INFORMATION: Synthetic

<400> SEQUENCE: 152

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Lys Val Ala Trp Lys Ala Asp Gly Ser Pro
        35                  40                  45

Val Asn Thr Gly Val Glu Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Ala Glu Cys Ser
            100                 105

<210> SEQ ID NO 153
<211> LENGTH: 106
<212> TYPE: PRT
<213> ORGANISM: Artificial Sequence
<220> FEATURE:
<223> OTHER INFORMATION: Synthetic

<400> SEQUENCE: 153

Gly Gln Pro Lys Ala Ala Pro Thr Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Lys Val Ala Trp Lys Ala Asp Ser Ser Pro
        35                  40                  45

Ala Lys Ala Gly Val Glu Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Lys Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 154
<211> LENGTH: 98
<212> TYPE: PRT
<213> ORGANISM: Artificial Sequence
<220> FEATURE:
<223> OTHER INFORMATION: Synthetic

<400> SEQUENCE: 154

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

-continued

Gly Val His Thr Phe Pro Ala Val Leu Gln Ser Ser Gly Leu Tyr Ser
 50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val

<210> SEQ ID NO 155
<211> LENGTH: 113
<212> TYPE: PRT
<213> ORGANISM: Artificial Sequence
<220> FEATURE:
<223> OTHER INFORMATION: Synthetic

<400> SEQUENCE: 155

Pro Cys Pro Ala Pro Glu Leu Leu Gly Gly Pro Ser Val Phe Leu Phe
 1               5                  10                  15

Pro Pro Lys Pro Lys Asp Thr Leu Met Ile Ser Arg Thr Pro Glu Val
                 20                  25                  30

Thr Cys Val Val Val Asp Val Ser His Glu Asp Pro Glu Val Lys Phe
             35                  40                  45

Asn Trp Tyr Val Asp Gly Val Glu Val His Asn Ala Lys Thr Lys Pro
 50                  55                  60

Arg Glu Glu Gln Tyr Asn Ser Thr Tyr Arg Val Val Ser Val Leu Thr
 65                  70                  75                  80

Val Leu His Gln Asp Trp Leu Asn Gly Lys Glu Tyr Lys Cys Lys Val
                 85                  90                  95

Ser Asn Lys Ala Leu Pro Ala Pro Ile Glu Lys Thr Ile Ser Lys Ala
                100                 105                 110

Lys

<210> SEQ ID NO 156
<211> LENGTH: 113
<212> TYPE: PRT
<213> ORGANISM: Artificial Sequence
<220> FEATURE:
<223> OTHER INFORMATION: Synthetic

<400> SEQUENCE: 156

Pro Cys Pro Ala Pro Glu Ala Ala Gly Gly Pro Ser Val Phe Leu Phe
 1               5                  10                  15

Pro Pro Lys Pro Lys Asp Thr Leu Met Ile Ser Arg Thr Pro Glu Val
                 20                  25                  30

Thr Cys Val Val Val Asp Val Ser His Glu Asp Pro Glu Val Lys Phe
             35                  40                  45

Asn Trp Tyr Val Asp Gly Val Glu Val His Asn Ala Lys Thr Lys Pro
 50                  55                  60

Arg Glu Glu Gln Tyr Asn Ser Thr Tyr Arg Val Val Ser Val Leu Thr
 65                  70                  75                  80

Val Leu His Gln Asp Trp Leu Asn Gly Lys Glu Tyr Lys Cys Lys Val
                 85                  90                  95

Ser Asn Lys Ala Leu Gly Ala Pro Ile Glu Lys Thr Ile Ser Lys Ala
                100                 105                 110

Lys

<210> SEQ ID NO 157

```
<211> LENGTH: 113
<212> TYPE: PRT
<213> ORGANISM: Artificial Sequence
<220> FEATURE:
<223> OTHER INFORMATION: Synthetic

<400> SEQUENCE: 157

Pro Cys Pro Ala Pro Glu Phe Glu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Ser Ile Glu Lys Thr Ile Ser Lys Ala
            100                 105                 110

Lys

<210> SEQ ID NO 158
<211> LENGTH: 113
<212> TYPE: PRT
<213> ORGANISM: Artificial Sequence
<220> FEATURE:
<223> OTHER INFORMATION: Synthetic

<400> SEQUENCE: 158

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Ala Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys

<210> SEQ ID NO 159
<211> LENGTH: 113
<212> TYPE: PRT
<213> ORGANISM: Artificial Sequence
<220> FEATURE:
<223> OTHER INFORMATION: Synthetic

<400> SEQUENCE: 159

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30
```

Thr Cys Val Val Asp Val Ser His Glu Asp Pro Glu Val Lys Phe
            35                  40                  45

Asn Trp Tyr Val Asp Gly Val Glu Val His Asn Ala Lys Thr Lys Pro
 50                  55                  60

Arg Glu Glu Gln Tyr Gln Ser Thr Tyr Arg Val Val Ser Val Leu Thr
 65                  70                  75                  80

Val Leu His Gln Asp Trp Leu Asn Gly Lys Glu Tyr Lys Cys Lys Val
                 85                  90                  95

Ser Asn Lys Ala Leu Pro Ala Pro Ile Glu Lys Thr Ile Ser Lys Ala
            100                 105                 110

Lys

<210> SEQ ID NO 160
<211> LENGTH: 113
<212> TYPE: PRT
<213> ORGANISM: Artificial Sequence
<220> FEATURE:
<223> OTHER INFORMATION: Synthetic

<400> SEQUENCE: 160

Pro Cys Pro Ala Pro Glu Ala Ala Gly Gly Pro Ser Val Phe Leu Phe
 1               5                  10                  15

Pro Pro Lys Pro Lys Asp Thr Leu Met Ile Ser Arg Thr Pro Glu Val
            20                  25                  30

Thr Cys Val Val Asp Val Ser His Glu Asp Pro Glu Val Lys Phe
            35                  40                  45

Asn Trp Tyr Val Asp Gly Val Glu Val His Asn Ala Lys Thr Lys Pro
 50                  55                  60

Arg Glu Glu Gln Tyr Asn Ser Thr Tyr Arg Val Val Ser Val Leu Thr
 65                  70                  75                  80

Val Leu His Gln Asp Trp Leu Asn Gly Lys Glu Tyr Lys Cys Lys Val
                 85                  90                  95

Ser Asn Lys Ala Leu Pro Ala Pro Ile Glu Lys Thr Ile Ser Lys Ala
            100                 105                 110

Lys

<210> SEQ ID NO 161
<211> LENGTH: 112
<212> TYPE: PRT
<213> ORGANISM: Artificial Sequence
<220> FEATURE:
<223> OTHER INFORMATION: Synthetic

<400> SEQUENCE: 161

Pro Ser Pro Ala Pro Pro Val Ala Gly Pro Ser Val Phe Leu Phe Pro
 1               5                  10                  15

Pro Lys Pro Lys Asp Thr Leu Met Ile Ser Arg Thr Pro Glu Val Thr
            20                  25                  30

Cys Val Val Val Asp Val Ser His Glu Asp Pro Glu Val Gln Phe Asn
            35                  40                  45

Trp Tyr Val Asp Gly Val Glu Val His Asn Ala Lys Thr Lys Pro Arg
 50                  55                  60

Glu Glu Gln Phe Asn Ser Thr Phe Arg Val Val Ser Val Leu Thr Val
 65                  70                  75                  80

Val His Gln Asp Trp Leu Asn Gly Lys Glu Tyr Lys Cys Lys Val Ser
                 85                  90                  95

Asn Lys Gly Leu Pro Ala Pro Ile Glu Lys Thr Ile Ser Lys Thr Lys
            100                 105                 110

<210> SEQ ID NO 162
<211> LENGTH: 107
<212> TYPE: PRT
<213> ORGANISM: Artificial Sequence
<220> FEATURE:
<223> OTHER INFORMATION: Synthetic

<400> SEQUENCE: 162

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 163
<211> LENGTH: 107
<212> TYPE: PRT
<213> ORGANISM: Artificial Sequence
<220> FEATURE:
<223> OTHER INFORMATION: Synthetic

<400> SEQUENCE: 163

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 164
<211> LENGTH: 107
<212> TYPE: PRT
<213> ORGANISM: Artificial Sequence
<220> FEATURE:
<223> OTHER INFORMATION: Synthetic

<400> SEQUENCE: 164

Gly Gln Pro Arg Glu Pro Gln Val Tyr Thr Leu Pro Pro Ser Arg Asp
1               5                   10                  15

Glu Leu Thr Lys Asn Gln Val Ser Leu Trp Cys Leu Val Lys Gly Phe

```
                 20                  25                  30

Tyr Pro Ser Asp Ile Ala Val Glu Trp Glu Ser Asn Gly Gln Pro Glu
            35                  40                  45

Asn Asn Tyr Lys Thr Thr Pro Pro Val Leu Asp Ser Asp Gly Ser Phe
         50                  55                  60

Phe Leu Tyr Ser Lys Leu Thr Val Asp Lys Ser Arg Trp Gln Gln Gly
 65                  70                  75                  80

Asn Val Phe Ser Cys Ser Val Met His Glu Ala Leu His Asn His Tyr
                 85                  90                  95

Thr Gln Lys Ser Leu Ser Leu Ser Pro Gly Lys
            100                 105

<210> SEQ ID NO 165
<211> LENGTH: 107
<212> TYPE: PRT
<213> ORGANISM: Artificial Sequence
<220> FEATURE:
<223> OTHER INFORMATION: Synthetic

<400> SEQUENCE: 165

Gly Gln Pro Arg Glu Pro Gln Val Tyr Thr Leu Pro Pro Ser Arg Asp
 1               5                  10                  15

Glu Leu Thr Lys Asn Gln Val Ser Leu Ser Cys Ala Val Lys Gly Phe
            20                  25                  30

Tyr Pro Ser Asp Ile Ala Val Glu Trp Glu Ser Asn Gly Gln Pro Glu
            35                  40                  45

Asn Asn Tyr Lys Thr Thr Pro Pro Val Leu Asp Ser Asp Gly Ser Phe
         50                  55                  60

Phe Leu Val Ser Lys Leu Thr Val Asp Lys Ser Arg Trp Gln Gln Gly
 65                  70                  75                  80

Asn Val Phe Ser Cys Ser Val Met His Glu Ala Leu His Asn His Tyr
                 85                  90                  95

Thr Gln Lys Ser Leu Ser Leu Ser Pro Gly Lys
            100                 105

<210> SEQ ID NO 166
<211> LENGTH: 107
<212> TYPE: PRT
<213> ORGANISM: Artificial Sequence
<220> FEATURE:
<223> OTHER INFORMATION: Synthetic

<400> SEQUENCE: 166

Gly Gln Pro Arg Glu Pro Gln Val Tyr Thr Leu Pro Pro Cys Arg Asp
 1               5                  10                  15

Glu Leu Thr Lys Asn Gln Val Ser Leu Trp Cys Leu Val Lys Gly Phe
            20                  25                  30

Tyr Pro Ser Asp Ile Ala Val Glu Trp Glu Ser Asn Gly Gln Pro Glu
            35                  40                  45

Asn Asn Tyr Lys Thr Thr Pro Pro Val Leu Asp Ser Asp Gly Ser Phe
         50                  55                  60

Phe Leu Tyr Ser Lys Leu Thr Val Asp Lys Ser Arg Trp Gln Gln Gly
 65                  70                  75                  80

Asn Val Phe Ser Cys Ser Val Met His Glu Ala Leu His Asn His Tyr
                 85                  90                  95

Thr Gln Lys Ser Leu Ser Leu Ser Pro Gly Lys
            100                 105
```

<210> SEQ ID NO 167
<211> LENGTH: 107
<212> TYPE: PRT
<213> ORGANISM: Artificial Sequence
<220> FEATURE:
<223> OTHER INFORMATION: Synthetic

<400> SEQUENCE: 167

```
Gly Gln Pro Arg Glu Pro Gln Val Cys Thr Leu Pro Pro Ser Arg Asp
1               5                   10                  15

Glu Leu Thr Lys Asn Gln Val Ser Leu Ser Cys Ala Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Val Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105
```

<210> SEQ ID NO 168
<211> LENGTH: 107
<212> TYPE: PRT
<213> ORGANISM: Artificial Sequence
<220> FEATURE:
<223> OTHER INFORMATION: Synthetic

<400> SEQUENCE: 168

```
Gly Gln Pro Arg Glu Pro Gln Val Tyr Thr Leu Pro Pro Cys Arg Asp
1               5                   10                  15

Glu Leu Thr Lys Asn Gln Val Ser Leu Trp Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105
```

<210> SEQ ID NO 169
<211> LENGTH: 107
<212> TYPE: PRT
<213> ORGANISM: Artificial Sequence
<220> FEATURE:
<223> OTHER INFORMATION: Synthetic

<400> SEQUENCE: 169

```
Gly Gln Pro Arg Glu Pro Gln Val Cys Thr Leu Pro Pro Ser Arg Asp
1               5                   10                  15

Glu Leu Thr Lys Asn Gln Val Ser Leu Ser Cys Ala Val Lys Gly Phe
            20                  25                  30

Tyr Pro Ser Asp Ile Ala Val Glu Trp Glu Ser Asn Gly Gln Pro Glu
```

```
                35                  40                  45
Asn Asn Tyr Lys Thr Thr Pro Pro Val Leu Asp Ser Asp Gly Ser Phe
            50                  55                  60
Phe Leu Val Ser Lys Leu Thr Val Asp Lys Ser Arg Trp Gln Gln Gly
 65                 70                  75                  80
Asn Val Phe Ser Cys Ser Val Met His Glu Ala Leu His Asn Arg Phe
                85                  90                  95
Thr Gln Lys Ser Leu Ser Leu Ser Pro Gly Lys
            100                 105
```

<210> SEQ ID NO 170
<211> LENGTH: 107
<212> TYPE: PRT
<213> ORGANISM: Artificial Sequence
<220> FEATURE:
<223> OTHER INFORMATION: Synthetic

<400> SEQUENCE: 170

```
Gly Gln Pro Arg Glu Pro Gln Val Tyr Thr Leu Pro Pro Ser Arg Asp
 1               5                  10                  15
Glu Leu Thr Lys Asn Gln Val Ser Leu Trp Cys Leu Val Lys Gly Phe
            20                  25                  30
Tyr Pro Ser Asp Ile Ala Val Glu Trp Glu Ser Asn Gly Gln Pro Glu
            35                  40                  45
Asn Asn Tyr Asp Thr Thr Pro Pro Val Leu Asp Ser Asp Gly Ser Phe
            50                  55                  60
Phe Leu Tyr Ser Asp Leu Thr Val Asp Lys Ser Arg Trp Gln Gln Gly
 65                 70                  75                  80
Asn Val Phe Ser Cys Ser Val Met His Glu Ala Leu His Asn His Tyr
                85                  90                  95
Thr Gln Lys Ser Leu Ser Leu Ser Pro Gly Lys
            100                 105
```

<210> SEQ ID NO 171
<211> LENGTH: 107
<212> TYPE: PRT
<213> ORGANISM: Artificial Sequence
<220> FEATURE:
<223> OTHER INFORMATION: Synthetic

<400> SEQUENCE: 171

```
Gly Gln Pro Arg Glu Pro Gln Val Tyr Thr Leu Pro Pro Ser Arg Asp
 1               5                  10                  15
Glu Leu Thr Lys Asn Gln Val Ser Leu Thr Cys Arg Val Lys Gly Phe
            20                  25                  30
Tyr Pro Ser Asp Ile Ala Val Glu Trp Glu Ser Asn Gly Gln Pro Glu
            35                  40                  45
Asn Asn Tyr Lys Thr Thr Pro Pro Val Leu Lys Ser Asp Gly Ser Phe
            50                  55                  60
Phe Leu Ala Ser Lys Leu Thr Val Asp Lys Ser Arg Trp Gln Gln Gly
 65                 70                  75                  80
Asn Val Phe Ser Cys Ser Val Met His Glu Ala Leu His Asn His Tyr
                85                  90                  95
Thr Gln Lys Ser Leu Ser Leu Ser Pro Gly Lys
            100                 105
```

<210> SEQ ID NO 172
<211> LENGTH: 107

<212> TYPE: PRT
<213> ORGANISM: Artificial Sequence
<220> FEATURE:
<223> OTHER INFORMATION: Synthetic

<400> SEQUENCE: 172

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Asp Thr Thr Pro Pro Val Leu Asp Ser Asp Gly Ser Phe
    50                  55                  60

Phe Leu Tyr Ser Asp Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 173
<211> LENGTH: 107
<212> TYPE: PRT
<213> ORGANISM: Artificial Sequence
<220> FEATURE:
<223> OTHER INFORMATION: Synthetic

<400> SEQUENCE: 173

Gly Gln Pro Arg Glu Pro Gln Val Tyr Thr Leu Pro Pro Ser Arg Lys
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Lys Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 174
<211> LENGTH: 107
<212> TYPE: PRT
<213> ORGANISM: Artificial Sequence
<220> FEATURE:
<223> OTHER INFORMATION: Synthetic

<400> SEQUENCE: 174

Gly Gln Pro Arg Glu Pro Gln Val Tyr Thr Leu Pro Pro Ser Arg Asp
1               5                   10                  15

Glu Leu Thr Lys Asn Gln Val Ser Leu Ser Cys Ala Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe

```
                    50                  55                  60
Phe Leu Val Ser Lys Leu Thr Val Asp Lys Ser Arg Trp Gln Gln Gly
 65                  70                  75                  80

Asn Val Phe Ser Cys Ser Val Met His Glu Ala Leu His Asn His Tyr
                 85                  90                  95

Thr Gln Lys Ser Leu Ser Leu Ser Pro Gly Lys
            100                 105

<210> SEQ ID NO 175
<211> LENGTH: 107
<212> TYPE: PRT
<213> ORGANISM: Artificial Sequence
<220> FEATURE:
<223> OTHER INFORMATION: Synthetic

<400> SEQUENCE: 175

Gly Gln Pro Arg Glu Pro Gln Val Tyr Thr Leu Pro Pro Ser Arg Asp
  1               5                  10                  15

Glu Leu Thr Lys Asn Gln Val Ser Leu Trp Cys Leu Val Lys Gly Phe
                 20                  25                  30

Tyr Pro Ser Asp Ile Ala Val Glu Trp Glu Ser Asn Gly Gln Pro Glu
             35                  40                  45

Asn Asn Tyr Lys Thr Thr Pro Pro Val Leu Asp Ser Asp Gly Ser Phe
         50                  55                  60

Phe Leu Tyr Ser Lys Leu Thr Val Asp Lys Ser Arg Trp Gln Gln Gly
 65                  70                  75                  80

Asn Val Phe Ser Cys Ser Val Met His Glu Ala Leu His Asn His Tyr
                 85                  90                  95

Thr Gln Lys Ser Leu Ser Leu Ser Pro Gly Lys
            100                 105

<210> SEQ ID NO 176
<211> LENGTH: 107
<212> TYPE: PRT
<213> ORGANISM: Artificial Sequence
<220> FEATURE:
<223> OTHER INFORMATION: Synthetic

<400> SEQUENCE: 176

Gly Gln Pro Arg Glu Pro Gln Val Cys Thr Leu Pro Pro Ser Arg Asp
  1               5                  10                  15

Glu Leu Thr Lys Asn Gln Val Ser Leu Ser Cys Ala Val Lys Gly Phe
                 20                  25                  30

Tyr Pro Ser Asp Ile Ala Val Glu Trp Glu Ser Asn Gly Gln Pro Glu
             35                  40                  45

Asn Asn Tyr Lys Thr Thr Pro Pro Val Leu Asp Ser Asp Gly Ser Phe
         50                  55                  60

Phe Leu Val Ser Lys Leu Thr Val Asp Lys Ser Arg Trp Gln Gln Gly
 65                  70                  75                  80

Asn Val Phe Ser Cys Ser Val Met His Glu Ala Leu His Asn His Tyr
                 85                  90                  95

Thr Gln Lys Ser Leu Ser Leu Ser Pro Gly Lys
            100                 105

<210> SEQ ID NO 177
<211> LENGTH: 107
<212> TYPE: PRT
<213> ORGANISM: Artificial Sequence
<220> FEATURE:
```

<223> OTHER INFORMATION: Synthetic

<400> SEQUENCE: 177

Gly Gln Pro Arg Glu Pro Gln Val Tyr Thr Leu Pro Pro Cys Arg Asp
1               5                   10                  15

Glu Leu Thr Lys Asn Gln Val Ser Leu Trp Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 178
<211> LENGTH: 107
<212> TYPE: PRT
<213> ORGANISM: Artificial Sequence
<220> FEATURE:
<223> OTHER INFORMATION: Synthetic

<400> SEQUENCE: 178

Gly Gln Pro Arg Glu Pro Gln Val Cys Thr Leu Pro Pro Ser Arg Asp
1               5                   10                  15

Glu Leu Thr Lys Asn Gln Val Ser Leu Ser Cys Ala Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Val Ser Lys Leu Thr Val Asp Lys Ser Arg Trp Gln Gln Gly
65                  70                  75                  80

Asn Val Phe Ser Cys Ser Val Met His Glu Ala Leu His Asn Arg Phe
                85                  90                  95

Thr Gln Lys Ser Leu Ser Leu Ser Pro Gly Lys
            100                 105

<210> SEQ ID NO 179
<211> LENGTH: 107
<212> TYPE: PRT
<213> ORGANISM: Artificial Sequence
<220> FEATURE:
<223> OTHER INFORMATION: Synthetic

<400> SEQUENCE: 179

Gly Gln Pro Arg Glu Pro Gln Val Tyr Thr Leu Pro Pro Cys Arg Asp
1               5                   10                  15

Glu Leu Thr Lys Asn Gln Val Ser Leu Trp Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly

```
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 180
<211> LENGTH: 107
<212> TYPE: PRT
<213> ORGANISM: Artificial Sequence
<220> FEATURE:
<223> OTHER INFORMATION: Synthetic

<400> SEQUENCE: 180

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Arg Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Lys Ser Asp Gly Ser Phe
    50                  55                  60

Phe Leu Ala Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 181
<211> LENGTH: 107
<212> TYPE: PRT
<213> ORGANISM: Artificial Sequence
<220> FEATURE:
<223> OTHER INFORMATION: Synthetic

<400> SEQUENCE: 181

Gly Gln Pro Arg Glu Pro Gln Val Tyr Thr Leu Pro Pro Ser Arg Asp
1               5                   10                  15

Glu Leu Thr Lys Asn Gln Val Ser Leu Trp Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Asp Thr Thr Pro Pro Val Leu Asp Ser Asp Gly Ser Phe
    50                  55                  60

Phe Leu Tyr Ser Asp Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 182
<211> LENGTH: 107
<212> TYPE: PRT
<213> ORGANISM: Artificial Sequence
<220> FEATURE:
<223> OTHER INFORMATION: Synthetic

<400> SEQUENCE: 182
```

Gly Gln Pro Arg Glu Pro Gln Val Tyr Thr Leu Pro Pro Ser Arg Lys
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Lys Ser Asp Gly Ser Phe
    50                  55                  60

Phe Leu Tyr Ser Lys Leu Thr Val Asp Lys Ser Arg Trp Gln Gln Gly
65              70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 183
<211> LENGTH: 107
<212> TYPE: PRT
<213> ORGANISM: Artificial Sequence
<220> FEATURE:
<223> OTHER INFORMATION: Synthetic

<400> SEQUENCE: 183

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Asp Thr Thr Pro Pro Val Leu Asp Ser Asp Gly Ser Phe
    50                  55                  60

Phe Leu Tyr Ser Asp Leu Thr Val Asp Lys Ser Arg Trp Gln Gln Gly
65              70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 184
<211> LENGTH: 258
<212> TYPE: PRT
<213> ORGANISM: Artificial Sequence
<220> FEATURE:
<223> OTHER INFORMATION: Synthetic

<400> SEQUENCE: 184

Val Pro Arg Trp Arg Gln Gln Trp Ser Gly Pro Gly Thr Thr Lys Arg
1               5                   10                  15

Phe Pro Glu Thr Val Leu Ala Arg Cys Val Lys Tyr Thr Glu Ile His
            20                  25                  30

Pro Glu Met Arg His Val Asp Cys Gln Ser Val Trp Asp Ala Phe Lys
        35                  40                  45

Gly Ala Phe Ile Ser Lys His Pro Cys Asn Ile Thr Glu Glu Asp Tyr
    50                  55                  60

Gln Pro Leu Met Lys Leu Gly Thr Gln Thr Val Pro Cys Asn Lys Ile
65              70                  75                  80

Leu Leu Trp Ser Arg Ile Lys Asp Leu Ala His Gln Phe Thr Gln Val

```
                    85                  90                  95
Gln Arg Asp Met Phe Thr Leu Glu Asp Thr Leu Leu Gly Tyr Leu Ala
                100                 105                 110

Asp Asp Leu Thr Trp Cys Gly Glu Phe Asn Thr Ser Lys Ile Asn Tyr
            115                 120                 125

Gln Ser Cys Pro Asp Trp Arg Lys Asp Cys Ser Asn Asn Pro Val Ser
        130                 135                 140

Val Phe Trp Lys Thr Val Ser Arg Arg Phe Ala Glu Ala Ala Cys Asp
145                 150                 155                 160

Val Val His Val Met Leu Asn Gly Ser Arg Ser Lys Ile Phe Asp Lys
                165                 170                 175

Asn Ser Thr Phe Gly Ser Val Glu Val His Asn Leu Gln Pro Glu Lys
            180                 185                 190

Val Gln Thr Leu Glu Ala Trp Val Ile His Gly Gly Arg Glu Asp Ser
        195                 200                 205

Arg Asp Leu Cys Gln Asp Pro Thr Ile Lys Glu Leu Glu Ser Ile Ile
210                 215                 220

Ser Lys Arg Asn Ile Gln Phe Ser Cys Lys Asn Ile Tyr Arg Pro Asp
225                 230                 235                 240

Lys Phe Leu Gln Cys Val Lys Asn Pro Glu Asp Ser Ser Cys Thr Ser
                245                 250                 255

Glu Ile

<210> SEQ ID NO 185
<211> LENGTH: 54
<212> TYPE: PRT
<213> ORGANISM: Artificial Sequence
<220> FEATURE:
<223> OTHER INFORMATION: Synthetic

<400> SEQUENCE: 185

Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
            20                  25                  30

Pro Pro Leu Thr Cys Gln Arg Tyr Cys Asn Ala Ser Val Thr Asn Ser
        35                  40                  45

Val Lys Gly Thr Asn Ala
    50

<210> SEQ ID NO 186
<211> LENGTH: 220
<212> TYPE: PRT
<213> ORGANISM: Artificial Sequence
<220> FEATURE:
<223> OTHER INFORMATION: Synthetic

<400> SEQUENCE: 186

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Gln
        35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
```

```
                65                  70                  75                  80
Leu Gln Ile Thr Asp Val Lys Leu Gln Asp Ala Gly Val Tyr Arg Cys
                    85                  90                  95

Met Ile Ser Tyr Gly Gly Ala Asp Tyr Lys Arg Ile Thr Val Lys Val
                    100                 105                 110

Asn Ala Pro Tyr Asn Lys Ile Asn Gln Arg Ile Leu Val Val Asp Pro
                    115                 120                 125

Val Thr Ser Glu His Glu Leu Thr Cys Gln Ala Glu Gly Tyr Pro Lys
                    130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                    165                 170                 175

Ser Thr Leu Arg Ile Asn Thr Thr Asn Glu Ile Phe Tyr Cys Thr
                    180                 185                 190

Phe Arg Arg Leu Asp Pro Glu Glu Asn His Thr Ala Glu Leu Val Ile
                    195                 200                 205

Pro Glu Leu Pro Leu Ala His Pro Pro Asn Glu Arg
                    210                 215                 220

<210> SEQ ID NO 187
<211> LENGTH: 204
<212> TYPE: PRT
<213> ORGANISM: Artificial Sequence
<220> FEATURE:
<223> OTHER INFORMATION: Synthetic

<400> SEQUENCE: 187

Ser Gly Pro Val Lys Glu Leu Val Gly Ser Val Gly Gly Ala Val Thr
1               5                   10                  15

Phe Pro Leu Lys Ser Lys Val Lys Gln Val Asp Ser Ile Val Trp Thr
                    20                  25                  30

Phe Asn Thr Thr Pro Leu Val Thr Ile Gln Pro Glu Gly Gly Thr Ile
                    35                  40                  45

Ile Val Thr Gln Asn Arg Asn Arg Glu Arg Val Asp Phe Pro Asp Gly
                    50                  55                  60

Gly Tyr Ser Leu Lys Leu Ser Lys Leu Lys Lys Asn Asp Ser Gly Ile
65                  70                  75                  80

Tyr Tyr Val Gly Ile Tyr Ser Ser Ser Leu Gln Gln Pro Ser Thr Gln
                    85                  90                  95

Glu Tyr Val Leu His Val Tyr Glu His Leu Ser Lys Pro Lys Val Thr
                    100                 105                 110

Met Gly Leu Gln Ser Asn Lys Asn Gly Thr Cys Val Thr Asn Leu Thr
                    115                 120                 125

Cys Cys Met Glu His Gly Glu Glu Asp Val Ile Tyr Thr Trp Lys Ala
                    130                 135                 140

Leu Gly Gln Ala Ala Asn Glu Ser His Asn Gly Ser Ile Leu Pro Ile
145                 150                 155                 160

Ser Trp Arg Trp Gly Glu Ser Asp Met Thr Phe Ile Cys Val Ala Arg
                    165                 170                 175

Asn Pro Val Ser Arg Asn Phe Ser Ser Pro Ile Leu Ala Arg Lys Leu
                    180                 185                 190

Cys Glu Gly Ala Ala Asp Asp Pro Asp Ser Ser Met
                    195                 200
```

```
<210> SEQ ID NO 188
<211> LENGTH: 651
<212> TYPE: PRT
<213> ORGANISM: Artificial Sequence
<220> FEATURE:
<223> OTHER INFORMATION: Synthetic

<400> SEQUENCE: 188

Lys Leu Thr Ile Glu Ser Thr Pro Phe Asn Val Ala Glu Gly Lys Glu
1               5                   10                  15

Val Leu Leu Val His Asn Leu Pro Gln His Leu Phe Gly Tyr Ser
            20                  25                  30

Trp Tyr Lys Gly Glu Arg Val Asp Gly Asn Arg Gln Ile Ile Gly Tyr
        35                  40                  45

Val Ile Gly Thr Gln Gln Ala Thr Pro Gly Pro Ala Tyr Ser Gly Arg
    50                  55                  60

Glu Ile Ile Tyr Pro Asn Ala Ser Leu Leu Ile Gln Asn Ile Ile Gln
65                  70                  75                  80

Asn Asp Thr Gly Phe Tyr Thr Leu His Val Ile Lys Ser Asp Leu Val
                85                  90                  95

Asn Glu Glu Ala Thr Gly Gln Phe Arg Val Tyr Pro Glu Leu Pro Lys
            100                 105                 110

Pro Ser Ile Ser Ser Asn Asn Ser Lys Pro Val Glu Asp Lys Asp Ala
        115                 120                 125

Val Ala Phe Thr Cys Glu Pro Glu Thr Gln Asp Ala Thr Tyr Leu Trp
    130                 135                 140

Trp Val Asn Asn Gln Ser Leu Pro Val Ser Pro Arg Leu Gln Leu Ser
145                 150                 155                 160

Asn Gly Asn Arg Thr Leu Thr Leu Phe Asn Val Thr Arg Asn Asp Thr
                165                 170                 175

Ala Ser Tyr Lys Cys Glu Thr Gln Asn Pro Val Ser Ala Arg Arg Ser
            180                 185                 190

Asp Ser Val Ile Leu Asn Val Leu Tyr Gly Pro Asp Ala Pro Thr Ile
        195                 200                 205

Ser Pro Leu Asn Thr Ser Tyr Arg Ser Gly Glu Asn Leu Asn Leu Ser
    210                 215                 220

Cys His Ala Ala Ser Asn Pro Pro Ala Gln Tyr Ser Trp Phe Val Asn
225                 230                 235                 240

Gly Thr Phe Gln Gln Ser Thr Gln Glu Leu Phe Ile Pro Asn Ile Thr
                245                 250                 255

Val Asn Asn Ser Gly Ser Tyr Thr Cys Gln Ala His Asn Ser Asp Thr
            260                 265                 270

Gly Leu Asn Arg Thr Thr Val Thr Thr Ile Thr Val Tyr Ala Glu Pro
        275                 280                 285

Pro Lys Pro Phe Ile Thr Ser Asn Asn Ser Asn Pro Val Glu Asp Glu
    290                 295                 300

Asp Ala Val Ala Leu Thr Cys Glu Pro Glu Ile Gln Asn Thr Thr Tyr
305                 310                 315                 320

Leu Trp Trp Val Asn Asn Gln Ser Leu Pro Val Ser Pro Arg Leu Gln
                325                 330                 335

Leu Ser Asn Asp Asn Arg Thr Leu Thr Leu Leu Ser Val Thr Arg Asn
            340                 345                 350

Asp Val Gly Pro Tyr Glu Cys Gly Ile Gln Asn Lys Leu Ser Val Asp
        355                 360                 365

His Ser Asp Pro Val Ile Leu Asn Val Leu Tyr Gly Pro Asp Asp Pro
```

```
                370                 375                 380
Thr Ile Ser Pro Ser Tyr Thr Tyr Tyr Arg Pro Gly Val Asn Leu Ser
385                 390                 395                 400

Leu Ser Cys His Ala Ala Ser Asn Pro Pro Ala Gln Tyr Ser Trp Leu
                405                 410                 415

Ile Asp Gly Asn Ile Gln Gln His Thr Gln Glu Leu Phe Ile Ser Asn
                420                 425                 430

Ile Thr Glu Lys Asn Ser Gly Leu Tyr Thr Cys Gln Ala Asn Asn Ser
                435                 440                 445

Ala Ser Gly His Ser Arg Thr Thr Val Lys Thr Ile Thr Val Ser Ala
                450                 455                 460

Glu Leu Pro Lys Pro Ser Ile Ser Ser Asn Asn Ser Lys Pro Val Glu
465                 470                 475                 480

Asp Lys Asp Ala Val Ala Phe Thr Cys Glu Pro Glu Ala Gln Asn Thr
                485                 490                 495

Thr Tyr Leu Trp Trp Val Asn Gly Gln Ser Leu Pro Val Ser Pro Arg
                500                 505                 510

Leu Gln Leu Ser Asn Gly Asn Arg Thr Leu Thr Leu Phe Asn Val Thr
                515                 520                 525

Arg Asn Asp Ala Arg Ala Tyr Val Cys Gly Ile Gln Asn Ser Val Ser
530                 535                 540

Ala Asn Arg Ser Asp Pro Val Thr Leu Asp Val Leu Tyr Gly Pro Asp
545                 550                 555                 560

Thr Pro Ile Ile Ser Pro Pro Asp Ser Ser Tyr Leu Ser Gly Ala Asn
                565                 570                 575

Leu Asn Leu Ser Cys His Ser Ala Ser Asn Pro Ser Pro Gln Tyr Ser
                580                 585                 590

Trp Arg Ile Asn Gly Ile Pro Gln Gln His Thr Gln Val Leu Phe Ile
                595                 600                 605

Ala Lys Ile Thr Pro Asn Asn Asn Gly Thr Tyr Ala Cys Phe Val Ser
                610                 615                 620

Asn Leu Ala Thr Gly Arg Asn Asn Ser Ile Val Lys Ser Ile Thr Val
625                 630                 635                 640

Ser Ala Ser Gly Thr Ser Pro Gly Leu Ser Ala
                645                 650

<210> SEQ ID NO 189
<211> LENGTH: 104
<212> TYPE: PRT
<213> ORGANISM: Artificial Sequence
<220> FEATURE:
<223> OTHER INFORMATION: Synthetic

<400> SEQUENCE: 189

Asp Gly Asn Glu Glu Met Gly Gly Ile Thr Gln Thr Pro Tyr Lys Val
1               5                   10                  15

Ser Ile Ser Gly Thr Thr Val Ile Leu Thr Cys Pro Gln Tyr Pro Gly
                20                  25                  30

Ser Glu Ile Leu Trp Gln His Asn Asp Lys Asn Ile Gly Gly Asp Glu
            35                  40                  45

Asp Asp Lys Asn Ile Gly Ser Asp Glu Asp His Leu Ser Leu Lys Glu
        50                  55                  60

Phe Ser Glu Leu Glu Gln Ser Gly Tyr Tyr Val Cys Tyr Pro Arg Gly
65                  70                  75                  80

Ser Lys Pro Glu Asp Ala Asn Phe Tyr Leu Tyr Leu Arg Ala Arg Val
```

```
                    85                  90                  95

Cys Glu Asn Cys Met Glu Met Asp
                100

<210> SEQ ID NO 190
<211> LENGTH: 14
<212> TYPE: PRT
<213> ORGANISM: Artificial Sequence
<220> FEATURE:
<223> OTHER INFORMATION: Synthetic

<400> SEQUENCE: 190

His Gly Asn Phe Gly Asn Ser Tyr Val Ser Trp Gly Ala Tyr
1               5                   10

<210> SEQ ID NO 191
<211> LENGTH: 14
<212> TYPE: PRT
<213> ORGANISM: Artificial Sequence
<220> FEATURE:
<223> OTHER INFORMATION: Synthetic

<400> SEQUENCE: 191

His Gly Asn Phe Gly Asn Ser Tyr Val Ser Trp Phe Gly Tyr
1               5                   10

<210> SEQ ID NO 192
<211> LENGTH: 112
<212> TYPE: PRT
<213> ORGANISM: Artificial Sequence
<220> FEATURE:
<223> OTHER INFORMATION: Synthetic

<400> SEQUENCE: 192

Pro Cys Pro Ala Pro Pro Val Ala Gly Pro Ser Val Phe Leu Phe Pro
1               5                   10                  15

Pro Lys Pro Lys Asp Thr Leu Met Ile Ser Arg Thr Pro Glu Val Thr
            20                  25                  30

Cys Val Val Val Asp Val Ser His Glu Ala Pro Glu Val Gln Phe Asn
        35                  40                  45

Trp Tyr Val Asp Gly Val Glu Val His Asn Ala Lys Thr Lys Pro Arg
    50                  55                  60

Glu Glu Gln Phe Asn Ser Thr Phe Arg Val Val Ser Val Leu Thr Val
65                  70                  75                  80

Val His Gln Asp Trp Leu Asn Gly Lys Glu Tyr Lys Cys Lys Val Ser
                85                  90                  95

Asn Lys Gly Leu Pro Ala Pro Ile Glu Lys Thr Ile Ser Lys Thr Lys
                100                 105                 110

<210> SEQ ID NO 193
<211> LENGTH: 118
<212> TYPE: PRT
<213> ORGANISM: Artificial Sequence
<220> FEATURE:
<223> OTHER INFORMATION: Synthetic

<400> SEQUENCE: 193

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Ser Tyr
            20                  25                  30

Trp Ile Asn Trp Val Lys Gln Arg Pro Gly Gln Gly Leu Glu Trp Ile
```

```
                35                  40                  45
Gly Asn Ile Tyr Pro Ser Asp Ser Tyr Thr Asn Tyr Asn Gln Lys Phe
         50                  55                  60
Lys Asp Lys Ala Thr Leu Thr Val Asp Lys Ser Ser Thr Ala Tyr
 65                  70                  75                  80
Met Gln Leu Ser Ser Pro Thr Ser Glu Asp Ser Ala Val Tyr Tyr Cys
                 85                  90                  95
Thr Arg Ser Trp Arg Gly Asn Ser Phe Asp Tyr Trp Gly Gln Gly Thr
                100                 105                 110
Thr Leu Thr Val Ser Ser
            115

<210> SEQ ID NO 194
<211> LENGTH: 113
<212> TYPE: PRT
<213> ORGANISM: Artificial Sequence
<220> FEATURE:
<223> OTHER INFORMATION: Synthetic

<400> SEQUENCE: 194

Asp Ile Val Met Thr Gln Ser Pro Ser Ser Leu Thr Val Thr Ala Gly
  1               5                  10                  15
Glu Lys Val Thr Met Ser Cys Lys Ser Ser Gln Ser Leu Leu Asn Ser
                 20                  25                  30
Gly Asn Gln Lys Asn Tyr Leu Thr Trp Tyr Gln Gln Lys Pro Gly Gln
                 35                  40                  45
Pro Pro Lys Leu Leu Ile Tyr Trp Ala Ser Thr Arg Glu Ser Gly Val
         50                  55                  60
Pro Asp Arg Phe Thr Gly Ser Gly Ser Gly Thr Asp Phe Thr Leu Thr
 65                  70                  75                  80
Ile Ser Ser Val Gln Ala Glu Asp Leu Ala Val Tyr Tyr Cys Gln Asn
                 85                  90                  95
Asp Tyr Ser Tyr Pro Phe Thr Phe Gly Ser Gly Thr Lys Leu Glu Ile
                100                 105                 110
Lys

<210> SEQ ID NO 195
<211> LENGTH: 261
<212> TYPE: PRT
<213> ORGANISM: Artificial Sequence
<220> FEATURE:
<223> OTHER INFORMATION: Synthetic

<400> SEQUENCE: 195

Met Ala Val Thr Ala Cys Gln Gly Leu Gly Phe Val Val Ser Leu Ile
  1               5                  10                  15
Gly Ile Ala Gly Ile Ile Ala Ala Thr Cys Met Asp Gln Trp Ser Thr
                 20                  25                  30
Gln Asp Leu Tyr Asn Asn Pro Val Thr Ala Val Phe Asn Tyr Gln Gly
                 35                  40                  45
Leu Trp Arg Ser Cys Val Arg Glu Ser Gly Phe Thr Glu Cys Arg
         50                  55                  60
Gly Tyr Phe Thr Leu Leu Gly Leu Pro Ala Met Leu Gln Ala Val Arg
 65                  70                  75                  80
Ala Leu Met Ile Val Gly Ile Val Leu Gly Ala Ile Gly Leu Leu Val
                 85                  90                  95
Ser Ile Phe Ala Leu Lys Cys Ile Arg Ile Gly Ser Met Glu Asp Ser
```

|     |     |     |     | 100 |     |     |     | 105 |     |     |     | 110 |     |     |
| --- | --- | --- | --- | --- | --- | --- | --- | --- | --- | --- | --- | --- | --- | --- |
| Ala | Lys | Ala | Asn | Met | Thr | Leu | Thr | Ser | Gly | Ile | Met | Phe | Ile | Val | Ser |
|     |     |     | 115 |     |     |     |     | 120 |     |     |     |     | 125 |     |     |
| Gly | Leu | Cys | Ala | Ile | Ala | Gly | Val | Ser | Val | Phe | Ala | Asn | Met | Leu | Val |
|     |     |     | 130 |     |     |     |     | 135 |     |     |     |     | 140 |     |     |
| Thr | Asn | Phe | Trp | Met | Ser | Thr | Ala | Asn | Met | Tyr | Thr | Gly | Met | Gly | Gly |
| 145 |     |     |     |     | 150 |     |     |     |     | 155 |     |     |     |     | 160 |
| Met | Val | Gln | Thr | Val | Gln | Thr | Arg | Tyr | Thr | Phe | Gly | Ala | Ala | Leu | Phe |
|     |     |     |     | 165 |     |     |     |     | 170 |     |     |     |     | 175 |     |
| Val | Gly | Trp | Val | Ala | Gly | Gly | Leu | Thr | Leu | Ile | Gly | Gly | Val | Met | Met |
|     |     |     |     | 180 |     |     |     |     | 185 |     |     |     |     | 190 |     |
| Cys | Ile | Ala | Cys | Arg | Gly | Leu | Ala | Pro | Glu | Glu | Thr | Asn | Tyr | Lys | Ala |
|     |     |     | 195 |     |     |     |     | 200 |     |     |     |     | 205 |     |     |
| Val | Ser | Tyr | His | Ala | Ser | Gly | His | Ser | Val | Ala | Tyr | Lys | Pro | Gly | Gly |
|     |     |     | 210 |     |     |     |     | 215 |     |     |     |     | 220 |     |     |
| Phe | Lys | Ala | Ser | Thr | Gly | Phe | Gly | Ser | Asn | Thr | Lys | Asn | Lys | Lys | Ile |
| 225 |     |     |     |     | 230 |     |     |     |     | 235 |     |     |     |     | 240 |
| Tyr | Asp | Gly | Gly | Ala | Arg | Thr | Glu | Asp | Glu | Val | Gln | Ser | Tyr | Pro | Ser |
|     |     |     |     | 245 |     |     |     |     | 250 |     |     |     |     | 255 |     |
| Lys | His | Asp | Tyr | Val |
|     |     |     |     | 260 |